US012698286B2

(12) United States Patent
Kakuuchi et al.

(10) Patent No.: US 12,698,286 B2
(45) Date of Patent: Aug. 4, 2026

(54) COMPOUND HAVING KDM5 INHIBITORY ACTIVITY AND PHARMACEUTICAL USE THEREOF

(71) Applicant: ONO PHARMACEUTICAL CO., LTD., Osaka (JP)

(72) Inventors: Akito Kakuuchi, Osaka (JP); Shuhei Umemura, Osaka (JP); Mats Svensson, New York, NY (US); Anatoly Ruvinsky, Lexington, MA (US); Daigo Inoyama, Edgewater, NJ (US); Goran Krilov, Long Island City, NY (US); Hidenori Takahashi, Lagrangeville, NY (US); Kyle Konze, Brooklyn, NY (US); Andreas Verras, New York, NY (US); Simon Crumpler, Saffron Walden (GB); Maelle Vallade, Saffron Walden (GB); Calum Macleod, Saffron Walden (GB); James N. Sanderson, Saffron Walden (GB); Richard J. Bull, Saffron Walden (GB); Simon Gaines, Saffron Walden (GB)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 1131 days.

(21) Appl. No.: 17/623,706

(22) PCT Filed: Jul. 16, 2020

(86) PCT No.: PCT/JP2020/028771
§ 371 (c)(1),
(2) Date: Dec. 29, 2021

(87) PCT Pub. No.: WO2021/010492
PCT Pub. Date: Jan. 21, 2021

(65) Prior Publication Data

US 2022/0289751 A1 Sep. 15, 2022

Related U.S. Application Data

(60) Provisional application No. 62/875,091, filed on Jul. 17, 2019.

(51) Int. Cl.

| | |
|---|---|
| ***C07D 487/04*** | (2006.01) |
| ***A61K 31/4155*** | (2006.01) |
| ***A61K 31/427*** | (2006.01) |
| ***A61K 31/4439*** | (2006.01) |
| ***A61K 31/519*** | (2006.01) |
| ***A61K 31/53*** | (2006.01) |
| ***C07D 401/14*** | (2006.01) |
| ***C07D 403/12*** | (2006.01) |
| ***C07D 471/04*** | (2006.01) |
| ***C07D 487/10*** | (2006.01) |

(52) U.S. Cl.
CPC ........ *C07D 487/04* (2013.01); *A61K 31/4155* (2013.01); *A61K 31/427* (2013.01); *A61K 31/4439* (2013.01); *A61K 31/519* (2013.01); *A61K 31/53* (2013.01); *C07D 401/14* (2013.01); *C07D 403/12* (2013.01); *C07D 471/04* (2013.01); *C07D 487/10* (2013.01)

(58) Field of Classification Search
CPC .......... A61P 25/28; A61P 35/00; A61P 43/00; C07D 401/14; C07D 403/06; C07D 403/12; C07D 403/14; C07D 413/14; C07D 471/04; C07D 487/04; C07D 487/10; C07D 498/10
See application file for complete search history.

(56) References Cited

U.S. PATENT DOCUMENTS

| | | | | |
|---|---|---|---|---|
| 11,691,968 B2 * | 7/2023 | Kakuuchi | A61K 31/4155 548/240 |
| 2004/0235844 A1 | 11/2004 | Goodacre | |
| 2006/0135767 A1 | 6/2006 | Feng et al. | |
| 2015/0291592 A1 * | 10/2015 | Brochu | A61P 31/12 544/405 |
| 2023/0271952 A1 * | 8/2023 | Kakuuchi | A61P 35/00 548/240 |

FOREIGN PATENT DOCUMENTS

| | | |
|---|---|---|
| CN | 108341819 A | 7/2018 |
| EP | 1 140 828 A1 | 10/2001 |

(Continued)

OTHER PUBLICATIONS

Leadem et al. Cancer Res. Mar. 1, 2018; 78(5): 1127-1139. (Year: 2018).*

(Continued)

*Primary Examiner* — Kara R. McMillian
(74) *Attorney, Agent, or Firm* — Sughrue Mion, PLLC

(57) ABSTRACT

The compound disclosed is a KDM5 inhibitor represented by the general formula (Z):

(Z)

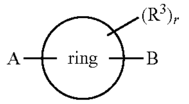

wherein all symbols have the same meanings as the definitions described in the specification, or a salt thereof, and is useful as a prophylactic and/or therapeutic agent for cancer, Huntington's disease, or Alzheimer's disease and the like.

7 Claims, No Drawings

(56) References Cited

FOREIGN PATENT DOCUMENTS

| | | | |
|---|---|---|---|
| WO | 00/39089 | A1 | 7/2000 |
| WO | 2016/057924 | A1 | 4/2016 |
| WO | 2021/223699 | A1 | 11/2021 |

OTHER PUBLICATIONS

Gehling et al. Bioorg. Med. Chem. Lett. 26 (2016) 4350-4354. (Year: 2016).*

International Search Report (PCT/ISA/210) issued Oct. 27, 2020 by the International Searching Authority in counterpart International Application No. PCT/JP2020/028771.

Written Opinion (PCT/ISA/237) issued Oct. 27, 2020 by the International Searching Authority in counterpart International Application No. PCT/JP2020/028771.

Communication issued on Jun. 30, 2023 by the European Patent Office for European Patent Application No. 20841280.9.

* cited by examiner

COMPOUND HAVING KDM5 INHIBITORY ACTIVITY AND PHARMACEUTICAL USE THEREOF

CROSS-REFERENCE TO RELATED APPLICATIONS

This is a U.S. National Stage of International Application No. PCT/JP2020/028771 filed on Jul. 16, 2020, claiming priority from U.S. Provisional Application No. 62-875,091 filed Jul. 17, 2019, the entire disclosures of which are incorporated by reference herein.

FIELD

The present invention relates to a compound represented by the general formula (Z) described hereinbelow having KDM5 inhibitory activity, or a salt thereof, and pharmaceutical use thereof.

BACKGROUND

Eukaryotic DNA exists in the nucleus as a chromatin structure that is a complex with histone proteins. Histone proteins are subject to modifications such as methylation, acetylation and phosphorylation through various enzymes, and changes in such modifications are known to induce chromatin remodelling and transcriptional alterations. Epigenetic modifications including histone methylation reversely regulate gene expression without altering any nucleotide sequence and play an important role in physiological processes.

KDM5 proteins are members of JARID histone demethylase protein family, which demethylates tri-methylation of the fourth lysine residue of histone H3 protein (H3K4me3). In mammalian species including humans, there are four subfamilies: KDM5A, KDM5B, KDM5C, and KDM5D, which have five conserved domains, namely JmjN, ARID, JmjC, PHDs, and C5HC2 zinc finger. The KDM5 family is widely distributed in blood cells and various organs in vivo, and particularly, is known to be highly expressed in cancer tissues. Epigenetic aberrations in cancer cells are known to be involved in the cell proliferation and metastasis, and KDM5 inhibitors have been reported to have efficacy against cancer cells. The involvement of epigenetic abnormalities, including histone modifications has also been reported in other pathologies such as neuropsychiatric disorders and metabolic diseases. Therefore, compounds with KDM5 inhibitory activity may improve the epigenetic abnormalities and be useful for the prevention and treatment of these diseases.

In arts related to the present invention, WO2014139326 reports that compounds represented by the formula (A) are useful as inhibitors of one or more histone demethylases such as KDM5.

Formula (A)

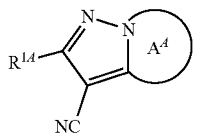

(A)

a pharmaceutically acceptable salt thereof, wherein:

$R^{1A}$ is —$R^A$, halogen atom, —$OR^A$, —$SR^A$, —$N(R^{1A})_2$, —CN;

each $R^A$ is independently hydrogen or an optionally substituted group selected from C1-6 aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-3 heteroatoms independently selected from nitrogen, oxygen, or sulfur, a 4-7 membered saturated or partially unsaturated heterocyclic ring having 1-2 heteroatoms independently selected from nitrogen, oxygen, or sulfur, a 7-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

each $R^{1A}$ is independently —$R^A$, —$C(O)R^A$, —$CO_2R^A$;

Ring $A^A$ is

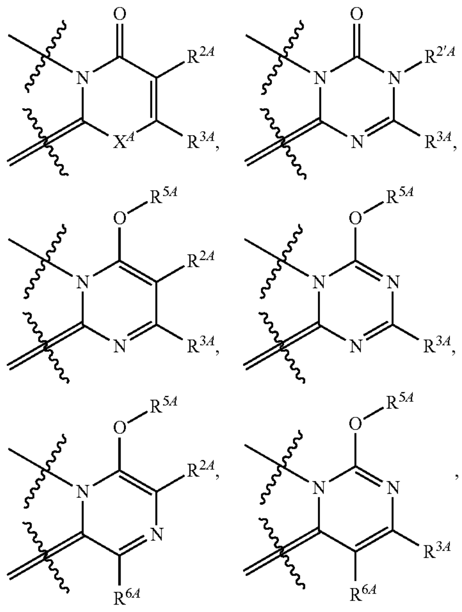

, or

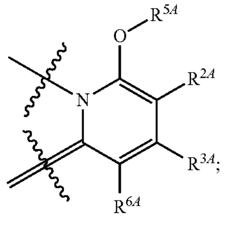

$R^{2A}$ and $R^{3A}$ are independently —$R^A$, halogen atom, —$OR^A$, —$SR^A$, —$N(R'^A)_2$, —CN;

$R^{2'A}$ is —$R^A$, —$OR^A$, —$SR^A$, —$N(R'^A)_2$, —$C(O)R^A$, —$CO_2R^A$;

$X^A$ is —$N(R^{4A})$—, —O—, or —S—;

$R^{4A}$ is —$R^A$, —$C(O)R^A$, —$CO_2R^A$, or —$S(O)_2R$;

$R^{5A}$ is $R^A$, —$C(O)R^A$, —$CO_2R^A$;

and $R^{6A}$ is —$R^A$, halogen atom, —$OR^A$, —$SR^A$, —$N(R^A)_2$, —CN (where the definitions of the groups are excerpted).

Further, WO2016057924 reports that compounds represented by the formula (B) are useful as inhibitors of one or more histone demethylases such as KDM5.

Formula (B)

(B)

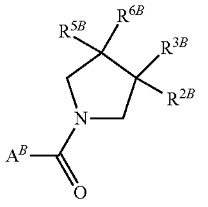

or a salt thereof, wherein:

$A^B$ is selected from the group consisting of:

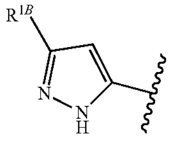

and

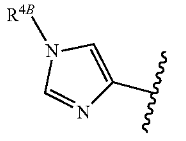

$R^{1B}$ is alkyl, cyclic group, or the like;

$R^{2B}$ is optionally substituted cyclic group, —$OR^{aA}$, —$C(O)N(R^{aA})_2$, or $NR^{aA}R^{bA}$;

$R^{aB}$ and $R^{bB}$ are each independently selected from H, optionally substituted alkyl group, and optionally substituted cyclic group, etc.;

$R^{3B}$ is H or alkyl;

$R^{4B}$ is H, alkyl, or cyclic group; and $R^{5B}$ is H, halo, or alkyl, and $R^{6B}$ is H, alkyl, cyclic group;

or $R^{5B}$ and $R^{6B}$ taken together to form cyclic group (where the definitions of the groups are excerpted).

However, none of the background art documents disclose the compound described hereinbelow in the present invention or a salt thereof or pharmaceutical use thereof.

CITATION LIST

Patent Literature

[PTL 1] WO 2014/139326

[PTL 2] WO 2016/057924

SUMMARY

Technical Problem

For example, a compound having KDM5 inhibitory activity for the treatment or prevention of diseases such as cancer, Huntington's disease, Alzheimer's disease and the like has been desired.

Solution to Problem

The inventors of the present invention have carried out extensive studies in order to achieve the above object, and as a result, found that the compound represented by the general formula (Z) described hereinafter, or a salt thereof can achieve the above object. The inventors have carried out further researches and completed the present invention.

That is, the present invention relates to:

[1] A compound represented by the general formula (Z):

(Z)

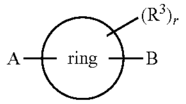

wherein ring represents a 3- to 10-membered mono or bicyclic hetero ring containing 1 to 4 nitrogen atoms, one oxygen atom and/or one sulfur atom, which may be substituted with 1 to 3 substituent(s) selected from a C1-4 alkyl, C1-4 haloalkyl, halogen atom, oxo or 5- or 6-membered monocyclic carbocycle;

a plurality of the substituents may be the same or different;

A represents $R^1$ or $R^{1-1}$-$L^1$-;

B represents $R^2$ or $R^{2-1}$-$L^2$-;

$R^1$ represents a hydrogen atom, C1-4 alkyl, nitrite, halogen atom, carbamoyl, C1-4 alkylaminocarbonyl, C1-4 dialkylaminocarbonyl, 5- or 6-membered monocyclic heterocycle which may be substituted with 1 to 4 $R^4$, or 5-isopropyl-1H-pyrazole-3-carbonyl;

$R^4$ represents a C1-4 alkyl, C2-6 acyl, or 5- or 6-membered monocyclic heterocycle which may be substituted with 1 to 4 C1-4 alkyl;

$R^2$ represents a hydrogen atom, or C1-4 alkyl;

$R^3$ represents a hydrogen atom, C1-4 alkyl which may be substituted with 1 to 3 $R^5$, C1-4 alkoxy which may be substituted with 1 to 3 $R^6$, hydroxy which may be substituted with $R^7$, amino which may be substituted with 1 or 2 $R^8$, 5- or 6-membered monocyclic carbocycle which may be substituted with 1 to 4 $R^9$, 4- to 6-membered monocyclic heterocycle which may be substituted with 1 to 4 $R^{10}$, or 4- to 15-membered bicyclic heterocycle which may be substituted with 1 to 4 $R^{11}$;

$R^5$ represents a C1-4 alkyl, halogen atom, or 5- or 6-membered monocyclic carbocycle;

$R^6$ represents a C1-4 alkyl, halogen atom, or 5- or 6-membered monocyclic carbocycle;

$R^7$ represents a 5- or 6-membered monocyclic carbocycle which may be substituted with 1 to 4 $R^{12}$, 5- or 6-membered monocyclic heterocycle which may be substituted with 1 to 4 $R^{13}$, benzyl, or 2-(2-tetrahydrofuryl)ethyl;

$R^8$ represents a C1-4 alkyl, or 2-(2-tetrahydrofuryl)ethyl;

$R^9$ represents a C1-4 alkyl, acetylaminomethyl, acetylaminoethyl, or 5- or 6-membered monocyclic heterocycle;

$R^{10}$ represents a C1-6 alkyl, C1-4 halo alkyl, C1-4 alkoxy-C1-4 alkyl, C3-8 cycloalkyl-C1-4 alkyl, benzyl, 5- or 6-membered monocyclic carbocycle, 5- or 6-membered monocyclic heterocycle, acetylaminomethyl, acetylaminoethyl, cyclopropylcarbonylaminoethyl, N-methyl-cyclopropylcarbonylaminoethyl, tert-butylcarbonylaminoethyl, N-methyl-tert-butylcarbonylaminoethyl, tert-butoxycarbonylaminoethyl, 1-phenylethyl, or 2-hydroxy-1-phenylethyl;

$R^{11}$ represents a C1-4 alkyl, or 5- or 6-membered monocyclic heterocycle;

$R^{12}$ represents a halogen atom, or C1-4 alkyl;

$R^{13}$ represents a C1-4 alkyl;

when being substituted with the plurality of $R^4$, $R^5$, $R^6$, $R^8$, $R^9$, $R^{10}$, $R^{11}$, $R^{12}$ or $R^{13}$, they may be the same or different;

$R^{1-1}$ represents a C3-8 cycloalkyl which may be substituted with 1 to 4 $R^{5-1}$, 5- or 6-membered monocyclic heterocycle which may be substituted with 1 to 4 $R^{6-1}$, or 4- to 15-membered bicyclic heterocycle which may be substituted with 1 to 4 $R^{7-1}$;

$R^{5-1}$ represents a C1-4 alkyl, C3-8 cycloalkyl, C1-4 haloalkyl, or halogen atom;

$R^{6-1}$ represents a C1-4 alkyl which may be substituted with 1 to 4 $R^{8-1}$, C3-8 cycloalkyl, C3-8 cycloalkyl which is substituted with C1-4 alkyl, C1-4 haloalkyl, or halogen atom;

$R^{7-1}$ represents a C1-4 alkyl, C3-8 cycloalkyl, C1-4 haloalkyl, or halogen atom;

$R^{8-1}$ represents a hydroxy, halogen atom, nitrile, benzyloxy, or 5- or 6-membered monocyclic carbocycle;

$L^1$ represents a bond, or carbonyl(—C(═O)—);

$L^2$ represents a bond, carbonyl(—C(═O)—), $—(CH_2)_n—NR^{9-1}C(═O)—$, or $—C(═O)NR^{10-1}—$;

$R^{9-1}$ represents a hydrogen atom, or C1-4 alkyl;

$R^{10-1}$ represents a hydrogen atom, or C1-4 alkyl;

n represents an integer of 0 to 3;

$R^{2-1}$ represents a hydrogen atom, C1-6 alkyl which may be substituted with 1 to 4 $R^{11-1}$, C1-4 alkoxy which may be substituted with 1 to 4 $R^{12-1}$, 3- to 8-membered monocyclic carbocycle which may be substituted with 1 to 4 $R^{13-1}$, 4- to 15-membered bicyclic carbocycle which may be substituted with 1 to 4 $R^{14-1}$, 5- or 6-membered monocyclic heterocycle which may be substituted with 1 to 4 $R^{15-1}$, or $—S(O)_m—$(C1-4 alkyl);

$R^{11-1}$ represents a hydroxy, halogen atom, or C3-8 cycloalkyl;

$R^{12-1}$ represents a hydroxy, halogen atom, or C3-8 cycloalkyl;

$R^{13-1}$ represents a C1-4 alkyl, C3-8 cycloalkyl, halogen atom, or C1-4 haloalkyl;

$R^{14-1}$ represents a C1-4 alkyl, C3-8 cycloalkyl, halogen atom, or C1-4 haloalkyl;

$R^{15-1}$ represents a C1-4 alkyl, C1-4 alkoxy, C1-4 haloalkyl, C3-8 cycloalkyl, halogen atom, phenyl which may be substituted with 1 to 4 $R^{16-1}$, phenoxy, pyridin-2-yl, 1-methylpyrazol-4-yl, or oxo;

$R^{16-1}$ represents a C1-4 alkyl, or C1-4 alkoxy;

m represents an integer of 0 to 2;

when being substituted with the plurality of $R^{5-1}$, $R^{6-1}$, $R^{7-1}$, $R^{8-1}$, $R^{11-1}$, $R^{12-1}$, $R^{13-1}$, $R^{14-1}$, $R^{15-1}$ or $R^{16-1}$, they may be the same or different; and r represents an integer of 0 to 1;

or a salt thereof;

[2] The compound according to the preceding item [1], wherein the compound represented by the general formula (Z) is represented by the general formula (I):

(I)

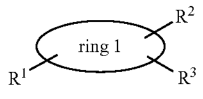

wherein the general formula (I) represents (I-1)

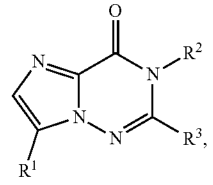

(I-2)

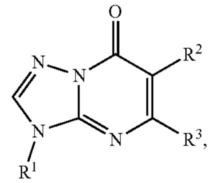

(I-3)

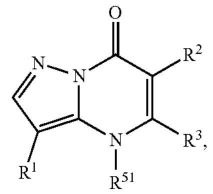

(I-4)

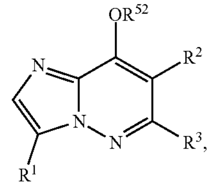

(I-5)

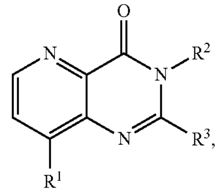

(I-6)

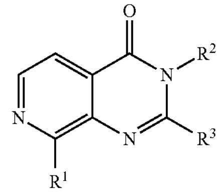

or (I-7)

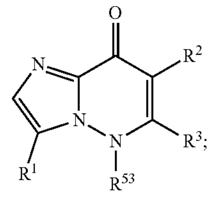

$R^{51}$ represents a hydrogen atom, or C1-4 alkyl;

$R^{52}$ represents a C1-4 alkyl;

$R^{53}$ represents a hydrogen atom, or C1-4 alkyl; and other symbols represent the same meaning as described in the preceding item [1]; or a salt thereof;

[3] The compound according to the preceding item [1] or [2], wherein the compound represented by the general formula (Z) or (I) is represented by the general formula (I-1), (I-5) or (I-7):

(I-1)

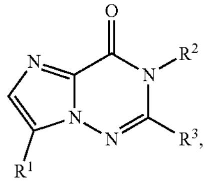

(I-5)

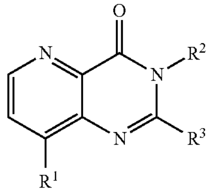

or (I-7)

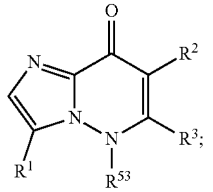

wherein all symbols represent the same meaning as described in the preceding item [1] or [2];

or a salt thereof;

[4] The compound according to any one of the preceding items [1] to [3], wherein the compound is represented by the general formula (I-1-1):

(I-1-1)

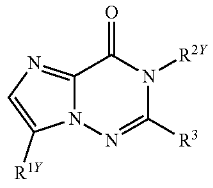

wherein $R^{1Y}$ represents a 5- or 6-membered monocyclic heterocycle which may be substituted with 1 to 4 $R^4$;

$R^{2Y}$ represents a C1-4 alkyl; and other symbols represent the same meaning as described in the preceding item [1];

or a salt thereof;

[5] The compound according to any one of the preceding items [1] to [4], wherein the compound is:

(1) 7-(1H-imidazol-5-yl)-3-isopropyl-2-(3-phenyl azetidin-1-yl)imidazo[2,1-f][1,2,4]triazin-4(3H)-one;

(2) 2-(1-(cyclopropylmethyl)-1H-pyrazol-4-yl)-7-(1H-imidazol-5-yl)-3-isopropylimidazo[2,1-f][1,2,4]triazin-4(3H)-one;

(3) 2-(1-(Cyclopropylmethyl)-1H-pyrazol-4-yl)-3-isopropyl-7-(1H-pyrazol-4-yl)imidazo[2,1-f][1,2,4]triazin-4(3H)-one;

(4) 3-Isopropyl-2-(1-methyl-1H-indol-5-yl)-7-(1H-pyrazol-4-yl)imidazo[2,1-f][1,2,4]triazin-4(3H)-one;

(5) 7-(1H-imidazol-5-yl)-3-isopropyl-2-(thiophen-2-yl)imidazo[2,1-f][1,2,4]triazin-4(3H)-one, 0.25 eq formate salt;

(6) 3-Isopropyl-7-(1H-pyrazol-4-yl)-2-(thiophen-2-yl)imidazo[2,1-f][1,2,4]triazin-4(3H)-one;

(7) N-(2-(4-(3-isopropyl-4-oxo-7-(1H-pyrazol-4-yl)-3,4-dihydroimidazo[2,1-f][1,2,4]triazin-2-yl)-1H-pyrazol-1-yl)ethyl)acetamide;

(8) 3-Isopropyl-2-methyl-7-(1-(5-methylpyridin-2-yl)-1H-pyrazol-4-yl)imidazo[2,1-f][1,2,4]triazin-4(3H)-one or (9) N-(2-(4-(7-(1H-Imidazol-4-yl)-3-isopropyl-4-oxo-3,4-dihydroimidazo[2,1-f][1,2,4]triazin-2-yl)-1H-pyrazol-1-yl)ethyl)acetamide or a salt thereof;

[6] The compound according to any one of the preceding items [1] to [3], wherein the compound is represented by the general formula (I-5-1):

(I-5-1)

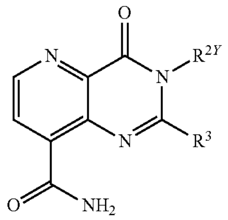

wherein all symbols represent the same meaning as described in the preceding item [1] or [4];

or a salt thereof;

[7] The compound according to any one of the preceding items [1] to [3] and [6], wherein the compound is:

(1) 2-(1-(Cyclopropylmethyl)-1H-pyrazol-4-yl)-3-isopropyl-4-oxo-3,4-dihydropyrido[3,2-d]pyrimidine-8-carboxamide; or (2) 3-isopropyl-4-oxo-2-phenyl-3,4-dihydropyrido[3,2-d]pyrimidine-8-carboxamide or a salt thereof;

[8] The compound according to any one of the preceding items [1] to [3], wherein the compound is represented by the general formula (I-7-1):

(I-7-1)

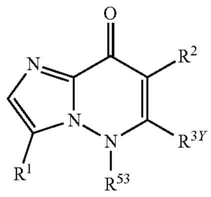

wherein $R^{3Y}$ represents a 5- or 6-membered monocyclic carbocycle which may be substituted with 1 to 4 $R^9$, 4- to 6-membered monocyclic heterocycle which may be substituted with 1 to 4 $R^m$, or 4- to 15-membered bicyclic heterocycle which may be substituted with 1 to 4 $R^{11}$; and other symbols represent the same meaning as described in the preceding item [1] or [2];

or a salt thereof;

[9] The compound according to any one of the preceding items [1] to [3] and [8], wherein the compound is:

(1) 7-Isopropyl-8-oxo-6-phenyl-5,8-dihydroimidazo[1,2-b]pyridazine-3-carbonitrile;

or a salt thereof;

[10] The compound according to the preceding item [1], wherein the compound represented by the general formula (Z) is represented by the general formula (II):

(II)

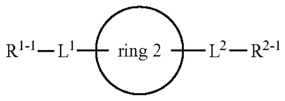

wherein the general formula (II) represents:

(II-1)

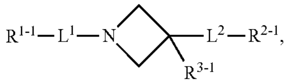

(II-2)

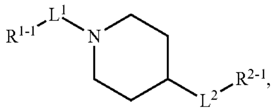

(II-3)

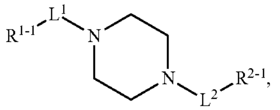

(II-4)

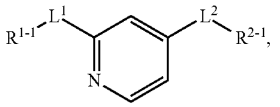

(II-5)

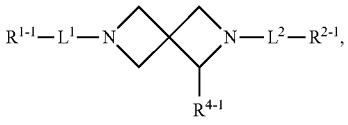

(II-6)

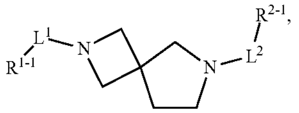

(II-7)

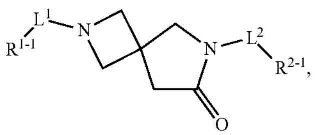

(II-8)

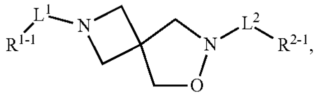

(II-9)

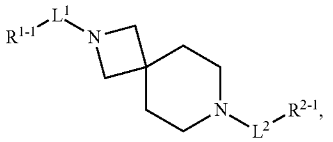

(II-10)

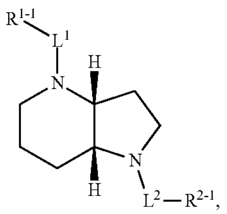

-continued (II-11)

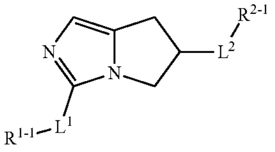

or (II-12)

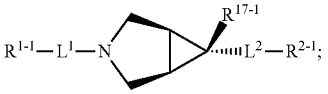

$R^{3-1}$ represents a hydrogen atom, C1-4 alkyl, C1-4 haloalkyl, or halogen atom;

$R^{4-1}$ represents a hydrogen atom, C1-4 alkyl, or 5- or 6-membered monocyclic carbocycle;

$R^{17-1}$ represents a hydrogen atom, or C1-4 alkyl;

represents α-configuration;

represents β-configuration;

represents α-configuration, β-configuration or the mixture of α-configuration and β-configuration; and other symbols represent the same meaning as described in the preceding item [1];

or a salt thereof;

[11] The compound according to the preceding item [1] or [10], wherein the compound represented by the general formula (Z) or (II) is represented by the general formula (II-1), (II-5), (II-8) or (II-12):

(II-1)

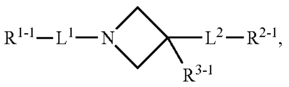

(II-5)

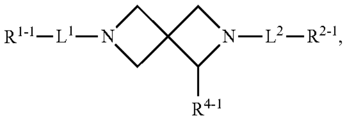

(II-8)

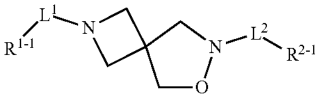

or (II-12)

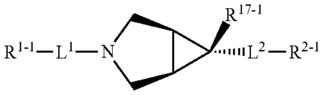

wherein all symbols represent the same meaning as described in the preceding item [1] or [10];

or a salt thereof;

[12] The compound according to the preceding item [1], [10] or [11], wherein the compound is represented by the general formula (II-1-1):

(II-1-1)

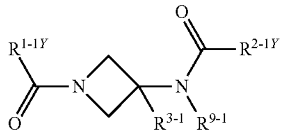

wherein $R^{1-1Y}$ represents

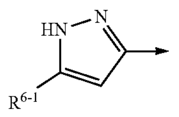

or

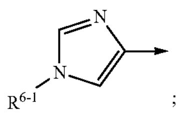

;

in the group, the arrow indicates the binding to the carbon atom of carbonyl;

$R^{2-1Y}$ represents a 3- to 8-membered monocyclic carbocycle which may be substituted with 1 to 4 $R^{13-1}$ or 4- to 15-membered bicyclic carbocycle which may be substituted with 1 to 4 $R^{14-1}$; and other symbols represent the same meaning as described in the preceding item [1];

or a salt thereof;

[13] The compound according to any one of the preceding items [1] and [10] to [12], wherein the compound is:

(1) N-(1-(5-Isopropyl-1H-pyrazole-3-carbonyl)azetidin-3-yl)cyclopropanecarboxamide;

or a salt thereof;

[14] The compound according to the preceding item [1], [10] or [11], wherein the compound is represented by the general formula (II-5-1):

(II-5-1)

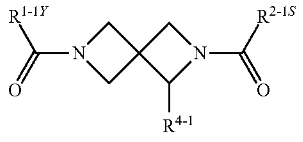

wherein $R^{2-1S}$ represents a 3- to 8-membered monocyclic carbocycle which may be substituted with 1 to 4 $R^{13-1}$, 4- to 15-membered bicyclic carbocycle which may be substituted with 1 to 4 $R^{14-1}$ or 5- or 6-membered monocyclic heterocycle which may be substituted with 1 to 4 $R^{15-1}$; and other symbols represent the same meaning as described in the preceding item [10] or [12];

or a salt thereof;

[15] The compound according to the preceding item [1], [10], [11] or [14], wherein the compound is:

(1) (5-cyclohexyl-1H-pyrazol-3-yl)(6-(cyclopropanecarbonyl)-2,6-diazaspiro[3.3]heptan-2-yl)methanone;

(2) (6-(Cyclopropanecarbonyl)-2,6-diazaspiro[3.3]heptan-2-yl)(1-isopropyl-1H-imidazol-4-yl)methanone;

(3) (5-Isopropyl-1H-pyrazol-3-yl)(6-(1-methylcyclopropane-1-carbonyl)-2,6-diazaspiro[3.3]heptan-2-yl)methanone;

(4) (5-Isopropyl-1H-pyrazol-3-yl)(6-(thiophene-2-carbonyl)-2,6-diazaspiro[3.3]heptan-2-yl)methanone; or (5) [2-(4-Fluoro-1-methyl-pyrazole-3-carbonyl)-2,6-diazaspiro[3.3]heptan-6-yl]-(5-isopropyl-1H-pyrazol-3-yl)methanone or a salt thereof;

[16] The compound according to the preceding item [1], [10] or [11], wherein the compound is represented by the general formula (II-8-1):

(II-8-1)

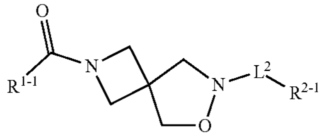

wherein all symbols represent the same meaning as described in the preceding item [1];

or a salt thereof;

[17] The compound according to the preceding item [1], [10], [11] or [16], wherein the compound is:

(1) 1-[2-(5-Isopropyl-1H-pyrazole-3-carbonyl)-6-oxa-2,7-diazaspiro[3.4]octan-7-yl]-2,2-dimethyl-propan-1-one;

or a salt thereof;

[18] The compound according to preceding item [1], [10] or [11], wherein the compound is represented by the general formula (II-12-1):

(II-12-1)

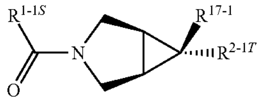

wherein $R^{1-1S}$ represents a 5-membered monocyclic aromatic hetero ring containing 1 to 4 nitrogen atoms, one oxygen atom and/or one sulfur atom which may be substituted with 1 to 4 $R^{6-1}$;

$R^{2-1T}$ represents a 5- or 6-membered monocyclic heterocycle which may be substituted with 1 to 4 $R^{15-1}$; and other symbols represent the same meaning as described in the preceding item [10];

or a salt thereof;

[19] The compound according to the preceding item [1], [10], [11] or [18], wherein the compound is:

(1) (5-isopropyl-1H-pyrazol-3-yl)((1R,5S,6r)-6-(5-methyl-4-phenylisoxazol-3-yl)-3-azabicyclo[3.1.0]hexan-3-yl)methanone;

or a salt thereof;

[20] A pharmaceutical composition comprising the compound represented by the general formula (Z) according to the preceding item [1] or a salt thereof, and a pharmaceutically acceptable carrier;

[21] The pharmaceutical composition according to the preceding item [20], which is KDM5 inhibitor;

[22] The pharmaceutical composition according to the preceding item [20] or [21], which is a prophylactic and/or therapeutic agent for KDM5-related disease;

[23-1] The pharmaceutical composition according to the preceding item [22], wherein the KDM5-related disease is hyperproliferative disease, cancer, stroke, diabetes, hepatomegaly, cardiovascular disease, multiple sclerosis, Huntington's disease, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders, myeloproliferative disorder, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, or hepatitis;

[23-2] The pharmaceutical composition according to the preceding item [22], wherein the KDM5-related disease is cancer, or Alzheimer's disease.

[24] A prophylactic and/or therapeutic agent for KDM5-related disease, comprising the compound represented by the general formula (Z) according to the preceding item [1] or a salt thereof as an active component, wherein the prophylactic and/or therapeutic agent is administered together with at least one drug selected from the group consisting of donepezil hydrochloride, galantamine hydrobromide, huperzine A, idebenone, levacecarnine hydrochloride, memantine hydrochloride, memantine hydrochloride/donepezil hydrochloride, proteolytic peptide fraction from porcine brain protein, rivastigmine tartrate, tacrine hydrochloride and aducanumab;

[25] A method for prophylaxis and/or therapy of KDM5-related disease, comprising administering to a mammal an effective amount of the compound represented by the general formula (Z) according to the preceding item [1] or a salt thereof;

[26] The compound represented by the general formula (Z) according to the preceding item [1] or a salt thereof for use in prophylaxis and/or therapy of KDM5-related disease;

[27] Use of the compound represented by the general formula (Z) according to the preceding item [1] or a salt thereof for manufacturing of a prophylactic and/or therapeutic agent for KDM5-related disease; and

[28] A compound represented by the general formula selected from the group consisting of the general formula (I-1-1), (I-5-1), (I-7-1), (II-1-1), (II-5-1), (II-8-1) and (II-12-1):

(I-1-1)

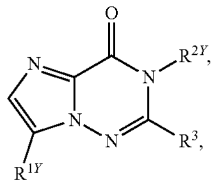

(I-5-1)

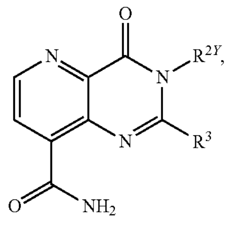

-continued (I-7-1)

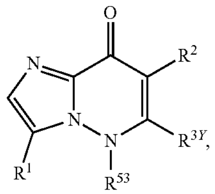

(II-1-1)

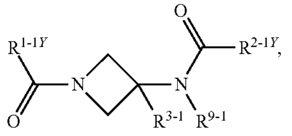

(II-5-1)

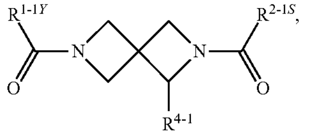

(II-8-1)

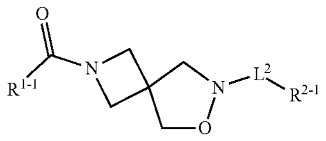

and (II-12-1)

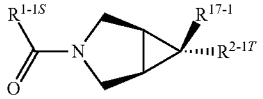

wherein $R^1$ represents a hydrogen atom, C1-4 alkyl, nitrile, halogen atom, carbamoyl, C1-4 alkylaminocarbonyl, C1-4 dialkylaminocarbonyl, 5- or 6-membered monocyclic heterocycle which may be substituted with 1 to 4 $R^4$, or 5-isopropyl-1H-pyrazole-3-carbonyl;

$R^4$ represents a C1-4 alkyl, C2-6 acyl, or 5- or 6-membered monocyclic heterocycle which may be substituted with 1 to 4 C1-4 alkyl;

$R^2$ represents a hydrogen atom, or C1-4 alkyl;

$R^3$ represents a hydrogen atom, C1-4 alkyl which may be substituted with 1 to 3 $R^5$, C1-4 alkoxy which may be substituted with 1 to 3 $R^6$, hydroxy which may be substituted with $R^7$, amino which may be substituted with 1 or 2 $R^8$, 5- or 6-membered monocyclic carbocycle which may be substituted with 1 to 4 $R^9$, 4- to 6-membered monocyclic heterocycle which may be substituted with 1 to 4 $R^{19}$, or 4- to 15-membered bicyclic heterocycle which may be substituted with 1 to 4 $R^{11}$;

$R^5$ represents a C1-4 alkyl, halogen atom, or 5- or 6-membered monocyclic carbocycle;

$R^6$ represents a C1-4 alkyl, halogen atom, or 5- or 6-membered monocyclic carbocycle;

$R^7$ represents a 5- or 6-membered monocyclic carbocycle which may be substituted with 1 to 4 $R^{12}$, 5- or 6-membered monocyclic heterocycle which may be substituted with 1 to 4 $R^{13}$, benzyl, or 2-(2-tetrahydrofuryl)ethyl;

$R^8$ represents a C1-4 alkyl, or 2-(2-tetrahydrofuryl)ethyl;

$R^9$ represents a C1-4 alkyl, acetylaminomethyl, acetylaminoethyl, or 5- or 6-membered monocyclic heterocycle;

$R^{10}$ represents a C1-6 alkyl, C1-4 haloalkyl, C1-4 alkoxy-C1-4 alkyl, C3-8 cycloalkyl-C1-4 alkyl, benzyl, 5- or 6-membered monocyclic carbocycle, 5- or 6-membered monocyclic heterocycle, acetylaminomethyl, acetylaminoethyl, cyclopropylcarbonylaminoethyl, N-methyl-cyclopropylcarbonylaminoethyl, tert-butylcarbonylaminoethyl, N-methyl-tert-butylcarbonylaminoethyl, tert-butoxycarbonylaminoethyl, 1-phenylethyl, or 2-hydroxy-1-phenylethyl;

$R^{11}$ represents a C1-4 alkyl, or 5- or 6-membered monocyclic heterocycle;

$R^{12}$ represents a halogen atom, or C1-4 alkyl;

$R^{13}$ represents a C1-4 alkyl;

when being substituted with the plurality of $R^4$, $R^5$, $R^6$, $R^8$, $R^9$, $R^{10}$, $R^{11}$, $R^{12}$ or $R^{13}$, they may be the same or different;

$R^{1-1}$ represents a C3-8 cycloalkyl which may be substituted with 1 to 4 $R^{5-1}$, 5- or 6-membered monocyclic heterocycle which may be substituted with 1 to 4 $R^{6-1}$, or 4- to 15-membered bicyclic heterocycle which may be substituted with 1 to 4 $R^{7-1}$;

$R^{5-1}$ represents a C1-4 alkyl, C3-8 cycloalkyl, C1-4 haloalkyl, or halogen atom;

$R^{6-1}$ represents a C1-4 alkyl which may be substituted with 1 to 4 $R^{8-1}$, C3-8 cycloalkyl, C3-8 cycloalkyl which is substituted with C1-4 alkyl, C1-4 haloalkyl, or halogen atom;

$R^{7-1}$ represents a C1-4 alkyl, C3-8 cycloalkyl, C1-4 haloalkyl, or halogen atom;

$R^{8-1}$ represents a hydroxy, halogen atom, nitrile, benzyloxy, or 5- or 6-membered monocyclic carbocycle;

$L^2$ represents a bond, carbonyl($-C(=O)-$), $-(CH_2)_n-$ $NR^{9-1}C(=O)-$, or $-C(=O)NR^{10-1}-$;

$R^{9-1}$ represents a hydrogen atom, or C1-4 alkyl;

$R^{10-1}$ represents a hydrogen atom, or C1-4 alkyl;

n represents an integer of 0 to 3;

$R^{2-1}$ represents a hydrogen atom, C1-6 alkyl which may be substituted with 1 to 4 $R^{11-1}$, C1-4 alkoxy which may be substituted with 1 to 4 $R^{12-1}$, 3- to 8-membered monocyclic carbocycle which may be substituted with 1 to 4 $R^{13-1}$, 4- to 15-membered bicyclic carbocycle which may be substituted with 1 to 4 $R^{14-1}$, 5- or 6-membered monocyclic heterocycle which may be substituted with 1 to 4 $R^{15-1}$, or $-S(O)_m-$(C1-4 alkyl);

$R^{11-1}$ represents a hydroxy, halogen atom, or C3-8 cycloalkyl;

$R^{12-1}$ represents a hydroxy, halogen atom, or C3-8 cycloalkyl;

$R^{13-1}$ represents a C1-4 alkyl, C3-8 cycloalkyl, halogen atom, or C1-4 haloalkyl;

$R^{14-1}$ represents a C1-4 alkyl, C3-8 cycloalkyl, halogen atom, or C1-4 haloalkyl;

$R^{15-1}$ represents a C1-4 alkyl, C1-4 alkoxy, C1-4 haloalkyl, C3-8 cycloalkyl, halogen atom, phenyl which may be substituted with 1 to 4 $R^{16-1}$, phenoxy, pyridin-2-yl, 1-methylpyrazol-4-yl, or oxo;

$R^{16-1}$ represents a C1-4 alkyl, or C1-4 alkoxy;

m represents an integer of 0 to 2;

when being substituted with the plurality of $R^{5-1}$, $R^{6-1}$, $R^{7-1}$, $R^{8-1}$, $R^{11-1}$, $R^{12-1}$, $R^{13-1}$, $R^{14-1}$, $R^{15-1}$ or $R^{16-1}$, they may be the same or different;

$R^{53}$ represents a hydrogen atom, or C1-4 alkyl;

$R^{1Y}$ represents a 5- or 6-membered monocyclic heterocycle which may be substituted with 1 to 4 $R^4$;

$R^{2Y}$ represents a C1-4 alkyl;

$R^{3Y}$ represents a 5- or 6-membered monocyclic carbocycle which may be substituted with 1 to 4 $R^9$, 4- to 6-membered monocyclic heterocycle which may be substituted with 1 to 4 $R^{10}$, or 4- to 15-membered bicyclic heterocycle which may be substituted with 1 to 4 $R^{11}$;

$R^{3-1}$ represents a hydrogen atom, C1-4 alkyl, C1-4 haloalkyl, or halogen atom;

$R^{4-1}$ represents a hydrogen atom, C1-4 alkyl, or 5- or 6-membered monocyclic carbocycle;

$R^{17-1}$ represents a hydrogen atom, or C1-4 alkyl;

represents α-configuration;

represents β-configuration;

represents α-configuration, β-configuration or the mixture of α-configuration and β-configuration;

$R^{1-1Y}$ represents

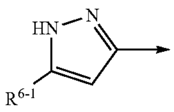

or

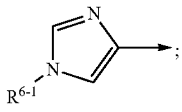

;

in the group, the arrow indicates the binding to the carbon atom of carbonyl;

$R^{2-1Y}$ represents a 3- to 8-membered monocyclic carbocycle which may be substituted with 1 to 4 $R^{13-1}$ or 4- to 15-membered bicyclic carbocycle which may be substituted with 1 to 4 $R^{14-1}$;

$R^{2-1S}$ represents a 3- to 8-membered monocyclic carbocycle which may be substituted with 1 to 4 $R^{13-1}$, 4- to 15-membered bicyclic carbocycle which may be substituted with 1 to 4 $R^{14-1}$ or 5- or 6-membered monocyclic heterocycle which may be substituted with 1 to 4 $R^{15-1}$;

wherein $R^{1-1S}$ represents 5-membered monocyclic aromatic hetero ring containing 1 to 4 nitrogen atoms, one oxygen atom and/or one sulfur atom which may be substituted with 1 to 4 $R^{6-1}$;

$R^{2-1T}$ represents 5- or 6-membered monocyclic heterocycle which may be substituted with 1 to 4 $R^{15-1}$;

or a salt thereof.

Advantageous Effects of Invention

The compound represented by the general formula (Z) or a salt thereof (hereinafter collectively referred to as the present compound) as disclosed herein has KDM5 inhibitory activity. Therefore, the present compound can be used as a therapeutic and/or prophylactic agent for diseases such as hyperproliferative disease, cancer, stroke, diabetes, hepatomegaly, cardiovascular disease, multiple sclerosis, Huntington's disease, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders, myeloproliferative disorder, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, or hepatitis.

DESCRIPTION OF EMBODIMENTS

Examples of "halogen atom" as used herein include a fluorine atom, chlorine atom, bromine atom and iodine atom.

Examples of "C1-4 alkyl" as used herein include methyl, ethyl, propyl, isopropyl, butyl, sec-butyl, text-butyl and isobutyl groups.

Examples of "C1-6 alkyl" as used herein include methyl, ethyl, propyl, isopropyl, butyl, sec-butyl, tert-butyl, isobutyl, pentyl, isopentyl, neopentyl, sec-pentyl, tert-pentyl, hexyl, isohexyl, neohexyl, sec-hexyl and tert-hexyl groups and the like.

Examples of "C1-4 alkoxy" as used herein include methoxy, ethoxy, propoxy, isopropoxy, butoxy, sec-butoxy, tert-butoxy and isobutoxy groups.

Examples of "C1-4 alkoxy-C1-4 alkyl" as used herein include methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl, butoxymethyl, butoxyethyl, butoxypropyl and butoxybutyl groups.

Examples of "C1-4 haloalkyl" as used herein include fluoromethyl, difluoromethyl, trifluoromethyl, chloromethyl, dichloromethyl, trichloromethyl, 2,2,2-trifluoroethyl, perfluoroethyl, 3,3,3-trifluoropropyl, perfluoropropyl, perfluoro(isopropyl), perfluorobutyl, perfluoro(sec-butyl), perfluoro(tert-butyl) and perfluoro(isobutyl) groups and the like.

Examples of "C3-8 cycloalkyl" as used herein include cyclopropyl, cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.2.0]hexyl, bicyclo[2.1.1]hexyl, bicyclo[4.1.0]heptyl, bicyclo[3.2.0]heptyl, bicyclo[2.2.1]heptyl and bicyclo[3.1.1]heptyl and bicyclo[2.2.2]octane groups and the like.

Examples of "C3-8 cycloalkyl-C1-4 alkyl" as used herein include cyclopropylmethyl, cyclopropylethyl, cyclopropylpropyl, cyclopropylbutyl, cyclobutylmethyl, cyclobutylethyl, cyclobutylpropyl, cyclobutylbutyl, cyclopentylmethyl, cyclopentylethyl, cyclopentylpropyl, cyclopentylbutyl, cyclohexylmethyl, cyclohexylethyl, cyclohexylpropyl and cyclohexylbutyl groups and the like.

Examples of "C3-8 cycloalkyl which is substituted with C1-4 alkyl" as used herein include 1-methylcyclopropyl, 2-methylcyclopropyl, 2,2-dimethylcyclopropyl, 1-ethylcyclopropyl, 1-propylcyclopropyl, 1-butylcyclopropyl, 1-methylcyclobutyl, 2-methylcyclobutyl, 3-methylcyclobutyl, 2,2-dimethylcyclobutyl, 3,3-dimethylcyclobutyl, 1-ethylcyclobutyl, 1-propylcyclobutyl, 1-butylcyclobutyl, 1-methylcyclopentyl, 2-methylcyclopentyl, 3-methylcyclopentyl, 2,2-dimethylcyclopentyl, 3,3-dimethylcyclopentyl, 1-ethylcyclopentyl, 1-propylcyclopentyl, 1-butylcyclopentyl, 1-methylcyclohexyl, 2-methylcyclohexyl, 3-methylcyclohexyl, 4-methylcyclohexyl, 2,2-dimethylcyclohexyl, 3,3-dimethylcyclohexyl, 4,4-dimethylcyclohexyl, 1-ethylcyclohexyl, 1-propylcyclohexyl, 1-butylcyclohexyl, 1-methylcycloheptyl, 2-methylcycloheptyl, 3-methylcycloheptyl, 4-methylcycloheptyl, 2,2-dimethylcycloheptyl, 3,3-dimethylcycloheptyl, 4,4-dimethylcycloheptyl, 1-ethylcycloheptyl, 1-propylcycloheptyl, 1-butylcycloheptyl, 1-methylcyclooctyl, 2-methylcyclooctyl, 3-methylcyclooctyl, 4-methylcyclooctyl, 5-methylcyclooctyl, 2,2-dimethylcyclooctyl, 3,3-dimethylcyclooctyl, 5,4-dimethylcyclooctyl, 4,5-dimethylcyclooctyl, 1-ethylcyclooctyl, 1-propylcyclooctyl, and 1-butylcyclooctyl groups and the like.

Examples of "C1-4 alkylaminocarbonyl" as used herein include methylaminocarbonyl, ethylaminocarbonyl, propylaminocarbonyl, isopropylaminocarbonyl, butylaminocarbonyl, sec-butylaminocarbonyl, tert-butylaminocarbonyl and isobutylaminocarbonyl groups.

Examples of "C1-4 dialkylaminocarbonyl" as used herein include dimethylaminocarbonyl, diethylaminocarbonyl, N-methyl-N-ethylaminocarbonyl, dipropylaminocarbonyl, diisopropylaminocarbonyl, dibutylaminocarbonyl, di-sec-butylaminocarbonyl, di-tert-butylaminocarbonyl and diisobutylaminocarbonyl groups and the like.

Examples of "$-S(O)_m-$(C1-4 alkyl)" as used herein include methylthio, ethylthio, propylthio, isopropylthio, butylthio, sec-butylthio, tert-butylthio, isobutylthio, methylsulfinyl, ethylsulfinyl, propylsulfinyl, isopropylsulfinyl, butylsulfinyl, sec-butylsulfonyl, tert-butylsulfinyl, isobutylsulfinyl, methylsulfonyl, ethylsulfonyl, propylsulfonyl, isopropylsulfonyl, butylsulfonyl, sec-butylsulfonyl, tert-butylsulfonyl and isobutylsulfonyl groups.

Examples of "C2-6 acyl" as used herein include acetyl, propanoyl, butanoyl, isobutanoyl, pentanoyl, isopentanoyl, neopentanoyl, hexanoyl, isohexanoyl and neohexanoyl groups and the like.

Examples of "3- to 8-membered monocyclic carbocycle" as used herein include cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, and benzene rings and the like.

Examples of "5- or 6-membered monocyclic carbocycle" as used herein include cyclopentane, cyclohexane, cyclopentene, cyclohexene, cyclopentadiene, cyclohexadiene and benzene rings.

Examples of "4- to 15-membered bicyclic carbocycle" as used herein include bicyclo[1.1.0]butane, bicyclo[1.1.1]pentane, spiro[2.2]pentane, bicyclo[3.1.0]hexane, spiro[2.3]hexane, bicyclo[3.2.0]heptane, indene, dihydroindene, naphthalene, dihydronaphthalene, and tetrahydronaphthalene rings and the like.

Examples of "4- to 6-membered monocyclic heterocycle" as used herein include "4- to 6-membered monocyclic heterocycle containing 1 to 4 nitrogen atoms, 1 or 2 oxygen atoms and/or one sulfur atom" and the like. Examples of the "4- to 6-membered monocyclic heterocycle containing 1 to 4 nitrogen atoms, 1 or 2 oxygen atoms and/or one sulfur atom" include azetidine, pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane and dioxole rings and the like.

Examples of "5- or 6-membered monocyclic heterocycle" as used herein include "5- to 6-membered monocyclic heterocycle containing 1 to 4 nitrogen atoms, 1 or 2 oxygen atoms and/or one sulfur atom" and the like. Examples of the "5- to 6-membered monocyclic heterocycle containing 1 to 4 nitrogen atoms, 1 or 2 oxygen atoms and/or one sulfur atom" include pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane and dioxole rings and the like.

Examples of "4- to 15-membered bicyclic heterocycle" as used herein include "4- to 15-membered bicyclic heterocycle containing 1 to 4 nitrogen atoms, 1 or 2 oxygen atoms and/or one sulfur atom" and the like. Examples of the "4- to 15-membered bicyclic heterocycle containing 1 to 4 nitrogen atoms, 1 or 2 oxygen atoms and/or one sulfur atom" include indole, benzimidazole, benztriazole, indazole, benzofuran, benzothiophene, benzoxazole, benzooxazine, indoline, dihydrobenzimidazole, dihydrobenztriazole, dihydroindazole, dihydrobenzofuran, dihydrobenzothiophene, dihydrobenzoxazole and dihydrobenzooxazine rings and the like.

Examples of the "5-membered monocyclic aromatic hetero ring containing 1 to 4 nitrogen atoms, one oxygen atom and/or one sulfur atom" include pyrrole, imidazole, triazole, tetrazole, pyrazole, furan, thiophene, oxazole, isoxazole, thiazole, isothiazole, furazan, oxadiazole and thiadiazole rings and the like.

Examples of the "3- to 10-membered mono or bicyclic hetero ring containing 1 to 4 nitrogen atoms, one oxygen atom and/or one sulfur atom" include 3,4-dihydroimidazo [2,1-f][1,2,4]triazine, 3,7-dihydro-[1,2,4]triazolo[1,5-a]pyrimidine, 4,7-dihydropyrazolo[1,5-a]pyrimidine, imidazo[1,2-b]pyridazine, 3,4-dihydropyrido[3,2-d]pyrimidine, 3,4-dihydropyrido[3,4-d]pyrimidine, 5,8-dihydroimidazo[1,2-b] pyridazine, azetidine, piperidine, piperazine, pyridine, 2,6-diazaspiro[3.3]heptane, 2,6-diazaspiro[3.4]octane, 2,6-diazaspiro[3.4]octane, 6-oxa-2,7-diazaspiro[3.4]octane, 2,7-diazaspiro[3.5]nonane, octahydro-1H-pyrrolo[3,2-b]pyridine, 6,7-dihydro-5H-pyrrolo[1,2-c]imidazole and 3-azabicyclo[3.1.0]hexane rings and the like.

In the present invention, unless particularly stated, the symbol:

indicates that the bond projects above the plane of the paper (i.e., β-configuration), and the symbol:

In the present invention, unless particularly stated, the symbol:

indicates that the bond projects below the plane of the paper (i.e., α-configuration), and the symbol:

indicates that the bond is the α-configuration, β-configuration or the mixture of these configurations at arbitrary proportions, as apparent to a person skilled in the art.

In the present invention, A is preferably, $R^1$.

In the present invention, A is also preferably, $R^{1-1}$-$L^1$-.

In the present invention, B is preferably, $R^2$.

In the present invention, B is also preferably, $R^{2A}$-$L^2$-.

In the present invention, $R^1$ is preferably, for example, a hydrogen atom, nitrile, carbamoyl or 5- or 6-membered monocyclic heterocycle which may be substituted with 1 to 4 $R^4$, and more preferably, for example, a hydrogen atom, carbamoyl or 5- or 6-membered monocyclic heterocycle which may be substituted with 1 to 4 $R^4$.

In the present invention, $R^2$ is preferably, a C1-4 alkyl.

In the present invention, $R^3$ is preferably, for example, a C1-4 alkyl which may be substituted with 1 to 3 $R^5$, C1-4 alkoxy which may be substituted with 1 to 3 $R^6$, hydroxy which may be substituted with $R^7$, amino which may be substituted with 1 or 2 $R^8$, 5- or 6-membered monocyclic carbocycle which may be substituted with 1 to 4 $R^9$, 4- to 6-membered monocyclic heterocycle which may be substituted with 1 to 4 $R^{10}$, or 4- to 15-membered bicyclic heterocycle which may be substituted with 1 to 4 $R^{11}$ and more preferably, for example, 5- or 6-membered monocyclic carbocycle which may be substituted with 1 to 4 $R^9$, 4- to 6-membered monocyclic heterocycle which may be substituted with 1 to 4 $R^{10}$, or 4- to 15-membered bicyclic heterocycle which may be substituted with 1 to 4 $R^{11}$.

In the present invention, $R^{1-1}$ is preferably, for example, a 5- or 6-membered monocyclic heterocycle which may be substituted with 1 to 4 $R^{6-1}$, and more preferably, for example,

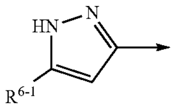

or

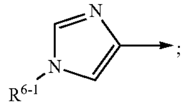

;

in the group, the arrow indicates the binding to the carbon atom of carbonyl;

or 5-membered monocyclic aromatic hetero ring containing 1 to 4 nitrogen atoms, one oxygen atom and/or one sulfur atom which may be substituted with 1 to 4 $R^{6-1}$.

In the present invention, $L^1$ is preferably, a bond.

In the present invention, $L^1$ is also preferably, a carbonyl (—C(═O)—).

In the present invention, $L^2$ is preferably, a bond.

In the present invention, $L^2$ is also preferably, a carbonyl (—C(═O)—).

In the present invention, $L^2$ is also preferably, $-(CH_2)_n-NR^{9-1}C(=O)-$.

In the present invention, n is preferably, for example, an integer of 0 to 1 and more preferably, for example, zero.

In the present invention, $R^{2-1}$ is preferably, for example, a 3- to 8-membered monocyclic carbocycle which may be substituted with 1 to 4 $R^{13-1}$, 4- to 15-membered bicyclic carbocycle which may be substituted with 1 to 4 $R^{14-1}$ or 5- or 6-membered monocyclic heterocycle which may be substituted with 1 to 4 $R^{15-1}$, and more preferably, for example, 3- to 8-membered monocyclic carbocycle which may be substituted with 1 to 4 $R^{13-1}$ or 4- to 15-membered bicyclic carbocycle which may be substituted with 1 to 4 $R^{14-1}$. $R^{2-1}$ is also preferably, for example, 5- or 6-membered monocyclic heterocycle which may be substituted with 1 to 4 $R^{15-1}$.

In the present invention, examples of the general formula (Z) preferably include the general formula (I):

(I)

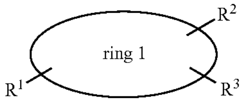

wherein all symbols have the same meanings as above, or the general formula (II):

(II)

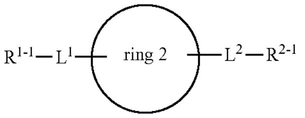

wherein all symbols have the same meanings as above.

In the present invention, examples of the general formula (Z) preferably include the general formula (I-1), (I-2), (I-3), (I-4), (I-5), (I-6) or (I-7):

(I-1)

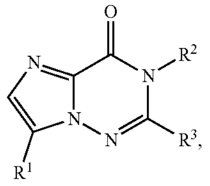

(I-2)

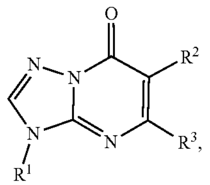

(I-3)

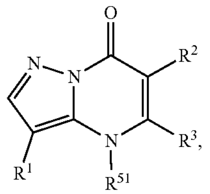

-continued (I-4)

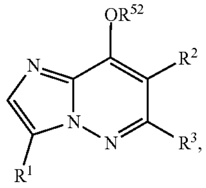

(I-5)

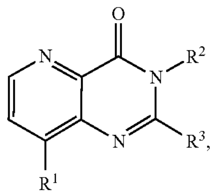

(I-6)

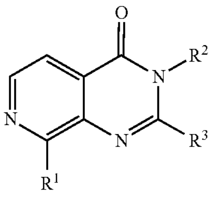

or (I-7)

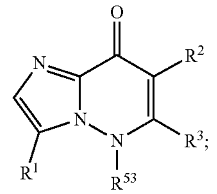

wherein all symbols have the same meanings as above.

In the present invention, examples of the general formula (Z) preferably include the general formula (II-1), (II-2), (II-3), (II-4), (II-5), (II-6), (II-7), (II-8), (II-9), (II-10), (II-11) or (II-12):

(II-1)

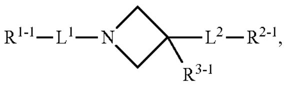

(II-2)

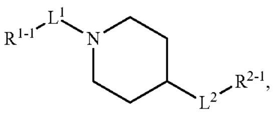

(II-3)

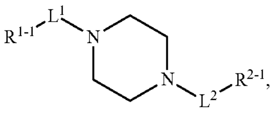

(II-4)

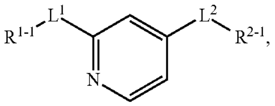

(II-5)

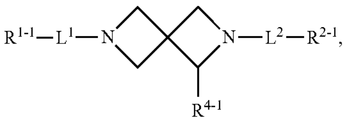

-continued (II-6)

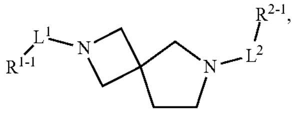

(II-7)

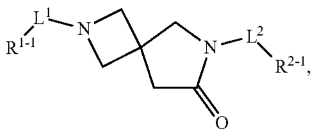

(II-8)

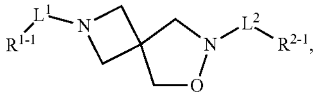

(II-9)

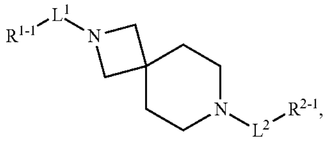

(II-10)

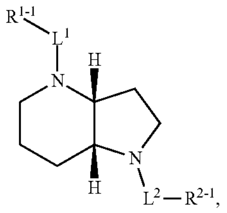

(II-11)

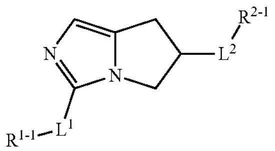

or (II-12)

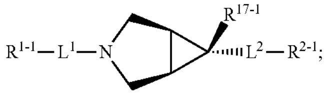

wherein all symbols have the same meanings as above.

In the present invention, examples of the general formula (Z) preferably include the general formula (I-A):

(I-A)

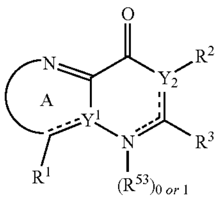

wherein Ring A represents

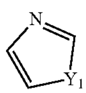

or

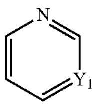

each of $Y_1$ and $Y_2$ represents carbon atom or nitrogen atom, the dotted lines represent double or single bonds and other symbols have the same meanings as above.

In the present invention, examples of the general formula (Z) or the general formula (I-A) preferably include the general formula (I-1), (I-5) or (I-7):

(I-1)

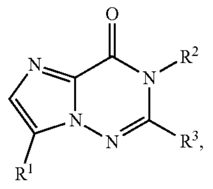

(I-5)

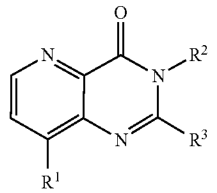

or (I-7)

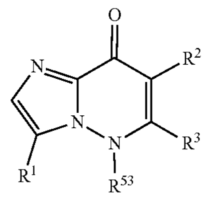

wherein all symbols have the same meanings as above.

In the present invention, examples of the general formula (Z) preferably include the general formula (II-A):

(II-A)

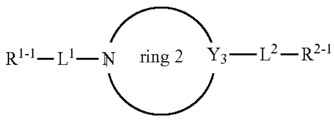

wherein ring 2 represents a saturated hetero ring containing one or two nitrogen atoms selected form piperazine, 2,6-diazaspiro[3.3]heptane, 2,6-diazaspiro[3.4]octane, 6-oxa-2,7-diazaspiro[3.4]octane, 2,7-diazaspiro[3.5]nonane, (3aR,7aR)-octahydro-1H-pyrrolo[3,2-b]pyridine, azetidine, piperidine and (1R,5S,6r)-3-azabicyclo[3.1.0]hexane, each of which may be substituted, $Y_3$ represents carbon atom or nitrogen atom, and other symbols have the same meanings as above.

In the present invention, examples of the general formula (Z) or general formula (II-A) preferably include the general formula (II-1), (II-5), (II-8) or (II-12):

(II-1)

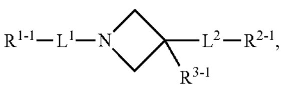

-continued (II-5)

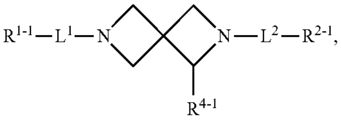

(II-8)

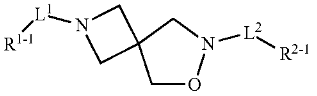

or (II-12)

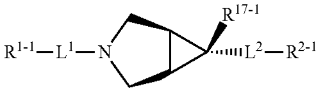

wherein all symbols have the same meanings as above.

In the present invention, examples of the general formula (Z) preferably include the general formula (I-1-1), (I-5-1), (I-7-1), (II-1-1), (II-5-1), (II-8-1) or (II-12-1):

(I-1-1)

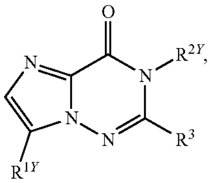

(I-5-1)

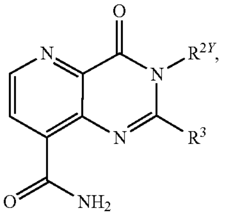

(I-7-1)

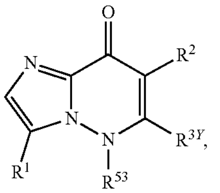

(II-1-1)

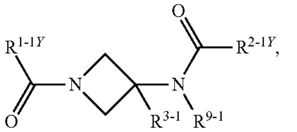

(II-5-1)

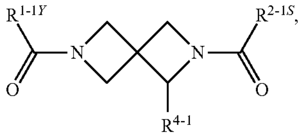

(II-8-1)

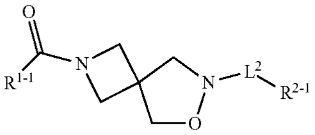

or

-continued (II-12-1)

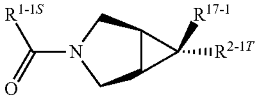

wherein all symbols have the same meanings as above.

In the present invention, examples of the general formula (Z) preferably include the general formula (I-1-1):

(I-1-1)

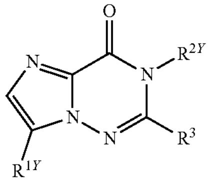

wherein all symbols have the same meanings as above.

In the present invention, examples of the general formula (Z) preferably include the general formula (I-5-1):

(I-5-1)

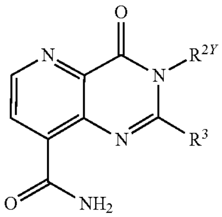

wherein all symbols have the same meanings as above.

In the present invention, examples of the general formula (Z) preferably include the general formula (I-7-1):

(I-7-1)

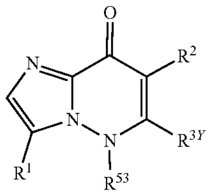

wherein all symbols have the same meanings as above.

In the present invention, examples of the general formula (Z) preferably include the general formula (II-1-1):

(II-1-1)

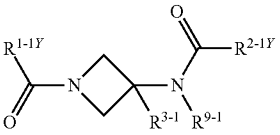

wherein all symbols have the same meanings as above.

In the present invention, examples of the general formula (Z) preferably include the general formula (II-5-1):

(II-5-1)

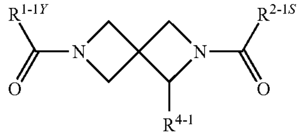

wherein all symbols have the same meanings as above.

In the present invention, examples of the general formula (Z) preferably include the general formula (II-8-1):

(II-8-1)

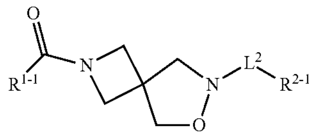

wherein all symbols have the same meanings as above.

In the present invention, examples of the general formula (Z) preferably include the general formula (II-12-1):

(II-12-1)

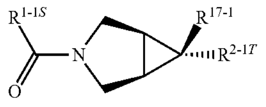

wherein all symbols have the same meanings as above.

In the present invention, or in the general formula (Z), (I), (I-1) or (I-1-1), the compound is preferably, for example:

(1) 7-(1H-imidazol-5-yl)-3-isopropyl-2-(3-phenylazetidin-1-yl)imidazo[2,1-f][1,2,4]triazin-4(3H)-one;

(2) 2-(1-(cyclopropylmethyl)-1H-pyrazol-4-yl)-7-(1H-imidazol-5-yl)-3-isopropylimidazo[2,1-f][1,2,4]triazin-4(3H)-one;

(3) 2-(1-(Cyclopropylmethyl)-1H-pyrazol-4-yl)-3-isopropyl-7-(1H-pyrazol-4-yl)imidazo[2,1-f][1,2,4]triazin-4(3H)-one;

(4) 3-Isopropyl-2-(1-methyl-1H-indol-5-yl)-7-(1H-pyrazol-4-yl)imidazo[2,1-f][1,2,4]triazin-4(3H)-one;

(5) 7-(1H-imidazol-5-yl)-3-isopropyl-2-(thiophen-2-yl)imidazo[2,1-f][1,2,4]triazin-4(3H)-one, 0.25 eq formate salt;

(6) 3-Isopropyl-7-(1H-pyrazol-4-yl)-2-(thiophen-2-yl)imidazo[2,1-f][1,2,4]triazin-4(3H)-one;

(7) N-(2-(4-(3-isopropyl-4-oxo-7-(1H-pyrazol-4-yl)-3,4-dihydroimidazo[2,1-f][1,2,4]triazin-2-yl)-1H-pyrazol-1-yl)ethyl)acetamide;

(8) 3-Isopropyl-2-methyl-7-(1-(5-methylpyridin-2-yl)-1H-pyrazol-4-yl)imidazo[2,1-f][1,2,4]triazin-4(3H)-one or (9) N-(2-(4-(7-(1H-Imidazol-4-yl)-3-isopropyl-4-oxo-3,4-dihydroimidazo[2,1-f][1,2,4]triazin-2-yl)-1H-pyrazol-1-yl)ethyl)acetamide or a salt thereof.

In the present invention, or in the general formula (Z), (I), (I-5) or (I-5-1), the compound is preferably, for example:

(1) 2-(1-(Cyclopropylmethyl)-1H-pyrazol-4-yl)-3-isopropyl-4-oxo-3,4-dihydropyrido[3,2-d]pyrimidine-8-carboxamide; or (2) 3-isopropyl-4-oxo-2-phenyl-3,4-dihydropyrido[3,2-d]pyrimidine-8-carboxamide;

or a salt thereof.

In the present invention, or in the general formula (Z), (I), (I-7) or (I-7-1), the compound is preferably, for example:

(1) 7-Isopropyl-8-oxo-6-phenyl-5,8-dihydroimidazo[1,2-b]pyridazine-3-carbonitrile;

or a salt thereof.

In the present invention, or in the general formula (Z), (II), (II-1) or (II-1-1), the compound is preferably, for example:

(1) N-(1-(5-Isopropyl-1H-pyrazole-3-carbonyl)azetidin-3-yl)cyclopropanecarboxamide;

or a salt thereof.

In the present invention, or in the general formula (Z), (II), (II-5) or (II-5-1), the compound is preferably, for example:

(1) (5-cyclohexyl-1H-pyrazol-3-yl)(6-(cyclopropanecarbonyl)-2,6-diazaspiro[3.3]heptan-2-yl)methanone;

(2) (6-(Cyclopropanecarbonyl)-2,6-diazaspiro[3.3]heptan-2-yl)(1-isopropyl-1H-imidazol-4-yl)methanone;

(3) (5-Isopropyl-1H-pyrazol-3-yl)(6-(1-methylcyclopropane-1-carbonyl)-2,6-diazaspiro[3.3]heptan-2-yl)methanone;

(4) (5-Isopropyl-1H-pyrazol-3-yl)(6-(thiophene-2-carbonyl)-2,6-diazaspiro[3.3]heptan-2-yl)methanone or (5) [2-(4-Fluoro-1-methyl-pyrazole-3-carbonyl)-2,6-diazaspiro[3.3]heptan-6-yl]-(5-isopropyl-1H-pyrazol-3-yl)methanone or a salt thereof.

In the present invention, or in the general formula (Z), (II), (II-8) or (II-8-1), the compound is preferably, for example:

(1) 1-[2-(5-Isopropyl-1H-pyrazole-3-carbonyl)-6-oxa-2,7-diazaspiro[3.4]octan-7-yl]-2,2-dimethyl-propan-1-one;

or a salt thereof.

In the present invention, or in the general formula (Z), (II), (II-12) or (II-12-1), the compound is preferably, for example:

(1) (5-isopropyl-1H-pyrazol-3-yl)((1R,5 S,6r)-6-(5-methyl-4-phenylisoxazol-3-yl)-3-azabicyclo[3.1.0]hexan-3-yl)methanone;

or a salt thereof.

[Isomers]

The present invention encompasses all isomers unless otherwise particularly stated. For example, alkyl groups, alkoxy groups and the like include linear and branched groups. Moreover, the present invention encompasses isomers for double bonds, rings and condensed rings (E-forms, Z-forms, cis forms and trans forms), isomers due to asymmetrical carbon atoms (R and S forms, a and configurations, enantiomers and diastereomers), optically active substances having optical rotating activity (D, L, d and 1 forms), polar substances which can be separated by chromatography (high polarity substances and low polarity substances), equilibrium compounds, rotamers, mixtures thereof at arbitrary proportions and racemic mixtures. The present invention also encompasses tautomers.

[Salt and Solvate]

A salt of the compound represented by the general formula (Z) disclosed herein encompasses all pharmacologically acceptable salts. The pharmacologically acceptable salt is preferably a water-soluble salt with low toxicity. Examples of appropriate salts include acid addition salts (such as inorganic acid salt[e.g., hydrochloride, hydrobromide, hydroiodide, sulphate, phosphate, nitrate and the like], organic acid salts [e.g., acetate, trifluoroacetate, lactate, tartrate, oxalate, fumarate, maleate, benzoate, citrate, methanesulphonate, ethanesulphonate, benzenesulphonate, toluenesulphonate, isethionate, glucuronate, gluconate and the like], salts with acidic natural amino acids [e.g., aspartate, glutamate and the like] and the like) and the like.

A salt also encompasses quaternary ammonium salts. The quaternary ammonium salt represents a compound represented by the general formula (Z) in which a nitrogen atom thereof is quaternised with an $R^0$ group. The $R^0$ group as used herein represents, for example, a C1-8 alkyl group which may be substituted with a phenyl group.

The compound represented by the general formula (Z) can be converted to the salt, N-oxide and solvate according to well-known methods.

The N-oxide of the compound represented by the general formula (Z) represents the compound represented by the general formula (Z) in which a nitrogen atom is oxidized. The N-oxide may form salts such as acid addition salts as described above.

The compound represented by the general formula (Z), a salt thereof or an N-oxide thereof may form a solvate with, for example, water or an alcoholic solvent (such as ethanol). The solvate preferably has low toxicity and is water soluble.

The compound represented by the general formula (Z) and a salt thereof may be in the form of without forming a solvate or may be in the form of a solvate with a pharmaceutically acceptable solvent such as water and ethanol. The solvate is preferably a hydrate. The compound represented by the general formula (Z) or a salt thereof can be converted to the solvate according to well-known methods.

The compound represented by the general formula (Z) and a salt thereof may form a co-crystal with an appropriate co-crystal former. The co-crystal is preferably pharmaceutically acceptable as formed with a pharmaceutically acceptable co-crystal former. A co-crystal is defined to be a crystal typically formed of two or more molecules by intermolecular interaction that is not ionic bonding. The co-crystal may be a complex of a neutral molecule and a salt. Co-crystals may be prepared according to well-known methods such as melt crystallization, recrystallization from a solvent or physical grinding of components together. Appropriate co-crystal formers include those disclosed in WO2006/007448.

In the present invention, all the recitations on the present compound encompass the compound represented by the general formula (Z), a salt thereof, a solvate (such as hydrate) thereof, an N-oxide thereof or a co-crystal thereof, or a solvate (such as hydrate), N-oxide or co-crystal of a salt of the compound represented by the general formula (Z).

Namely, in the present invention, the compound represented by the general formula (Z) or a salt thereof encompasses a solvate (such as hydrate), N-oxide or co-crystal of the compound represented by the general formula (Z) or a solvate (such as hydrate), N-oxide or co-crystal of a salt of the compound represented by the general formula (Z).

[Prodrug]

The prodrug of the compound represented by the general formula (Z) refers to a compound which is converted in vivo to the compound represented by the general formula (Z) by the reaction with enzymes, gastric acid and the like. Examples of the prodrug of the compound represented by the general formula (Z) include, when the compound represented by the general formula (Z) has an amino group, compounds in which the amino group is acylated, alkylated or phosphorylated (e.g., compounds represented by the general formula (Z) in which the amino group thereof is converted to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl or the like); when the compound represented by the general formula (Z) has a hydroxy group, compounds in which the hydroxy group is acylated, alkylated, phosphorylated or converted to borate (e.g., compounds represented by the general formula (Z) in which the hydroxy group thereof is converted to acetyl, palmitoyl, propanoyl, pivaloyl, succinyl, fumaryl, alanyl, dimethylaminomethylcarbonyl or the like) and the like. The prodrug of the compound represented by the general formula (Z) may be the one which is converted to the compound represented by the general formula (Z) under the physiological condition such as those disclosed in "Iyakuhin no Kaihatsu", vol. 7 "Bunshi Sekkei", p. 163-198, 1990, Hirokawa Shoten Co. The prodrug of the compound represented by the general formula (Z) can be produced by the methods well known per se. The prodrug of the compound represented by the general formula (Z) may form, similarly to the compound represented by the general formula (Z), for example, salts such as acid addition salts, or may form solvates with water or an alcoholic solvent (such as ethanol).

[Labelled Compound]

In the present invention, the compound represented by the general formula (Z), or a salt thereof encompasses a so-called labelled compound in which some or all atoms constituting the compound is substituted with an isotope thereof. The labelled compound may be produced according to the methods well known per se. Examples of isotopes which may be used for labelling suitably include, but are not limited to, $^{2}H$, $^{3}H$, $^{13}C$, $^{14}C$, $^{15}N$, $^{16}N$, $^{17}O$, $^{18}O$, $^{35}S$, $^{36}Cl$, $^{77}Br$, $^{125}I$ and the like.

[Production Method]

[Method for Producing Compound of the Present Invention]

The compound represented by the general formula (I) or (II), or a salt thereof may be produced by well-known methods, for example, methods described in the following methods represented in Scheme I to XII, methods equivalent to these methods, methods described in Examples, methods equivalent to those described in Examples, or methods described in Comprehensive Organic Transformations: A Guide to Functional Group Preparations, 2nd Edition (Richard C. Larock, John Wiley & Sons Inc., 1999), methods adapted from the foregoing or methods combining the foregoing without limitation. In the production methods described hereinbelow, raw material compounds may be those forming salts. Examples of the salts include those mentioned above as salts of the compound represented by the general formula (I) or (II).

Cross Coupling

Cross coupling is known. For example, it includes the method (1) Suzuki-Miyaura coupling, (2) Stille coupling, and (3) Negishi coupling.

These methods are explained as follows.

(1) Suzuki-Miyaura coupling is well known method to make a carbon-carbon bond using an organoboron compound and aryl halide, and can be carried out by, for example, reacting in an organic solvent (e.g., benzene, toluene, dimethylformamide, 1,4-dioxane, tetrahydrofuran, methanol, acetonitrile, dimethoxyethane, acetone or mixed solvents thereof), with a base (e.g., sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide, tetrabutylammonium fluoride and the like) or aqueous solutions thereof or mixtures thereof in the presence of a catalyst (e.g., bis(di-tert-butyl(4-dimethylaminophenyl)phosphine)dichloropalladium ($(A\text{-taPhos})_2PdCl_2$), tetrakis(triphenylphosphine)

palladium ($Pd(PPh_3)_4$), bis(tri-tert-butylphosphine) palladium ($Pd(tBu)_3$), bis(triphenylphosphine)palladium dichloride ($PdCl_2(PPh_3)_2$), palladium acetate ($Pd(OAc)_2$), palladium black, palladium on carbon, 1,1'-bis(diphenylphosphinoferrocene)dichloropalladium ($PdCl_2(dppf)$), diallylpalladium dichloride ($PdCl_2(allyl)_2$), iodophenyl bis (triphenylphosphine)palladium ($PhPdI(PPh_3)_2$), (tris(dibenzylideneacetone)dipalladium ($Pd_2(dba)_3$) and the like) with or without a ligand (e.g., triphenylphosphine ($PPh_3$), tributylphosphine ($PBu_3$), tricyclohexylphosphine ($PCy_3$), 1,1'-bis(diphenylphosphino)ferrocene (DPPF), 1,2-bis(diphenylphosphino)ethane (DPPE), (PCy2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2',4',6'-triisopropylbiphenyl (XPhos) and the like) at room temperature to 150° C.

(2) Stille coupling is well known method to make a carbon-carbon bond using an organotin compound and an aryl halide, and can be carried out by, for example, reacting in an organic solvent (e.g., benzene, toluene, dimethylformamide, 1,4-dioxane, tetrahydrofuran, methanol, acetonitrile, dimethoxyethane, acetone or mixed solvents thereof), with an additive (e.g., tetrabutylammoium fluoride, tetrabutylammonium chloride, cesium fluoride, lithium fluoride, lithium chloride, potassium fluoride, copper chloride, copper bromide, copper iodide, copper oxide and the like) or mixtures thereof in a presence of a catalyst (e.g., bis(di-tert-butyl(4-dimethylaminophenyl)phosphine)dichloropalladium ($(A\text{-}taPhos)_2PdCl_2$), tetrakis(triphenylphosphine)palladium ($Pd(PPh_3)_4$), bis(tri-tert-butylphosphine)palladium ($Pd(tBu)_3$), bis(triphenylphosphine)palladium dichloride ($PdCl_2(PPh_3)_2$), palladium acetate ($Pd(OAc)_2$), palladium black, palladium on carbon, 1,1'-bis(diphenylphosphinoferrocene)dichloropalladium ($PdCl_2(dppf)$), diallylpalladium dichloride ($PdCl_2(allyl)_2$), iodophenyl bis(triphenylphosphine)palladium ($PhPdI(PPh_3)_2$), (tris(dibenzylideneacetone)dipalladium ($Pd_2(dba)_3$) and the like) with or without a ligand (e.g., triphenylphosphine ($PPh_3$), tributylphosphine (PBu3), tricyclohexylphosphine ($PCy_3$), 1,1'-bis(diphenylphosphino)ferrocene (DPPF), 1,2-bis(diphenylphosphino)ethane (DPPE), 2-Dicyclohexylphosphino-2',6'-diisopropoxybiphenyl (RuPhos), 2-Dicyclohexylphosphino-2',6'-dimethoxybiphenyl (SPhos), 2-Dicyclohexylphosphino-2',4',6'-triisopropylbiphenyl (XPhos), tri(2-furyl)phosphine (trp) and the like) at room temperature to 150° C.

(3) Negishi coupling is well known method to make a carbon-carbon bond using an organozinc compound and an aryl halide, and can be carried out by, for example, reacting in an organic solvent (e.g., benzene, toluene, dimethylformamide, 1,4-dioxane, tetrahydrofuran, methanol, acetonitrile, dimethoxyethane, acetone or mixed solvents thereof) in the presence of a catalyst (e.g., bis(di-tert-butyl(4-dimethylaminophenyl)phosphine)dichloropalladium ($(A\text{-}taPhos)_2PdCl_2$), tetrakis(triphenylphosphine)palladium ($Pd(PPh_3)_4$), bis(tri-tert-butylphosphine)palladium ($Pd(tBu)_3$), bis(triphenylphosphine)palladium dichloride ($PdCl_2(PPh_3)_2$), palladium acetate ($Pd(OAc)_2$), palladium black, 1,1'-bis(diphenylphosphinoferrocene)dichloropalladium ($PdCl_2(dppf)$), diallylpalladium dichloride ($PdCl_2(allyl)_2$), iodophenyl bis(triphenylphosphine)palladium ($PhPdI(PPh_3)_2$), (tris(dibenzylideneacetone)dipalladium ($Pd_2(dba)_3$), nickel chloride ($NiCl_2$), nickel(II) bis(acetylacetonate) ($Ni(acac)_2$) and the like) with or without a ligand (e.g., triphenylphosphine ($PPh_3$), tributylphosphine ($PBu_3$), 2-Dicyclohexylphosphino-2',6'-diisopropoxybiphenyl (RuPhos), 2-Dicyclohexylphosphino-2',6'-dimethoxybiphenyl (SPhos), 2-Dicyclohexylphosphino-2',4',6'-triisopropylbiphenyl (XPhos), tri(2-furyl)phosphine (trp), terpyridine and the like) at room temperature to 150° C.

Amidation

The amidation is known. For example, it includes the method (1) via an acyl halide, (2) via a mixed acid anhydride, (3) using a condensing agent, and (4) via an ester.

These methods are explained as follows.

(1) The method via an acyl halide may be carried out, for example, by reacting a carboxylic acid with an acyl halide (e.g., oxalyl chloride or thionyl chloride) in an organic solvent (e.g., chloroform, dichloromethane, diethyl ether or tetrahydrofuran) or without a solvent at about −20° C. to reflux temperature. And then, the obtained acyl halide derivative may be reacted with an amine in an organic solvent (e.g., chloroform, dichloromethane, diethyl ether or tetrahydrofuran) in the presence of a base (e.g., pyridine, triethylamine, dimethylaniline, dimethylaminopyridine or diisopropylethylamine or the like.) at about 0 to 40° C. As an alternative, the obtained acyl halide derivative may be reacted with an amine in an organic solvent (e.g., dioxane, tetrahydrofuran) using an alkaline aqueous solution (e.g., odium hydrogen carbonate, sodium hydroxide) at about −78 to 40° C.

(2) The method via a mixed acid anhydride may be carried out, for example, by reacting a carboxylic acid with an acyl halide (e.g., pivaloyl chloride) or a sulfonyl chloride (e.g., p-toluenesulfonyl chloride or methanesulfonyl chloride and the like) or an chloroformate (e.g., ethyl chloroformate, isobutyl chloroformate or phenyl chloroformate and the like) in an organic solvent (e.g., chloroform, dichloromethane, diethyl ether, tetrahydrofuran and the like) or without a solvent, in the presence of a base (e.g., pyridine, triethylamine, dimethylaniline, dimethylaminopyridine or diisopropylethylamine) at about 0 to 40° C. And then the obtained mixed acid anhydride derivative may be reacted with an amine in an organic solvent (e.g., chloroform, methylene chloride, diethyl ether or tetrahydrofuran), at about 0 to 40° C.

(3) The method using a condensing agent may be carried out, for example, by reacting a carboxylic acid and an amine in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl] carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzotiazole (HOBt), at about 0 to 40° C.

(4) The method via an ester may be carried out with an ester and large excess amount of amine in an organic solvent (e.g., benzene, toluene, xylene and the like) or without a solvent at 60 to 150° C.

Ester can be easily prepared from the corresponding carboxylic acid by treating with diazoalkane, heating in alcohol with a catalytic acid, acyl halide and alcohol, or mixed acid anhydride and alcohol.

The reaction described in (1), (2), (3) and (4) may be carried out under an inert atmosphere (e.g., argon, nitrogen) to avoid water in order to obtain a preferable result.

Oxidative Halogenation

Oxidative halogenation is known. For example, it includes the method (1) Oxidative chlorination, (2) Oxidative bromination, and (3) Oxidative iodination.

These methods are explained as follows.

(1) Oxidative chlorination can be carried out with a chlorination reagent (e.g., N-chlorosccinimide, N-chlorophthalimide, trichloroisocyanuclic acid and the like) and a solvent (e.g., DMF, DMA, THF, DME, $CH_3CN$ or mixed solvents thereof) at 0° C. to 100° C. under inert atmosphere.

(2) Oxidative bromination can be carried out with a bromination reagent (e.g., N-bromosccinimide, N-bromophthalimide, pyridinium bromide perbromide, bromine and the like) and a solvent (e.g., DMF, DMA, THF, DME, $CH_3CN$ or mixed solvents thereof) at 0° C. to 80° C. under inert atmosphere.

(3) Oxidative iodination can be carried out with an iodination reagent (e.g., N-iodosccinimide, N-iodosaccharin, iodine and the like) and a solvent (e.g., dimethylformamide, dimethylacetamide, tetrahydrofuran, dimethoxyethane, acetonitrile or mixed solvents thereof) at −20° C. to 40° C. under inert atmosphere.

Dehydrative Halogenation

Dehydrative halogenation is known. For example, it includes the method (1) Dehydrative chlorination, and (2) Dehydrative bromination.

These methods are explained as follows.

(1) Dehydrative chlorination is carried out using $POCl_3$ in a solvent (e.g., benzene, toluene, xylene and the like) or without a solvent at room temperature to 150° C. under inert atmosphere (e.g., nitrogen and argon).

(2) Dehydrative bromination is carried out using $POBr_3$ with or without a solvent (e.g., benzene, toluene, xylene and the like) at room temperature to 150° C. under inert atmosphere (e.g., nitrogen and argon).

SnAr Replacement

The SnAr replacement is known. For example, it includes the method (1) SnAr replacement with alcohol, and (2) SnAr replacement with amine.

These methods are explained as follows.

(1) SnAr replacement with alcohol can be carried out with an aryl halide and an alcohol using a base (e.g., sodium hydride, potassium carbonate, potassium tert-butoxide, sodium methoxide, sodium ethoxide, tripotassium phosphate and like that) in a solvent (e.g., dioxane, tetrahydrofuran, dimethoxyethane, dimethylformamide and the like or mixed solvents thereof) at 0° C. to 40° C.

(2) SnAr replacement with amine can be carried out with an aryl halide and an amine using a base (e.g., trimethylamine, diisopropylethylamine, potassium carbonate, tripotassium phosphate, potassium tert-butoxide and like that) in a solvent (isopropanol, dioxane, tetrahydrofuran, dimethoxyethane, dimethylformamide and the like) or mixed solvents thereof at 80° C. to 150° C.

Imidazotriazinone Cyclization

Imidazotriazinone cyclization include the followings (1) via an iminochloride, and (2) via an orthoester.

(1) The method via an iminochloride can be carried out with an ester of 1-amino-2-imidazole carboxylic acid and an iminochloride with a base (e.g., potassium carbonate, sodium methoxide, trimethylamine and like that) and catalytic 4-dimethylpyridine (DMAP) in a solvent (e.g., acetonitrile, N,N-dimethylformamide, N,N-dimethylacetamide, tetrahydrofuran, dimethoxyethene and like that or mixed solvent thereof) at 50° C. to 120° C.

(2) The method via an orthoester can be carried out with 1-amino-2-imidazole carboxamide and an orthoester with a solvent (e.g., benzene, toluene, xylene and the like or mixed solvent thereof) or without solvent at 80° C. to 150° C.

Deprotection of Protective Group of Amino Moiety

Deprotection of protective group of amino moiety can be conducted by suitable condition of each protective group.

For example, a deprotection of tert-butoxycarbonyl (Boc) group can be conducted with acidic reagent (e.g., hydrogen chloride in dioxane, trifluoroacetic acid or methane sulfonic acid and the like) in solvent (e.g., dioxane or dichloromethane and the like) at 0° C. to 40° C.

For example, a deprotection of benzyloxycarbonyl (Z) group can be conducted by hydrogenation in a presence of a catalyst (e.g., palladium on carbon, palladium hydroxide and the like) in a solvent (e.g., methanol, ethanol and the like) or mixed solvent thereof at room temperature to 80° C. under hydrogen atmosphere.

Deprotection of protective group of amino moiety is well known and well described in T. W. Greene, Protective Groups in Organic Synthesis, Wiley, New York, 1999.

Deprotection of Protective Group of Carboxylic Acid

Deprotection of protective group of carboxylic acid can be conducted by suitable condition of each protective group.

For example, a deprotection of methyl group can be conducted with aqueous basic condition (e.g., aqueous sodium hydroxide, aqueous potassium hydroxide and the like) in a solvent (e.g., methanol, ethanol and the like) at room temperature to 80° C.

For example, a deprotection of tert-butyl group can be conducted with an acid (e.g., trifluoroacetic acid, methane sulfonic acid, hydrogen chloride in acetic acid and the like) in a solvent (e.g., dichloromethane, dioxane and the like) at room temperature to 40° C.

For example, a deprotection of benzyl group can be conducted by hydrogenation in a presence of a catalyst (e.g., palladium on carbon, palladium hydroxide and the like) in a solvent (e.g., methanol, ethanol and the like) or mixed solvents thereof at room temperature to 80° C. under hydrogen atmosphere.

Deprotection of protective group of carboxylic acid is well known and well described in T. W. Greene, Protective Groups in Organic Synthesis, Wiley, New York, 1999.

Urea Formation

The urea formation includes followings (1) via an isocyanate, and (2) via a carbonylation reagent.

(1) The method via an isocyanate can be conducted with an amine and an isocyanate in a solvent (e.g., dichloromethane, acetonitrile, dioxane and the like) or mixed solvents thereof at 0° C. to room temperature.

(2) The method via a carbonylation reagent is a 2-step reaction and can be conducted with two amines and a carbonylation reagent (e.g., CDI, phosgene, triphosgene and the like). The first step can be conducted with one amine and a carbonylation reagent in a solvent (e.g., DCM, $CH_3CN$, dioxane and the like or mixed solvents thereof) at 0° C. to room temperature under inert atmosphere. The second step can be carried out with adding the other amine into the reaction at room temperature to 100° C. under inert atmosphere.

Protective Groups in Scheme I to XII $P^1$ in Scheme I to XII represents a protective group of carboxylic acid.

$P^1$ includes methyl, ethyl, propyl, tert-butyl, phenyl, benzyl, allyl and the like.

$P^2$ in Scheme I to XII represents a protective group of amino group.

$P^2$ includes benzyloxycarbonyl (Z), tert-butoxycarbonyl (Boc), allyloxycarbonyl (Alloc), 1-methyl-1-(4-biphenyl) ethoxycarbonyl (Bpoc), trifluoroacetyl, 9-fluorenyl-methoxycarbonyl (Fmoc), benzyl (Bn), p-methoxybenzyl (MPM), benzyloxymethyl (BOM) or 2-(trimethylsilyl) ethoxymethyl (SEM) and the like.

Metals and Halogens in Scheme I to XII

M in Scheme I, II and IV represents $B(OH)_2$,

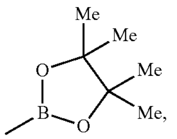

$SnBu_3$, ZnCl, ZnBr or ZnI.

$X^1$ and $X^2$ in Scheme I to IV represent Cl, Br or I.

$X^3$ in Scheme IV represents Cl, Br, I, O-mesyl, O-tosyl or O-nosyl.

Scheme I to V describe the synthesis of the compound represented by the general formula (I).

Scheme I

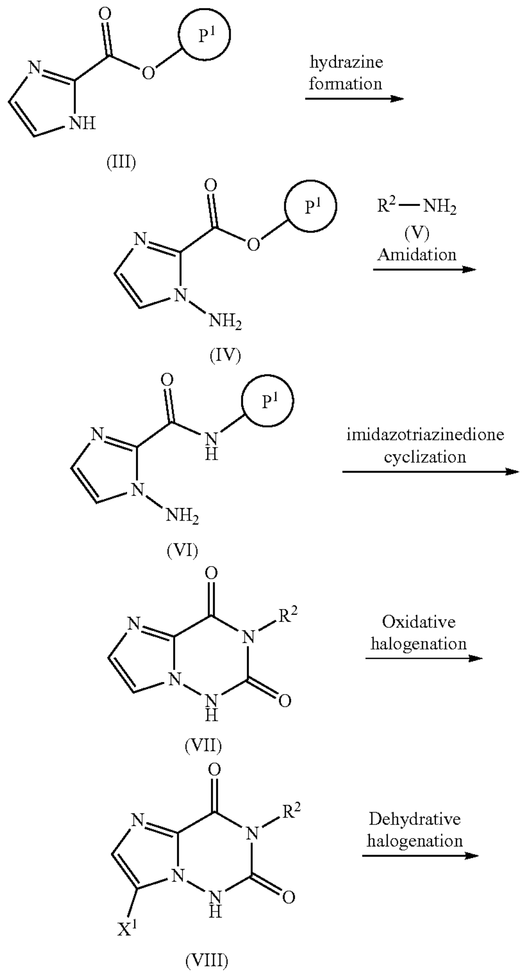

(III) (IV) (VI) (VII) (VIII)

-continued

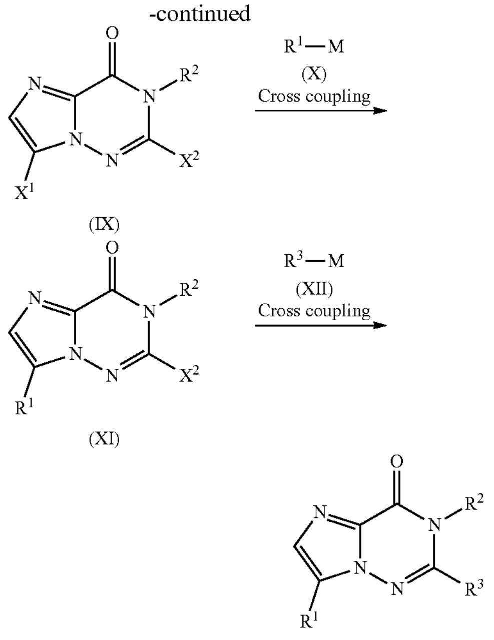

(IX) (XI) (I-1)

When $R^3$ in the compound represented by the general formula (I-1) is not $OR^7$, $NHR^8$, nor $N(R^8)_2$, the compound represented by the general formula (I-1) can be produced by the method described in Scheme I.

The compound represented by the general formula (I-1) can be produced by subjecting the compound represented by the general formula (XI) and the compound represented by the general formula (XII) to cross coupling described above.

The compound represented by the general formula (XI) can be produced by subjecting the compound represented by the general formula (IX) and the compound represented by the general formula (X) to cross coupling described above.

The compound represented by the general formula (IX) can be produced by subjecting the compound represented by the general formula (VIII) to dehydrative halogenation described above.

The compound represented by the general formula (VIII) can be produced by subjecting the compound represented by the general formula (VII) to oxidative halogenation described above.

The compound represented by the general formula (VII) can be produced by subjecting the compound represented by the general formula (VI) to imidazotriazine dione cyclization.

Imidazotriazine dione cyclization can be carried out with an alkyl or aryl chloroformate (e.g., ethyl chloroformate, isobutyl chloroformate, phenyl chloroformete and the like) and a solvent (e.g., acetonitrile, DMF, toluene and the like) or mixed solvents thereof at 100° C. to 150° C.

The compound represented by the general formula (VI) can be produced by subjecting the compound represented by the general formula (IV) and the compound represented by the general formula (V) to amidation described above.

The compound represented by the general formula (IV) can be produced by subjecting the compound represented by the general formula (III) to hydrazine formation.

Hydrazine formation can be carried out with a base (e.g., BuLi, LDA, LiHMDS and the like) and O-(diphenylphosphinyl)hydroxylamine in a solvent (e.g., DMF, THF and the like) or mixed solvents thereof at 0° C. to 25° C. under inert atmosphere.

Scheme II

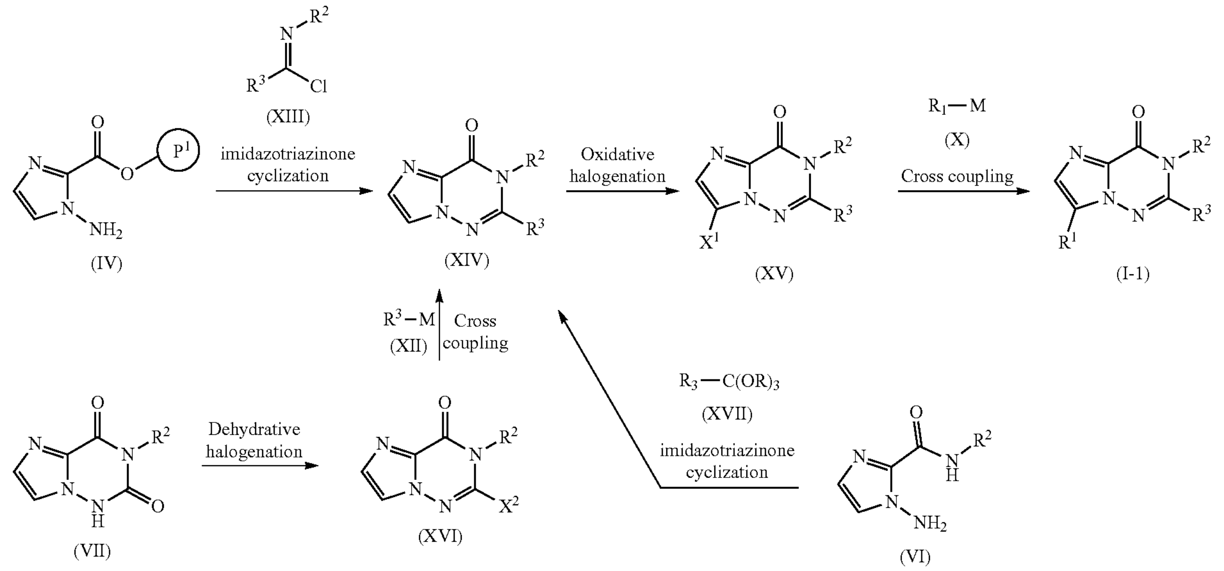

Alternatively, the compound represented by the general formula (I-1) in Scheme I can be produced another method described in Scheme II.

The compound represented by the general formula (I-1) can be produced by subjecting the compound represented by the general formula (XV) and the compound represented by the general formula (X) to a cross coupling described above.

The compound represented by the general formula (XV) can be produced by subjecting the compound represented by the general formula (XIV) to oxidative halogenation described above.

The compound represented by the general formula (XIV) can be produced by subjecting the compound represented by the general formula (IV) and the compound represented by the general formula (XIII) to imidazotriazinone cyclization described above.

Alternatively, the compound represented by the general formula (XIV) can be produced by subjecting the compound represented by the general formula (XVI) and the compound represented by the general formula (XII) to cross coupling described above.

The compound represented by the general formula (XVI) can be produced by subjecting the compound represented by the general formula (VII) to dehydrative halogenation described above.

Alternatively, the compound represented by the general formula (XIV) can be produced by subjecting the compound represented by the general formula (VI) and the compound represented by the general formula (XVII) to imidazotriazinone cyclization described above.

Scheme III

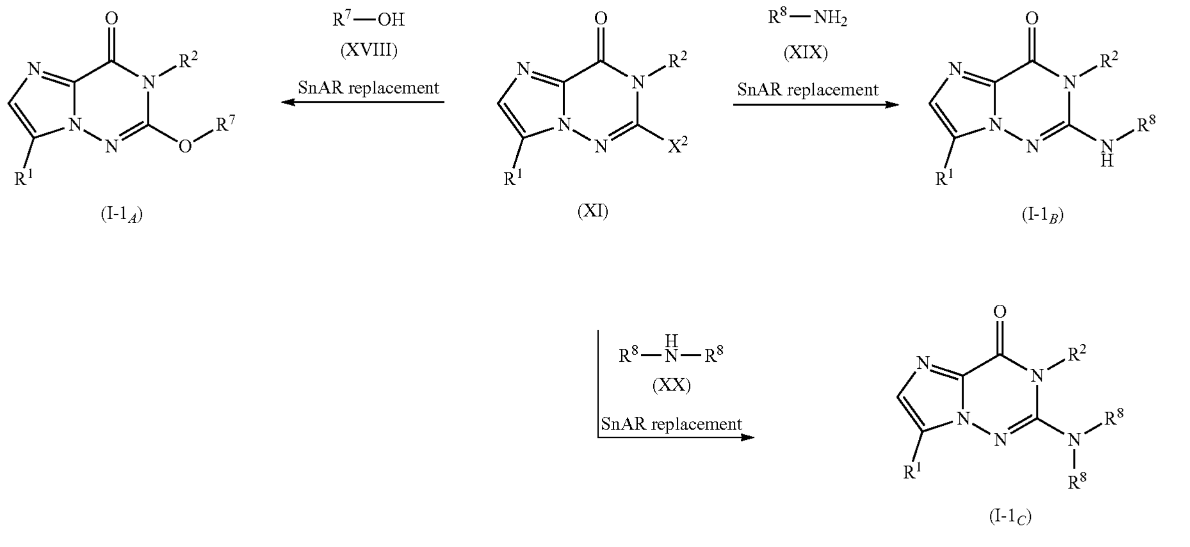

When $R^3$ in the compound represented by the general formula (I-1) in Scheme I is $OR^7$, $NHR^8$ or $N(R^8)_2$, the compound represented by the general formula (I-1) can be described as the compound represented by the general formula ($I-1_A$), ($I-1_B$) or ($I-1_C$) in Scheme II, respectively.

The compound represented by the general formula ($I-1_A$), ($I-1_B$) and ($I-1_C$) can be produced by subjecting the compound represented by the general formula (XI) with the compounds represented by the general formula (XVIII), (XIX) and (XX), respectively, to SnAr replacement described above.

Scheme IV

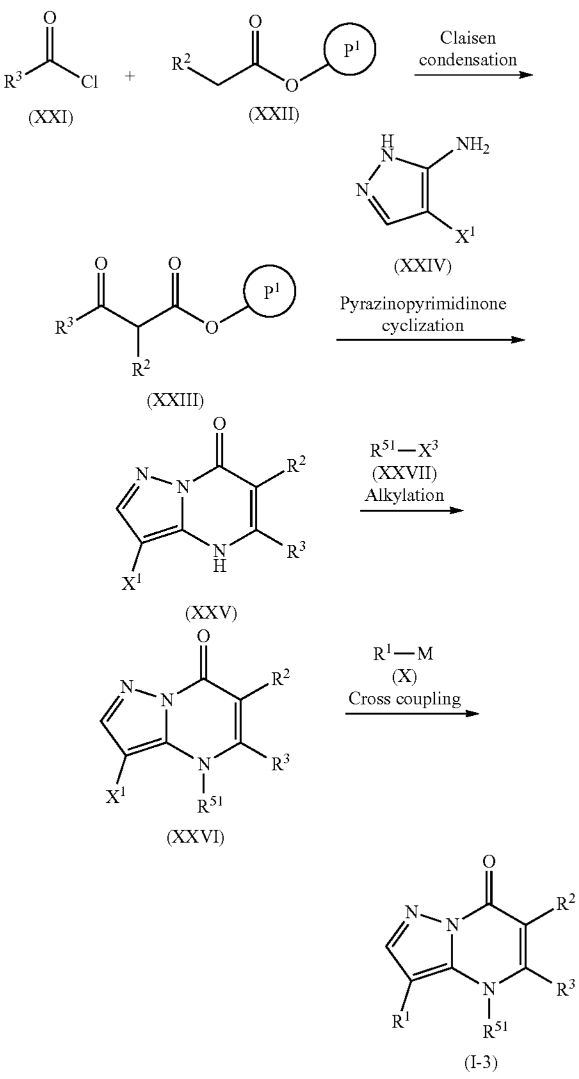

(XXI) (XXII) (XXIV) (XXIII) (XXV) (XXVI) (I-3)

The compound represented by the general formula (I-3) in Scheme IV can be produced by the subjecting the compound represented by the general formula (XXVI) and the compound represented by the general formula (X) to cross coupling.

The compound represented by the general formula (XXVI) can be produced by subjecting the compound represented by the general formula (XXV) and the compound represented by the general formula (XXVII) to alkylation.

Alkylation can be carried out with an alkylation agent (e.g., alkyl halide, alkyl mesylate, alkyl tosylate and like that) and a base (e.g., sodium hydride, potassium hydride, potassium tert-butoxide, sodium methoxide, potassium carbonate, tripotassium phosphate and like that) in a solvent (e.g., tetrahydrofuran, dimethoxyethane, dioxane and the like) or mixed solvents thereof at 0° C. to 60° C. under inert atmosphere.

The compound represented by the general formula (XXV) can be produced by subjecting the compound represented by the general formula (XXIII) and the compound represented by the general formula (XXIV) to a pyrazolopyrimidinone cyclization.

Pyrazolopyrimidinone cyclization can be carried out with a beta-ketoester and a 3-aminpyrazole derivative with titanium tetrachloride in a solvent (e.g., tetrahydrofuran, 2-methyltetrahydrofuran, dimethoxyethane, dioxane, benzene, toluene, xylene and the like) or mixed solvents thereof at 60° C. to 120° C. under inert atmosphere.

The compound represented by the general formula (XXIII) can be produced by subjecting the compound represented by the general formula (XXI) and the compound represented by the general formula (XXII) to Claisen condensation.

Claisen condensation can be carried out with a nucleophilic carbonyl compound (e.g., ketone, ester or aldehyde which have hydrogen atoms at their alpha position) and an ester or acid chloride with a base (e.g., LDA, LiHMDS, sodium hydride, potassium tert-butoxide, trimethylamine and the like) in a solvent (e.g., dichloromethane, tetrahydrofuran, diethylether, dimethylformamide, dimethoxyethane and the like) at −78° C. to room temperature under inert atmosphere.

Scheme V

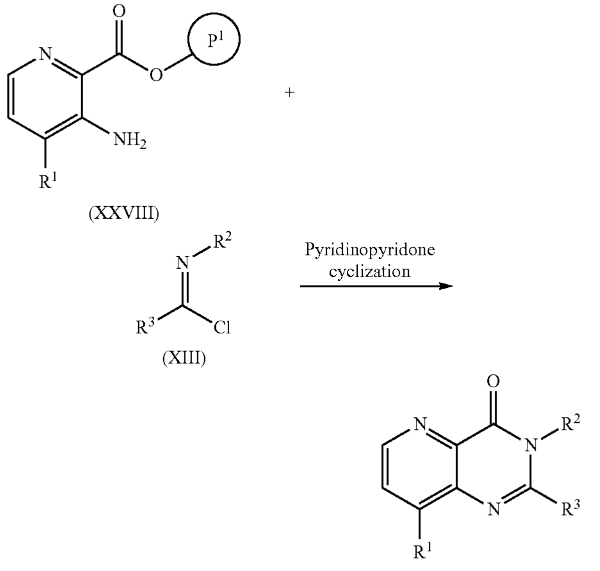

(XXVIII) (XIII) (I-5)

The compound represented by the general formula (I-5) in Scheme V can be produced by the general formula (XXVIII) and the compound represented by the general formula (XIII) to pyridinopiridazinone cyclization.

Pyridinopiridazinone cyclization can be carried out with an ester of a 3-amino nicotinic acid derivative and an iminochloride with a base (e.g., potassium carbonate, tripotassium phosphate and the like) in a solvent (e.g., acetonitrile, tetrahydrofuran, dimethylformamide and the like) or mixed solvents thereof at 50° C. to 100° C.

Typical synthetic methods of the compound represented by the general formula (XXVIII) are described in Chemical and Pharmaceutical bulletin, vol 31, #10, p 3490-3464, U.S. Pat. No. 5,591,742 (1997) or US2019/194174.

Scheme VI to XII describe the synthesis of the compound represented by the general formula (II).

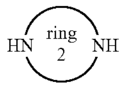

represents a saturated hetero ring containing two nitrogen atoms (e.g., piperazine, 2,6-diazaspiro[3.3]heptane, 2,6-diazaspiro[3.4]octane, 6-oxa-2,7-diazaspiro[3.4]octane, 2,7-diazaspiro[3.5]nonane, (3aR,7aR)-octahydro-1H-pyrrolo[3,2-b]pyridine and the like).

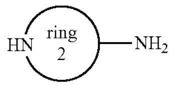

represents a saturated hetero ring containing one nitrogen atom and substituted with an amino group (e.g., azetidin-3-amine, piperidin-4-amine and the like).

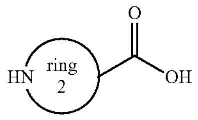

represents a saturated hetero ring containing one nitrogen atom and substituted with a carboxyl group (e.g., azetidine-3-carboxylic acid, piperidine-4-carboxylic acid, (1R,5S,6r)-3-azabicyclo[3.1.0]hexane-6-carboxylic acid and the like).

Scheme VI

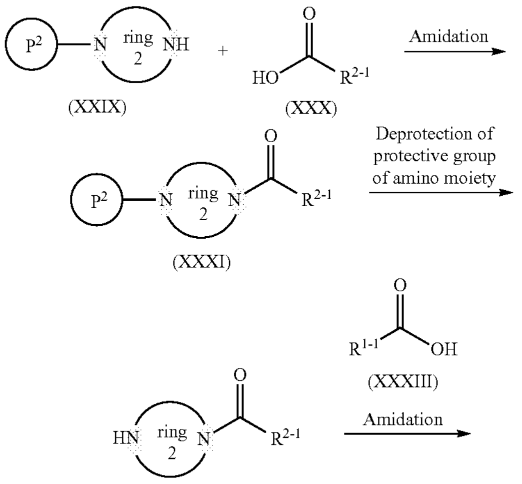

-continued

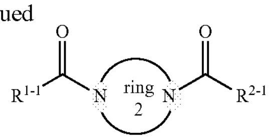

($II_A$)

When $L^1$ and $L^2$ are —C(═O)—, the compounds represented by the general structure (II-3), (II-5), (II-6), (II-9) and (II-10) can be described as ($II_A$) in Scheme VI, respectively.

The compound represented by the general formula ($II_A$) can be produced by subjecting the compound represented by the general formula (XXXII) and the compound represented by the general formula (XXXIII) to amidation described above.

The compound represented by the general formula (XXXII) can be produced by subjecting the compound represented by the general formula (XXXI) to deprotection of protective group of the amino moiety described above.

The compound represented by the general formula (XXXI) can be produced by subjecting the compound represented by the general formula (XXIX) and the compound represented by the general formula (XXX) to amidation described above.

Scheme VII

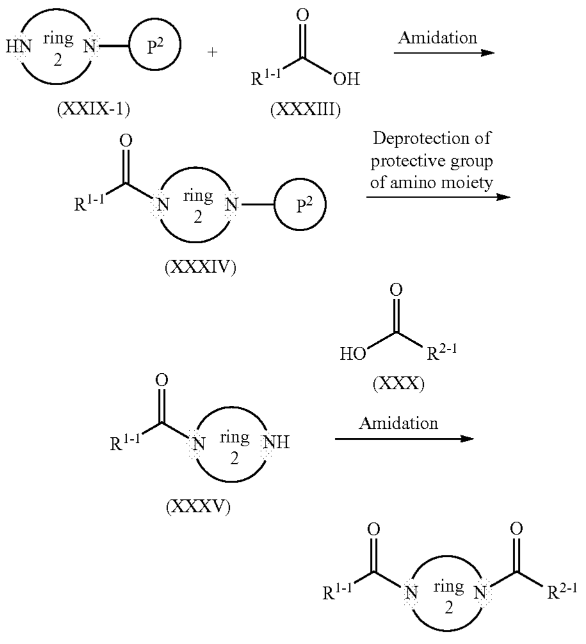

Alternatively, the compound represented by the general formula ($II_A$) can be produced by subjecting the compound represented by the general formula (XXX) and the compound represented by the general formula (XXXV) to amidation described above.

The compound represented by the general formula (XXXV) can be produced by subjecting the compound represented by the general formula (XXXIV) to deprotection of protective group of the amino moiety described above.

The compound represented by the general formula (XXXIV) can be produced by subjecting the compound represented by the general formula (XXXIII) and the compound represented by the general formula (XXIX-1) to amidation described above.

Scheme VIII

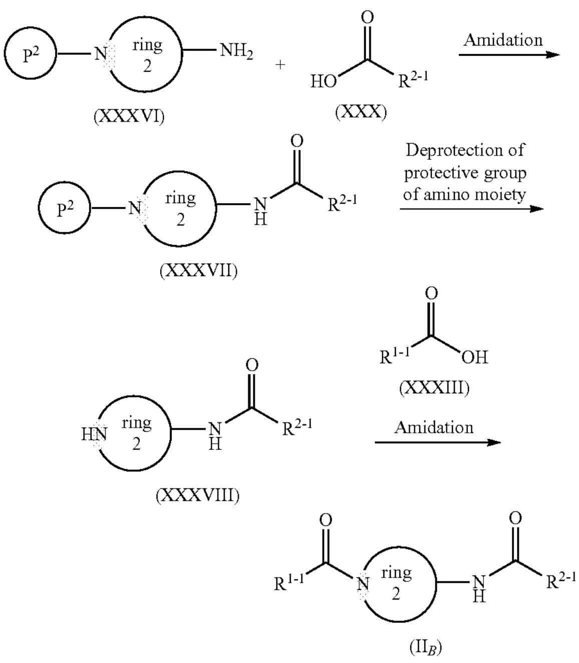

(XXXVI) (XXX) (XXXVII) (XXXIII) (XXXVIII) ($II_B$)

When $L^1$ is —C(═O)— and $L^2$ is —N(H)C(═O)—, the compounds represented by the general formula (II-1) and (II-2) can be described as ($II_B$) in Scheme VIII, respectively.

The compound represented by the general formula ($II_B$) can be produced by subjecting the compound represented by the general formula (XXXVIII) and the compound represented by the general formula (XXXIII) to amidation described above.

The compound represented by the general formula (XXXVIII) can be produced by subjecting the compound represented by the general formula (XXXVII) to deprotection of protective group of the amino moiety described above.

The compound represented by the general formula (XXXVII) can be produced by subjecting the compound represented by the general formula (XXX) and the compound represented by the general formula (XXXVI) to amidation described above.

Scheme IX

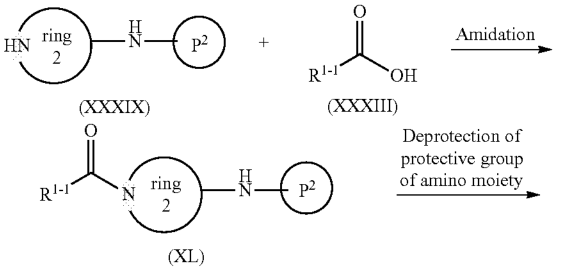

(XXXIX) (XXXIII) (XL)

-continued

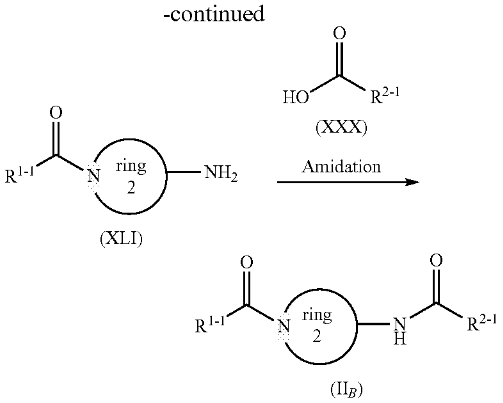

(XXX) (XLI) ($II_B$)

Alternatively, the compound represented by the general formula ($II_B$) can be produced by subjecting the compound represented by the general formula (XXX) and the compound represented by the general formula (XLI) to amidation described above.

The compound represented by the general formula (XLI) can be produced by subjecting the compound represented by the general formula (XL) to deprotection of protective group of the amino moiety described above.

The compound represented by the general formula (XL) can be produced by subjecting the compound represented by the general formula (XXXIII) and the compound represented by the general formula (XXXIX) to amidation described above.

Scheme X

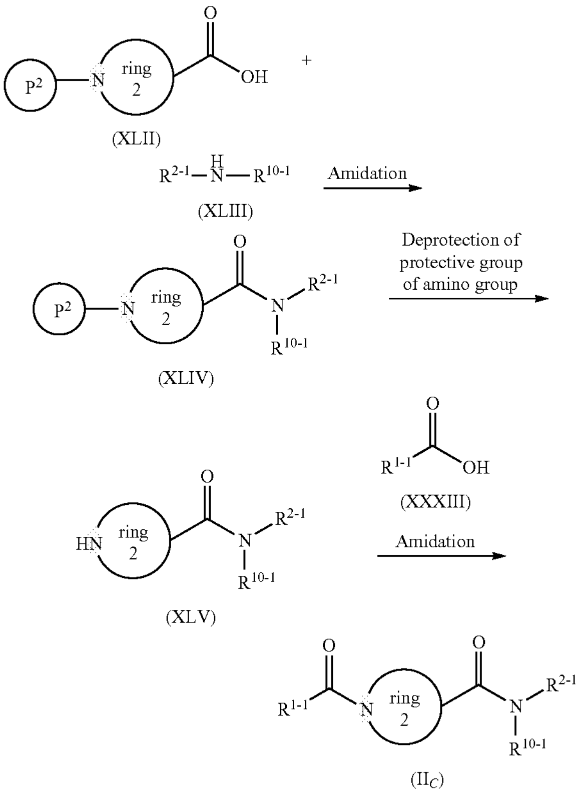

(XLII) (XLIII) (XLIV) (XXXIII) (XLV) ($II_C$)

When $L^1$ is —C(═O)— and $L^2$ is —C(═O)N($R^{10-1}$)—, the compounds represented by the general formula (II-1), (II-2) and (II-12) can be described as ($II_C$) in Scheme X, respectively.

The compound represented by the general formula ($II_C$) can be produced by subjecting the compound represented by the general formula (XXXIII) and the compound represented by the general formula (XLV) to amidation described above.

The compound represented by the general formula (XLV) can be produced by subjecting the compound represented by the general formula (XLIV) to deprotection of protective group of the amino moiety described above.

The compound represented by the general formula (XLIV) can be produced by subjecting the compound represented by the general formula (XLIII) and the compound represented by the general formula (XLII) to amidation described above.

Scheme XI

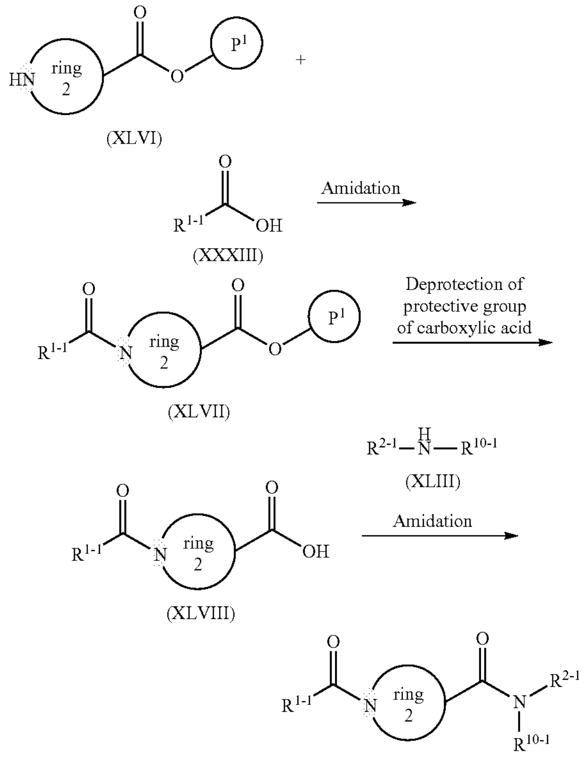

($II_C$)

Alternatively, the compound represented by the general formula ($II_C$) can be produced by subjecting the compound represented by the general formula (XLVIII) and the compound represented by the general formula (XLVIII) to amidation described above.

The compound represented by the general formula (XLVIII) can be produced by subjecting the compound represented by the general formula (XLVII) to deprotection of protective group of the carboxylic acid described above.

The compound represented by the general formula (XLVII) can be produced by subjecting the compound represented by the general formula (XXXIII) and the compound represented by the general formula (XLVI) to amidation described above.

Scheme XII

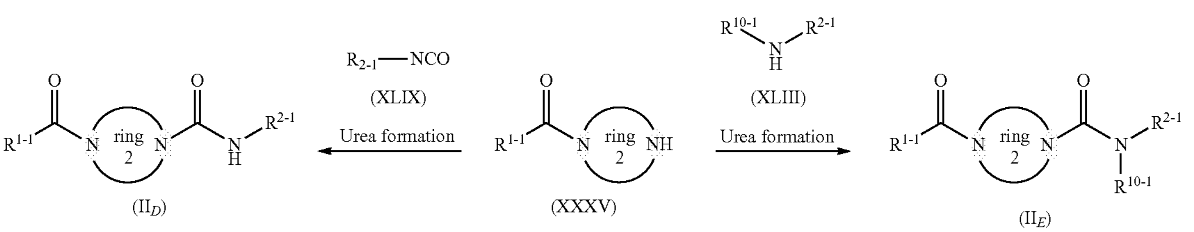

When $L^1$ is —C(═O)— and $L^2$ is C(═O)N(H)—, the compounds represented by the general formula (II-3), (II-5), (II-6), (II-8), (II-9) and (II-10) can be described as ($II_D$) or ($II_E$) in Scheme XII, respectively.

The compound represented by the general formula ($II_D$) can be produced by subjecting the compound represented by the general formula (XXXV) and the compound represented by the general formula (XLIX) to urea formation described above.

The compound represented by the general formula ($II_E$) can be produced by subjecting the compound represented by the general formula (XXXV) and the compound represented by the general formula (XLIII) to urea formation described above.

The respective compounds represented by the general formula (III), (V), (X), (XII), (XIII), (XVII), (XVIII), (XIX), (XX), (XXI), (XXII), (XXIV), (XXVII), (XXVIII), (XXIX), (XXIX-1), (XXX), (XXXIII), (XXXVI), (XXXIX), (XLII), (XLIII), (XLVI) and (XLIX) in Scheme I to XII can be available commercially or easily prepared from commercial chemicals by well-known method described in, for example, Comprehensive Organic Transformations: A Guide to Functional Group Preparations, 2nd Edition (Richard C. Larock, John Wiley & Sons Inc., 1999) and the like.

In the reactions exemplified herein, any heating means such as water bath, oil bath, sand bath and microwave may be used.

In the reactions exemplified herein, a solid phase-supported reagent supported on a polymer (such as polystyrene, polyacrylamide, polypropylene and polyethylene glycol) may be used, if appropriate.

The products from the reactions exemplified herein may be purified by a conventional purification means, for example, distillation under normal or reduced pressure, chromatography (such as high performance liquid chromatography, thin layer chromatography or column chromatography) using silica gel, ion exchange resin, scavenger resin or magnesium silicate, or by washing or recrystallization. Purification may be carried out after each reaction step or after a series of reactions.

[Toxicity]

The present compound has low toxicity and thus can be safely used as a medicament.

[Application to Medicaments]

The present compound has KDM5 inhibitory activity, and thus can be used as an agent for prophylaxis and/or therapy of KDM5-related diseases in mammals, particularly in humans.

Examples of such diseases include hyperproliferative disease, cancer, stroke, diabetes, hepatomegaly, cardiovascular disease, multiple sclerosis, Huntington's disease, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders, myeloproliferative disorder, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, and hepatitis and the like.

Among others, the present compound is useful for prophylaxis and/or therapy of cancer, Huntington's disease, Alzheimer's disease, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, or hepatitis. The present compound is particularly suitable for prophylaxis and/or therapy of cancer and Alzheimer's disease.

In addition to having a strong KDM5 inhibitory activity, the present compound is excellent in permeability in wild type MDCK cell lines.

Upon using the present compound for pharmaceutical purposes, the present compound may be used not only as a single drug but also as a combined drug with an additional active component, for example, those listed hereinbelow, for the purposes of, for example, (1) supplementing and/or enhancement of the effect thereof for prophylaxis, therapy and/or amelioration of symptoms, (2) improvement of the kinetics and absorption, reduction of the dosage thereof and/or (3) alleviation of side-effects thereof.

When the present compound is used for prophylaxis and/or therapy of Alzheimer's disease, examples of the drugs which may be used in combination with the present compound include symptomatic agents, for example, those known to modify cholinergic transmission such as M1 and M3 muscarinic receptor agonists or allosteric modulators, M2 muscarinic antagonists, M4 agonists or positive allosteric modulators (PAMs), acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-$HT_4$ receptor agonists or partial agonists, histamine H3 antagonists, 5-$HT_6$ receptor antagonists or $5HT_{1A}$ receptor ligands and NMDA receptor antagonists or modulators, 5-$HT_{2A}$ antagonists, 5-$HT_7$ antagonists, D1 agonists or PAMs, D4 agonists or PAMs, D5 agonists or PAMs, GABA-A a5 inverse agonists or negative allosteric modulators (NAMs), GABA-A a2/3 agonists or PAMs, mGluR2 modulators (PAMs or NAMs), mGluR3 PAMs, mGluR5 PAMs, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASCI inhibitors, AMPA modulators, SIRT1 activators or inhibitors, AT4 antagonists, GalR1 antagonists, GalR3 ligands, adenosine A1 antagonists, adenosine A2a antagonists, a2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation/kinase inhibitors, tau dephosphorylation/phosphatase activators, mitogen-activated protein kinase kinase 4 (MKK4/MEK4/MAP2K4) inhibitors, c-Jun N-terminal kinase (JNK) inhibitors, casein kinase inhibitors, MK2 (mitogen activated protein kinase-activated protein kinase 2) inhibitors, MARK (microtubule affinity regulating kinase) inhibitors, CDK5 (cyclin dependent kinase 5) inhibitors, GSK-3 (glycogen synthase kinase-3) inhibitors and tau-tubulin kinase-1 (TTBK1) inhibitors. Further examples of such other therapeutic agents may be calcium channel blockers, HMG-CoA (3-hydroxy-3-methylglutaryl-CoA) reductase inhibitors (statins) and lipid lowering agents, NGF (nerve growth factor) mimics, antioxidants, GPR3 ligands, plasmin activators, neprilysin (NEP) activators, IDE (insulin degrading enzyme) activators, melatonin MT1 and/or MT2 agonists, TLX/NR2E1 (tailless X receptor) ligands, GluR1 ligands, RAGE (receptor for advanced glycation end-products) antagonists, EGFR (epidermal growth factor receptor) inhibitors, FPRL-1 (formyl peptide-like receptor-1) ligands, GABA antagonists, and MICAL (molecule interacting with casL) inhibitors, e.g. oxoreductase inhibitors, CB1 antagonists/inverse agonists, non-steroidal anti-inflammatory drugs (NSAIDs), anti-inflammatory agents (for example agents that could be used to treat neuroinflammation either by enhancing or reducing neuroinflammation), amyloid precursor protein (APP) ligands, anti-amyloid vaccines and/or antibodies, agents that promote or enhance amyloid efflux and/or clearance, histone deacetylase (HDAC) inhibitors, EP2 antagonists, 11-beta HSD1 (hydroxy steroid dehydrogenase) inhibitors, liver X receptor (LXR) agonists or PAMs, lipoprotein receptor-related protein (LRP) mimics and/or ligands and/or enhancers and/or inhibitors, butyryl cholinesterase inhibitors, kynurinic acid antagonists and/or inhibitors of kynurenine aminotransferease (KAT), orphanin FQ/nociceptin (NOP)/opioid-like receptor 1 (ORL1) antagonists, excitatory amino acid transporter (EAAT) ligands (activators or inhibitors), and plasminogen activator inhibitor-1 (PAI-1) inhibitors, niacin and/or GPR109 agonists or PAMs in combination with cholesterol lowering agents and/or HMGCoA reductase inhibitors (statins), dimebolin or similar agents, antihistamines, metal binding/chelating agents, antibiotics, growth hormone secretagogues, cholesterol lowering agents, vitamin E, cholesterol absorption inhibitors, cholesterol efflux promoters and/or activators, and insulin upregulating agents, and the like.

The present compound may alternatively be used in combination with, for example, donepezil hydrochloride, galantamine hydrobromide, huperzine A, idebenone, levacecarnine hydrochloride, memantine hydrochloride, memantine hydrochloride/donepezil hydrochloride, proteolytic peptide fraction from porcine brain protein, rivastigmine tartrate, tacrine hydrochloride, aducanumab (genetical recombination) or the like.

The combined drug of the present compound and an additional drug may be administered in the form of a concomitant drug containing both components in one formulation, or separate formulations may be administered by the same or different routes of administration. It is not necessary that separate formulations are administered simultaneously and separate formulations may be administered sequentially with a time difference. When the formulations are sequentially administered, the order or administration is not particularly limited and may be appropriately adjusted so that desired efficacy of drugs can be obtained.

The dosage of the additional drug which is used in combination with the present compound may be appropriately increased or decreased according to the clinical dosage thereof or a similar drug. The ratio between the present compound and the additional drug may be appropriately adjusted by considering the age and weight of the subject, the administration method, the time of administration, the target disease and condition and the like. Generally, 1 part by weight of the present compound may be combined with the additional drug in an amount ranging from 0.01 to 100 parts by weight. A plurality of the additional drug may be used. The additional drug may be, in addition to those mentioned above, a drug having the same mechanism as those mentioned above. Such an additional drug includes not only the one which has been discovered by now but also the one which will be discovered in future.

The dosage of the present compound may vary according to the age, weight, condition, therapeutic effect, administration method, treatment period and the like. The present compound may be orally administered to an adult once to several times daily at the amount of 0.1 mg to 300 mg per administration, parenterally administered to an adult once to several times daily at the amount of 0.1 mg to 150 mg per administration or intravenously and continuously administered over 1 hour to 24 hours daily.

As described above, the dosage may vary according to various conditions, and thus the amount less than the dosage described above may be sufficient in some cases and the amount exceeding the above dosage may be required in other cases.

When the present compound is used for prophylaxis and/or therapy of the above diseases as a single drug or a combined drug with the additional drug, the present substance which is an active component is generally formulated with a pharmaceutically acceptable carrier such as various additives or solvents and the obtained formulation is administered systemically or locally and orally or parenterally. The pharmaceutically acceptable carrier as used herein means a substance other than an active component that is generally used for medicinal formulations. The pharmaceutically acceptable carrier preferably does not exhibit pharmacological activity, is harmless and does not prevent the therapeutic effect of the active component at the dosage of the formulation. The pharmaceutically acceptable carrier may also be used in order to increase the usefulness of the active component and the formulation, to facilitate production of the formulation, to stabilize the quality or to improve the usability. Specifically, the substances described in "Iyalcuhin Tenkabutsu Jiten", 2000, Yakuji Nippo Ltd. (Ed. IPEC Japan) may be appropriately selected according to the need.

Examples of the dosage form include oral administration formulations (examples: tablets, capsules, granules, powders, oral liquids, syrups, oral jelly formulations and the like), oral cavity formulations (examples: tablets for the oral cavity, spray formulations for the oral cavity, semi-solid formulations for the oral cavity, oral rinse and the like), formulations for injection (examples: injections and the like), formulations for dialysis (examples: agents for dialysis and the like), formulations for inhalation (examples: agents for inhalation and the like), ophthalmic formulations (examples: ophthalmic solutions, ophthalmic ointments and the like), otological formulations (examples: ear drops and the like), nasologic formulations (examples: nasal drops and the like), rectal formulations (examples: suppositories, semisolid formulations for rectal administration, enema formulations and the like), vaginal formulations (examples: vaginal tablets, vaginal suppositories and the like), skin formulations (examples: topical solid formulations, topical liquids, spray formulations, ointments, creams, gels, plasters and pressure sensitive adhesives and the like) and the like.

[Oral Administration Formulations]

Examples of an oral administration formulation include tablets, capsules, granules, powders, oral liquids, syrups, oral jelly formulations and the like. The oral administration formulation may be classified into rapidly disintegrating formulations for which the release of an active component from the formulations is not particularly controlled and release-controlled formulations for which the release is controlled according to the purposes by adjusting the dosage design and production method, such as enteric formulations and sustained release formulations. The enteric formulations refer to a formulation which is designed to release an active component mainly in the small intestine rather than in the stomach with the purpose of prevention of decomposition of the active component in the stomach or reduction of stimulation of the stomach by the active component. The enteric formulation may be generally produced by providing a coating of an acid-insoluble enteric base. The sustained release formulations refer to a formulation for which the release rate, release time and release site of an active component from the formulation is controlled with the purpose of reduction in the frequency of administration or reduction of side effects. The sustained release formulation may be generally produced by using an appropriate agent for sustained release. Among the oral administration formulations, capsules, granules, tablets may be provided with an appropriate coating film of a saccharide, sugar alcohol, polymer compound and the like with the purpose of easy ingestion or prevention of decomposition of an active component.

(1) Tablets

Tablets are an orally administered solid formulation having a certain shape. Examples thereof include those generally referred to as tablets such as plain tablets, film-coated tablets, sugar-coated tablets, multilayered tablets and dry-coated tablets as well as orally disintegrating tablets, chewable tablets, effervescent tablets, dispersible tablets, soluble tablets and the like. Plain tablets may be generally produced according to the following procedure (a), (b) or (c):

(a) An active component is mixed with an additive such as a vehicle, a binding agent and a disintegrating agent to obtain a homogeneous mixture which is granulated by an appropriate method using water or a solution containing a binding agent, mixed with a lubricant and the like, compressed and moulded;

(b) An active component is mixed with an additive such as a vehicle, a binding agent and a disintegrating agent to obtain a homogeneous mixture which is then directly compressed and moulded, or granules prepared with an additive are mixed with an active component, a lubricant and the like to obtain a homogeneous mixture which is then compressed and moulded;

(c) An active component is mixed with an additive such as a vehicle and a binding agent to obtain a homogeneous mixture which is then wetted and kneaded with a solvent, moulded in a certain mould and dried by an appropriate method. Film-coated tablets may be generally produced by providing appropriate thin coating films of a polymer and the like to plain tablets. Sugar-coated tablets may be generally produced by providing coating films containing a saccharide or sugar alcohol to plain tablets. Multilayerd tablets may be produced by stacking layers of powder granules having different compositions and compressing and moulding the product according to an appropriate method. Dry-coated tablets may be produced by coating inner core tablets with outer layers having different compositions. Tablets may be formed as enteric tablets or sustained release tablets according to appropriate well-known methods. Orally disintegrating tablets, chewable tablets, effervescent tablets, dispersible tablets and soluble tablets are the tablets to which unique functions are imparted by appropriately selecting additives, and may be produced according to the production procedures described above for the tablets. Orally disintegrating tablets refer to a tablet ingested by rapid dissolution or disintegration in the oral cavity; chewable tablets refer to a tablet ingested by chewing; effervescent tablets refer to a tablet which is dissolved or dispersed in water with rapid effervescence; dispersible tablets refer to a tablet which is ingested after dispersion in water; and the soluble tablets refer to a tablet which is ingested after dissolution in water. The effervescent tablets may be produced by using an additive which is an appropriate acidic substance, carbonate salt, hydrogen carbonate salt and the like.

(2) Capsules

Capsules are a formulation containing a capsule shell filled with an active component or an active component coated with a capsule base. Examples thereof include hard capsules, soft capsules and the like. Hard capsules may be produced by mixing an active component with an additive such as a vehicle to obtain a homogeneous mixture, or obtaining granules or moulded substance by an appropriate method, which is then directly, or after appropriately being moulded, added to a capsule shell. Soft capsules may be produced by capsulating and moulding a mixture of an active component and an additive into a certain shape with an appropriate capsule base such as gelatine having an increased plasticity by addition of glycerol, D-sorbitol or the like. Capsules may be formed as enteric capsules or sustained release capsules according to appropriate well-known methods. An capsule base may be added with a colorant, a preservative or the like.

(3) Granules

Granules are a granulated formulation. Examples thereof include those generally referred to as granules as well as effervescent granules. Granules may be generally produced according to the following procedure (a), (b) or (c):

(a) A powder active component is mixed with an additive such as a vehicle, a binding agent or a disintegrating agent to obtain a homogeneous mixture which is then granulated by an appropriate method;

(b) A granulated active component is mixed with an additive such as a vehicle to obtain a homogeneous mixture;

(c) A granulated active component is mixed with an additive such as a vehicle to obtain a homogeneous mixture which is then granulated by an appropriate method. Granules may be optionally provided with a film or may be formed as enteric granules or sustained release granules using appropriate well-known methods. Effervescent granules may be produced by using an additive which is an appropriate acidic substance, carbonate salt, hydrogen carbonate salt and the like. The effervescent granules refer to a granule which is dissolved or dispersed in water with rapid effervescence. The granules may also be formed as fine granules by controlling the particle size.

(4) Powders

Powders are powdery formulations and may be generally produced by mixing an active component with an additive such as a vehicle to obtain a homogeneous mixture.

(5) Oral Liquids

Oral liquids are a formulation in the form of solution or flowable and viscous gel. Examples thereof include those generally referred to as oral liquids as well as elixirs, suspensions, emulsions, lemonades and the like. Oral liquids may be generally produced by mixing an active component with an additive and purified water to homogeneously dissolve, emulsify or suspend the active component and optionally filtering the product. Elixirs refer to a clear oral liquid containing ethanol having sweet taste and aroma. Elixirs may be generally produced by dissolving a solid active component or an infusion thereof in ethanol, purified water, a flavouring agent and sucrose, an additional saccharide or a sweetening agent and obtaining a clear liquid by filtration or other methods. Suspensions refer to an oral liquid in which an active component is finely and homogeneously suspended. Suspensions may be generally produced by suspending a solid active component in a suspending agent or an additional additive and purified water or oil and homogenising the whole product according to an appropriate method. Emulsions refer to an oral liquid in which an active component is finely and homogeneously emulsified. Emulsions may be generally produced by adding an emulsifying agent and purified water to a liquid active component and emulsifying and homogenising the whole product according to an appropriate method. Lemonades refer to a clear oral liquid having sweet taste and sour taste.

(6) Syrups

Syrups are a viscous liquid or solid formulation containing a saccharide or a sweetening agent. Examples thereof include agents for syrups. Syrups may be generally produced by dissolving, mixing, suspending or emulsifying an active component in a solution of sucrose, other saccharides or a sweetening agent or solely a syrup and optionally boiling the product followed by filtering while heating. Formulations for syrups refer to a granular or powdery formulation to which water is added to provide syrups and may be sometimes referred to as dry syrups. Formulations for syrups may be generally produced according to the production procedures described above for the granules or powders by using a saccharide or a sweetening agent as an additive.

(7) Oral Jelly Formulations

Oral jelly formulations are a shaped gel formulation without flowability. Oral jelly formulations may be generally produced by mixing an active component with an additive and a polymer gel base, allowing formation of gel and shaping into a certain shape according to appropriate methods.

[Oral Cavity Formulations]

(1) Tablets for the Oral Cavity

Tablets for the oral cavity are a formulation having a certain shape which is administered to the oral cavity. Examples thereof include troches, sublingual tablets, buccal tablets, adhering tablets, chewing gum tablets and the like. Tablets for the oral cavity may be generally produced according to the production procedures described for the tablets. Troches refer to a tablet for the oral cavity which is gradually dissolved or disintegrated in the oral cavity and is applied locally to the oral cavity or pharynx; sublingual tablets refer to a tablet for the oral cavity to be rapidly dissolved under the tongue to allow absorption of an active component through oral mucosa; buccal tablets refer to a tablet for the oral cavity to be gradually dissolved between the molars and cheeks to allow absorption of an active component through oral mucosa; adhering tablets refer to a tablet for the oral cavity which is adhered to oral mucosa; and chewing gum tablets refer to a tablet for the oral cavity to be chewed to release an active component.

(2) Spray Formulations for the Oral Cavity

Spray formulations for the oral cavity are a formulation to spray an active component in the form of mist, powder, foam or paste. Spray formulations for the oral cavity may be generally produced by dissolving or suspending an active component and an additive in a solvent or the like, optionally filtering thereof and packing the product into a container together with liquefied gas or compressed gas, or by preparing a solution or suspension with an active component and an additive and packing the product into a container to which a spraying pump is attached.

(3) Semi-Solid Formulations for the Oral Cavity

Semi-solid formulations for the oral cavity are a formulation to be applied to the oral mucosa. Examples thereof include creams, gels, ointments and the like. Semi-solid formulations for the oral cavity may be generally produced by emulsifying an active component together with an additive in purified water and an oil component such as petrolatum, or by mixing an active component and an additive with a base such as a polymer gel or an oil or fat and obtaining a homogeneous mixture. Creams refer to a semi-solid formulation in the form of an oil-in-water or water-in-oil emulsion and lipophilic formulations in the form of a water-in-oil emulsion may also be referred to as oil-based creams. Creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion. Gels refer to a gel formulation and examples thereof include water-based gels, oil-based gels and the like. Water-based gels may be produced by dissolving or suspending an active component in an additive such as a polymer compound and purified water and allowing cross-linking by heating and cooling or addition of a gel-forming agent. Oil-based gels may be produced by mixing an active component with a liquid oil base such as a glycol or a higher alcohol and an additive. Ointments refer to a semi-solid formulation containing an active component dissolved or dispersed in a base. Examples thereof include oil- or fat-based ointments, water-soluble ointments and the like. Oil- or fat-based ointments may be generally produced by melting an oil- or fat-based base such as an oil or fat, a wax and a hydrocarbon including paraffin by heating, dissolving or dispersing an active component therein and mixing and kneading to obtain a homogeneous mixture. Water-soluble ointments may be generally produced by melting a water-soluble base such as macrogol by heating and mixing and kneading an active component therein to obtain a homogeneous mixture.

(4) Oral Rinses

Oral rinses are a liquid formulation to be applied locally to the oral cavity or pharynx and may include solid formulations which are dissolved upon use. Oral rinses may be generally produced by homogeneously dissolving an active component in a solvent and an additive and optionally filtering the solution. Solid formulations which are dissolved upon use may be generally produced according to the production procedures described for the tablets and granules.

[Formulations for Injection]

(1) Injections

Injections are an aseptic formulation in the form of solution, suspension or emulsion or solid to be dissolved or suspended upon use, which are directly administered to body tissues and organs such as under the skin, in the muscle or to a vessel. Examples thereof include those generally referred to as injections as well as lyophilised injections, powder injections, pre-filled syringes, cartridges, transfusions, implantable injections, sustained release injections and the like. Injections may be generally produced according to the following procedure (a) or (b):

(a) An active component or a mixture of an active component with an additive is dissolved, suspended or emulsified in water for injection or another aqueous solvent or a non-aqueous solvent and the product is packed into a container for injection which is then sterilised;

(b) An active component or a mixture of an active component with an additive is dissolved, suspended or emulsified in water for injection or another aqueous solvent or a non-aqueous solvent and the product is subjected to aseptic filtration or the product is homogeneously prepared in an aseptic manner and is charged into a container for injection which is then sealed. Lyophilised injections may be generally produced by dissolving an active component or an active component together with an additive such as a vehicle in water for injection, subjecting the solution to aseptic filtration, charging the solution in a container for injection followed by lyophilisation or lyophilising the solution in a container dedicated for lyophilisation followed by packing the product in a container for injection. Powder injections may be generally produced by aseptic filtration and crystallization to obtain powder which is directly or a mixture thereof with a sterilized additive is charged into a container for injection. Pre-filled syringes may be generally produced by charging an active component or a solution, suspension or emulsion of an active component and an additive into a syringe. Cartridges refer to an injection in the form of a cartridge containing a drug solution to be placed in a dedicated syringe. Cartridges containing a drug solution may be generally produced by charging an active component or a solution, suspension or emulsion of an active component and an additive into a cartridge. Transfusions refer to an injection generally of 100 mL of more which is intravenously administered. Implantable injections refer to an injection in the form of a solid or gel, which is to be applied using an implantable tool or by surgery under the skin or in the muscle in order to release an active component over a long period of time. Implantable injections may be generally produced by forming a pellet, microsphere or gel with a biodegradable polymer compound. Sustained release injections refer to an injection applied in the muscle in order to release an active component over a long period of time and may be generally produced by dissolving or suspending an active component in a vegetable oil or obtaining a microsphere suspension with a biodegradable polymer compound.

[Formulations for Dialysis]

(1) Agents for Dialysis

Agents for dialysis are a liquid formulation or a solid formulation dissolved upon use to be used for peritoneal dialysis or haemodialysis. Examples thereof include agents for peritoneal dialysis, agents for haemodialysis and the like. Agents for peritoneal dialysis refer to an aseptic agent for dialysis used for peritoneal dialysis and may be generally produced by charging a solution of an active component and an additive in a solvent at a certain volume or a mixture of an active component and an additive into a container, sealing the same and optionally sterilizing the same. Solid formulations to be dissolved upon use may be generally produced according to the production procedures described above for the tablets and granules. Agents for haemodialysis refer to an agent for dialysis used for haemodialysis and may be generally produced by charging a solution of an active component and an additive in a solvent at a certain volume or a mixture of an active component and an additive into a container. Solid formulations to be dissolved upon use may be generally produced according to the production procedures described above for the tablets and granules.

[Formulations for Inhalation]

(1) Agents for Inhalation

Agents for inhalation are a formulation applied to the bronchus or lung by inhaling aerosols of an active component. Examples thereof include powder agents for inhalation, liquid agents for inhalation, aerosols for inhalation and the like. Powder agents for inhalation refer to a formulation to be inhaled as aerosols of solid particles at a predetermined amount, and may be generally produced by preparing fine particles of an active component and optionally mixing thereof with an additive such as lactose to obtain a homogeneous mixture. Liquid agents for inhalation refer to a liquid agent for inhalation to be applied by a nebuliser and the like and may be generally produced by homogeneously dissolving or suspending an active component in a solvent, an appropriate tonicity agent, a pH-controlling agent and the like and optionally filtering the product. Aerosols for inhalation refer to a metered-dose agent for inhalation to spray a predetermined amount of active component packed in a container together with a propellant. Aerosols for inhalation may be generally produced by preparing a solution or suspension from an active component, a solvent, an appropriate dispersant, a stabilising agent and the like and charging the product in a pressure resistant container attached with a flow regulating valve together with a liquid propellant.

[Ophthalmic Formulations]

(1) Ophthalmic Solutions

Ophthalmic solutions are a liquid aseptic formulation or a solid aseptic formulation to be dissolved or suspended upon use, which is applied to ophthalmic tissue such as conjunctival sac. Ophthalmic solutions may be generally produced by charging a solution or suspension of an active component and an additive in a solvent or the like at a certain volume or a mixture of an active component and an additive in a container.

(2) Ophthalmic Ointments

Ophthalmic ointments are a semi-solid aseptic formulation to be applied to ophthalmic tissue such as conjunctival sac, and may be generally produced by charging a homogeneous mixture of a base such as petrolatum and a solution or fine powder of an active component in a container.

[Otological Formulations]

(1) Ear Drops

Ear drops are a liquid or semi-solid formulation or a solid formulation to be dissolved or suspended upon use, which is administered to the external ear or middle ear. Ear drops are generally produced by charging a solution or suspension of an active component and an additive in a solvent or like at a certain volume or a mixture of an active component and an additive in a container.

[Nasologic Formulations]

(1) Nasal Drops

Nasal drops are a formulation to be administered to the nasal cavity or nasal mucosa and examples thereof include nasal powders, nasal liquids and the like. Nasal powders refer to a fine powder nasal drop to be administered to the nasal cavity and may be generally produced by making appropriately fine powder of an active component and optionally mixing the active component with an additive to obtain a homogeneous mixture. Nasal liquids refer to a nasal drop which is liquid or solid to be dissolved or suspended upon use and is administered to the nasal cavity. Nasal liquids may be generally produced by dissolving or suspending an active component in a solvent and an additive and optionally filtering the product. An additive for nasal liquids which may be used includes a tonicity agent, a pH controlling agent and the like.

[Rectal Formulations]

(1) Suppositories

Suppositories are a semi-solid formulation having a certain shape, which is applied in the rectum and releases an active component by melting at body temperature or gradually dissolving or dispersing in water. Suppositories may be generally produced by dissolving or homogeneously dispersing a homogeneous mixture of an active component with an additive such as a dispersant and an emulsifying agent in a base liquefied by heating and the like, charging a predetermined amount of the product in a container and solidifying/moulding the same. A base for suppositories which may be generally used includes oil- or fat-based bases and hydrophilic bases.

(2) Semi-Solid Formulations for Rectal Administration

Semi-solid formulations for rectal administration are a formulation applied around or in the anus and examples thereof include rectal creams, rectal gels, rectal ointments and the like. Semi-solid formulations for rectal administration may be generally produced by emulsifying an active component together with an additive in purified water and an oil component such as petrolatum, or by homogeneously mixing an active component and an additive with a base which is a polymer gel or an oil or fat. Rectal creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion. Rectal gels refer to a gel formulation and examples thereof include water-based gels, oil-based gels and the like. Water-based gels may be produced by dissolving or suspending an active component in an additive such as a polymer compound and purified water and allowing crosslinking by heating and cooling or addition of a gel-forming agent. Oil-based gels may be produced by mixing an active component with a liquid oil base such as a glycol or a higher alcohol and an additive. Rectal ointments refer to a semi-solid formulation containing an active component dissolved or suspended in a base and examples thereof include oil- or fat-based ointments, water-soluble ointments and the like. Oil- or fat-based ointments may be generally produced by melting an oil- or fat-based base such as an oil or fat, a wax and a hydrocarbon including paraffin by heating, dissolving or suspending an active component therein and mixing and kneading to obtain a homogeneous mixture. Water-soluble ointments may be generally produced by melting a water-soluble base such as macrogol by heating and mixing and kneading an active component therein to obtain a homogeneous mixture.

(3) Enema Formulations

Enema formulations are a liquid or viscous gel formulation to be applied through the anus. Enema formulations are generally produced by dissolving or suspending an active component in a solvent or the like at a certain volume using purified water or an appropriate aqueous solvent and charging the product in a container. An additive which may be used for enema formulations includes a dispersant, a stabilising agent, a pH controlling agent and the like.

[Vaginal Formulations]

(1) Vaginal Tablets

Vaginal tablets are a solid formulation having a certain shape, which is applied in the vagina and releases an active component by gradually dissolving or dispersing in water. Vaginal tablets may be generally produced according to the production procedures described above for the tablets.

(2) Vaginal Suppositories

Vaginal suppositories are a semi-solid formulation having a certain shape, which is applied in the vagina and releases an active component by melting at body temperature or gradually dissolving or dispersing in water. Vaginal suppositories may be generally produced according to the production procedures described above for the rectal suppositories and the like.

[Skin Formulations]

(1) Topical Solid Formulations

Topical solid formulations are a solid formulation to be applied or spread on skin including the scalp or nails and examples thereof include topical powders. Topical powders refer to a topical solid powder formulation and may be generally produced by mixing an active component with an additive such as a vehicle to obtain a homogeneous mixture which is then formed into powders.

(2) Topical Liquids

Topical liquids are a liquid formulation to be applied on skin including the scalp or nails and examples thereof include liniments, lotions and the like. Topical liquids may be generally produced by dissolving, emulsifying or suspending an active component in a solvent, an additive and the like and optionally filtering the product. Liniments refer to a liquid or muddy topical liquid to be rubbed into the skin. Lotions refer to a topical liquid containing an active component dissolved, emulsified or finely dispersed in an aqueous liquid. Lotions may be generally produced by preparing a solution, suspension or emulsion of an active component, an additive and purified water to obtain a homogeneous product.

(3) Spray Formulations

Spray formulations are a formulation to spray an active component in the form of mist, powder, foam or paste on the skin and examples thereof include topical aerosols, pump spray formulations and the like. Spray formulations may be generally produced by preparing a solution or suspension of an active component, optionally filtering the product and charging the product in a container. Topical aerosols refer to a spray formulation which sprays an active component together with liquefied gas or compressed gas packed in a container. Topical aerosols may be generally produced by preparing a solution or suspension of an active component and packing the product into a pressure resistant container attached with a continuous injection valve together with a liquid propellant. An additive such as a dispersant and a stabilising agent may be optionally added to topical aerosols. Pump spray formulations refer to a spray formulation which sprays an active component in a container by means of a pump. Pump spray formulations may be generally produced by dissolving or suspending an active component and an additive and charging the product in a container to which a pump is attached.

(4) Ointments

Ointments are a semi-solid formulation to be applied on the skin containing an active component dissolved or dispersed in a base. Examples thereof include oil- or fat-based ointments, water soluble ointments and the like. Oil- or fat-based ointments may be generally produced by melting an oil- or fat-based base such as an oil or fat, a wax and a hydrocarbon including paraffin by heating, dissolving or suspending an active component therein and mixing and kneading to obtain a homogeneous mixture. Water soluble ointments may be generally produced by melting a water-soluble base such as macrogol by heating and mixing and kneading an active component therein to obtain a homogeneous mixture.

(5) Creams

Creams are a semi-solid formulation in the form of an oil-in-water or water-in-oil emulsion to be applied on the skin and lipophilic formulations in the form of a water-in-oil emulsion may also be referred to as oil-based creams. Creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion.

(6) Gels

Gels are a gel formulation to be applied on the skin and examples thereof include water-based gels and oil-based gels. Water-based gels may be generally produced by dissolving or suspending an active component in an additive such as a polymer compound and purified water and allowing crosslinking by heating and cooling or addition of a gel-forming agent. Oil-based gels may be produced by mixing an active component with a liquid oil base such as a glycol or a higher alcohol and an additive.

(7) Plasters and Pressure Sensitive Adhesives

Plasters and pressure sensitive adhesives are a formulation to be adhered on the skin and examples thereof include tapes and cataplasms. Plasters and pressure sensitive adhesives may be generally produced by homogeneously mixing an active component with a base which is a polymer compound or a mixture thereof, spreading the mixture on a support or a liner (release material) and shaping the same. Plasters and pressure sensitive adhesives may be formed as transdermal absorption formulations by using a release-controlled film. An additive such as an adhesive or an absorption-promoting agent may be optionally used for plasters and pressure sensitive adhesives. Tapes refer to a plaster and pressure sensitive adhesive containing a base that contains little water and examples thereof include plasters and the like. Tapes may be generally produced with a base which is a water insoluble natural or synthetic polymer compound such as a resin, a plastic, a rubber or the like by spreading on a fabric or spreading on or incorporating into a plastic film an active component or a homogeneous mixture of an active component and an additive and shaping the product. Tapes may also be produced by incorporating a mixture of an active component and a base or another additive into a release material made of a release-controlled film, a support and a liner (release material) and shaping the same. Cataplasms refer to a plaster and pressure sensitive adhesive containing a base which contains water and may be generally produced by homogeneously mixing an active component with a liquid substance such as purified water or glycerol or homogeneously mixing and kneading a natural or synthetic polymer compound such as a water soluble polymer or a water-absorbable polymer and purified water together with an active component, spreading the mixture on a fabric or the like and shaping the same.

Unless otherwise defined, all technical and scientific terms and abbreviations used herein have the same meanings as those commonly understood by a person skilled in the art to which the present invention belongs.

Contents of all patent literatures and non patent literatures or references explicitly cited herein may be incorporated herein as a part of the present specification.

EXAMPLES

The present invention is hereinafter specifically described by way of Examples and Biological Examples which do not limit the present invention. The present compounds and compounds described in Examples are denominated according to the IUPAC nomenclature. Naming according to the IUPAC nomenclature can be done using, for example, ACD/Name (version 2019.2.0, available from Advanced Chemistry Development Inc.), ACD/Name Batch (version 12.02.45356, available from Advanced Chemistry Development Inc.) or ChemDraw Professional (version 17.1.0.105 or 18.0.0.231, available from PerkinElmer Inc.) In each of the following Examples, the name of the objective compound of the Example is described subsequently to the number of the Example, and the compound is sometimes referred to as the "title compound".

Analytical Methods $^1$H NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Avance 400 MHz, 5 mm QNP probe H, C, F, P, single Z gradient, two channel instrument running TopSpin 2.1 or on a Bruker Avance III 400 MHz, 5 mm BBFO Plus probe, single Z gradient, two channel instrument running TopSpin 3.1. Shifts are given in ppm relative to tetramethylsilane (δ=0 ppm).

The Liquid Chromatography Mass Spectroscopy (LCMS) systems used are:

Method 1

ACQUITY UPLC (binary pump/PDA detector)+ZQ Mass Spectrometer with an ACQUITY UPLC BEH $C_{18}$ 1.7 μM, 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 2

ACQUITY H-Class (quaternary pump/PDA detector)+QDa Mass Spectrometer, ACQUITY UPLC CSH $C_{18}$ 1.7 μm, 50×2.1 mm at 40° C. Elution with A: water+0.1% formic acid; B: acetonitrile+0.1% formic acid. Gradient:

| Gradient - Time | flow mL/min | % A | % B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV diode array 190-400 nm. MS ionization method—Electrospray (positive and negative ion).

Method 3

ACQUITY i-Class (quarternary pump/PDA detector)+Quattro Micro Mass Spectrometer with an ACQUITY UPLC BEH $C_{18}$ 1.7 μM, 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 4

ACQUITY H-Class (quaternary pump/PDA detector)+QDa Mass Spectrometer, ACQUITY BEH $C_{18}$ 1.7 μm, 50×2.1 mm at 40° C. Elution with A: 7.66 mM ammonia in water; B: 7.66 mM ammonia in acetonitrile. Gradient:

| Gradient - Time | flow mL/min | % A | % B |
|---|---|---|---|
| 0.00 | 0.8 | 97 | 3 |
| 1.50 | 0.8 | 3 | 97 |
| 1.90 | 0.8 | 3 | 97 |
| 2.00 | 0.8 | 97 | 3 |
| 2.50 | 0.8 | 97 | 3 |

Detection—MS, UV diode array 190-400 nm. MS ionization method—Electrospray (positive and negative ion).

Method 5

ACQUITY Classic+996 PDA detector+Waters ZMD Mass Spectrometer, ACQUITY UPLC CSH $C_{18}$ 1.7 μm, 50×2.1 mm at 40° C. Elution with A: water+0.1% formic acid; B: acetonitrile+0.1% formic acid. Gradient:

| Gradient - Time | flow mL/min | % A | % B |
|---|---|---|---|
| 0.00 | 1.0 | 97 | 3 |
| 0.15 | 1.0 | 97 | 3 |
| 2.30 | 1.0 | 1 | 99 |
| 2.40 | 1.0 | 1 | 99 |
| 2.50 | 1.0 | 97 | 3 |

Detection—MS, UV diode array 190-400 nm. MS ionization method—Electrospray (positive and negative ion).

Method 6

ACQUITY Classic+996 PDA detector+Waters ZMD Mass Spectrometer, ACQUITY UPLC BEH $C_{18}$ 1.7 μm, 50×2.1 mm at 40° C. Elution with A: 0.1% aqueous ammonia (v/v); B: 0.1% ammonia in acetonitrile (v/v). Gradient:

| Gradient - Time | flow mL/min | % A | % B |
|---|---|---|---|
| 0.00 | 1.0 | 97 | 3 |
| 0.15 | 1.0 | 97 | 3 |
| 2.30 | 1.0 | 1 | 99 |
| 2.40 | 1.0 | 1 | 99 |
| 2.50 | 1.0 | 97 | 3 |

Detection—MS, UV diode array 190-450 nm. MS ionization method—Electrospray (positive and negative ion).

Method 7

ACQUITY UPLC (binary pump/PDA detector)+Waters SQD2, single quadrapole UPLC-MS with an ACQUITY UPLC HSS $C_{18}$ 1.81 μm, 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 8

ACQUITY UPLC (binary pump/PDA detector)+Waters SQD2, single quadrapole UPLC-MS with an ACQUITY UPLC BEH Shield RP18 1.7 μm, 100×2.1 mm, maintained at 40° C. Elution with A: water+10 mM ammonium bicarbonate; B: acetonitrile. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 9

ACQUITY UPLC (binary pump/PDA detector)+ZQ Mass Spectrometer with an ACQUITY UPLC BEH $C_{18}$ 1.7 μm, 100×2.1 mm, maintained at 40° C. Elution with A: 0.1% aqueous ammonia (v/v); B: 0.1% ammonia in acetonitrile (v/v). Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 10

HP1100 (quaternary pump/PDA detector)+ZQ Mass Spectrometer, Waters Xbridge BEH C18 3.5 μm, 50×4.6 mm at 40° C. Elution with A: 7.66 mM ammonia in water; B: 7.66 mM ammonia in acetonitrile. Gradient:

| Gradient - Time | flow mL/min | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, UV diode array 190-450 nm. MS ionization method—Electrospray (positive and negative ion).

Method 11

Simadzu LC20-MS2010, Agilent Pursit 5 C18 20×2.0 mm at 50° C. Elution with A: 1.5 mL of TFA in 4 L water; B: 0.75 mL of TFA in acetonitrile. Gradient:

| Gradient - Time | flow mL/min | % A | % B |
|---|---|---|---|
| 0.00 | 1.5 | 95 | 5 |
| 0.70 | 1.5 | 5 | 95 |
| 1.10 | 1.5 | 5 | 95 |
| 1.11 | 1.5 | 95 | 5 |
| 1.50 | 2.0 | 95 | 5 |

Detection—MS, UV 220, 254 nm. MS ionization method—Electrospray (positive ion).

Reverse phase preparative HPLC purification was performed using a Waters Fractionlynx preparative HPLC system (2525 pump, 2996/2998 UV/VIS detector, 2767 liquid handler) or Gilson preparative HPLC system (322 pump, 155 UV/VIS detector, GX-281 liquid handler). The column used for the preparative purification of the compounds was a Waters Sunfire OBD, Phenomenex Luna Phenyl Hexyl, or Waters Xbridge Phenyl at 10 μm 19×150 mm unless otherwise stated. Appropriate focused gradients were selected based on acetonitrile and MeOH solvent systems under either acidic or basic conditions. The standard gradient used was 5% MeCN to 20% over 1 min, hold 2.5 min, to 80% MeCN over 12.5 min, hold 7.5 min followed by 3 min re-equilibration at initial conditions. A flow rate of 20 ml/min is used. Compounds were screened analytically prior to the purification step. Each sample was run under both acidic and basic conditions (2 μl injection, 5/95 gradient for 5 min). A decision was then made as to what pH and which gradient to use depending on where the desired product elutes and the separation achieved. The modifiers used under acidic/basic conditions were formic acid (0.1% V/V) and ammonium bicarbonate (10 mM) respectively or TFA (0.1% V/V) if Method Development was required. The purification was controlled by Waters Fractionlynx software through monitoring at 210 to 400 nm and triggered a threshold collection value at 260 run and the presence of target molecular ion as observed under ESI conditions. Collected fractions were analysed by LCMS (Waters ACQUITY systems with Waters SQD). The fractions that contained the desired product were dried overnight by Genevac lyopholisation. Some of the compounds may have gone through a second purification process in order to achieve the required purity due to complex mixtures. A more focused gradient or isocratic conditions may have been used for the more challenging separations.

Separation of enantiomers by Supercritical Fluid Chromatography (SFC) was performed using either Waters Thar Prep100 preparative SFC system (P200 $CO_2$ pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module). Where the Waters 2767 liquid handler was used it acted as both auto-sampler and fraction collector.

The compounds were purified using an appropriate column from YMC Amylose-C, YMC Cellulose-C, YMC Cellulose-SC, Phenomenex LUX Cellulose-3 or Phenomenex LUX Cellulose-4 at 10×250 mm, 5 μm unless otherwise stated.

Appropriate isocratic methods were selected based on methanol, ethanol or isopropanol solvent systems under un-modified or basic conditions. The standard method used was modifier/$CO_2$, 100 ml/min (or as appropriate), 120 Bar backpressure, 40° C. column temperature where the specific modifier composition was as stated by the method development.

All compounds were screened analytically prior to the purification step. Each sample was run under both unmodified and basic conditions (5.0 μl injection, 5/55 gradient for 5 minutes) across ethanol, methanol and isopropanol. If necessary, secondary screen across extended solvents such as acetonitrile, ethyl acetate and THF may also be reviewed. A decision was then made as to what pH and which isocratic condition to use depending on where the desired product elutes and the separation achieved.

The modifier used under basic conditions was diethylamine (0.1% V/V). Alternate modifiers such as formic acid (0.1% V/V), acetic acid (0.1% V/V), etc may be used as an acidic modifier.

The purification was controlled either by Waters Fractionlynx or Waters Chromscope software through monitoring at 210 to 400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation.

All samples have been pre-purified by achiral systems and purity checked before SFC chiral purification.

Some of the compounds may have gone through a second purification process in order to achieve the required % ee or % de purity.

Reverse phase chromatography was performed on a $C_{18}$ cartridge eluting with a gradient of MeCN/$H_2O$ with a modifier of either 0.1% formic acid or 0.1% $NH_4OH$.

Abbreviations

2-MeTHF=2-methyl tetrahydrofuran;
4A MS=molecular sieves, 4A;
DAST=N,N-diethylaminosulfur trifluorid;
DCM=dichloromethane;
DE=diethyl ether;
DEA=diethylamine;
DIPEA=diisopropyl ethylamine;
DMF=N,N-dimethylformamide;
DMP=Dess-Martin periodinane;
DMSO=dimethyl sulfoxide;
dppf=1,1'-Ferrocenebis(diphenylphosphine);
EA=ethyl acetate;
EDCI=1-Ethyl-3-(3-dimethylaminopropyl)carbodiimide;
HATU=1-[Bis(dimethylamino)methylene]-1H-1,2,3-triazolo[4,5-b]pyridinium 3-oxide hexafluorophosphate;
MTBE=methyl tert-butyl ether;
NBS=N-bromosuccinimide;
NCS=N-chlorosuccinimide;
PE=petroleum ether;
TBHP=tert-butyl hydroperoxide;
TEA=triethylamine;
TFA=trifluoroacetic acid;
THF=tetrahydrofuran;
TLC=thin layer chromatography and
X-Phos=2-Dicyclohexylphosphino-2',4',6'-triisopropylbiphenyl.

Suzuki-Miyaura General Procedure 1

A mixture of the aryl chloride or bromide (1.0 eq), the boronic acid or ester (1.3 eq.), potassium carbonate (2.0 eq), XPhos (0.1 eq) and XPhosPdG2 (0.1 eq) in dioxan/water (10:1, 100 mM) was degassed and stirred at 80° C. for 16 h. Further boronic acid, XPhos and XPhosPdG2 were added if required for completion of the reaction. Water and DCM were added and the phases separated. The aqueous phase was extracted with DCM (×2) and the combined organic phase was washed with a saturated aqueous $NaHCO_3$ solution and brine, dried ($MgSO_4$) and concentrated in vacuo. The residue was dissolved in DCM, preadsorbed onto ISOLUTE® HM-N column (Biotage) and purified by silica gel chromatography eluting with (2N $NH_3$/MeOH) in DCM.

Suzuki-Miyaura General Procedure 2

A mixture of the aryl chloride or bromide (1.0 eq), the boronic acid or ester (1.3 eq.), cesium carbonate (2.5 eq), $Pd(PPh_3)_4$ (0.1 eq) in dioxan/water (10:1, 100 mM) was degassed and stirred at 80° C. for 16 h. Further boronic acid, and $Pd(PPh_3)_4$ were added if required for completion of the reaction. Water and DCM were added and the phases separated. The aqueous phase was extracted with DCM (×2) and the combined organic phase was washed with a saturated aqueous $NaHCO_3$ solution and brine, dried ($MgSO_4$) and concentrated in vacuo. The residue was dissolved in DCM, preadsorbed onto ISOLUTE® HM-N column (Biotage) and purified by silica gel chromatography eluting with a gradient of 2N $NH_3$/MeOH in DCM.

THP Deprotection Procedure 1

A suspension of the THP protected compound in MeOH (100 mM) was treated with 1N HCl (aq) (5 eq.) and the reaction mixture was stirred at rt until judged complete by LC-MS (3-24 h). The reaction was diluted with water and freeze dried. The resulting off white solid purified by reverse phase chromatography to afford the title compound.

Trityl Deprotection Procedure 1

A suspension of the trityl protected compound in MeOH (200 mM) was treated with 1N HCl (aq) (5 eq.) and the reaction mixture was stirred at rt for 21 h. The solid was filtered off, washed with MeOH and dried at the pump. Further purification was by reverse phase chromatography to afford the title compound.

Trityl Deprotection Procedure 2

A solution of the trityl protected compound in TFA/DCM (1:1, final concentration 100 mM) was stirred at rt. After completion of the reaction by LCMS the reaction mixture was diluted with toluene and the volatiles evaporated in vacuo. The residue was azeotroped with toluene (×2) then purified by reverse phase chromatography to afford the title compound.

SnAr and Deprotection General Procedure 1

A mixture of 2-chloro-3-isopropyl-7-(1-trityl-1H-imidazol-4-yl)imidazo[2,1-f][1,2,4]triazin-4(3H)-one (1.0 eq), and the amine hydrochloride salt (1.2 eq) in IPA (190 mM concentration) was treated with triethylamine (1.5 eq) and heated at 120° C. for 1 h under microwave irradiation. 1N HCl (aq) (6.5 eq) was added and the reaction mixture was stirred at rt for 16 h. The solid was filtered off, washed with IPA and water and dried at the pump before being dissolved up in MeCN/$H_2O$/formic acid and purified by reverse phase chromatography (C18 cartridge) eluting with 10-98% MeCN/$H_2O$+0.1% formic acid.

SnAr and Deprotection General Procedure 2

A mixture of 2-chloro-3-isopropyl-7-(1-trityl-1H-imidazol-4-yl)imidazo[2,1-f][1,2,4]triazin-4(3H)-one (1.0 eq), and the amine hydrochloride salt (1.2 eq) in IPA (190 mM concentration) was treated with triethylamine (1.5 eq) and heated at 120° C. for 1 h under microwave irradiation. TFA (6.5 eq) and a drop of water were added and the reaction mixture was stirred at rt for 16 h. The solid was filtered off, washed with IPA and water and dried at the pump before being dissolved up in DMSO/formic acid and purified by reverse phase chromatography (C18 cartridge) eluting with 10-98% MeCN/$H_2O$+0.1% formic acid.

SnAr General Procedure 3

A mixture of 2-chloro-3-isopropyl-7-(1-trityl-1H-imidazol-4-yl)imidazo[2,1-f][1,2,4]triazin-4(3H)-one (1.0 eq), and the amine or the amine hydrochloride salt (1.0 eq) in dioxane (0.2 mM) was treated with triethylamine (5 eq) and heated at 100° C. Further amine or the amine hydrochloride salt was added if required for completion of the reaction. The reaction was cooled down to rt and the white precipitate was filtered off. The volatiles were concentrated in vacuo. The residue was dissolved in DCM and purified by silica gel chromatography eluting with a gradient of MeOH in DCM.

Bromination General Procedure 1

To a solution of aryl (1.0 eq) in dry DMF (0.1 M), N-bromosuccinimide (1.0 eq) was added in one portion. The resulting solution was stirred at room temperature for 2 h. Additional N-bromosuccinimide was added if required for completion of the reaction (judged by LC-MS analysis). The reaction was partitioned between DCM and saturated aqueous $NaHCO_3$ solution. The organic phase was washed with saturated aqueous $NaHCO_3$ solution (×2), water, dried ($MgSO_4$), and concentrated in vacuo. The residue was dissolved in DCM and purified by silica gel chromatography, when necessary, eluting with a gradient of EtOAc in DCM.

General Procedure for Nitrile Hydrolysis

A suspension of the nitrile (1 eq.) and Parkin's catalyst (5 mol %) in EtOH/$H_2O$ (9:1, 0.34 M) was heated at 80° C. until judged complete by LC-MS. The reaction mixture was diluted with DCM, preadsorbed onto ISOLUTE® HM-N column (Biotage) and purified by silica gel chromatography eluting with a gradient of MeOH in DCM.

EXAMPLES

Example 1

2-(Furan-2-yl)-7-(1H-imidazol-5-yl)-3-isopropylimidazo[2,1-f][1,2,4]triazin-4(3H)-one Formate Salt (0.6 eq)

Ethyl 1-amino-1H-imidazole-2-carboxylate

A solution of ethyl imidazole-2-carboxylate (65.0 g, 0.463 mol) in DMF (2 L) was cooled in an ice/water bath and treated dropwise with lithium bis(trimethylsilyl)amide (1 M in THF, 510 mL, 0.510 mol) keeping the internal temperature to 10-15° C. O-(diphenylphosphinyl)hydroxylamine (119 g, 0.510 mol) was added to the resulting solution portionwise. The resulting mixture was stirred mechanically for 16 h. The reaction was quenched with water and evaporated in vacuo. The residue was triturated with EtOAc (×4), filtered and the solid washed with EtOAc. The combined filtrates were evaporated to give a brown solid, which was dissolved in DCM and passed through a pad of silica gel, eluted with DCM, followed by 5% MeOH in DCM. The relevant fractions were collected and concentrated in vacuo to give a pale yellow semi solid. The solid was triturated with Et2O and filtered to afford the title compound as a white solid (61.2 g, 84%).

$^1H$ NMR (400 MHz, $CDCl_3$) δ, ppm, 7.19 (1H, d, J=1.0 Hz), 7.07 (1H, d, J=1.0 Hz), 5.81 (2H, s), 4.43 (2H, q, J=7.1 Hz), 1.43 (3H, t, J=7.1 Hz).

1-Amino-N-isopropyl-1H-imidazole-2-carboxamide

Ethyl 1-amino-1H-imidazole-2-carboxylate (20 g, 0.13 mol) was dissolved in isopropylamine (120 mL, 13 mol) and heated at reflux for 48 h. After completion of the reaction, the reaction was concentrated in vacuo to give a yellow oil which crystallised on standing (21.7 g, quant.)

$^1H$ NMR (400 MHz, $CDCl_3$) δ, ppm, 7.09 (1H, d, J=1.1 Hz), 6.92 (1H, d, J=1.1 Hz), 6.12 (2H, s), 4.24-4.15 (1H, m), 1.26 (6H, d, J=6.6 Hz).

3-Isopropylimidazo[2,1-f][1,2,4]triazine-2,4 (1H, 3H)-dione, hydrogen chloride Phenyl chloroformate (17.8 mL, 0.14 mol) was added to a solution of 1-amino-N-isopropyl-1H-imidazole-2-carboxamide (22.0 g, 0.13 mol) in acetonitrile (500 mL) and heated at reflux for 54 h. The product precipitated as a white solid, which was filtered off then washed with acetonitrile. The filtrate was concentrated (to ~40 mL) in vacuo and the residue was transferred into two 25 mL microwave reactor vials, which were each heated at 180° C. for 45 min in a microwave reactor. The resulting brown suspension was diluted with MeCN (100 mL) and refluxed for 16 h. The resulting white suspension was filtered and washed with acetonitrile to afford the title compound as a white solid. A total of 25.8 g (quantitative yield) was isolated from the two filtrations.

$^1$H NMR (400 MHz, DMSO) δ, ppm, 7.78 (1H, d, J=1.4 Hz), 7.73 (1H, d, J=1.4 Hz), 5.12-4.99 (1H, m), 1.43 (6H, d, J=7.1 Hz).

3-Isopropylimidazo[2,1-f][1,2,4]triazine-2,4(1H, 3H)-dione, triethylamine Salt

3-Isopropylimidazo[2,1-f][1,2,4]triazine-2,4 (1H,3H)-dione, hydrogen chloride (16.7 g, 72.6 mmol) was suspended in MeOH (380 mL). Triethylamine (20.2 mL, 140 mmol) was added and the reaction mixture was stirred at room temperature until complete dissolution of the solid (30-45 min). The reaction was concentrated in vacuo and the residue was partitioned between DCM and water. The aqueous layer was extracted with DCM (×4). The combined organic layers were dried ($MgSO_4$), and concentrated in vacuo to afford the title compound as an orange paste, (21.4 g, quant.)

$^1$H NMR (400 MHz, $CDCl_3$) δ, ppm 7.28 (1H, d, J=0.9 Hz), 7.21 (1H, d, J=0.9 Hz), 5.37-5.26 (1H, m), 3.16 (6H, q, J=7.3 Hz), 1.52 (6H, d, J=7.4 Hz), 1.34 (9H, t, J=7.3 Hz).

7-Iodo-3-isopropylimidazo[2,1-f][1,2,4]triazine-2,4 (1H,3H)-dione, triethylamine Salt To a solution of 3-Isopropylimidazo[2,1-f][1,2,4]triazine-2,4 (1H,3H)-dione, triethylamine salt (21.4 g, 72.6 mmol) in MeOH (380 mL), N-iodosuccinimide (16.3 g, 72.6 mmol) was added in one portion. The resulting orange solution was stirred at room temperature for 3 h. Additional N-iodosuccinimide (1.80 g, 7.98 mmol) was added in one portion, after stirring for 1 h at room temperature the reaction was judged complete by LC-MS analysis. The reaction was concentrated in vacuo and partitioned between DCM and saturated aqueous $NaHCO_3$ solution. The organic phase was washed with saturated aqueous $NaHCO_3$ solution (×3), water, dried ($MgSO_4$), and concentrated in vacuo to afford a pale brown oil, which crystalized on standing (20.9 g, 68%).

$^1$H NMR (400 MHz, $CDCl_3$) S, ppm 13.50 (1H, s), 7.33 (1H, s), 5.34-5.24 (1H, m), 3.26 (6H, q, J=7.2 Hz), 1.50 (6H, d, J=7.0 Hz), 1.37 (9H, t, J=7.3 Hz).

2-Chloro-7-iodo-3-isopropylimidazo[2,1-f][1,2,4] triazin-4(3H)-one

A suspension of 7-Iodo-3-isopropylimidazo[2,1-f][1,2,4] triazine-2,4 (1H,3H)-dione, triethylamine salt (9.45 g, 22.4 mmol) in phosphorous oxychloride (20.9 mL) was stirred at 80° C. for 43 h. The reaction was diluted with toluene, concentrated in vacuo then azeotroped with toluene (×2). The residue was partitioned between DCM and saturated aqueous $NaHCO_3$ solution. The phases were separated and the aqueous phase was extracted with DCM (×2). The combined organic phases were washed with water, brine, dried ($MgSO_4$) and concentrated in vacuo to afford a brown solid. The crude product was purified by silica gel chromatography eluting with 0-40% EtOAc in cyclohexane to give the title compound as an off white solid (5.3 g, 70%).

LCMS Method 2: r.t. 1.30 mins, [MH+] 339, 341.

4-(tributylstannyl)-1-trityl-1H-imidazole

Ethyl magnesium bromide (3M in diethyl ether, 4.58 mL, 13.8 mmol) was added dropwise to a solution of 4-iodo-1-trityl-1H-imidazole (5.00 g, 11.5 mmol) in DCM (100 mL) under an Ar atmosphere. The reaction was stirred for 1 h before tributyltin chloride (3.73 mL, 13.8 mmol) was added to the reaction. The resulting white suspension was stirred overnight. The reaction was concentrated under reduced pressure. The concentrate was dry loaded with ISOLUTE® HM-N column (Biotage) onto a 200 g $SiO_2$ cartridge eluting with 0-20% EtOAc in cyclohexane. Concentration of the target containing fractions afforded a clear oil which solidified under high-vac to afford a white solid (4.038 g, 59% yield)

$^1$H NMR (400 MHz, $CDCl_3$) δ, ppm 7.63 (1H, s), 7.32-7.30 (9H, m), 7.15-7.12 (6H, m), 6.76 (1H, d, J=1.1 Hz), 1.54-1.46 (6H, m), 1.39-1.23 (12H, m), 1.03-0.98 (6H, m), 0.84 (9H, t, J=7.3 Hz).

2-Chloro-3-isopropyl-7-(1-trityl-1H-imidazol-4-yl) imidazo[2,1-f][1,2,4]triazin-4(3H)-one A solution of 2-chloro-7-iodo-3-isopropylimidazo[2,1-f] [1,2,4]triazin-4(3H)-one (2.80 g, 8.27 mmol), 4-(tributylstannyl)-1-trityl-1H-imidazole (5.98 g, 9.93 mmol) and CuI (79 mg, 0.41 mmol) in 1,4-dioxane (28 mL) was bubbled with Ar for 15 min before $Pd(PPh_3)_4$ (960 mg, 0.827 mmol) was added. The resulting suspension was heated at 100° C. for 18 h. The reaction mixture was concentrated in vacuo and loaded with DCM onto a 220 g $SiO_2$ cartridge and eluted with 0-100% EtOAc in cyclohexane. Concentration of the product containing fractions afforded the title compound as a yellow solid (3.73 g, 72%).

$^1$H NMR (400 MHz, $CDCl_3$) 5, ppm 7.94 (1H, s), 7.66 (1H, d, J=1.4 Hz), 7.51 (1H, d, J=1.4 Hz), 7.39-7.36 (9H, m), 7.21-7.18 (6H, m), 5.21 (1H, s), 1.63 (6H, d, J=7.0 Hz).

2-(Furan-2-yl)-3-isopropyl-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 2-furylboronic acid using Suzuki-Miyaura General Procedure 1 to afford the title compound as a white foam, 44 mg (55%).

LCMS Method 4: r.t. 1.76 mins, [$MH^+$] 553

2-(Furan-2-yl)-7-(1H-imidazol-5-yl)-3-isopropylimidazo[2,1-f][1,2,4]triazin-4(3H)-one, 0.6 eq Formate Salt Prepared from 2-(Furan-2-yl)-3-isopropyl-7-(1-trityl-1H-imidazol-4-yl)imidazo[2,1-f][1,2,4]triazin-4(3H)-one using Trityl Deprotection Procedure 1 and purification by reverse phase preparative HPLC to afford the title compound as a white solid after lyophilisation, 4.5 mg (19%).

$^1$H NMR (400 MHz, $d_6$-DMSO) δ, ppm 12.39 (1H, s), 8.23 (0.6H, s), 8.06 (1H, dd, J=0.8, 1.8 Hz), 7.82 (1H, d, J=1.1 Hz), 7.75 (1H, s), 7.70 (1H, d, J=1.0 Hz), 7.22 (1H, dd, J=0.8, 3.4 Hz), 6.79 (1H, dd, J=1.8, 3.4 Hz), 4.25 (1H, hept, J=6.8 Hz), 1.57 (6H, d, J=6.8 Hz). LCMS Method 1: r.t. 2.53 mins, [$MH^+$] 311.1

Example 2

7-(1H-imidazol-5-yl)-3-isopropyl-2-phenylimidazo [2,1-f][1,2,4]triazin-4(3H)-one, 0.6 eq Formate Salt 3-Isopropyl-2-phenyl-7-(1-trityl-1H-imidazol-4-yl) imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and phenyl boronic acid by Suzuki-Miyaura General Procedure 1 to give the title compound as a pale yellow glass, 25 mg (31%).

LCMS Method 4: r.t. 1.81 mins, $[MH^+]$ 563

7-(1H-imidazol-5-yl)-3-isopropyl-2-phenylimidazo[2,1-f][1,2,4]triazin-4(3H)-one, 0.6 eq Formate Salt Prepared from 3-Isopropyl-2-phenyl-7-(1-trityl-1H-imidazol-4-yl)imidazo[2,1-f][1,2,4]triazin-4(3H)-one by Trityl Deprotection Procedure 1 to give the title compound as a white solid, 4.1 mg (32%).

$^1$H NMR (400 MHz, $d_6$-DMSO) δ, ppm 12.30 (1H, s), 8.35 (0.6H, s), 7.78 (1H, d, J=1.1 Hz), 7.75-7.71 (3H, m), 7.64-7.59 (3H, m), 7.53 (1H, d, J=0.9 Hz), 4.07 (1H, hept, J=6.8 Hz), 1.50 (6H, d, J=6.8 Hz).

LCMS Method 1: r.t. 2.80 mins, $[MH^+]$ 321.1

Example 3

7-(1H-imidazol-5-yl)-3-isopropyl-2-(5-methylfuran-2-yl)imidazo[2,1-f][1,2,4]triazin-4(3H)-one 3-Isopropyl-2-(5-methylfuran-2-yl)-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 5-methy-2-furanboronic acid by Suzuki-Miyaura General Procedure 1 to give the title compound as an off-white foam, 66 mg (61%).

LCMS Method 4: r.t. 1.82 mins, $[MH^+]$ 567

7-(1H-imidazol-5-yl)-3-isopropyl-2-(5-methylfuran-2-yl)imidazo[2,1-f][1,2,4]triazin-4(3H)-one Prepared from 3-Isopropyl-2-(5-methylfuran-2-yl)-7-(1-trityl-1H-imidazol-4-yl)imidazo[2,1-f][1,2,4]triazin-4(3H)-one by Trityl Deprotection Procedure 1 except that TFA (11 eq.) was also added to the reaction mixture. Purification was by reverse phase chromatography (C18 cartridge) eluting with 10-98% $MeCN/H_2O$+0.1% formic acid to give the title compound as a white solid, 17 mg (45%).

$^1$H NMR (400 MHz, $d_6$-DMSO) δ, ppm 8.60 (1H, s), 7.94 (1H, s), 7.91 (1H, d, J=1.1 Hz), 7.16 (1H, d, J=3.3 Hz), 6.42 (1H, dd, J=1.0, 3.3 Hz), 4.36 (1H, hept, J=6.7 Hz), 2.42 (3H, s), 1.58 (6H, d, J=6.7 Hz).

LCMS Method 1: r.t. 2.83 mins, $[MH^+]$ 325.1

Example 4

7-(1H-imidazol-5-yl)-3-isopropyl-2-(3-methylazetidin-1-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 3-methylazetidine hydrochloride by SnAr and Deprotection General Procedure 2 starting with a 100 mg 2-chloro-3-isopropyl-7-(1-trityl-1H-imidazol-4-yl)imidazo[2,1-f][1,2,4]triazin-4(3H)-one except that the reaction mixture was heated at 120° C. for 30 mins under microwave irradiation then treated with another portion of the amine (0.5 eq) and triethylamine (0.8 eq) and heated for another 30 mins at 120° C. under microwave irradiation. DCM (0.5 mL) was added 6 h after the addition of TFA and the mixture stirred at rt for a further 40 h. The title compound was isolated as a white solid, 45 mg (75%).

$^1$H NMR (400 MHz, $d_6$-DMSO) δ, ppm 12.56 (1H, s), 7.87 (1H, s), 7.74 (1H, s), 7.62 (1H, s), 4.44-4.34 (1H, hept, J=6.7 Hz), 4.25 (2H, t, J=7.9 Hz), 3.79 (2H, t, J=7.0 Hz), 2.82-2.73 (1H, m), 1.53 (6H, d, J=6.7 Hz), 1.24 (3H, d, J=6.7 Hz).

LCMS Method 1: r.t. 2.65 mins, $[MH^+]$ 314.1

Example 5

7-(1H-imidazol-5-yl)-3-isopropyl-2-(2-(tetrahydrofuran-2-yl)ethoxy)imidazo[2,1-f][1,2,4]triazin-4(3H)-one 3-isopropyl-2-(2-(tetrahydrofuran-2-yl)ethoxy)-7-(1-trityl-1H-imidazol-4-yl)imidazo[2,1-f][1,2,4]triazin-4(3H)-one A solution of 2-(Tetrahydrofuran-2-yl)ethan-1-ol (111 mg, 0.96 mmol) in dry DMF (2.0 mL) under nitrogen was treated with sodium hydride (60% dispersion in oil, 38 mg, 0.96 mmol) and stirred at rt. After 10 mins a portion (0.9 mL) of the mixture was added to a solution of 2-chloro-3-isopropyl-7-(1-trityl-1H-imidazol-4-yl)imidazo[2,1-f][1,2,4]triazin-4(3H)-one (200 mg, 0.38 mmol) in dry DMF (2.0 mL) under argon and the reaction mixture was stirred at rt for 30 mins. Another portion (0.5 mL) of the solution of the alkoxide was added and the reaction mixture stirred for a further 30 mins then diluted with EtOAc and saturated aqueous ammonium chloride solution. The phases were separated and the aqueous phase was extracted with EtOAc (×2). The combined organic phase was washed with water, saturated aqueous sodium bicarbonate solution and brine, dried ($MgSO_4$) and concentrated in vacuo to a yellow gum. The gum was dissolved in DCM, preadsorbed onto ISOLUTE® HM-N column (Biotage) and purified by silica gel chromatography (40 g cartridge) eluting with 0-4% (2N $NH_3$/MeOH) in DCM to afford the title compound as a white foam (116 mg, 50%). LCMS Method 5: r.t. 2.02 mins, $[MH^+]$ 601.

7-(1H-imidazol-5-yl)-3-isopropyl-2-(2-(tetrahydrofuran-2-yl)ethoxy)imidazo[2,1-f][1,2,4]triazin-4(3H)-one Prepared from 3-isopropyl-2-(2-(tetrahydrofuran-2-yl)ethoxy)-7-(1-trityl-1H-imidazol-4-yl)imidazo[2,1-f][1,2,4]triazin-4(3H)-one using Trityl Deprotection Procedure 2 to afford the title compound as a white solid (43 mg, 63%).

$^1$H NMR (400 MHz, $d_6$-DMSO) δ, ppm 12.39 (1H, s), 7.82 (1H, d, J=0.9 Hz), 7.77 (1H, s), 7.66 (1H, s), 5.24 (1H, hept, J=6.9 Hz), 4.62-4.53 (2H, m), 4.02-3.94 (1H, m), 3.84-3.77 (1H, m), 3.67-3.61 (1H, m), 2.12-1.96 (3H, m), 1.93-1.78 (2H, m), 1.58-1.49 (1H, m), 1.45 (6H, d, J=6.9 Hz).

LCMS Method 1: r.t. 2.77 mins, $[MH^+]$ 359.1

The enantiomers of EXAMPLE 5 were separated by chiral SFC using a YMC Amylose-C column eluting with 20% EtOH (+0.1% diethylamine): 80% $CO_2$, 15 mL/min, 120 bar, 40° C., DAD 230 nm to afford EXAMPLE 6 and EXAMPLE 7.

Example 6

Enantiomer A: 17 mg of a white solid

Analytical SFC using YMC Amylose-C (4.6×250 mm, 5 micron) eluting with 20% EtOH (+0.1% diethylamine): 80% $CO_2$, 5.0 mL/min, 120 bar, 40° C., DAD 230 nm retention time 2.1 min Example 7

Enantiomer B: 16 mg of a white solid

Analytical SFC using YMC Amylose-C (4.6×250 mm, 5 micron) eluting with 20% EtOH (+0.1% diethylamine): 80% $CO_2$, 5.0 mL/min, 120 bar, 40° C., DAD 230 nm retention time 3.2 min Example 8

7-(1H-imidazol-5-yl)-3-isopropyl-2-(3-phenylazetidin-1-yl)imidazo[2,1-f][1,2,4]triazin-4(3H)-one Prepared by SnAr and Deprotection General Procedure 2 starting with a 100 mg of 2-chloro-3-isopropyl-7-(1-trityl-1H-imidazol-4-yl)imidazo[2,1-f][1,2,4]triazin-4(3H)-one and 3-phenylazetidine hydrochloride except that 2.5 eq triethylamine were used the reaction mixture was heated at 120° C. for 30 mins under microwave irradiation. A second portion (5.0 eq) of TFA was added 24 h after the first portion and the mixture stirred at rt for 7.5 h then at 50° C. for 16 h. The title compound was isolated as a white solid (27 mg, 38%).

$^1$H NMR (400 MHz, $d_6$-DMSO) δ, ppm 12.27 (1H, s), 7.79 (11-1, s), 7.74 (1H, s), 7.62 (1H, s), 7.46 (2H, d, J=7.6 Hz), 7.38 (2H, t, J=7.5 Hz), 7.28 (1H, t, J=7.3 Hz), 4.54 (2H, t, J=8.2 Hz), 4.48 (1H, hept, J=6.5 Hz), 4.26 (2H, t, J=7.5 Hz), 4.00 (11-1, quin, J=7.8 Hz), 1.56 (6H, d, J=6.7 Hz).

LCMS Method 1: r.t. 3.30 mins, [$MH^+$] 376.1

Example 9

7-(1H-imidazol-5-yl)-3-isopropyl-2-(methyl(2-(tetrahydrofuran-2-yl)ethyl)amino)imidazo[2,1-f][1,2,4]triazin-4(3H)-one Prepared by SnAr and Deprotection General Procedure 2 starting with a 200 mg of 2-chloro-3-isopropyl-7-(1-trityl-1H-imidazol-4-yl)imidazo[2,1-f][1,2,4]triazin-4(3H)-one and N-methyl-2-tetrahydrofuran-2-yl-ethanamine hydrochloride except that the reaction mixture was heated at 120° C. for 90 mins under microwave irradiation then at 80° C. for 72 h under conventional heating. A further portion (0.8 eq) of the amine hydrochloride salt and triethylamine (1.5 eq) were added and the reaction mixture was heated at 120° C. for 60 mins under microwave irradiation. The reaction mixture was treated with 8.2 eq TFA. The title compound was isolated as a white solid (57 mg, 40%).

$^1$H NMR (400 MHz, $d_6$-DMSO) δ, ppm 8.02 (1H, s), 7.77 (1H, d, J=1.0 Hz), 7.68 (1H, s), 4.70 (1H, hept, J=6.8 Hz), 3.82-3.71 (2H, m), 3.61-3.55 (1H, m), 3.21-3.12 (1H, m), 2.84 (3H, s), 1.99-1.90 (1H, m), 1.88-1.71 (4H, m), 1.57 (6H, d, J=6.8 Hz), 1.48-1.38 (1H, m) plus 1 proton obscured by water peak.

LCMS Method 1: r.t. 2.81 mins, [$MH^+$] 372.2

The enantiomers of EXAMPLE 9 were separated by chiral SFC using a YMC Cellulose-C column eluting with 40% MeCN (+0.1% diethylamine): 60% $CO_2$, 15 mL/min, 120 bar, 40° C., DAD 230 nm to afford EXAMPLE 10 and EXAMPLE 11.

Example 10

Enantiomer A: 8 mg of a fawn solid

Analytical SFC using YMC Cellulose-C (4.6×250 mm, 5 micron) eluting with 40% MeCN (+0.1% diethylamine): 60% $CO_2$, 5.0 mL/min, 120 bar, 40° C., DAD 230 nm retention time 4.1 min Example 11

Enantiomer B: 8 mg of a fawn solid

Analytical SFC using YMC Cellulose-C (4.6×250 mm, 5 micron) eluting with 40% MeCN (+0.1% diethylamine) 60% $CO_2$, 5.0 mL/min, 120 bar, 40° C., DAD 230 nm retention time 4.8 min Example 12

7-(1H-imidazol-5-yl)-3-isopropyl-2-(1-methyl-1H-imidazol-4-yl)imidazo[2,1-f][1,2,4]triazin-4(3H)-one 3-isopropyl-2-(1-methyl-1H-imidazol-4-yl)-7-(1-trityl-1H-imidazol-4-yl)imidazo[2,1-f][1,2,4]triazin-4(3H)-one A mixture of 2-chloro-3-isopropyl-7-(1-trityl-1H-imidazol-4-yl)imidazo[2,1-f][1,2,4]triazin-4(3H)-one (100 mg, 0.19 mmol), N-Methyl-4-(tributylstannyl)imidazole (85 mg, 76 μL, 0.23 mmol) and copper (I) iodide (1.8 mg, 0.010 mmol) in dry dioxane (2.0 mL) was degassed then treated with tetrakis(triphenylphosphine)palladium (0) (22 mg, 0.019 mmol) and stirred at 100° C. for 16 h. A further portion of N-Methyl-4-(tributylstannyl)imidazole (30 μL, 0.090 mmol) and tetrakis(triphenylphosphine)palladium (0) (19 mg, 0.016 mmol) was added and the reaction mixture stirred at 100° C. for 3 h. The reaction mixture was diluted with DCM and water and the phases were separated. The aqueous phase was extracted with DCM (×2) and the combined organic phase was washed with saturated aqueous sodium bicarbonate solution and brine, dried ($MgSO_4$) and concentrated in vacuo to a yellow oil. The oil was purified by silica gel chromatography (40 g cartridge) eluting with 0-4% (2N $NH_3$/MeOH) in DCM to afford the title compound as a milky gum (35 mg, 32%).

LCMS Method 5: r.t. 1.63 mins, [$MH^+$] 567.

7-(1H-imidazol-5-yl)-3-isopropyl-2-(1-methyl-1H-imidazol-4-yl)imidazo[2,1-f][1,2,4]triazin-4(3H)-one Prepared from 3-isopropyl-2-(1-methyl-1H-imidazol-4-yl)-7-(1-trityl-1H-imidazol-4-yl)imidazo[2,1-f][1,2,4]triazin-4(3H)-one by Trityl Deprotection Procedure 2 to afford the title compound as a white solid (9 mg, 47%).

$^1$H NMR (400 MHz, $d_6$-DMSO) δ, ppm 12.35 (1H, s), 7.92 (1H, d, J=1.1 Hz), 7.88 (1H, d, J=1.2 Hz), 7.81 (1H, d, J=0.9 Hz), 7.76 (1H, s), 7.72 (1H, s), 4.98 (1H, hept, J=6.7 Hz), 3.79 (3H, s), 1.56 (6H, d, J=6.8 Hz).

LCMS Method 1: r.t. 1.99 mins, [$MH^+$] 325.1

Example 13

(S)-7-(1H-imidazol-5-yl)-3-isopropyl-2-(3-phenylpyrrolidin-1-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and (3S)-3-phenylpyrrolidine hydrochlodide by SnAr and Deprotection General Procedure 1 to afford the title compound as a white solid (34 mg, 45%).

$^1$H NMR (400 MHz, $d_6$-DMSO) δ, ppm 12.31 (1H, s), 7.79 (1H, s), 7.69 (1H, s), 7.62 (1H, s), 7.42-7.34 (4H, m), 7.27 (1H, tt, J=1.9, 6.8 Hz), 4.63 (1H, hept, J=6.6 Hz), 3.85-3.73 (2H, m), 3.62-3.46 (3H, m), 2.40-2.32 (1H, m), 2.15-2.05 (1H, m), 1.66 (3H, d, J=6.7 Hz), 1.50 (3H, d, J=6.6 Hz).

LCMS Method 3: r.t. 3.38 mins, [$MH^+$] 390.3

Example 14

(R)-7-(1H-imidazol-5-yl)-3-isopropyl-2-(3-phenylpyrrolidin-1-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and (3R)-3-phenylpyrrolidine hydrochlodide by SnAr and Deprotection General Procedure 2 except that the reaction mixture was heated at 100° C. for 1 h under microwave irradiation. The title compound was isolated as a white solid (28 mg, 25%).

$^1$H NMR (400 MHz, $d_6$-DMSO) δ, ppm 12.70 (1H, s), 7.90 (1H, s), 7.71 (1H, d, J=0.8 Hz), 7.64 (1H, s), 7.42-7.34 (4H, m), 7.27 (1H, tt, J=1.9, 6.9 Hz), 4.63 (1H, hept, J=6.7 Hz), 3.85-3.73 (2H, m), 3.62-3.46 (3H, m), 2.40-2.32 (1H, m), 2.15-2.05 (1H, m), 1.66 (3H, d, J=6.7 Hz), 1.50 (3H, d, J=6.6 Hz).

LCMS Method 1: r.t. 3.40 mins, [$MH^+$] 390.1

Example 15

(R)-7-(1H-imidazol-5-yl)-3-isopropyl-24 (2-(tetrahydrofuran-2-yl)ethyl)amino)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 2-[(2R)-tetrahydrofuran-2-yl]ethanamine hydrochlodide by SnAr and Deprotection General Procedure 1 except that the reaction mixture was heated for 30 mins under microwave irradiation. At the end of the reaction little solid was isolated by filtration so the filtrate was diluted with (2N $NH_3$/MeOH) in DCM and a saturated aqueous $NaHCO_3$ solution and the phases were separated. The aqueous phase was extracted with DCM (×2) and the combined organic phase was washed with a saturated aqueous $NaHCO_3$ solution and brine, dried ($MgSO_4$) and concentrated in vacuo. The residue was dissolved in MeOH/DCM, preadsorbed onto ISOLUTE® HM-N column (Biotage) and purified by silica gel chromatography eluting with a gradient of 0-10% 2N $NH_3$/MeOH in DCM to afford the title compound (21 mg, 30%) as a white solid.

$^1$H NMR (400 MHz, $d_6$-DMSO) δ, ppm 12.32 (1H, s), 7.80-7.77 (2H, m), 7.55 (1H, s), 6.80 (1H, t, J=5.0 Hz), 4.76-4.68 (1H, m), 3.92-3.85 (1H, m), 3.85-3.79 (1H, m), 3.69-3.62 (1H, m), 3.52-3.34 (2H, m), 2.05-1.96 (1H, m), 1.91-1.78 (4H, m), 1.52 (6H, d, J=6.8 Hz), 1.49-1.43 (1H, m).

LCMS Method 3: r.t. 2.57 mins, [$MH^+$] 358.4

Example 16

7-(1H-imidazol-5-yl)-3-isopropyl-2-(3-(methoxymethyl)azetidin-1-yl)imidazo[2,1-f][1,2,4]triazin-4(3H)-one 0.6 eq Formate Salt Prepared from 2-chloro-3-isopropyl-7-(1-trityl-1H-imidazol-4-yl)imidazo[2,1-f][1,2,4]triazin-4(3H)-one and 3-methoxymethyl azetidine hydrochlodide by SnAr and Deprotection General Procedure 1 except that the reaction mixture was heated for 30 mins under microwave irradiation. At the end of the reaction the mixture was freeze-dried and the residue dissolved in 2N $NH_3$/MeOH in DCM, preadsorbed onto ISOLUTE® HM-N column (Biotage) and purified by silica gel chromatography eluting with a gradient of 0-10% 2N $NH_3$/MeOH in DCM. Further purification was by reverse phase chromatography ($C_{18}$ cartridge) eluting with 10-98% MeCN/$H_2O$+0.1% formic acid to afford the title compound (34 mg, 52%) as a white solid.

$^1$H NMR (400 MHz, $d_6$-DMSO) δ, ppm 12.31 (1H, s), 8.18 (0.6H, s), 7.80 (1H, d, J=0.9 Hz), 7.72 (1H, s), 7.61 (1H, s), 4.37 (1H, hept, J=6.7 Hz), 4.22 (2H, t, J=8.1 Hz), 3.93 (2H, dd, J=6.2, 7.8 Hz), 3.55 (2H, d, J=6.7 Hz), 3.29 (3H, s), 2.97-2.86 (1H, m), 1.53 (6H, d, J=6.7 Hz).

LCMS Method 1: r.t. 2.58 mins, [$MH^+$] 344.2

Example 17

7-(1H-imidazol-5-yl)-3-isopropyl-2-(3-(2,2,2-trifluoroethyl)azetidin-1-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 3-(2,2,2-trifluoroethyl)azetidine hydrochlodide by SnAr and Deprotection General Procedure 1 except that 1.1 eq of the amine hydrochloride salt was used and the reaction mixture was heated for 30 mins under microwave irradiation. At the end of the reaction the mixture the solid was filtered off, dissolved in 2N $NH_3$/MeOH in DCM, preadsorbed onto ISOLUTE® HM-N column (Biotage) and purified by silica gel chromatography eluting with a gradient of 0-10% 2N $NH_3$/MeOH in DCM to afford the title compound (21 mg, 22%) as a white solid.

$^1$H NMR (400 MHz, $d_6$-DMSO) δ, ppm 12.33 (1H, s), 7.80 (1H, d, J=0.8 Hz), 7.72 (1H, s), 7.61 (1H, s), 4.40 (1H, hept, J=6.7 Hz), 4.29 (2H, t, J=8.0 Hz), 4.02 (2H, t, J=7.3 Hz), 2.99 (1H, hept, J=7.4 Hz), 2.78-2.65 (2H, m), 1.53 (6H, d, J=6.7 Hz).

LCMS Method 1: r.t. 3.03 mins, [$MH^+$] 382.2

Example 18

2-(Indolin-5-yl)-3-isopropyl-7-(1H-pyrazol-4-yl)imidazo[2,1-f][1,2,4]triazin-4 (31-1)-one

2-Chloro-3-isopropylimidazo[2,1-f][1,2,4]triazin-4(3H)-one

3-Isopropylimidazo[2,1-f][1,2,4]triazine-2,4 (1H,3H)-dione (460 mg, 2.37 mmol) was suspended in phosphorus oxychloride (5.0 mL) and stirred at 120° C. for 48 h. $POCl_3$ was added (5 mL) and it was stirred at 120° C. until the completion of the reaction was observed by LCMS. Water was added to the mixture and $NaHCO_3$ was added at 40° C. slowly portionwise to reach pH=6. DCM was added and the phases separated. The aqueous was extracted with DCM (×2) using a phase separator cartridge and the combined organic phase was concentrated in vacuo to afford the title compound (285 mg, 57%) as a pale yellow solid. $^1$H NMR (400 MHz, $CDCl_3$) δ, ppm 7.54-7.52 (2H, m), 5.24-5.24 (1H, m), 1.67 (6H, d, J=6.9 Hz).

tert-Butyl 5-(3-isopropyl-4-oxo-3,4-dihydroimidazo[2,1-f][1,2,4]triazin-2-yl) indoline-1-carboxylate Prepared from 2-chloro-3-isopropylimidazo[2,1-f][1,2,4]triazin-4(3H)-one and tert-butyl 5-(4,4,5,5-tetramethyl-1,3, 2-dioxaborolan-2-yl) indoline-1-carboxylate using Suzuki-Miyaura General Procedure 1. Purification by silica gel chromatography eluting with 0-75% EtOAc in cyclohexane afforded the title compound (116 mg, 31%) as a colourless gum. LCMS Method 4: r.t. 1.55 mins, [MH$^+$] 396.

tert-Butyl 5-(7-bromo-3-isopropyl-4-oxo-3,4-dihydroimidazo[2,1-f][1,2,4]triazin-2-yl) indoline-1-carboxylate A solution of tert-butyl 5-(3-isopropyl-4-oxo-3,4-dihydroimidazo[2,1-f][1,2,4]triazin-2-yl) indoline-1-carboxylate (114 mg, 0.29 mmol) in dry DMF (2.0 mL) was treated with NBS (38 mg, 0.22 mmol) and the reaction mixture was stirred at rt for 16 h. A further portion (15 mg, 0.085 mmol) of NBS was added and the reaction mixture stirred for 2 h. EtOAc and water were added and the phases separated. The aqueous phase was extracted with EtOAc (×2) and the combined organic phase was washed with water, a saturated aqueous $NaHCO_3$ solution and brine, dried ($MgSO_4$) and concentrated in vacuo. The residue was dissolved in MeOH/DCM, preadsorbed onto ISOLUTE® HM-N column (Biotage) and purified by silica gel chromatography eluting with 0-100% EtOAc in cyclohexane to afford the title compound (97 mg, 71%) as a golden gum.

LCMS Method 4: r.t. 1.68 mins, [MH$^+$] 474, 476.

tert-Butyl 5-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl) indoline-1-carboxylate Prepared from tert-butyl 5-(7-bromo-3-isopropyl-4-oxo-3,4-dihydroimidazo[2,1-f][1,2,4]triazin-2-yl) indoline-1-carboxylate and 1-tetrahydropyran-2-yl-4-(4,4,5,5-tetramethyl-1,3,2-dioxaborolan-2-yl)pyrazole using Suzuki-Miyaura General Procedure 1 except that a 9:1 ratio of dioxane:water was used. Purification by silica gel chromatography eluting with 0-100% EtOAc in cyclohexane afforded the title compound (68 mg, 62%) as a colourless glass.

LCMS Method 4: r.t. 1.68 mins, [MH$^+$] 546

2-(Indolin-5-yl)-3-isopropyl-7-(1H-pyrazol-4-yl) imidazo[2,1-f][1,2,4]triazin-4(3H)-one A solution of text-butyl 5-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl) indoline-1-carboxylate (66 mg, 0.12 mmol) in MeOH (1.2 mL) was treated with 1N HCl (aq) (1.2 mL) and the reaction mixture was stirred at rt for 18 h. Conc. HCl (1.2 mL) was added and the reaction mixture stirred at rt for 4 h. Water was added and the solution freeze-dried. Purification by reverse phase preparative HPLC gave the title compound (18 mg, 41%) as a white solid.

$^1$H NMR (400 MHz, $d_6$-DMSO) δ, ppm 8.16 (2H, s), 7.78 (1H, s), 7.35 (1H, d, J=1.4 Hz), 7.26 (1H, dd, J=1.7, 8.0 Hz), 6.68 (1H, d, J=8.1 Hz), 4.29 (1H, hept, J=6.8 Hz), 3.56 (2H, t, J=8.6 Hz), 3.04 (2H, t, J=8.6 Hz), 1.50 (6H, d, J=6.8 Hz) plus 2 exchangeable protons not observed.

LCMS Method 7: r.t. 3.07 mins, [MH$^+$] 362.2

Example 19

2-(1-(Cyclopropylmethyl)-1H-pyrazol-4-yl)-7-(1H-imidazol-5-yl)-3-isopropylimidazo[2,1-f][1,2,4]triazin-4(3H)-one 2-(1-(Cyclopropylmethyl)-1H-pyrazol-4-yl)-3-isopropylimidazo[2,1-f][1,2,4]triazin-4(3H)-one A solution of ethyl 1-amino-1H-imidazole-2-carboxylate (1.83 g, 11.8 mmol) in dry MeCN (35 mL) was treated with 1-(cyclopropylmethyl)-N-isopropyl-1H-pyrazole-4-carbimidoyl chloride (3.19 g, 14.2 mmol) and the reaction mixture was stirred at 50° C. under argon. After 2 h a further 1.33 g (5.9 mmol) 1-(cyclopropylmethyl)-N-isopropyl-1H-pyrazole-4-carbimidoyl chloride was added and the reaction mixture was stirred at 50° C. for 1 h. DMAP (0.029 mg, 0.24 mmol) and potassium carbonate (1.63 g, 11.8 mmol) was added and the reaction mixture was stirred at reflux for 16 h becoming a very thick precipitate. MeCN (10 mL) was added to aid stirring and stirring at reflux continued for 6 h. A further 10 mL MeCN was added and reaction mixture stirred for 1.5 h then another 10 mL MeCN was added and stirring at reflux continued for 24 h. Another portion of DMAP (0.029 mmol, 0.24 mmol) was added and the reaction mixture stirred at reflux for 16 h then another portion of potassium carbonate (1.63 g, 11.8 mmol) and MeCN (10 mL) were added and stirring at reflux was continued for 7 h whereupon LCMS indicated the reaction was complete. The reaction mixture was concentrated in vacuo and the residue partitioned between EtOAc and water. The phases were separated and the aqueous phase was extracted with EtOAc (×2). The combined organic phase was washed with brine, dried ($MgSO_4$) and concentrated in vacuo to a dark brown solid. The solid was dissolved in MeOH/DCM, preadsorbed onto ISOLUTE® HM-N column (Biotage) and purified by silica gel chromatography eluting with 0-5% IPA in DCM to afford the title compound (1.49 g, 42%) as a golden viscous oil.

$^1$H NMR (400 MHz, $d_6$-DMSO) δ, ppm 8.24 (1H, s), 7.94 (1H, d, J=1.0 Hz), 7.80 (1H, d, J=0.6 Hz), 7.51 (1H, d, J=1.1 Hz), 4.51 (1H, hept, J=6.8 Hz), 4.07 (2H, d, J=7.2 Hz), 1.54 (6H, d, J=6.8 Hz), 1.35-1.25 (1H, m), 0.59-0.53 (2H, m), 0.43-0.38 (2H, m).

LCMS Method 1: r.t. 3.44 mins, [MH$^+$] 299.3

7-Bromo-2-(1-(cyclopropylmethyl)-1H-pyrazol-4-yl)-3-isopropylimidazo[2,1-f][1,2,4]triazin-4(3H)-one A solution of 2-(1-(cyclopropylmethyl)-1H-pyrazol-4-yl)-3-isopropylimidazo[2,1-f][1,2,4]triazin-4(3H)-one (1.49 g, 5.0 mmol) in dry DMF (35 mL) under argon was treated with NBS (0.89 g, 5.0 mmol) and the reaction mixture was stirred at rt for 18 h. A further portion (87 mg, 0.49 mmol) of NBS was added and the reaction mixture stirred for 1 h. EtOAc and water were added and the phases separated. The aqueous phase was extracted with EtOAc (×2) and the combined organic phase was washed with water, a saturated aqueous $NaHCO_3$ solution and brine, dried ($MgSO_4$) and concentrated in vacuo. The residue was dissolved in MeOH/DCM, preadsorbed onto ISOLUTE® HM-N column (Biotage) and purified by silica gel chromatography (80 g cartridge) eluting with 0-75% EtOAc in cyclohexane. The product was treated with ether and re-evaporated (×2) to afford the title compound (1.38 g, 73%) as a white solid.

$^1$H NMR (400 MHz, $CDCl_3$) δ, ppm 7.95 (1H, s), 7.77 (1H, d, J=0.6 Hz), 7.51 (1H, s), 4.73-4.66 (1H, m), 4.08 (2H, d, J=7.3 Hz), 1.67 (6H, d, J=6.8 Hz), 1.41-1.34 (1H, m), 0.78-0.73 (2H, m), 0.49-0.45 (2H, m).

LCMS Method 7: r.t. 4.16 mins, [$MH^+$] 377.0, 379.2

2-(1-(Cyclopropylmethyl)-1H-pyrazol-4-yl)-3-isopropyl-7-(1-trityl-1H-imidazol-4-yl)imidazo[2,1-f][1,2,4]triazin-4(3H)-one A solution of 4-iodo-1-trityl-1H-imidazole (127 mg, 0.29 mmol) in dry THF under argon was treated dropwise with ethylmagnesium bromide (3.0 M solution in ether, 0.11 mL, 0.35 mmol) and stirred at rt for 30 mins zinc chloride (2.0 M solution in 2-methyl THF, 0.29 mL, 0.58 mmol) was added dropwise generating a creamy suspension that was stirred at rt for 2 h. 7-Bromo-2-(1-(cyclopropylmethyl)-1H-pyrazol-4-yl)-3-isopropylimidazo[2,1-f][1,2,4]triazin-4(3H)-one (100 mg, 0.27 mmol) was added, the reaction mixture was degassed and then Tetrakis(triphenylphosphine)palladium(0) (15 mg, 0.013 mmol) was added and the reaction mixture was stirred at reflux for 3 h. A further 15 mg (0.013 mmol) of tetrakis(triphenylphosphine)palladium(0) was added and the reaction mixture was stirred at reflux for 16 h before cooling to rt. EtOAc and saturated aqueous ammonium chloride solution were added and the small quantity of insoluble solid dissolved on addition of a bit of MeOH/DCM. The phases were separated and the aqueous phase was extracted with EtOAc (×2). The combined organic phase was washed with water, saturated aqueous sodium bicarbonate solution and brine, dried ($MgSO_4$) and concentrated in vacuo to a golden oil. The gum was dissolved in DCM, and purified by silica gel chromatography (25 g cartridge) eluting with 0-100% EtOAc in cyclohexane to afford the title compound (69 mg, 43%) as a cream coloured gum.

LCMS Method 5: r.t. 1.84 mins, $[MH]^+$ 607.

2-(1-(Cyclopropylmethyl)-1H-pyrazol-4-yl)-7-(1H-imidazol-5-yl)-3-isopropylimidazo[2,1-f][1,2,4]triazin-4(3H)-one (Assumed bis HCl Salt)

A solution of 2-(1-(cyclopropylmethyl)-1H-pyrazol-4-yl)-3-isopropyl-7-(1-trityl-1H-imidazol-4-yl)imidazo[2,1-f][1,2,4]triazin-4(3H)-one (69 mg, 0.11 mmol) in MeOH (1.0 mL) was treated with 1N HCl (aq) (0.34 mL, 0.34 mmol) and the reaction mixture was stirred at rt for 16 h. The solid was filtered off, washed with MeOH then ether and dried to afford the title compound (17 mg, 41%) as a white solid.

$^1$H NMR (400 MHz, $d_6$-DMSO) δ, ppm 9.17 (1H, s), 8.40 (1H, s), 8.08 (1H, s), 8.06 (1H, d, J=1.2 Hz), 7.96 (1H, d, J=0.6 Hz), 4.63 (1H, hept, J=6.7 Hz), 4.10 (2H, d, J=7.2 Hz), 1.59 (6H, d, J=6.7 Hz), 1.38-1.28 (1H, m), 0.61-0.55 (2H, m), 0.46-0.41 (2H, m) plus three exchangeable protons not observed.

LCMS Method 3: r.t. 2.60 mins, [$MH^+$] 365.1

Example 20

2-(1-(Cyclopropylmethyl)-1H-pyrazol-4-yl)-3-isopropyl-7-(1H-pyrazol-4-yl)imidazo[2,1-f][1,2,4]triazin-4(3H)-one A mixture of 7-bromo-2-(1-(cyclopropylmethyl)-1H-pyrazol-4-yl)-3-isopropylimidazo[2,1-f][1,2,4]triazin-4(3H)-one (150 mg, 0.40 mmol), 1H-pyrazole-4-boronic acid (67 mg, 0.60 mmol), sodium carbonate (126 mg, 1.2 mmol) in DMF (1.2 mL) and water (0.3 mL) was degassed then treated with [1,1'-bis(diphenylphosphino)ferrocene]dichloropalladium (II) (29 mg, 0.040 mmol) and stirred at 100° C. for 3 h. Another portion of [1,1'-Bis(diphenylphosphino)ferrocene]dichloropalladium (II) (29 mg, 0.040 mmol) was added and the reaction mixture stirred at 100° C. for another 2 h. Another portion of 1H-pyrazole-4-boronic acid (67 mg, 0.60 mmol), and sodium carbonate (126 mg, 1.2 mmol) were added and the reaction mixture stirred at 100° C. for 18 h. EtOAc and water were added, the mixture was filtered through Celite® and the phases separated. The aqueous phase was extracted with EtOAc (×2) and the combined organic phase was washed with water, a saturated aqueous $NaHCO_3$ solution and brine, dried ($MgSO_4$) and concentrated in vacuo. The residue was dissolved up in MeOH/DCM, preadsorbed onto ISOLUTE® HM-N column (Biotage) and purified by silica gel chromatography (25 g cartridge) eluting with 0-5% MeOH/DCM to give a pink solid (25 mg). The solid residue from the initial filtration was washed repeatedly with 10% MeOH/DCM. The solution was washed with water and the aqueous extracted with DCM (×2). The combined DCM extracts were washed with a saturated aqueous $NaHCO_3$ solution and brine, dried ($MgSO_4$) and concentrated in vacuo to a solid (112 mg). The two solids were combined, taken up in MeOH/DCM, preadsorbed onto ISOLUTE® HM-N column (Biotage) and purified by silica gel chromatography (25 g cartridge) eluting with 0-5% MeOH/DCM to give a pink solid (89 mg). The solid was triturated with MeOH/DCM, filtered off, washed with MeOH/DCM then ether to afford the title compound. A second crop was obtained from the mother liquor by an identical trituration procedure. The two solids were combined, stirred in ether and filtered off to afford the title compound (46 mg, 32%) as a white solid.

$^1$H NMR (400 MHz, $d_6$-DMSO) δ, ppm 13.17 (1H, s), 8.37 (1H, s), 8.34 (1H, s), 8.11 (1H, s), 7.90 (1H, s), 7.76 (1H, s), 4.59 (1H, hept, J=6.6 Hz), 4.10 (2H, d, J=7.2 Hz), 1.58 (6H, d, J=6.7 Hz), 1.38-1.28 (1H, m), 0.60-0.55 (2H, m), 0.46-0.42 (2H, m).

LCMS Method 3: r.t. 3.27 mins, [$MH^+$] 365.1

Example 21

3-Isopropyl-2-(1-methyl-1H-indol-5-0)-7-(1H-pyrazol-4-yl)imidazo[2,1-f][1,2,4]triazin-4(3H)-one 2-Chloro-3-isopropyl-7-(1-(tetrahydro-2H-pyran-2-yl)-1H-pyrazol-4-yl)imidazo[2,1-f][1,2,4]triazin-4(3H)-one iPrMgCl (1.3 M in THF, 7.25 mL, 9.42 mmol) was added dropwise to a cooled (0° C.) solution of 4-iodo-1-(tetrahydro-2H-pyran-2-yl)-1H-pyrazole (2.38 g, 8.57 mmol) in THF (20 mL). The resulting white suspension was stirred for 10 min before $ZnCl_2$ (1.9M in 2-MeTHF, 5.86 mL, 11.1 mmol) was added dropwise. The resulting yellow solution was stirred for 30 minutes, before $Pd(PPh_3)_4$ (683 mg, 0.591 mmol) and 2-chloro-7-iodo-3-isopropylimidazo[2,1-f][1,2,4]triazin-4(3H)-one (2.00 g, 5.91 mmol) were added quickly to the reaction and the resulting solution was heated to reflux. After 15 min, the reaction was cooled and then diluted with DCM. The organic layer was washed with aqueous 10% citric acid solution and brine, dried ($Na_2SO_4$), filtered and concentrated in vacuo. The resulting yellow oil was loaded with DCM on to a 120 g $SiO_2$ cartridge and eluted with 10-70% EtOAc in DCM. Concentration of the product contacting fractions afforded the title compound as an off white solid (1.13 g, 53%).

$^1$H NMR (400 MHz, $CDCl_3$) δ, ppm 8.24 (1H, d, J=0.4 Hz), 8.03 (1H, d, J=0.6 Hz), 7.63 (1H, s), 5.47 (1H, dd, J=3.1, 9.1 Hz), 5.26 (1H, s), 4.13-4.07 (1H, m), 3.78-3.71 (1H, m), 2.24-2.05 (3H, m), 1.77-1.70 (2H, m), 1.70-1.62 (7H, m).

3-Isopropyl-2-(1-methyl-1H-indol-5-yl)-7-(1-(tetrahydro-2H-pyran-2-yl)-1H-pyrazol-4-yl)imidazo[2,1-f][1,2,4]triazin-4(3H)-one Prepared from 2-chloro-3-isopropyl-7-(1-(tetrahydro-2H-pyran-2-yl)-1H-pyrazol-4-yl)imidazo[2,1-f][1,2,4]triazin-4(3H)-one and 1-methylimidazole-5-boronic acid using Suzuki-Miyaura General Procedure 1 to afford the title compound as a white fluffy solid, 146 mg (77%).

$^1$H NMR (400 MHz, $CDCl_3$) δ, ppm 8.16 (1H, s), 8.03 (1H, s), 7.82 (1H, d, J=1.2 Hz), 7.66 (1H, s), 7.48 (1H, d, J=8.5 Hz), 7.38-7.33 (1H, m), 7.22 (1H, d, J=3.1 Hz), 6.63 (1H, d, J=3.1 Hz), 5.36 (1H, dd, J=2.2, 9.5 Hz), 4.39-4.27 (1H, m), 4.06-3.99 (1H, m), 3.90 (3H, s), 3.70-3.63 (1H, m), 2.16-2.01 (1H, m), 2.06-1.97 (2H, m), 1.78-1.55 (9H, m).

3-Isopropyl-2-(1-methyl-1H-indol-5-yl)-7-(1H-pyrazol-4-yl)imidazo[2,1-f][1,2,4]triazin-4(3H)-one Prepared from 3-isopropyl-2-(1-methyl-1H-indol-5-yl)-7-(1-(tetrahydro-2H-pyran-2-yl)-1H-pyrazol-4-yl)imidazo[2,1-f][1,2,4]triazin-4(3H)-one by THP Deprotection Procedure 0.1 to give the title compound as a white solid, 18 mg (15%).

$^1$H NMR (400 MHz, $d_6$-DMSO) δ, ppm 8.13 (2H, s), 7.91 (1H, d, J=1.2 Hz), 7.78 (1H, s), 7.65 (1H, d, J=8.5 Hz), 7.51 (1H, d, J=3.3 Hz), 7.45 (1H, dd, J=1.7, 8.5 Hz), 6.59 (1H, d, J=2.6 Hz), 4.24-4.13 (1H, m), 3.88 (3H, s), 1.49 (6H, d, J=6.8 Hz) plus one exchangeable not observed.

LCMS Method 1: r.t. 3.80 mins, [$MH^+$] 374.1

Example 22

7-(1H-Imidazol-5-yl)-3-isopropyl-2-(1-methyl-1H-pyrazol-3-yl)imidazo[2,1-f][1,2,4]triazin-4(3H)-one, 0.25 eq Formate Salt 3-Isopropyl-2-(1-methyl-1H-pyrazol-3-yl)-7-(1-trityl-H1-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 1-methyl-3-(4,4,5,5-tetramethyl-1,3,2-dioxaborolan-2-yl)-1H-pyrazole using Suzuki-Miyaura General Procedure 1 to afford the title compound as a white foam, 50 mg (46%).

LCMS Method 4: r.t. 1.64 mins, [$MH^+$] 567

7-(1H-Imidazol-5-yl)-3-isopropyl-2-(1-methyl-1H-pyrazol-3-yl)imidazo[2,1-f][1,2,4]triazin-4(3H)-one Prepared from 3-isopropyl-2-(1-methyl-1H-pyrazol-3-yl)-7-(1-trityl-1H-imidazol-4-yl)imidazo[2,1-f][1,2,4]triazin-4(3H)-one by Trityl Deprotection Procedure 1 to give the title compound as a white solid, 20.8 mg (71%).

$^1$H NMR (400 MHz, $d_6$-DMSO) δ, ppm 12.33 (1H, s), 8.24 (0.3H, s), 7.96 (1H, d, J=2.2 Hz), 7.81 (1H, s), 7.74 (1H, s), 7.66 (1H, s), 6.80 (1H, d, J=2.2 Hz), 4.72-4.64 (1H, m), 3.98 (3H, s), 1.54 (6H, d, J=6.8 Hz).

LCMS Method 1: r.t. 2.25 mins, [$MH^+$] 325.3

Example 23

7-(1H-Imidazol-5-yl)-3-isopropyl-2-(6-(piperidin-1-yl)pyridin-3-yl)imidazo[2,1-f][1,2,4]triazin-4(3H)-one 3-Isopropyl-2-(6-(piperidin-1-yl)pyridin-3-yl)-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 2-(1-piperidyl)-5-(4,4,5,5-tetramethyl-1,3,2-dioxaborolan-2-yl) pyridine using Suzuki-Miyaura General Procedure 1 to afford the title compound as a white foam, 46 mg (37%).

LCMS Method 4: r.t. 1.54 mins, [$MH^+$] 647

7-(1H-Imidazol-5-yl)-3-isopropyl-2-(6-(piperidin-1-yl)pyridin-3-yl)imidazo[2,1-f][1,2,4]triazin-4(3H)-one Prepared from 3-isopropyl-2-(6-(piperidin-1-yl)pyridin-3-yl)-7-(1-trityl-1H-imidazol-4-yl)imidazo[2,1-f][1,2,4]triazin-4(3H)-one by Trityl Deprotection Procedure 1 to give the title compound as a white solid, 5.5 mg (19%).

$^1$H NMR (400 MHz, $d_6$-DMSO) δ, ppm 12.32 (1H, s), 8.40 (1H, d, J=2.3 Hz), 7.81-7.77 (2H, m), 7.72 (1H, s), 7.61 (1H, s), 6.97 (1H, d, J=8.8 Hz), 4.33-4.23 (1H, m), 3.65 (4H, t, J=5.3 Hz), 1.68-1.55 (6H, m), 1.53 (6H, d, J=6.5 Hz).

LCMS Method 7: r.t. 3.06 mins, [$MH^+$] 405.0

Example 24

2-(3,5-Dimethylphenyl)-3-isopropyl-7-(1H-imidazol-4-yl)imidazo[2,1-f][1,2,4]triazin-4(3H)-one 2-(3,5-Dimethylphenyl)-3-isopropyl-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 3,5-dimethylbenzene boronic acid using Suzuki-Miyaura General Procedure 1 to afford the title compounds in a 2:1 ratio as a glassy solid, 28 mg (46%).

LCMS Method 4: r.t. 1.70 mins, [$MH^+$] 591 and r.t. 1.74, [$MH^+$] 607

2-(3,5-Dimethylphenyl)-3-isopropyl-7-(1H-imidazol-4-yl)imidazo[2,1-f][1,2,4]triazin-4(3H)-one Prepared from 2-(3,5-dimethylphenyl)-3-isopropyl-7-(1-trityl-1H-imidazol-4-yl)imidazo[2,1-f][1,2,4]triazin-4(3H)-one by Trityl Deprotection Procedure 1 to give the title compounds as white solids, 6.3 mg (9% over two steps).

$^1$H NMR (400 MHz, $d_6$-DMSO) δ, ppm 12.26 (1H, s), 7.78 (1H, s), 7.73 (1H, s), 7.54 (1H, s), 7.31 (2H, s), 7.25 (1H, s), 4.12-4.02 (1H, m), 2.38 (6H, s), 1.49 (6H, d, J=6.8 Hz).

LCMS Method 1: r.t. 3.35 mins, [$MH^+$] 349.3

Example 25

2-(1-(Cyclohexylmethyl)-1H-pyrazol-4-yl)-7-(1H-imidazol-5-yl)-3-isopropylimidazo[2,1-f][1,2,4]triazin-4(3H)-one 2-(1-(Cyclohexylmethyl)-1H-imidazol-4-yl)-3-isopropyl-7-(1-trityl-1H-imidazol-4-yl)imidazo[2,1-f][1,2,4]triazin-4(3H)-one iPrMgCl (1.3 M in THF, 0.532 mL, 0.691 mmol) was added dropwise to a cooled (0° C.) solution of 1-(cyclohexylmethyl)-4-iodo-1H-imidazole (167 mg, 0.576 mmol) in THF (2.5 mL). The reaction was stirred for 30 min before $ZnCl_2$ (1.9M in 2-MeTHF, 0.455 mL, 0.864 mmol) was added dropwise. The resulting yellow solution was stirred for 30 minutes, before 2-chloro-3-isopropyl-7-(1-trityl-1H-imidazol-4-yl)imidazo[2,1-f][1,2,4]triazin-4(3H)-one (100 mg, 0.192 mmol), XPhosPdG2 (15 mg, 10 mol %) and XPhos (9.0 mg, 10 mol %) were added quickly to the reaction and the resulting solution was heated to reflux. After 1 h, the reaction was cooled and then diluted with EtOAc. The organic layer was washed with 10% aq. citric acid, brine, dried ($Na_2SO_4$), and concentrated in vacuo. The crude mixture was loaded with DCM on to a 24 g $SiO_2$ cartridge and eluted with 0-10% MeOH in DCM. Concentration of the product contacting fractions afforded the title compound as a glassy solid (40 mg, 32%).

LCMS Method 4: r.t. 1.85 mins, [$MH^+$] 649

2-(1-(Cyclohexylmethyl)-1H-pyrazol-4-yl)-7-(1H-imidazol-5-yl)-3-isopropylimidazo[2,1-f][1,2,4]triazin-4(3H)-one Prepared from 2-(1-(cyclohexylmethyl)-1H-imidazol-4-yl)-3-isopropyl-7-(1-trityl-1H-imidazol-4-yl)imidazo[2,1-f][1,2,4]triazin-4(3H)-one by Trityl Deprotection Procedure 1 to give the title compound as a white solid, 5 mg (20%).

$^1$H NMR (400 MHz, $d_6$-DMSO) δ, ppm 12.37 (1H, s), 7.95 (1H, d, J=1.2 Hz), 7.90 (1H, d, J=1.3 Hz), 7.81 (1H, s), 7.76 (1H, s), 7.72 (1H, s), 5.07-4.97 (1H, m), 3.95 (2H, d, J=7.2 Hz), 1.85-1.56 (12H, m), 1.26-1.12 (3H, m), 1.04-0.92 (2H, m).

LCMS Method 1: r.t. 3.32 mins, [$MH^+$] 407.3

Example 26

7-(1H-Imidazol-5-yl)-3-isopropyl-2-(thiophen-2-yl)imidazo[2,1-f][1,2,4]triazin-4(3H)-one, 0.25 eq Formate Salt 3-Isopropyl-2-(thiophen-3-yl)-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 4,4,5,5-tetramethyl-2-(2-thienyl)-1,3,2-dioxaborolane using Suzuki-Miyaura General Procedure 1 to afford the title compound as a yellow oil, 106 mg. LCMS indicated 57% purity, the product was taken on without further purification LCMS Method 4: r.t. 1.92 mins, [$MH^+$] 569

7-(1H-imidazol-5-yl)-3-isopropyl-2-(thiophen-2-yl)imidazo[2,1-f][1,2,4]triazin-4(3H)-one, 0.25 eq Formate Salt Prepared from 3-isopropyl-2-(thiophen-3-yl)-7-(1-trityl-1H-imidazol-4-yl)imidazo[2,1-f][1,2,4]triazin-4(3H)-one by Trityl Deprotection Procedure 1 to give the title compound as a white solid, 15 mg (24% over two steps).

$^1$H NMR (400 MHz, $d_6$-DMSO) δ, ppm 12.37 (1H, s), 8.28 (0.2H, s), 7.92 (1H, d, J=4.9 Hz), 7.81 (1H, s), 7.74 (1H, s), 7.64-7.60 (2H, m), 7.29 (1H, dd, J=3.8, 4.8 Hz), 4.52-4.41 (1H, m), 1.57 (6H, d, J=6.7 Hz).

LCMS Method 1: r.t. 2.68 mins, [$MH^+$] 327.1

Example 27

3-Isopropyl-7-(1H-pyrazol-4-yl)-2-(thiophen-2-yl)imidazo[2,1-f][1,2,4]triazin-4(3H)-one 3-Isopropyl-7-(1-(tetrahydro-2H-pyran-2-yl)-1H-pyrazol-4-yl)-2-(thiophen-2-yl)imidazo[2,1-f][1,2,4]triazin-4(3H)-one Prepared from 2-chloro-3-isopropyl-7-(1-(tetrahydro-2H-pyran-2-yl)-1H-pyrazol-4-yl)imidazo[2,1-f][1,2,4]triazin-4(3H)-one and 4,4,5,5-tetramethyl-2-(2-thienyl)-1,3,2-dioxaborolane using Suzuki-Miyaura General Procedure 1 to afford the title compound as an off-white solid, 130 mg (76%).

LCMS Method 4: r.t. 1.44 mins, [$MH^+$] 411

3-Isopropyl-7-(1H-pyrazol-4-yl)-2-(thiophen-2-yl)imidazo[2,1-f][1,2,4]triazin-4(3H)-one Prepared from 3-isopropyl-7-(1-(tetrahydro-2H-pyran-2-yl)-1H-pyrazol-4-yl)-2-(thiophen-2-yl)imidazo[2,1-f][1,2,4]triazin-4(3H)-one by THP Deprotection Procedure 1 to give the title compound as a white solid, 22 mg (13%)

$^1$H NMR (400 MHz, $d_6$-DMSO) δ, ppm 13.17 (1H, s), 8.30 (1H, s), 8.10 (1H, s), 7.92 (1H, dd, J=1.2, 5.1 Hz), 7.79 (1H, s), 7.61 (1H, dd, J=1.2, 3.6 Hz), 7.29 (1H, dd, J=3.6, 5.1 Hz), 4.52-4.42 (1H, m), 1.57 (6H, d, J=6.8 Hz).

LCMS Method 1: r.t. 3.44 mins, [$MH^+$] 327.0

Example 28

7-(1H-Imidazol-4-yl)-3-isopropyl-2-(1-methyl-1H-pyrazol-4-yl)imidazo[2,1-f][1,2,4]triazin-4(3H)-one 3-Isopropyl-2-(1-methyl-1H-pyrazol-4-yl)-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 1-methyl-4-(4,4,5,5-tetramethyl-1,3,2-dioxaborolan-2-yl)pyrazole using Suzuki-Miyaura General Procedure 1 to afford the title compound as an off-white solid, 54 mg (24%).

LCMS Method 4: r.t. 1.59 mins, $[MH]^+$ 567

7-(1H-Imidazol-4-yl)-3-isopropyl-2-(1-methyl-1H-pyrazol-4-yl)imidazo[2,1-f][1,2,4]triazin-4(3H)-one Prepared from 3-isopropyl-2-(1-methyl-1H-pyrazol-4-yl)-7-(1-trityl-1H-imidazol-4-yl)imidazo[2,1-f][1,2,4]triazin-4(3H)-one by Trityl Deprotection Procedure 1 to give the title compound as a white solid, 2.6 mg (8%).

$^1$H NMR (400 MHz, $d_6$-DMSO) δ, ppm 12.38 (1H, s), 8.29 (1H, s), 7.87 (1H, s), 7.80 (1H, d, J=0.8 Hz), 7.71 (1H, s), 7.70 (1H, d, J=0.8 Hz), 4.62-4.51 (1H, m), 3.97 (3H, s), 1.56 (6H, d, J=6.8 Hz).

LCMS Method 1: r.t. 2.11 mins, [$MH^+$] 325

Example 29

7-(1H-Imidazol-4-yl)-3-isopropyl-2-(1-methyl-1H-indol-5-yl)imidazo[2,1-f][1,2,4]triazin-4(3H)-one, 0.3 eq Formate Salt 3-Isopropyl-2-(1-methyl-1H-indol-5-yl)-7-(1-trityl-1H-imidazol-4-yl)imidazo[2,1-f][1,2,4]triazin-4 (3H)-one Prepared from 2-chloro-3-isopropyl-7-(1-trityl-1H-imidazol-4-yl)imidazo[2,1-f][1,2,4]triazin-4(3H)-one and 1-methyl-5-(4,4,5,5-tetramethyl-1,3,2-dioxaborolan-2-yl) indole using Suzuki-Miyaura General Procedure 1 to afford the title compound as an off-white solid, 26 mg (14%).

LCMS Method 2: r.t. 1.67 mins, [$MH^+$] 616

7-(1H-Imidazol-4-yl)-3-isopropyl-2-(1-methyl-1H-indol-5-yl)imidazo[2,1-f][1,2,4]triazin-4(3H)-one, 0.3 eq Formate Salt Prepared from 3-isopropyl-2-(1-methyl-1H-indol-5-yl)-7-(1-trityl-1H-imidazol-4-yl)imidazo[2,1-f][1,2,4]triazin-4 (3H)-one by Trityl Deprotection Procedure 1 to give the title compound as a white solid, 3.6 mg (23%).

$^1$H NMR (400 MHz, $d_6$-DMSO) δ, ppm 12.26 (1H, s), 8.41 (0.3H, s), 7.91 (1H, d, J=1.2 Hz), 7.77 (1H, s), 7.74 (1H, s), 7.65 (1H, d, J=8.5 Hz), 7.55 (1H, s), 7.51 (1H, d, J=3.1 Hz), 7.45 (1H, dd, J=1.6, 8.4 Hz), 6.59 (1H, dd, J=0.7, 3.1 Hz), 4.24-4.13 (1H, m), 3.88 (3H, s), 1.49 (6H, d, J=6.8 Hz).

LCMS Method 1: r.t. 3.12 mins, [$MH^-$] 374.1

Example 30

2-(1-(Cyclopropylmethyl)-1H-pyrazol-4-yl)-3-isopropyl-4-oxo-3,4-dihydropyrido[3,2-d]pyrimidine-8-carboxamide Ethyl 2-amino-2-cyanoacetate A saturated solution of $NaHCO_3$ (440 ml at 1.2M, 0.528 mol) was carefully added to a suspension of ethyl (hydroxyimino)cyanoacetate (75 g, 0.528 mol) in water (300 mL). After 15 min sodium hydrosulfite (255 g, 1.46 mol) was added portion wise over a 30 min period. The reaction temperature was allowed to warm to 40° C. before it was cooled with an ice bath. After 1 h the ice bath was removed and the reaction was allowed to warm to rt. After 3 h the reaction was saturated with NaCl and extracted with $CHCl_3$ (4×500 mL). The combined organic layers were dried ($Na_2SO_4$) and concentrated in vacuo to afford the title compound as a black oil (26.60 g, 40%).

$^1$H NMR (300 MHz, $CDCl_3$) δ, ppm, 4.47 (1H, s), 4.34 (2H, q, J=7.1 Hz), 1.35 (3H, t, J=7.1 Hz) plus two exchangeables not observed.

Ethyl 2-cyano-2-formamidoacetate

A mixture of formic acid (16.3 ml, 433 mmol) and acetic anhydride (39.8 ml, 421 mmol) were heated to 55° C. under a nitrogen atmosphere for 2 h. The solution was allowed to cool and was added to THF (350 mL) and cooled to <10° C. A solution of ethyl 2-amino-2-cyanoacetate (30.0 g, 234 mmol) in THF (350 mL) was added via dropping funnel over a 30 min period. The reaction was allowed to warm to rt and was stirred overnight. The reaction was concentrated in vacuo (using azeotropic drying with toluene (3×100 mL)). The residue was taken up in DCM (20 mL) and loaded onto a 330 g $SiO_2$ cartridge and eluted with 0-40% EtOAc in cyclohexane. Concentration of the product containing fractions afforded the title compound as an off white solid (13.26 g, 36%)

$^1$H NMR (400 MHz, $CDCl_3$) δ, ppm 8.32 (1H, s), 6.48 (1H, s), 5.56 (1H, d, J=7.6 Hz), 4.39 (2H, q, J=7.2 Hz), 1.39 (3H, t, J=7.1 Hz).

Ethyl 3-amino-4-cyanopicolinate

A solution of ethyl 2-cyano-2-formamidoacetate (13.00 g, 83.26 mmol), acrylonitrile (32.9 mL, 499.55 mmol), TFA (6.4 mL, 83 mmol) in 1,2-dichloroethane (83 mL) was heated at reflux for 72 h. The reaction was cooled to rt and concentrated under vacuum. The resulting black residue was diluted with DCM (100 mL) and portioned with sat. aq. $NaHCO_3$ (100 mL). The organic layer was collected and the aqueous layer was extracted with DCM (2×100 mL). The combined organic layers were dried ($Na_2SO_4$) and concentrated in vacuo onto ISOLUTE® HM-N column (Biotage). This was loaded onto an 80 g $SiO_2$ cartridge and eluted with 20-50% EtOAc in cyclohexane. Concentration of the product containing fractions afforded the title compound (8.78 g, 55%) as a white solid $^1$H NMR (400 MHz, $CDCl_3$) δ, ppm 8.12 (1H, d, J=4.6 Hz), 7.45 (1H, d, J=4.6 Hz), 6.56-6.44 (2H, m), 4.49 (2H, q, J=7.1 Hz), 1.46 (3H, t, J=7.1 Hz).

1-(Cyclopropylmethyl)-1H-pyrazole-4-carboxylic Acid

Potassium carbonate (15.0 g, 107 mmol) and (bromomethyl)cyclopropane (14.0 mL, 143 mmol) were added to a solution of ethyl 4-pyrazolecarboxylate (10.0 g, 71.3 mmol). The resulting mixture was heated at reflux for 5 h. The reaction was cooled to rt, filtered and concentrated in vacuo. The resulting yellow oil was dissolved in THF (160 mL) and water (40 mL) and treated with $LiOH \cdot H_2O$ (12.0 g, 285 mmol) and heated to reflux for 72 h. The reaction was cooled to rt, diluted with 1 M HCl (300 mL) and extracted with EtOAc (3×300 mL). The combined organic layers were washed with brine (300 mL), dried ($MgSO_4$) and concentrated in vacuo to afford a white solid. The solid was triturated with diethyl ether/cyclohexane (1:1, 200 mL) to afford the title compound (7.32 g, 62%) as a white solid.

$^1$H NMR (400 MHz, $CDCl_3$) δ, ppm 8.09 (1H, s), 7.99 (1H, s), 4.03 (2H, d, J=7.2 Hz), 1.38-1.26 (1H, m), 0.74-0.68 (2H, m), 0.41 (2H, q, J=5.2 Hz) plus one exchangeable not observed.

1-(Cyclopropylmethyl)-N-isopropyl-1H-pyrazole-4-carboxamide

Oxalyl chloride (1.6 mL, 18.05 mmol) and DMF (9.3 μL, 0.120 mmol) were added to a stirring suspension of 1-(cyclopropylmethyl)-1H-pyrazole-4-carboxylic acid (2.00 g, 12.04 mmol) in DCM under nitrogen atmosphere. After 4 h, the resulting clear solution was concentrated in vacuo (using azeotropic drying with toluene (3×10 mL) to afford a colourless oil. The oil was dissolved in DCM (30 mL) and treated with a solution of isopropylamine (2.10 mL, 24.1 mmol) in DCM (20 mL). The resulting solution was stirred overnight. The reaction was diluted with DCM (40 mL), washed with sat. aq. $NH_4Cl$ (40 mL), dried ($Na_2SO_4$) and concentrated in vacuo to afford the title compound as a white solid (2.27 g, 91%).

$^1H$ NMR (400 MHz, $CDCl_3$) δ, ppm 7.97 (1H, s), 7.69 (1H, s), 5.53 (1H, d, J=5.7 Hz), 4.30-4.21 (1H, m), 3.98 (2H, d, J=7.2 Hz), 1.25-1.23 (7H, m), 0.71-0.65 (2H, m), 0.39 (2H, q, J=5.2 Hz).

2-(1-(Cyclopropylmethyl)-1H-pyrazol-4-yl)-3-isopropyl-4-oxo-3,4-dihydropyrido[3,2-d]pyrimidine-8-carbonitrile A solution 1-(cyclopropylmethyl)-N-isopropyl-1H-pyrazole-4-carboxamide (1.71 g, 8.25 mmol) in thionyl chloride (2 mL) was stirred at 80° C. for 2 h under an Ar atmosphere. The reaction was diluted with toluene (10 mL), and concentrated in vacuo (using azeotropic drying with toluene (2×10 mL) to yield 1-(cyclopropylmethyl)-N-isopropyl-1H-pyrazole-4-carbimidoyl chloride. The resulting yellow oil was used directly in the next step without further purification.

$^1H$ NMR (400 MHz, $CDCl_3$) δ, ppm 8.11 (1H, s), 7.89 (1H, s), 4.16-4.06 (1H, m), 3.98 (2H, d, J=7.7 Hz), 1.34-1.22 (7H, m), 0.72-0.66 (2H, m), 0.42-0.37 (2H, m).

A solution of 1-(cyclopropylmethyl)-N-isopropyl-1H-pyrazole-4-carbimidoyl chloride in MeCN (10 mL) was added to a solution of ethyl 3-amino-4-cyanopicolinate (1.50 g, 7.85 mmol) in MeCN (20 mL) under nitrogen atmosphere. The resulting solution was heated at 50° C. After 140 h, $K_2CO_3$ (4.34 g, 31.4 mmol) was added to the reaction mixture and the resulting mixture was heated at 82° C. for 40 h. The reaction was allowed to cool to rt and was diluted with water and extracted with EtOAc (3×). The combined organic layers were washed with brine, dried ($Na_2SO_4$) and concentrated in vacuo. The resulting solid was loaded with DCM onto an 80 g $SiO_2$ cartridge and eluted with 20-100% EtOAc in cyclohexane. Concentration of the product containing fractions afforded the title compound as an off-white solid (0.928 g, 26.5%).

$^1H$ NMR (400 MHz, $CDCl_3$) δ, ppm 8.86 (1H, d, J=4.5 Hz), 8.21 (1H, s), 7.89 (1H, s), 7.87 (1H, d, J=4.5 Hz), 5.06-4.94 (1H, m), 4.09 (2H, d, J=7.3 Hz), 1.76 (6H, d, J=6.8 Hz), 1.43-1.34 (1H, m), 0.78-0.72 (2H, m), 0.50-0.45 (2H, m).

2-(1-(Cyclopropylmethyl)-1H-pyrazol-4-yl)-3-isopropyl-4-oxo-3,4-dihydropyrido[3,2-d]pyrimidine-8-carboxamide Prepared from 2-(1-(cyclopropylmethyl)-1H-pyrazol-4-yl)-3-isopropyl-4-oxo-3,4-dihydropyrido[3,2-d]pyrimidine-8-carbonitrile using General procedure for nitrile hydrolysis to afford the title compound as a white solid (95 mg, 60%)

$^1H$ NMR (400 MHz, $d_6$-DMSO) δ, ppm 9.37 (1H, d, J=2.5 Hz), 8.86 (1H, d, J=4.5 Hz), 8.35 (1H, s), 8.24 (1H, d, J=4.5 Hz), 8.10 (1H, d, J=2.3 Hz), 7.91 (1H, s), 4.84-4.73 (1H, m), 4.10 (2H, d, J=7.2 Hz), 1.63 (6H, d, J=6.7 Hz), 1.36-1.27 (1H, m), 0.60-0.55 (2H, m), 0.46-0.41 (2H, m).

LCMS Method 1: r.t. 3.18 mins, [$MH^+$] 353.0

Example 31

3-isopropyl-4-oxo-2-phenyl-3,4-dihydropyrido[3,2-d]pyrimidine-8-carboxamide N-Isopropylbenzamide A solution of isopropylamine (7.40 mL, 86.2 mmol) in DCM (30 mL) was added dropwise to a solution of benzoyl chloride (5.00 mL, 43.1 mmol) in DCM (50 mL). After 30 min the reaction was quenched with water and extracted with DCM (3×50 mL). The combined organic layers were washed with brine, dried ($MgSO_4$) and concentrated in vacuo to afford the title compound as a white solid (6.36 g, 90%).

$^1H$ NMR (400 MHz, $CDCl_3$) δ, ppm 7.76-7.74 (2H, m), 7.50-7.45 (1H, m), 7.44-7.38 (2H, m), 6.03 (1H, s), 4.33-4.24 (1H, m), 1.27-1.25 (6H, m).

3-Isopropyl-4-oxo-2-phenyl-3,4-dihydropyrido[3,2-d]pyrimidine-8-carbonitrile

A solution of N-isopropylbenzamide (1.71 g, 10.46 mmol) in thionyl chloride (2 mL) was stirred at 80° C. for 2 h under an Ar atmosphere. The reaction was diluted with toluene (10 mL), and concentrated in vacuo (using azeotropic drying with toluene (2×10 mL)). The resulting N-isopropylbenzimidoyl chloride as yellow oil was used directly in the next step without further purification.

$^1H$ NMR (400 MHz, $CDCl_3$) δ, ppm 7.99 (2H, d, J=7.3 Hz), 7.46-7.37 (3H, m), 4.22-4.12 (1H, m), 1.29 (6H, d, J=6.4 Hz).

A solution of N-isopropylbenzimidoyl chloride in MeCN (10 mL) was added to a solution of ethyl 3-amino-4-cyanopicolinate (2.00 g, 10.46 mmol) in MeCN (30 mL) under a nitrogen atmosphere. The resulting solution was heated at 50° C. After 96 h, $K_2CO_3$ (5.78 g, 41.8 mmol) was added to the reaction mixture and the resulting mixture was heated at 82° C. for 50 h. The reaction was allowed to cool to rt and was diluted with water and extracted with EtOAc (3×). The combined organic layers were washed with brine, dried ($Na_2SO_4$) and concentrated in vacuo. The resulting solid was loaded with DCM onto a 220 g $SiO_2$ cartridge and eluted with 20-40% EtOAc in cyclohexane. Concentration of the product containing fractions afforded the title compound as an off-white solid (1.46 g, 48%).

$^1H$ NMR (400 MHz, $CDCl_3$) δ, ppm 8.95 (1H, d, J=4.5 Hz), 7.91 (1H, d, J=4.5 Hz), 7.60-7.55 (5H, m), 4.51-4.43 (1H, m), 1.64 (6H, d, J=6.8 Hz).

LCMS Method 1: r.t. 4.15 mins, [$MH^+$] 291.3

3-Isopropyl-4-oxo-2-phenyl-3,4-dihydropyrido[3,2-cl]pyrimidine-8-carboxamide

Prepared from 3-isopropyl-4-oxo-2-phenyl-3,4-dihydropyrido[3,2-d]pyrimidine-8-carbonitrile using General procedure for nitrile hydrolysis to afford the title compound as a white solid (92 mg, 86%)

$^1H$ NMR (400 MHz, $d_6$-DMSO) δ, ppm 9.21 (1H, s), 8.93 (1H, d, J=4.6 Hz), 8.26 (1H, d, J=4.6 Hz), 8.04 (1H, s), 7.71-7.68 (2H, m), 7.61-7.59 (3H, m), 4.28-4.18 (1H, m), 1.53 (6H, d, J=6.8 Hz).

LCMS Method 1: r.t. 3.40 mins, [$MH^+$] 309.1

Pyrazole Spirodiazetidine Synthesis tert-Butyl 6-(5-isopropyl-1H-pyrazole-3-carbonyl)-2,6-diazaspiro[3.3]heptane-2-carboxylate 5-Isopropyl-1H-pyrazole-3-carboxylic acid (1.6 g, 10.4 mmol) and tert-butyl 2,6-diazaspiro[3.3]heptane-2-carboxylate oxalate (3.0 g, 10.4 mmol) were suspended in DMF (30 mL). Triethylamine (5.8 mL, 41.6 mmol) was added, followed by portionwise addition of HATU (9.9 g, 26.0 mmol). The reaction was stirred at room temperature for 16 h. The solution was diluted with water and 2-methyl THF. The phases were separated, and the aqueous layer was extracted with 2-methyl THF (×2). The combined organic phase was washed with water (×2), followed by brine, and dried ($Na_2SO_4$) then concentrated in vacuo. The resulting material was triturated with ethyl acetate to afford the title compound as a white solid (2.0 g, 57%).

LCMS Method 4: r.t. 1.29 mins, [$MH^+$] 335.3.

Pyrazole Spirodiazetidine Amides (General Synthetic Route)

Pyrazole Spirodiazetidine Amide General Procedure 1 tert-Butyl 6-(5-isopropyl-1H-pyrazole-3-carbonyl)-2,6-diazaspiro[3.3]heptane-2-carboxylate (75 mg, 0.22 mmol) was suspended in DCM (1 mL). To this was added MsOH (30 μL, 0.45 mmol). The resulting solution was stirred at room temperature for 2-4 h. $Et_3N$ (0.13 mL, 0.90 mmol) was then added, followed by the carboxylic acid (0.25 mmol) then HATU (111 mg, 0.3 mmol). The reaction was stirred for a further 90 min-16 h at rt. The solvent was removed in vacuo and the samples were dissolved in 10% water in DMSO and purified by reverse phase preparative HPLC.

Pyrazole Spirodiazetidine Amide General Procedure 2 tert-Butyl 6-(5-isopropyl-1H-pyrazole-3-carbonyl)-2,6-di azaspiro[3.3]heptane-2-carboxylate (290 mg, 0.86 mmol) was deprotected using Amberlyst 15 Hydrogen Form (2 g) in MeOH (20 mL) over 2 h. To this suspension was added a 2 M solution of $NH_3$ in MeOH (20 mL), which was stirred for 1 h. The reaction mixture was filtered and concentrated to afford crude (5-isopropyl-1H-pyrazol-3-yl)(2,6-diazaspiro[3.3]heptan-2-yl)methanone. The isolated material was divided into portions and coupled to 4 carboxylic acids.

HATU (97 mg, 0.26 mmol) and the carboxylic acid (0.24 mmol) were dissolved in DCM (1 mL) and $Et_3N$ (35 μL, 0.26 mmol). The mixture was stirred for 10 min. To this was added a solution of (5-isopropyl-1H-pyrazol-3-yl)(2,6-diazaspiro[3.3]heptan-2-yl)methanone (50 mg, 0.21 mmol) and $Et_3N$ (35 μL, 0.26 mmol) in DCM (2 mL). The reaction mixture was stirred for 16 h then concentrated in vacuo, re-dissolved in 2-methyl THF and washed twice with water then brine and dried ($Na_2SO_4$). The resulting solution was concentrated in vacuo and purified.

Pyrazole Spirodiazetidine Amide General Procedure 3

As for Pyrazole Spirodiazetidine Amide General Procedure 2 except that after stirring for 16 h the reaction mixture was concentrated in vacuo and purified directly by reverse phase chromatography.

Pyrazole Spirodiazetidine Amide General Procedure 4

To a solution/suspension of carboxylic acid (1 eq) in DCM (0.2 M) was added triethylamine (2.4 eq) followed by HATU (1.2 eq). The reaction was stirred at room temperature for 15 minutes then (5-isopropyl-1H-pyrazol-3-yl)(2,6-diazaspiro[3.3]heptan-2-yl)methanone (1 eq) was added and the reaction was stirred at room temperature for 16 h. The reaction mixture was concentrated in vacuo to give the crude product.

Example 32

1-[2-(5-Isopropyl-1H-pyrazole-3-carbonyl)-2,6-diazaspiro[3.3]heptan-6-yl]propan-1-one Prepared from tert-butyl 6-(5-isopropyl-1H-pyrazole-3-carbonyl)-2,6-diazaspiro[3.3]heptane-2-carboxylate and propionic acid using Pyrazole Spirodiazetidine General Procedure 1. Reverse phase preparative HPLC afforded the title compound as a white solid (30 mg).

$^1H$ NMR (400 MHz, $d_6$-DMSO) δ, ppm 13.00 (1H, s), 6.37 (1H, s), 4.59 (2H, br s), 4.29-4.26 (2H, m), 4.14 (2H, br s), 4.03-4.00 (2H, m), 3.00-2.92 (1H, m), 2.04 (2H, q, J=7.5 Hz), 1.22 (6H, d, J=6.9 Hz), 0.96 (3H, t, J=7.5 Hz).

LCMS Method 8: r.t. 2.77 mins [$MH^+$] 291.3.

Example 33

(5-Isopropyl-1H-pyrazol-3-yl)-[2-(spiro[2.2]pentane-2-carbonyl)-2,6-diazaspiro[3.3]heptan-6-yl]methanone Prepared from text-butyl 6-(5-isopropyl-1H-pyrazole-3-carbonyl)-2,6-diazaspiro[3.3]heptane-2-carboxylate and spiro[2.2]pentane-2-carboxylic acid using Pyrazole Spirodiazetidine General Procedure 1. Reverse phase preparative HPLC afforded the title compound as a white solid (37 mg).

$^1H$ NMR (400 MHz, $d_6$-DMSO) δ, ppm 12.99 (1H, s), 6.37 (1H, s), 4.59 (2H, s), 4.38-4.37 (1H, m), 4.29-4.26 (1H, m), 4.16 (2H, s), 4.01 (2H, d, J=2.0 Hz), 2.96-2.92 (1H, m), 1.89-1.86 (1H, m), 1.27-1.18 (6H, m), 0.87-0.82 (4H, m), 0.72 (2H, s).

LCMS Method 8: r.t. 3.16 mins [$MH^+$] 329.0.

Example 34

1-[6-(5-Isopropyl-1H-pyrazole-3-carbonyl)-2,6-diazaspiro[3.3]heptan-2-yl]-2-methyl-propan-1-one Prepared from tert-butyl 6-(5-isopropyl-1H-pyrazole-3-carbonyl)-2,6-diazaspiro[3.3]heptane-2-carboxylate and 2-methylpropanoic acid using Pyrazole Spirodiazetidine General Procedure 1. Reverse phase preparative HPLC afforded the title compound as a white solid (10 mg).

$^1H$ NMR (400 MHz, $d_6$-DMSO) δ, ppm 12.99 (1H, s), 6.37 (1H, d, J=1.5 Hz), 4.62-4.59 (2H, m), 4.36-4.30 (2H, m), 4.16-4.14 (2H, m), 4.03-4.00 (2H, m), 3.03-2.92 (1H, m), 2.46-2.38 (1H, m), 1.23 (6H, d, J=6.9 Hz), 0.97 (6H, d, J=6.8 Hz).

LCMS Method 8: r.t. 3.01 mins [$MH^+$] 305.0.

Example 35

1-[6-(5-Isopropyl-1H-pyrazole-3-carbonyl)-2,6-diazaspiro[3.3]heptan-2-yl]-2,2-dimethyl-propan-1-one Prepared from tert-butyl 6-(5-isopropyl-1H-pyrazole-3-carbonyl)-2,6-diazaspiro[3.3]heptane-2-carboxylate and pivalic acid using pyrazole spirodiazetidine General Procedure 1. Reverse phase preparative HPLC afforded the title compound as a white solid (37 mg).

$^1H$ NMR (400 MHz, $d_6$-DMSO) δ, ppm 13.00 (1H, s), 6.37 (1H, s), 4.61 (2H, s), 4.54 (2H, br s), 4.17-4.15 (2H, m), 4.01 (2H, br s), 3.03-2.92 (1H, m), 1.23 (6H, d, J=6.9 Hz), 1.11 (9H, s).

LCMS Method 8: r.t. 3.23 mins [$MH^+$] 319.0.

Example 36

(5-Isopropyl-1H-pyrazol-3-yl)-[2-(4-methylthiophene-2-carbonyl)-2,6-diazaspiro[3.3]heptan-6-yl] methanone Prepared from tert-butyl 6-(5-isopropyl-1H-pyrazole-3-carbonyl)-2,6-diazaspiro[3.3]heptane-2-carboxylate and 4-methylthiophene-2-carboxylic acid using Pyrazole Spirodiazetidine General Procedure 2. Purified by reverse phase chromatography to afford the title compound as a white solid (20 mg, 26%)

$^1$H NMR (400 MHz, $d_6$-DMSO) δ, ppm 12.99 (1H, s), 7.39 (1H, s), 7.31 (1H, d, J=1.0 Hz), 6.37 (1H, d, J=1.2 Hz), 4.63 (4H, s), 4.21-4.17 (4H, m), 3.01-2.91 (1H, m), 2.23 (3H, s), 1.21 (6H, d, J=7.0 Hz).

LCMS Method 1: r.t. 3.46 mins [$MH^+$] 359.1.

Example 37

[2-(5-Isopropyl-1H-pyrazole-3-carbonyl)-2,6-diazaspiro[3.3]heptan-6-yl]-[1-(2,2,2-trifluoroethyl)pyrazol-3-yl]methanone Prepared from tert-butyl 6-(5-isopropyl-1H-pyrazole-3-carbonyl)-2,6-diazaspiro[3.3]heptane-2-carboxylate and 1-(2,2,2-trifluoroethyl)pyrazole-3-carboxylic acid using Pyrazole Spirodiazetidine General Procedure 2. Purified by reverse phase preparative HPLC to afford the title compound as a white solid after lyophilisation, 37.0 mg (42%).

$^1$H NMR (400 MHz, $d_6$-DMSO) δ, ppm 12.98 (1H, s), 7.93 (1H, d, J=2.4 Hz), 6.71 (1H, d, J=2.4 Hz), 6.36 (1H, s), 5.20 (2H, q, J=9.1 Hz), 4.62 (4H, d, J=5.4 Hz), 4.22-4.15 (4H, m), 3.00-2.91 (1H, m), 1.21 (6H, d, J=6.9 Hz).

LCMS Method 1: r.t. 3.32 mins [$MH^+$] 411.0.

Example 38

[1-(2,2-Difluoroethyl)pyrazol-3-yl]-[2-(5-isopropyl-1H-pyrazole-3-carbonyl)-2,6-diazaspiro[3.3]heptan-6-yl]methanone Prepared from tert-butyl 6-(5-isopropyl-1H-pyrazole-3-carbonyl)-2,6-diazaspiro[3.3]heptane-2-carboxylate and 1-(2,2-difluoroethyl)pyrazole-3-carboxylic acid using Pyrazole Spirodiazetidine General Procedure 2. Purified by reverse phase chromatography to afford the title compound as a white solid (18.3 mg, 22%)

$^1$H NMR (400 MHz, $d_6$-DMSO) δ, ppm 12.97 (1H, s), 7.88-7.87 (1H, m), 6.68 (1H, d, J=2.4 Hz), 6.43 (1H, tt, J=3.7, 54.8 Hz), 6.38 (1H, s), 4.70 (2H, dt, J=3.6, 15.0 Hz), 4.64 (4H, d, J=5.0 Hz), 4.22-4.18 (4H, m), 3.02-2.91 (1H, m), 1.23 (6H, d, J=7.0 Hz).

LCMS Method 7: r.t. 3.27 mins [$MH^+$] 393.0.

Example 39

[2-(1,4-Dimethylpyrazole-3-carbonyl)-2,6-diazaspiro[3.3]heptan-6-yl]-(5-isopropyl-1H-pyrazol-3-yl) methanone Prepared from tert-butyl 6-(5-isopropyl-1H-pyrazole-3-carbonyl)-2,6-diazaspiro[3.3]heptane-2-carboxylate and 1,4-dimethylpyrazole-3-carboxylic acid using Pyrazole Spirodiazetidine General Procedure 3. White solid after lyophilisation (46.7 mg, 61%)

$^1$H NMR (400 MHz, $d_6$-DMSO) δ, ppm 12.97 (1H, d, J=0.8 Hz), 7.53 (1H, s), 6.36 (1H, d, J=1.5 Hz), 4.62 (2H, s), 4.58 (2H, s), 4.17-4.14 (4H, m), 3.80 (3H, s), 2.99-2.92 (1H, m), 2.15 (3H, s), 1.21 (6H, d, J=7.0 Hz).

LCMS Method 1: r.t. 3.04 mins [$MH^+$] 357.1.

Example 40

N-Isopropyl-6-(5-isopropyl-1H-pyrazole-3-carbonyl)-2,6-diazaspiro[3.3]heptane-2-carboxamide tert-Butyl 6-(5-isopropyl-1H-pyrazole-3-carbonyl)-2,6-diazaspiro[3.3]heptane-2-carboxylate (50 mg, 0.15 mmol) was suspended in acetonitrile (1 mL). To this was added MsOH (50 μL, 0.75 mmol). The resulting solution was stirred at rt for 30 mins. $Et_3N$ (0.21 mL, 1.50 mmol) was added followed by isopropyl isocyanate (59 μL, 0.60 mmol). The reaction was stirred for a further 16 h at rt. The solvent was removed in vacuo and the samples were dissolved in 10% water in DMSO and purified by reverse phase preparative HPLC. This gave the title compound as a white solid (27.3 mg, 57%).

$^1$H NMR (400 MHz, $d_6$-DMSO) δ, ppm 12.97 (1H, s), 6.36 (1H, s), 6.10-6.05 (1H, m), 4.55 (2H, s), 4.10 (2H, s), 3.91 (4H, s), 3.73-3.62 (1H, m), 2.99-2.92 (1H, m), 1.21 (6H, d, J=6.9 Hz), 1.02 (6H, d, J=6.8 Hz).

LCMS Method 7: r.t. 2.98 mins [$MH^+$] 320.0.

Example 41

N-Ethyl-6-(5-isopropyl-1H-pyrazole-3-carbonyl)-2,6-diazaspiro[3.3]heptane-2-carboxamide tert-Butyl 6-(5-isopropyl-1H-pyrazole-3-carbonyl)-2,6-diazaspiro[3.3]heptane-2-carboxylate (100 mg, 0.30 mmol) was suspended in acetonitrile (1 mL). To this was added MsOH (100 μL, 1.5 mmol). The resulting solution was stirred at rt for 30 mins. $Et_3N$ (0.42 mL, 3.0 mmol) was then added, followed by ethyl isocyanate (50 μL, 3.0 mmol). The reaction was stirred for a further 1 h at rt. The solvent was removed in vacuo and the samples were dissolved in 10% water in DMSO and purified by reverse phase preparative HPLC to give the title compound as a white solid (47.6 mg, 52%).

$^1$H NMR (400 MHz, $d_6$-DMSO) δ, ppm 12.99 (1H, s), 6.35 (1H, s), 6.34-6.28 (1H, m), 4.56 (2H, s), 4.10 (2H, s), 3.96-3.87 (4H, m), 3.03-2.91 (3H, m), 1.21 (6H, d, J=6.8 Hz), 0.98 (3H, t, J=7.1 Hz).

LCMS Method 7: r.t. 2.92 mins [$MH^+$] 306.0.

Example 42

(5-Isopropyl-1H-pyrazol-3-yl)-[2-(pyrrolidine-1-carbonyl)-2,6-diazaspiro[3.3]heptan-6-yl]methanone tert-Butyl 6-(5-isopropyl-1H-pyrazole-3-carbonyl)-2,6-diazaspiro[3.3]heptane-2-carboxylate (200 mg, 0.60 mmol) was suspended in acetonitrile (3 mL) To this was added MsOH (80 μL, 1.2 mmol). The resulting solution was stirred at rt for 30 mins. $Et_3N$ (0.5 mL, 3.6 mmol) was then added, followed by CDI (160 mg, 1.0 mmol). An aliquot of half of the reaction mixture was removed. To the solution was added pyrrolidine (0.25 mL, 3.1 mmol). The reaction mixture was heated to 60° C. and stirred for 24 h, followed by 80° C. for 2 h and 100° C. for 3 h. The reaction mixture was then concentrated in vacuo and the samples were dissolved in 10% water in DMSO and purified by reverse phase preparative HPLC to give the title compound as a white solid (29.5 mg, 29%).

$^1$H NMR (400 MHz, $d_6$-DMSO) δ, ppm 12.98 (1H, s), 6.36 (1H, s), 4.55 (2H, s), 4.11 (2H, s), 4.04-4.01 (4H, m), 3.22-3.16 (4H, m), 2.99-2.91 (1H, m), 1.78-1.73 (4H, m), 1.21 (6H, d, J=6.9 Hz).

LCMS Method 7: r.t. 3.01 mins [$MH^+$]332.3.

Example 43

N-Ethyl-6-(5-isopropyl-1H-pyrazole-3-carbonyl)-N-methyl-2,6-diazaspiro[3.3]heptane-2-carboxamide tert-Butyl 6-(5-isopropyl-1H-pyrazole-3-carbonyl)-2,6-diazaspiro[3.3]heptane-2-carboxylate (100 mg, 0.30 mmol) was suspended in acetonitrile (2 mL). To this was added MsOH (80 μL, 1.2 mmol). The resulting solution was stirred at rt for 1 h. $Et_3N$ (0.3 mL, 2.4 mmol) was then added followed by CDI (53 mg, 0.33 mmol). The reaction mixture was heated to 100° C. and stirred for 4 h, followed by 120° C. for 2 h. N-ethylmethylamine (0.26 mL, 3.0 mmol) was then added and the reaction was heated to 120° C. for 8 h, followed by 150° C. for 3 h. The reaction mixture was then concentrated in vacuo and the sample was dissolved in 10% water in DMSO and purified by reverse phase preparative HPLC to give the title compound as a white solid (24.2 mg, 25%).

$^1$H NMR (400 MHz, $d_6$-DMSO) δ, ppm 12.97 (1H, s), 6.36 (1H, s), 4.56 (2H, s), 4.11 (2H, s), 4.06-4.00 (4H, m), 3.13 (2H, q, J=7.1 Hz), 3.00-2.90 (1H, m), 2.71 (3H, s), 1.21 (6H, d, J=7.0 Hz), 1.01 (3H, t, J=7.2 Hz).

LCMS Method 7: r.t. 2.99 mins [$MH^+$] 320.3.

Example 44

(1-Ethylpyrazol-3-yl)-[2-(5-isopropyl-1H-pyrazole-3-carbonyl)-2,6-diazaspiro[3.3]heptan-6-yl]methanone Prepared from text-butyl 6-(5-isopropyl-1H-pyrazole-3-carbonyl)-2,6-diazaspiro[3.3]heptane-2-carboxylate and 1-ethylpyrazole-3-carboxylic acid using Pyrazole Spirodiazetidine General Procedure 3 to give the title compound as a white solid after lyophilisation (46.7 mg, 61%)

$^1$H NMR (400 MHz, $d_6$-DMSO) δ, ppm 7.81-7.79 (1H, m), 6.58 (1H, d, J=2.3 Hz), 6.36 (1H, d, J=1.2 Hz), 4.63 (4H, d, J=3.7 Hz), 4.21-4.14 (6H, m), 2.99-2.92 (1H, m), 1.38 (3H, t, J=7.2 Hz), 1.21 (6H, d, J=7.2 Hz) plus one exchangeable proton not observed.

LCMS Method 1: r.t. 3.04 mins [$MH^+$] 357.1.

Example 45 tert-Butyl (2-(4-(3-isopropyl-4-oxo-7-(1H-pyrazol-4-yl)-3,4-dihydroimidazo[2,1-f][1,2,4]triazin-2-yl)-1H-pyrazol-1-yl)ethyl)carbamate tert-Butyl (2-(4-(4,4,5,5-tetramethyl-1,3,2-dioxaborolan-2-yl)-1H-pyrazol-1-yl)ethyl)carbamate A mixture of 4-(4,4,5,5-tetramethyl-1,3,2-dioxaborolan-2-yl)-1H-pyrazole (1.5 g, 7.73 mmol), tert-butyl (2-bromoethyl)carbamate (2.43 g, 10.82 mmol) and potassium carbonate (2.14 g, 15.46 mmol) in DMF (30 mL) was heated at 50° C. for 16 h. The reaction mixture was diluted with water and extracted with ethyl acetate (×3). The combined organic fractions were washed with brine, dried ($MgSO_4$) and concentrated in vacuo. The residue was purified by silica gel chromatography eluting with 0-100% ethyl acetate in cyclohexane to yield the title compound as a white solid (567 mg, 22%).

LCMS Method 5: r.t. 1.41 mins, [$MH^+$-56], 282, [$MH^+$-100] 238.

tert-Butyl (2-(4-(3-isopropyl-4-oxo-3,4-dihydroimidazo[2,1-f][1,2,4]triazin-2-yl)-1H-pyrazol-1-yl)ethyl)carbamate A mixture of 2-bromo-3-isopropylimidazo[2,1-f][1,2,4]triazin-4(3H)-one (90 mg, 0.35 mmol), tert-butyl (2-(4-(4,4,5,5-tetramethyl-1,3,2-dioxaborolan-2-yl)-1H-pyrazol-1-yl)ethyl)carbamate (165 mg, 0.49 mmol), tetrakis(triphenylphosphine)palladium(0) (40 mg, 0.04 mmol) and cesium carbonate (171 mg, 0.53 mmol) in dioxane (3 mL), and water (0.3 mL) was degassed with argon and the reaction mixture heated at 100° C. for 1 h. The reaction mixture was diluted with water and extracted with ethyl acetate (×3). The combined organic fractions were washed with brine, dried ($MgSO_4$) and concentrated in vacuo. The residue was purified by silica gel chromatography eluting with 0-4% MeOH in DCM to yield the title compound as a yellow oil (80 mg, 59%).

LCMS Method 2: r.t. 1.06 mins, [$MH^+$] 388.

tert-Butyl (2-(4-(7-bromo-3-isopropyl-4-oxo-3,4-dihydroimidazo[2,1-f][1,2,4]triazin-2-yl)-1H-pyrazol-1-yl)ethyl)carbamate To a solution of tert-butyl (2-(4-(3-isopropyl-4-oxo-3,4-dihydroimidazo[2,1-f][1,2,4]triazin-2-yl)-1H-pyrazol-1-yl)ethyl)carbamate (120 mg, 0.31 mmol) in DMF (3 mL) was added NBS (61 mg, 0.34 mmol) and the mixture stirred at rt for 16 h. The reaction mixture was diluted with water and extracted with ethyl acetate (×3). The combined organic fractions were washed with brine, dried ($MgSO_4$) and concentrated in vacuo to yield the title compound as a yellow oil (140 mg, 99%).

LCMS Method 2 r.t. 1.37 mins, [$MH^+$] 466 & 468 tert-Butyl (2-(4-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl)-1H-pyrazol-1-yl)ethyl)carbamate A mixture of tert-butyl (2-(4-(7-bromo-3-isopropyl-4-oxo-3,4-dihydroimidazo[2,1-f][1,2,4]triazin-2-yl)-1H-pyrazol-1-yl)ethyl)c arbamate (140 mg, 0.30 mmol), 1-(tetrahydro-2H-pyran-2-yl)-4-(4,4,5,5-tetramethyl-1,3,2-dioxaborolan-2-yl)-1H-pyrazole (100 mg, 0.36 mmol), tetrakis(triphenylphosphine)palladium(0) (35 mg, 0.03 mmol) and cesium carbonate (147 mg, 0.45 mmol) in dioxane (5 mL), and water (0.5 mL) was degassed with argon and the reaction mixture heated at 100° C. for 16 h. The reaction mixture was diluted with water and extracted with ethyl acetate (×3). The combined organic fractions were washed with brine, dried ($MgSO_4$) and concentrated in vacuo. The residue was purified by silica gel chromatography eluting with 0-5% MeOH in DCM to yield the title compound as a yellow oil (52 mg, 32%).

LCMS Method 4: r.t. 1.34 mins, [$MH^+$] 538 tert-Butyl (2-(4-(3-isopropyl-4-oxo-7-(1H-pyrazol-4-yl)-3,4-dihydroimidazo[2,1-f][1,2,4]triazin-2-yl)-1H-pyrazol-1-yl)ethyl)carbamate To a solution of text-butyl (2-(4-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl)-1H-pyrazol-1-yl)ethyl) carbamate (52 mg, 0.10 mmol) in MeOH (3 mL) was added HCl aq. (0.4 mL, 1M, 0.4 mmol) and the reaction mixture stirred at rt for 16 h. A further aliquot of HCl aq. was added (0.4 mL, 1M, 0.4 mmol) was added and the reaction mixture stirred at rt for 16 h. The reaction mixture was made basic with 7N $NH_3$ in MeOH and concentrated in vacuo. The residue was purified by silica gel chromatography eluting with 0-5% (7N $NH_3$/MeOH) in DCM. The product was re-purified by reverse phase preparative HPLC to afford the title compound as a white solid after lyophilisation (9 mg, 20%).

$^1$H NMR (400 MHz, $CDCl_3$) δ, ppm 8.17 (2H, s), 7.82 (1H, s), 7.79 (1H, s), 7.67 (1H, s), 4.94 (1H, br s), 4.67 (1H, sept, J=6.8 Hz), 4.36 (2H, d, J=5.7 Hz), 3.71-3.61 (2H, m), 1.69 (6H, d, J=6.8 Hz), 1.44 (9H, s) plus one exchangeable not observed.

LCMS Method 1 r.t. 3.46 mins, [$MH^+$] 454.3

Example 46

3-isopropyl-2-(1-(2-methoxyethyl)-1H-pyrazol-4-yl)-7-(1H-pyrazol-4-yl)imidazo[2,1-f][1,2,4]triazin-4(3H)-one 3-Isopropyl-2-(1-(2-methoxyethyl)-1H-pyrazol-4-yl)imidazo[2,1-f][1,2,4]triazin-4(3H)-one A mixture of 2-bromo-3-isopropylimidazo[2,1-f][1,2,4]triazin-4(3H)-one (100 mg, 0.39 mmol), 1-(2-methoxyethyl)-4-(4,4,5,5-tetramethyl-1,3,2-dioxaborolan-2-yl)-1H-pyrazole (137 mg, 0.55 mmol), tetrakis(triphenylphosphine)palladium(0) (45 mg, 0.04 mmol) and cesium carbonate (190 mg, 0.58 mmol) in dioxane (3 mL), and water (0.3 mL) was degassed with argon and the reaction mixture heated at 100° C. for 16 h. A further aliquot of tetrakis(triphenylphosphine)palladium(0) (45 mg, 0.04 mmol) was added and the reaction heated for 5 h. The reaction mixture was diluted with water and extracted with ethyl acetate (×3). The combined organic fractions were washed with brine, dried ($MgSO_4$) and concentrated in vacuo. The residue was purified by silica gel chromatography eluting with 0-5% MeOH in DCM to yield the title compound as a yellow oil (50 mg, 42%).

LCMS Method 2: r.t. 1.08 mins, [$MH^+$] 303.

7-Bromo-3-isopropyl-2-(1-(2-methoxyethyl)-1H-pyrazol-4-yl)imidazo[2,1-f][1,2,4]triazin-4(3H)-one To a solution of 3-isopropyl-2-(1-(2-methoxyethyl)-1H-pyrazol-4-yl)imidazo[2,1-f][1,2,4]triazin-4(3H)-one (50 mg, 0.17 mmol) in DMF (2 mL) was added NBS (32 mg, 0.18 mmol) and the mixture stirred at rt for 2 h. The reaction mixture was diluted with water and extracted with ethyl acetate (×3). The combined organic fractions were washed with brine, dried ($MgSO_4$) and concentrated in vacuo to yield the title compound as a yellow oil (45 mg, 71%).

LCMS Method 4: r.t. 1.15 mins, [$MH^+$] 381 & 383

3-Isopropyl-2-(1-(2-methoxyethyl)-1H-pyrazol-4-yl)-7-(1-(tetrahydro-2H-pyran-2-yl)-1H-pyrazol-4-yl)imidazo[2,1-f][1,2,4]triazin-4(3H)-one A mixture 7-bromo-3-isopropyl-2-(1-(2-methoxyethyl)-1H-pyrazol-4-yl)imidazo[2,1-f][1,2,4]triazin-4(3H)-one (45 mg, 0.12 mmol), 1-(tetrahydro-2H-pyran-2-yl)-4-(4,4,5,5-tetramethyl-1,3,2-dioxaborolan-2-yl)-1H-pyrazole (46 mg, 0.17 mmol), tetrakis(triphenylphosphine)palladium(0) (14 mg, 0.01 mmol) and cesium carbonate (58 mg, 0.18 mmol) in dioxane (3 mL), and water (0.3 mL) was degassed with argon and the reaction mixture heated at 100° C. for 16 h. The reaction mixture was diluted with water and extracted with ethyl acetate (×3). The combined organic fractions were washed with brine, dried ($MgSO_4$) and concentrated in vacuo to yield the title compound as a yellow oil (83 mg, 156%). Used crude in the next reaction.

LCMS Method 4: r.t. 1.21 mins, [$MH^+$] 453

3-Isopropyl-2-(1-(2-methoxyethyl)-1H-pyrazol-4-yl)-7-(1H-pyrazol-4-yl)imidazo[2,1-f][1,2,4]triazin-4(3H)-one To a solution of 3-isopropyl-2-(1-(2-methoxyethyl)-1H-pyrazol-4-yl)-7-(1-(tetrahydro-2H-pyran-2-yl)-1H-pyrazol-4-yl)imidazo[2,1-f][1,2,4]triazin-4(3H)-one (83 mg, ~0.12 mmol) in MeOH (3 mL) was added HCl aq. (2 mL, 1M, 2.00 mmol) and the reaction mixture stirred at rt for 16 h. The reaction mixture was concentrated in vacuo and the residue purified by reverse phase preparative HPLC to afford the title compound as a white solid after lyophilisation (10 mg, 23%).

$^1$H NMR (400 MHz, $d_6$-DMSO) δ, ppm 13.16 (1H, s), 8.29 (1H, s), 8.22 (2H, s), 7.91 (1H, s), 7.76 (1H, s), 4.57 (1H, sept, J=6.7 Hz), 4.40 (2H, t, J=5.3 Hz), 3.77 (2H, t, J=5.3 Hz), 3.27 (3H, s), 1.57 (6H, d, J=6.8 Hz), LCMS Method 1: r.t. 2.91 mins, [$MH^+$] 369

Example 47

N-(2-(4-(3-isopropyl-4-oxo-7-(1H-pyrazol-4-yl)-3,4-dihydroimidazo[2,1-f][1,2,4]triazin-2-yl)-1H-pyrazol-1-yl)ethyl)acetamide N-(2-(4-(3-Isopropyl-4-oxo-3,4-dihydroimidazo[2,1-f][1,2,4]triazin-2-yl)-1H-pyrazol-1-yl)ethyl)acetamide A mixture of 2-bromo-3-isopropylimidazo[2,1-f][1,2,4]triazin-4(3H)-one (100 mg, 0.39 mmol), N-(2-(4-(4,4,5,5-tetramethyl-1,3,2-dioxaborolan-2-yl)-1H-pyrazol-1-yl)ethyl)acetamide (100 mg, 0.36 mmol), tetrakis(triphenylphosphine)palladium(0) (34 mg, 0.03 mmol) and cesium carbonate (195 mg, 0.60 mmol) in dioxane (3 mL), and water (0.3 mL) was degassed with argon and the reaction mixture heated at 100° C. for 16 h. The reaction mixture was diluted with water and extracted with ethyl acetate (×3). The combined organic fractions were washed with brine, dried ($MgSO_4$) and concentrated in vacuo. The residue was purified by silica gel chromatography eluting with 0-10% MeOH in DCM to yield the title compound as a yellow oil (51 mg, 52%).

LCMS Method 4: r.t. 0.85 mins, [$MH^+$] 330.

N-(2-(4-(7-Bromo-3-isopropyl-4-oxo-3,4-dihydroimidazo[2,1-f][1,2,4]triazin-2-yl)-1H-pyrazol-1-yl)ethyl)acetamide To a solution of N-(2-(4-(3-isopropyl-4-oxo-3,4-dihydroimidazo[2,1-f][1,2,4]triazin-2-yl)-1H-pyrazol-1-yl)ethyl)acetamide (81 mg, 0.25 mmol) in DMF (3 mL) was added NBS (48 mg, 0.27 mmol) and the mixture stirred at rt for 1 h. The reaction mixture was diluted with water and extracted with ethyl acetate (×3). The combined organic fractions were washed with brine, dried ($MgSO_4$) and concentrated in vacuo to yield the title compound as a yellow oil. The aqueous phase was concentrated in vacuo and the residue extracted with ethyl acetate. The organic phase was concentrated in vacuo to give a second batch of product as a yellow oil. Both batches were combined to give the title compound (75 mg, 75%)

LCMS Method 5: r.t. 0.93 mins, [$MH^+$] 408 & 410

N-(2-(4-(3-Isopropyl-4-oxo-7-(1-(tetrahydro-2H-pyran-2-yl)-1H-pyrazol-4-yl)-3,4-dihydroimidazo[2,1-f][1,2,4]triazin-2-yl)-1H-pyrazol-1-yl)ethyl)acetamide A mixture N-(2-(4-(7-bromo-3-isopropyl-4-oxo-3,4-dihydroimidazo[2,1-f][1,2,4]triazin-2-yl)-1H-pyrazol-1-yl)ethyl)acetamide (75 mg, 0.18 mmol), 1-(tetrahydro-2H-pyran-2-yl)-4-(4,4,5,5-tetramethyl-1,3,2-dioxaborolan-2-yl)-1H-pyrazole (72 mg, 0.26 mmol), tetrakis(triphenylphosphine)palladium(0) (21 mg, 0.02 mmol) and cesium carbonate (90 mg, 0.28 mmol) in dioxane (3 mL), and water (0.3 mL) was degassed with argon and the reaction mixture heated at 100° C. for 2 h. The reaction mixture was diluted with water and extracted with ethyl acetate (×3). The combined organic fractions were washed with brine, dried ($MgSO_4$) and concentrated in vacuo The residue was purified by silica gel chromatography eluting with 0-10% MeOH in DCM to yield the title compound as a yellow oil (51 mg, 58%).

LCMS Method 4: r.t. 1.06 mins, [$MH^+$] 480

N-(2-(4-(3-Isopropyl-4-oxo-7-(1H-pyrazol-4-yl)-3,4-dihydroimidazo[2,1-f][1,2,4]triazin-2-yl)-1H-pyrazol-1-yl)ethyl)acetamide To a solution of N-(2-(4-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl)-1H-pyrazol-1-yl)ethyl)acetamide (51 mg, 0.11 mmol) in MeOH (3 mL) was added HCl aq. (1 mL, 1M, 1.00 mmol) and the reaction mixture stirred at rt for 16 h. The reaction mixture was made basic by addition of 7N $NH_3$ in MeOH concentrated in vacuo. The residue purified by silica gel chromatography eluting with 0-10% (7N $NH_3$/MeOH) in DCM to yield the title compound as a white solid (10 mg, 25%).

$^1$H NMR (400 MHz, $d_6$-DMSO) δ, ppm 13.17 (1H, s), 8.34 (1H, s), 8.27 (1H, s), 8.12 (1H, s), 8.02 (1H, t, J=5.6 Hz), 7.92 (1H, s), 7.76 (1H, s), 4.58 (1H, sept, J=6.8 Hz), 4.27 (2H, t, J=5.9 Hz), 3.50 (2H, q, J=5.9 Hz), 1.80 (3H, s), 1.56 (6H, d, J=6.8 Hz).

LCMS Method 1: r.t. 2.48 mins, [$MH^+$] 396

Example 48

3-Isopropyl-7-(1H-pyrazol-4-yl)-2-(1-(3,3,3-trifluoropropyl)-1H-pyrazol-4-yl)imidazo[2,1-f][1,2,4]triazin-4(3H)-one 3-Isopropyl-2-(1-(3,3,3-trifluoropropyl)-1H-pyrazol-4-yl)imidazo[2,1-f][1,2,4]triazin-4(3H)-one A mixture of 2-chloro-3-isopropylimidazo[2,1-f][1,2,4]triazin-4(3H)-one (200 mg, 0.94 mmol), 4-(4,4,5,5-tetramethyl-1,3,2-dioxaborolan-2-yl)-1-(3,3,3-trifluoropropyl)-1H-pyrazole (409 mg, 1.41 mmol), tetrakis(triphenylphosphine)palladium(0) (109 mg, 0.09 mmol) and cesium carbonate (613 mg, 1.88 mmol) in dioxane (5 mL), and water (0.5 mL) was degassed with argon and the reaction mixture heated at 100° C. for 16 h. A further aliquot of tetrakis(triphenylphosphine)palladium(0) (100 mg, 0.09 mmol) was added and the reaction heated for 3 h. The reaction mixture was diluted with water and extracted with ethyl acetate (×3). The combined organic fractions were washed with brine, dried ($MgSO_4$) and concentrated in vacuo. The residue was purified by silica gel chromatography eluting with 0-10% MeOH in DCM to yield the title compound as a yellow oil (100 mg, 31%).

LCMS Method 5: r.t. 1.18 mins, [$MH^+$] 341

7-Bromo-3-isopropyl-2-(1-(3,3,3-trifluoropropyl)-1H-pyrazol-4-yl)imidazo[2,1-f][1,2,4]triazin-4(3H)-one To a solution of 3-isopropyl-2-(1-(3,3,3-trifluoropropyl)-1H-pyrazol-4-yl)imidazo[2,1-f][1,2,4]triazin-4(3H)-one (99 mg, 0.29 mmol) in DMF (4 mL) was added NBS (57 mg, 0.32 mmol) and the mixture stirred at rt for 2 h. The reaction mixture was diluted with water and extracted with ethyl acetate (×3). The combined organic fractions were washed with brine, dried ($MgSO_4$) and concentrated in vacuo to yield the title compound as a yellow oil. (146 mg, 120%)

LCMS Method 4: r.t. 1.33 mins, [$MH^+$] 419 & 421

3-Isopropyl-7-(1-(tetrahydro-2H-pyran-2-yl)-1H-pyrazol-4-yl)-2-(1-(3,3,3-trifluoropropyl)-1H-pyrazol-4-yl)imidazo[2,1-f][1,2,4]triazin-4(3H)-one A mixture 7-bromo-3-isopropyl-2-(1-(3,3,3-trifluoropropyl)-1H-pyrazol-4-yl)imidazo[2,1-f][1,2,4]triazin-4(3H)-one (~122 mg, ~0.29 mmol), 1-(tetrahydro-2H-pyran-2-yl)-4-(4,4,5,5-tetramethyl-1,3,2-dioxaborolan-2-yl)-1H-pyrazole (136 mg, 0.49 mmol), tetrakis(triphenylphosphine)palladium(0) (40 mg, 0.03 mmol) and cesium carbonate (170 mg, 0.52 mmol) in dioxane (3 mL), and water (0.3 mL) was degassed with argon and the reaction mixture heated at 100° C. for 16 h. The reaction mixture was diluted with water and extracted with ethyl acetate (×3). The combined organic fractions were washed with brine, dried ($MgSO_4$) and concentrated in vacuo The residue was purified by silica gel chromatography eluting with 0-5% MeOH in DCM to yield the title compound as a yellow oil (100 mg, 58%).

LCMS Method 2: r.t. 1.25 mins, [$MH^+$] 491

3-Isopropyl-7-(1H-pyrazol-4-yl)-2-(1-(3,3,3-trifluoropropyl)-1H-pyrazol-4-yl)imidazo[2,1-f][1,2,4]triazin-4(3H)-one To a solution of 3-isopropyl-7-(1-(tetrahydro-2H-pyran-2-yl)-1H-pyrazol-4-yl)-2-(1-(3,3,3-trifluoropropyl)-1H-pyrazol-4-yl)imidazo[2,1-f][1,2,4]triazin-4(3H)-one (100 mg, 0.20 mmol) in MeOH (3 mL) was added HCl aq. (4 mL, 1M, 4.00 mmol) and the reaction mixture stirred at rt for 3 h. The reaction mixture was made basic by addition of 7N $NH_3$ in MeOH then concentrated in vacuo. The residue purified by silica gel chromatography eluting with 0-5% (7N $NH_3$/MeOH) in DCM. The residue was triturated with hot acetonitrile and collected by filtration to yield the title compound as a white solid (20 mg, 24%).

$^1H$ NMR (400 MHz, $d_6$-DMSO) δ, ppm 13.17 (1H, s), 8.42 (1H, s), 8.33 (1H, s), 8.12 (1H, s), 7.95 (1H, s), 7.77 (1H, s), 4.58-4.48 (3H, m), 3.04-2.91 (2H, m), 1.56 (6H, d, J=6.6 Hz).

LCMS Method 1: r.t. 3.54 mins, [$MH^+$] 407

Example 49

3-Isopropyl-2-(1-(1-phenylethyl)-1H-pyrazol-4-yl)-7-(1H-pyrazol-4-yl)imidazo[2,1-f][1,2,4]triazin-4(3H)-one 3-Isopropyl-2-(1-(1-phenylethyl)-1H-pyrazol-4-yl)imidazo[2,1-f][1,2,4]triazin-4(3H)-one A mixture of 2-chloro-3-isopropylimidazo[2,1-f][1,2,4]triazin-4(3H)-one (200 mg, 0.94 mmol), 1-(1-phenylethyl)-4-(4,4,5,5-tetramethyl-1,3,2-dioxaborolan-2-yl)-1H-pyrazole (421 mg, 1.41 mmol), tetrakis(triphenylphosphine)palladium(0) (109 mg, 0.09 mmol) and cesium carbonate (613 mg, 1.88 mmol) in dioxane (5 mL), and water (0.5 mL) was degassed with argon and the reaction mixture heated at 100° C. for 16 h. The reaction mixture was concentrated in vacuo onto ISOLUTE® HM-N column (Biotage) and the residue was purified by silica gel chromatography eluting with 0-10% MeOH in DCM to yield the title compound as a yellow oil (114 mg, 33%).

LCMS Method 5: r.t. 1.37 mins, [$MH^+$] 349

7-Bromo-3-isopropyl-2-(1-(1-phenylethyl)-1H-pyrazol-4-yl)imidazo[2,1-f][1,2,4]triazin-4(3H)-one To a solution of 3-isopropyl-2-(1-(1-phenylethyl)-1H-pyrazol-4-yl)imidazo[2,1-f][1,2,4]triazin-4(3H)-one (114 mg, 0.33 mmol) in DMF (3 mL) was added NBS (64 mg, 0.36 mmol) and the mixture stirred at rt for 2.5 h. The reaction mixture was diluted with water and extracted with ethyl acetate (×3). The combined organic fractions were washed with brine, dried ($MgSO_4$) and concentrated in vacuo to yield the title compound as a yellow oil. (149 mg, 105%)

LCMS Method 5: r.t. 1.56 mins, [$MH^+$] 427 & 429

3-Isopropyl-2-(1-(1-phenylethyl)-1H-pyrazol-4-yl)-7-(1-(tetrahydro-2H-pyran-2-yl)-1H-pyrazol-4-yl)imidazo[2,1-f][1,2,4]triazin-4(3H)-one A mixture 7-bromo-3-isopropyl-2-(1-(1-phenylethyl)-1H-pyrazol-4-yl)imidazo[2,1-f][1,2,4]triazin-4(3H)-one (~140 mg, ~0.32 mmol), 1-(tetrahydro-2H-pyran-2-yl)-4-(4,4,5,5-tetramethyl-1,3,2-dioxaborolan-2-yl)-1H-pyrazole (136 mg, 0.49 mmol), tetrakis(triphenylphosphine)palladium(0) (40 mg, 0.03 mmol) and cesium carbonate (170 mg, 0.52 mmol) in dioxane (3 mL), and water (0.3 mL) was degassed with argon and the reaction mixture heated at 100° C. for 2.5 h. The reaction mixture was concentrated in vacuo onto ISOLUTE® HM-N column (Biotage) and the residue purified by silica gel chromatography eluting with 0-10% MeOH in DCM. The residue was re-purified by silica gel chromatography eluting with 0-100% ethyl acetate in cyclohexane to yield the title compound as a yellow oil (44 mg, 25%).

LCMS Method 5: r.t. 1.59 mins, [$MH^+$] 499

3-Isopropyl-2-(1-(1-phenylethyl)-1H-pyrazol-4-yl)-7-(1H-pyrazol-4-yl)imidazo[2,1-f][1,2,4]triazin-4(3H)-one To a solution of 3-isopropyl-2-(1-(1-phenylethyl)-1H-pyrazol-4-yl)-7-(1-(tetrahydro-2H-pyran-2-yl)-1H-pyrazol-4-yl)imidazo[2,1-f][1,2,4]triazin-4(3H)-one (44 mg, 0.09 mmol) in MeOH (3 mL) was added HCl aq. (2 mL, 1M, 2.00 mmol) and the reaction mixture stirred at RT for 3 h. The reaction mixture was made basic by addition of 7N $NH_3$ in MeOH then concentrated in vacuo. The residue was purified by silica gel chromatography eluting with 0-10% MeOH in DCM to yield the title compound as a white solid (17 mg, 46%).

$^1H$ NMR (400 MHz, $d_6$-DMSO) δ, ppm 13.16 (1H, s), 8.47 (1H, s), 8.33 (1H, s), 8A1 (1H, s), 7.94 (1H, s), 7.76 (1H, s), 7.43-7.26 (5H, m), 5.79 (1H, q, J=7.0 Hz), 4.56 (1H, sept, J=6.8 Hz), 1.89 (3H, d, J=7.0 Hz), 1.56 (6H, t, J=7.1 Hz).

LCMS Method 9: r.t. 3.91 mins, [$MH^+$] 415

Example 50

7-(1H-Imidazol-4-yl)-2-(1-isopentyl-1H-pyrazol-4-yl)-3-isopropylimidazo[2,1-f][1,2,4]triazin-4(3H)-one 2-(1-Isopentyl-1H-pyrazol-4-yl)-3-isopropyl-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and (1-isopentylpyrazol-4-yl)boronic acid using Suzuki-Miyaura General Procedure 1 to afford the title compound as a yellow oil, (72 mg, 60%).

LCMS Method 2: r.t. 1.61 mins, [$MH^+$] 623

7-(1H-imidazol-4-yl)-2-(1-isopentyl-1H-pyrazol-4-yl)-3-isopropylimidazo[2,1-f][1,2,4]triazin-4(3H)-one Prepared from 2-(1-isopentyl-1H-pyrazol-4-yl)-3-isopropyl-7-(1-trityl-1H-imidazol-4-yl)imidazo[2,1-f][1,2,4]triazin-4(3H)-one by Trityl Deprotection Procedure 1 to yield the title compound as a white solid (20 mg, 45%)

$^1H$ NMR (400 MHz, $d_6$-DMSO) δ, ppm 12.34 (1H, s), 8.34 (1H, s), 7.89 (1H, s), 7.80 (1H, s), 7.71 (2H, s), 4.56 (1H, sept, J=6.9 Hz), 4.25 (2H, t, J=7.4 Hz), 1.76 (2H, q, J=7.4 Hz), 1.60-1.48 (7H, m), 0.93 (6H, d, J=6.7 Hz).

LCMS Method 1: r.t. 3.17 mins, [$MH^+$] 381

Example 51 tert-Butyl (2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)carbamate tert-Butyl (2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)carbamate Prepared from 2-chloro-3-isopropyl-7-(1-trityl-1H-imidazol-4-yl)imidazo[2,1-f][1,2,4]triazin-4(3H)-one and [1-[2-(tert-butoxycarbonylamino)ethyl]pyrazol-4-yl]boronic acid using Suzuki-Miyaura General Procedure 1 to afford the title compound as a yellow oil, (63 mg, 47%).

LCMS Method 2: r.t. 1.46 mins, [$MH^+$] 696 tert-Butyl (2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)carbamate A suspension of tert-butyl (2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)carbamate in MeOH (90 mM) was treated with 1N HCl (aq) (6 eq.) and the reaction mixture was stirred at rt for 21 h. The reaction was quenched with 7N ammonia in MeOH and the reaction evaporated to dryness. Purification was by reverse phase chromatography to afford the title compound as a white solid (8 mg, 27%)

$^1$H NMR (400 MHz, $d_6$-DMSO) δ, ppm 12.34 (1H, s), 8.26 (1H, s), 7.90 (1H, s), 7.80 (1H, s), 7.73 (1H, s), 7.71 (1H, s), 7.00 (1H, t, J=5.5 Hz), 4.60 (1H, sept, J=6.8 Hz), 4.26 (2H, t, J=6.1 Hz), 3.40 (2H, d, J=6.1 Hz), 1.57 (6H, d, J=6.8 Hz), 1.35 (9H, s).

LCMS Method 3: r.t. 2.71 mins, [$MH^+$] 454.3

Example 52

7-(1H-Imidazol-4-yl)-3-isopropyl-2-(4-(piperidin-1-yl)phenyl)imidazo[2,1-f][1,2,4]triazin-4(3H)-one 3-Isopropyl-2-(4-(piperidin-1-yl)phenyl)-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and [4-(1-piperidyl)phenyl]boronic acid using Suzuki-Miyaura General Procedure 1 to afford the title compound as a yellow oil, (68 mg, 55%).

LCMS Method 2: r.t. 1.74 mins, [$MH^+$] 646

7-(1H-Imidazol-4-yl)-3-isopropyl-2-(4-(piperidin-1-yl)phenyl)imidazo[2,1-f][1,2,4]triazin-4(3H)-one Prepared from 3-isopropyl-2-(4-(piperidin-1-yl)phenyl)-7-(1-trityl-1H-imidazol-4-yl)imidazo[2,1-f][1,2,4]triazin-4(3H)-one by Trityl Deprotection Procedure 1 to yield the title compound as a white solid (12 mg, 29%)

$^1$H NMR (400 MHz, $d_6$-DMSO) δ, ppm 12.29 (1H, s), 7.78 (1H, s), 7.71 (1H, s), 7.58 (1H, s), 7.51 (2H, d, J=8.6 Hz), 7.08 (2H, d, J=8.6 Hz), 4.27 (1H, sept, J=6.8 Hz), 3.33-3.27 (4H, m), 1.67-1.55 (6H, m), 1.51 (6H, d, J=6.8 Hz).

LCMS Method 1: r.t. 3.36 mins, [$MH^+$] 404.4

Example 53

7-(1H-Imidazol-4-yl)-2-(1H-indol-2-yl)-3-isopropylimidazo[2,1-f][1,2,4]triazin-4(3H)-one 2-(1H-Indol-2-yl)-3-isopropyl-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and indol-2-boronic acid using Suzuki-Miyaura General Procedure 1 to afford the title compound as a yellow oil, (49 mg, 43%).

LCMS Method 2 r.t. 1.67 mins, [$MH^+$] 602

7-(1H-Imidazol-4-yl)-2-(1H-indol-2-yl)-3-isopropylimidazo[2,1-f][1,2,4]triazin-4(3H)-one Prepared from 2-(1H-Indol-2-yl)-3-isopropyl-7-(1-trityl-1H-imidazol-4-yl)imidazo[2,1-f][1,2,4]triazin-4(3H)-one by Trityl Deprotection Procedure 1 to yield the title compound as a white solid (8 mg, 27%).

$^1$H NMR (400 MHz, $d_6$-DMSO) δ, ppm 12.38 (1H, s), 11.86 (1H, s), 7.85-7.74 (3H, m), 7.70 (1H, d, J=8.0 Hz), 7.56 (1H, d, J=8.0 Hz), 7.28 (1H, t, J=7.7 Hz), 7.14 (1H, t, J=7.7 Hz), 6.98 (1H, s), 4.59 (1H, sept, J=6.8 Hz), 1.60 (6H, d, J=6.8 Hz).

LCMS Method 1: r.t. 3.43 mins, [$MH^+$] 360.2

Example 54

2-(1-(2-Hydroxy-1-phenylethyl)-1H-pyrazol-4-yl)-3-isopropyl-7-(1H-pyrazol-4-yl)imidazo[2,1-f][1,2,4]triazin-4(3H)-one (2-Bromo-2-phenylethoxy)(tert-butyl)dimethylsilane To a solution of 2-bromo-2-phenylethan-1-ol (2.00 g, 9.95 mmol) in THF (50 mL) was added tert-butyldimethylsilyl chloride (1.80 g, 11.94 mmol) and imidazole (0.88 g, 12.93 mmol) and the resulting mixture stirred at rt for 16 h. The reaction mixture was diluted with water and extracted with ethyl acetate (×3). The combined organic fractions were dried ($MgSO_4$) and concentrated in vacuo to give the title compound as a colourless oil (3.3 g, quant).

$^1$H NMR (400 MHz, $CDCl_3$) δ, ppm 7.42-7.25 (5H, m), 4.91 (1H, t, J=6.9 Hz), 4.09 (1H, dd, J=10.8, 6.7 Hz), 3.99 (1H, dd, J=10.8, 7.1 Hz), 0.81 (9H, s), 0.00 (3H, s), −0.06 (3H, s).

1-(2-((tert-Butyldimethylsilyl)oxy)-1-phenylethyl)-4-(4,4,5,5-tetramethyl-1,3,2-dioxaborolan-2-yl)-1H-pyrazole A mixture of 4-(4,4,5,5-tetramethyl-1,3,2-dioxaborolan-2-yl)-1H-pyrazole (1.00 g, 5.15 mmol), (2-bromo-2-phenylethoxy)(tert-butyl)dimethylsilane (2.44 g, 7.73 mmol), cesium carbonate (5.04 g, 15.46 mmol) and potassium iodide (0.43 g, 2.58 mmol) in DMF (20 mL) was heated at 60° C. for 48 h. The reaction mixture was diluted with water and extracted with ethyl acetate (×3). The combined organic fractions were washed with brine, dried ($MgSO_4$) and concentrated in vacuo. The residue was purified by silica gel chromatography, eluting with 0-70% ethyl acetate in cyclohexane to yield the title compound as a white solid (394 mg, 18%).

$^1$H NMR (400 MHz, $CDCl_3$) δ, ppm 7.91 (1H, s), 7.86 (1H, s), 7.46-7.25 (5H, m), 5.47 (1H, dd, J=7.1, 5.6 Hz), 4.47

(1H, dd, J=10.6, 7.1 Hz), 4.25 (1H, dd, J=10.5, 5.6 Hz), 1.38 (12H, s), 0.87 (9H, s), 0.01 (3H, s), 0.00 (3H, s).

2-(1-(2-((tert-Butyldimethylsilyl)oxy)-1-phenylethyl)-1H-pyrazol-4-yl)-3-isopropyl-7-(1-(tetrahydro-2H-pyran-2-yl)-1H-pyrazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 1-(2-((tert-butyldimethylsilyl)oxy)-1-phenylethyl)-4-(4,4,5,5-tetramethyl-1,3,2-dioxaborolan-2-yl)-1H-pyrazole using Suzuki-Miyaura General Procedure 1 to afford the title compound as a yellow oil, (41 mg, 26%).

LCMS Method 4 r.t. 1.89 mins, [$MH^+$] 629

2-(1-(2-hydroxy-1-phenylethyl)-1H-pyrazol-4-yl)-3-isopropyl-7-(1H-pyrazol-4-yl)imidazo[2,1-f][1,2,4]triazin-4(3H)-one To a solution of 2-(1-(2-((tert-butyldimethylsilyl)oxy)-1-phenylethyl)-1H-pyrazol-4-yl)-3-isopropyl-7-(1-(tetrahydro-2H-pyran-2-yl)-1H-pyrazol-4-yl)imidazo[2,1-f][1,2,4]triazin-4(3H)-one (78 mg, 0.12 mmol) in MeOH (0.5 mL) was added HCl in dioxane (4N, 3 mL, 12.00 mmol) and the reaction mixture stirred at rt for 20 min. The reaction mixture was concentrated in vacuo and the residue purified by reverse phase chromatography to afford the title compound as a white solid (26 mg, 49%).

$^1$H NMR (400 MHz, $d_6$-DMSO) δ, ppm 13.18 (1H, s), 8.53 (1H, s), 8.24 (2H, s), 7.98 (1H, s), 7.77 (1H, s), 7.46-7.30 (5H, m), 5.64 (1H, dd, J=9.0, 4.8 Hz), 5.26 (1H, br, s), 4.60 (1H, sept, J=6.7 Hz), 4.36-4.28 (1H, m), 4.03-196 (1H, m), 1.58 (6H, t, J=6.6 Hz).

LCMS Method 8: r.t. 3.34 mins, [$MH^+$] 431.0

Example 55

2-(1-Cyclohexyl-1H-pyrazol-4-yl)-3-isopropyl-7-(1H-pyrazol-4-yl)imidazo[2,1-f][1,2,4]triazin-4(3H)-one 2-(1-Cyclohexyl-1H-pyrazol-4-yl)-3-isopropyl-7-(1-(tetrahydro-2H-pyran-2-yl)-1H-pyrazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 1-cyclohexyl-4-(4,4,5,5-tetramethyl-1,3,2-dioxaborolan-2-yl)pyrazole using Suzuki-Miyaura General Procedure 1 to afford the title compound as a yellow oil, (63 mg, 79%).

LCMS Method 4: r.t. 1.52 mins, [$MH^+$] 477

2-(1-Cyclohexyl-1H-pyrazol-4-yl)-3-isopropyl-7-(1H-pyrazol-4-yl)imidazo[2,1-f][1,2,4]triazin-4(3H)-one To a solution of 2-(1-cyclohexyl-1H-pyrazol-4-yl)-3-isopropyl-7-(1-(tetrahydro-2H-pyran-2-yl)-1H-pyrazol-4-yl)imidazo[2,1-f][1,2,4]triazin-4(3H)-one (63 mg, 0.13 mmol) in MeOH (2 mL) was added HCl aq. (1M, 3 mL, 3 mmol) and the reaction mixture stirred at rt for 3 h. The reaction mixture was concentrated in vacuo and the residue purified by reverse phase chromatography to afford the title compound as a white solid (24 mg, 46%).

$^1$H NMR (400 MHz, $d_6$-DMSO) δ, ppm 13.18 (1H, s), 8.36 (1H, s), 8.25 (2H, s), 7.91 (1H, s), 7.77 (1H, s), 4.59 (1H, sept, J=6.8 Hz), 4.30 (1H, tt, J=11.5, 3.7 Hz), 2.16-2.06 (2H, m), 1.91-1.66 (5H, m), 1.58 (6H, d, J=6.8 Hz), 1.51-1.36 (2H, m), 1.26 (1H, qt, J=12.6, 3.5 Hz).

LCMS Method 7: r.t. 4.05 mins, [$MH^+$] 393.0

Example 56

(5-Isopropyl-1H-pyrazol-3-yl)(3-(6-methyl-4-(p-tolyl)pyridin-2-yl)azetidin-1-yl)methanone tert-Butyl 3-(2-(3-methylisoxazol-5-yl)acetyl)azetidine-1-carboxylate To a solution of 3,5-dimethylisoxazole (2.6 mL, 26.2 mmol) in THF (75 mL) at −78° C. was added nBuLi (11.5 mL, 2.5 M, 28.82 mmol) at such a rate that temp remained below −60° C. The reaction mixture was allowed to warm to −40° C. then cooled to −78° C. and stirred for 45 min tert-butyl 3-(methoxy(methyl)carbamoyl)azetidine-1-carboxylate (3.20 g, 13.10 mmol) was added and the reaction allowed to warm to rt over 1 h. The reaction mixture was diluted with sat. aq. $NH_4Cl$ and extracted with ethyl acetate (×3). The combined organic fractions were washed with brine, dried ($MgSO_4$) and concentrated in vacuo. The residue was purified by silica gel chromatography eluting with 0-100% ethyl acetate in cyclohexane to yield the title compound as a colourless oil (2.49 g, 68%).

LCMS Method 5: r.t. 1.42 mins, $[M\text{-}tBu+2H]^+$225, $[M\text{-}Boc+2H]^+$181 tert-Butyl 3-(4-hydroxy-6-methylpyridin-2-yl)azetidine-1-carboxylate

To a solution of tert-butyl 3-(2-(3-methylisoxazol-5-yl)acetyl)azetidine-1-carboxylate (2.49 g, 8.88 mmol) in ethanol (25 mL) was added palladium on carbon (0.25 g, 10%) and the reaction mixture stirred under an atmosphere of hydrogen for 16 h. The reaction mixture was then heated at 45° C. for 4 h. The reaction mixture was filtered and the filtrate concentrated in vacuo. The residue was purified by silica gel chromatography eluting with 0-10% (7N $NH_3$/MeOH) in DCM then re-purified by silica gel chromatography eluting with 0-10% (7N $NH_3$/MeOH) in ethyl acetate to yield the title compound as a white solid (838 mg, 36%)

LCMS Method 5: r.t. 1.00 mins, $[M\text{-}tBu+2H]^+$209 tert-Butyl 3-(6-methyl-4-(((trifluoromethyl)sulfonyl)oxy)pyridin-2-yl)azetidine-1-carboxylate To a suspension of tert-butyl 3-(4-hydroxy-6-methylpyridin-2-yl)azetidine-1-carboxylate (828 mg, 3.11 mmol) and triethylamine (1.3 mL, 9.34 mmol) in DCM (30 mL) was added dropwise, trifluoromethanesulfonic anhydride (1.3 mL, 7.78 mmol) causing the solids to dissolve. The reaction mixture was stirred at rt for 16 h. The reaction mixture was diluted with water and extracted with ethyl acetate (×3). The combined organic fractions were dried ($MgSO_4$) and concentrated in vacuo. The residue was purified by silica gel chromatography eluting with 0-60% ethyl acetate in cyclohexane to yield the title compound as a yellow oil (396 mg, 32%).

LCMS Method 5: r.t. 2.04 mins, $[M\text{-}tBu+2H]^+$341 tert-Butyl 3-(6-methyl-4-(p-tolyl)pyridin-2-yl)azetidine-1-carboxylate

A mixture text-butyl 3-(6-methyl-4-(((trifluoromethyl)sulfonyl)oxy)pyridin-2-yl)azetidine-1-carboxylate (234 mg, 0.59 mmol), p-tolylboronic acid (112 mg, 0.83 mmol), tetrakis(triphenylphosphine)palladium(0) (68 mg, 0.06 mmol) and cesium carbonate (308 mg, 0.95 mmol) in dioxane (3 mL), and water (0.5 mL) was degassed with argon and the reaction mixture heated at 100° C. for 30 min The reaction mixture was diluted with water and extracted with ethyl acetate (×3). The combined organic fractions were washed with brine, dried ($MgSO_4$) and concentrated in vacuo. The residue was purified by silica gel chromatography eluting with 0-100% ethyl acetate in cyclohexane to yield the title compound as a yellow oil (152 mg, 76%).

LCMS Method 5: r.t. 1.35 mins, [$MH^+$] 339, [M-tBu+2H]$^+$283, [M-Boc+2H]$^+$239

2-(Azetidin-3-yl)-6-methyl-4-(p-tolyl)pyridine hydrochloride

To a solution of tert-butyl 3-(6-methyl-4-(p-tolyl)pyridin-2-yl)azetidine-1-carboxylate (150 mg, 0.44 mmol) in MeOH (1 mL) was added HCl in dioxane (2.6 mL, 4N, 10.4 mmol) and the reaction mixture stirred at rt for 30 min. The reaction mixture was concentrated in vacuo to give the title compound as a white solid (130 mg, 106%).

LCMS Method 5: r.t. 0.89 mins, [$MH^+$] 239

(5-Isopropyl-1H-pyrazol-3-yl)(3-(6-methyl-4-(p-tolyl)pyridin-2-yl)azetidin-1-yl)methanone To a suspension of 2-(azetidin-3-yl)-6-methyl-4-(p-tolyl) pyridine hydrochloride (122 mg, 0.44 mmol), 5-isopropyl-1H-pyrazole-3-carboxylic acid (103 mg, 0.67 mmol) and triethylamine (0.15 mmol, 1.11 mmol) in DMF (3 mL) was added HATU (270 mg, 0.71 mmol). DCM (2 mL) was added causing the solids to dissolve and the reaction mixture was stirred at rt for 1 h. The reaction mixture was diluted with water and extracted with ethyl acetate (×3). The combined organic fractions were washed with 5% LiCl aq., brine, dried ($MgSO_4$) and concentrated in vacuo. The residue was purified by silica gel chromatography eluting with 0-5% (7N $NH_3$/MeOH) in DCM to yield the title compound as a white solid (89 mg, 54%).

$^1$H NMR (400 MHz, $d_6$-DMSO) δ, ppm 12.97 (1H, s), 7.70 (2H, d, J=8.1 Hz), 7.50-7.42 (2H, m), 7.31 (2H, d, J=8.0 Hz), 6.40 (1H, d, J=1.8 Hz), 4.83 (1H, t, J=9.2 Hz), 4.65 (1H, dd, J=9.5, 6.3 Hz), 4.35 (1H, t, J=9.3 Hz), 4.20 (1H, dd, J=9.3, 6.1 Hz), 4.12-4.03 (1H, m), 2.97 (1H, sept, J=7.0 Hz), 2.53 (3H, s), 2.36 (3H, s), 1.23 (6H, d, J=6.6 Hz).

LCMS Method 1: r.t. 3.39 mins, [$MH^+$] 375.1

Example 57

(5-Isopropyl-1H-pyrazol-3-yl)(3-(6-methyl-4-(1-methyl-1H-pyrazol-4-yl)pyridin-2-yl)azetidin-1-yl)methanone tert-Butyl 3-(6-methyl-4-(1-methyl-1H-pyrazol-4-yl)pyridin-2-yl)azetidine-1-carboxylate A mixture tert-butyl 3-(6-methyl-4-(((trifluoromethyl)sulfonyl)oxy)pyridin-2-yl)azetidine-1-carboxylate (150 mg, 0.38 mmol), (1-methyl-1H-pyrazol-4-yl)boronic acid (67 mg, 0.53 mmol), tetrakis(triphenylphosphine)palladium(0) (44 mg, 0.04 mmol) and cesium carbonate (197 mg, 0.61 mmol) in dioxane (3 mL), and water (0.5 mL) was degassed with argon and the reaction mixture heated at 100° C. for 1.5 h The reaction mixture was diluted with water and extracted with ethyl acetate (×3). The combined organic fractions were washed with brine, dried ($MgSO_4$) and concentrated in vacuo. The residue was purified by silica gel chromatography eluting with 0-60% ethyl acetate in cyclohexane to yield the title compound as a yellow oil (112 mg, 68%).

LCMS Method 2: r.t. 0.82 mins, [$MH^+$] 329, [M-tBu+2H]$^+$273

2-(Azetidin-3-yl)-6-methyl-4-(1-methyl-1H-pyrazol-4-yl)pyridine

To a solution of Cert-butyl 3-(6-methyl-4-(1-methyl-1H-pyrazol-4-yl)pyridin-2-yl)azetidine-1-carboxylate (112 mg, 0.34 mmol) in MeOH (1 mL) was added HCl in dioxane (2 mL, 4N, 8 mmol mmol) and the reaction mixture stirred at rt for 30 min. The reaction mixture was concentrated in vacuo to give the title compound as a white solid (130 mg, quant).

$^1$H NMR (400 MHz, $d_6$-DMSO) δ, ppm 9.59-9.34 (2H, m), 8.78 (1H, s), 8.42 (1H, s), 8.37 (1H, s), 7.97 (1H, s), 4.52 (1H, quin, J=8.5 Hz), 4.40-4.31 (4H, m), 3.95 (3H, s), 2.68 (3H, s).

(5-Isopropyl-1H-pyrazol-3-yl)(3-(6-methyl-4-(1-methyl-1H-pyrazol-4-yl)pyridin-2-yl)azetidin-1-yl)methanone To a suspension of 2-(azetidin-3-yl)-6-methyl-4-(p-tolyl) pyridine hydrochloride (122 mg, 0.44 mmol), 5-isopropyl-1H-pyrazole-3-carboxylic acid (103 mg, 0.67 mmol) and triethylamine (0.15 mmol, 1.11 mmol) in DMF (3 mL) was added HATU (270 mg, 0.71 mmol). The reaction mixture was stirred at rt for 1 h. The reaction mixture was diluted with water and extracted with ethyl acetate (×3). The combined organic fractions were washed with 5% LiCl aq., brine, dried ($MgSO_4$) and concentrated in vacuo. The residue was purified by silica gel chromatography eluting with 0-5% (7N $NH_3$/MeOH) in DCM then re-purified by reverse phase preparative HPLC to yield the title compound as a white solid (13 mg, 10%).

$^1$H NMR (400 MHz, $CDCl_3$) δ, ppm 7.84 (1H, d, J=0.7 Hz), 7.74 (1H, s), 7.15 (1H, s), 7.13-7.12 (1H, m), 6.48 (1H, s), 4.88 (1H, t, J=9.1 Hz), 4.75 (1H, dd, J=6.5, 9.0 Hz), 4.57 (1H, t, J=9.4 Hz), 4.43 (1H, dd, J=6.3, 10.0 Hz), 4.08-4.01 (1H, m), 3.97 (3H, s), 3.02 (1H, sept, J=6.9 Hz), 2.55 (3H, s), 1.30 (6H, d, J=6.9 Hz) plus one exchangeable not observed.

LCMS Method 7: r.t. 2.47 mins, [$MH^+$] 365.0

Example 58

7-(1-Acetyl-1H-pyrazol-4-yl)-2-(1-isopentyl-1H-pyrazol-4-yl)-3-isopropylimidazo[2,1-f][1,2,4]triazin-4(3H)-one 2-(1-Isopentyl-1H-pyrazol-4-yl)-3-isopropyl-7-(1-(tetrahydro-2H-pyran-2-yl)-1H-pyrazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and (1-isopentylpyrazol-4-yl)boronic acid by Suzuki-Miyaura General Procedure 1 to give the title compound as a yellow oil (112 mg, 58%).

LCMS Method 2: r.t. 1.40 mins, [$MH^+$] 465.

2-(1-Isopentyl-1H-pyrazol-4-yl)-3-isopropyl-7-(1H-pyrazol-4-yl)imidazo[2,1-f][1,2,4]triazin-4(3H)-one Prepared from 2-(1-isopentyl-1H-pyrazol-4-yl)-3-isopropyl-7-(1-(tetrahydro-2H-pyran-2-yl)-1H-pyrazol-4-yl)imidazo[2,1-f][1,2,4]triazin-4(3H)-one by THP Deprotection Procedure 1 to give the title compound as a yellow solid (93 mg, quantitative yield).

LCMS Method 2: r.t. 1.18 mins, [$MH^+$] 381.

$^1$H NMR (400 MHz, $d_6$-DMSO) δ, ppm 8.39 (1H, s), 8.25 (2H, s), 7.91 (1H, d, J=0.6 Hz), 7.87 (1H, s), 4.65-4.55 (1H, m), 4.29-4.24 (2H, m), 1.76 (2H, dt, J=7.1, 7.2 Hz), 1.72-1.63 (1H, m), 1.57 (6H, d, J=6.9 Hz), 0.93 (6H, d, J=6.1 Hz) plus one exchangeable not observed.

7-(1-Acetyl-1H-pyrazol-4-yl)-2-(1-isopentyl-1H-pyrazol-4-yl)-3-isopropylimidazo[2,1-f][1,2,4]triazin-4(3H)-one 2-(1-Isopentyl-1H-pyrazol-4-yl)-3-isopropyl-7-(1H-pyrazol-4-yl)imidazo[2,1-f][1,2,4]triazin-4(3H)-one (20 mg, 0.05 mmol) was dissolved in pyridine (1.0 mL). Acetic anhydride (10 μL, 0.11 mmol) was added to the mixture at 0° C. The reaction mixture was stirred at rt for 1 h. The volatiles were concentrated in vacuo and the residue was purified by reverse phase chromatography to afford the title compound as a white solid (12 mg, 60%).

LCMS Method 1: r.t. 4.62 mins, [$MH^+$] 423.

$^1$H NMR (400 MHz, $CDCl_3$) δ, ppm 8.79 (1H, s), 8.17 (1H, s), 7.78 (1H, s), 7.76 (1H, s), 7.72 (1H, s), 4.69 (1H, hept, J=6.8 Hz), 4.28-4.24 (2H, m), 2.75 (3H, s), 1.92-1.85 (3H, m), 1.68 (6H, d, J=6.0 Hz), 1.02 (6H, d, J=6.5 Hz).

Example 59

(1-Cyclopropylpyrazol-3-yl)-[2-(5-isopropyl-1H-pyrazole-3-carbonyl)-2,6-diazaspiro[3.3]heptan-6-yl]methanone Prepared from (5-isopropyl-1H-pyrazol-3-yl)(2,6-diazaspiro[3.3]heptan-2-yl)methanone and 1-cyclopropylpyrazole-3-carboxylic acid using Pyrazole Spirodiazetidine Amide General Procedure 4. Purification of the crude product by reverse phase chromatography eluting with 10-98% MeCN in 0.1% $NH_4OH$ solution to afford the title compound as a white solid (60 mg, 76%).

$^1$H NMR (400 MHz, $d_6$-DMSO) δ, ppm 12.99 (1H, s), 7.86 (1H, d, J=2.3 Hz), 6.58 (1H, d, J=2.6 Hz), 6.36 (1H, d, J=1.7 Hz), 4.66-4.58 (4H, m), 4.21-4.13 (4H, m), 3.84-3.78 (1H, m), 3.01-2.91 (1H, m), 1.22 (6H, d, J=6.9 Hz), 1.11-0.96 (4H, m).

Example 60

2-(Furan-3-yl)-7-(1H-imidazol-4-yl)-3-isopropylimidazo[2,1-f][1,2,4]triazin-4(3H)-one 2-(Furan-3-yl)-3-isopropyl-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and furan-3-boronic acid by Suzuki-Miyaura General Procedure 1 to give the title compound as a white solid (26 mg, 24%).

$^1$H NMR (400 MHz, $CDCl_3$) δ, ppm 7.97 (1H, s), 7.64 (1H, d, J=1.4 Hz), 7.54 (1H, t, J=1.6 Hz), 7.52-7.50 (2H, m), 7.37-7.31 (9H, m), 7.18-7.13 (6H, m), 6.50 (1H, dd, J=0.9, 1.9 Hz), 4.59-4.48 (1H, m), 1.64 (6H, d, J=6.4 Hz).

2-(Furan-3-yl)-7-(1H-imidazol-4-yl)-3-isopropylimidazo[2,1-f][1,2,4]triazin-4(3H)-one Prepared from 2-(furan-3-yl)-3-isopropyl-7-(1-trityl-1H-imidazol-4-yl)imidazo[2,1-f][1,2,4]triazin-4(3H)-one by Trityl Deprotection Procedure 1 to give the title compound as a white solid (2.8 mg, 10%).

LCMS Method 1: r.t. 2.47 mins, [$MH^+$] 311.1

$^1$H NMR (400 MHz, $d_6$-DMSO) δ, ppm 12.34 (1H, s), 8.32-8.31 (1H, m), 7.94 (1H, t, J=1.7 Hz), 7.79 (1H, s), 7.72 (1H, s), 7.69 (1H, s), 6.92-6.90 (1H, m), 4.48-4.37 (1H, m), 1.56 (6H, d, J=7.4 Hz).

Example 61

3-Isopropyl-2-(methyl(2-(tetrahydrofuran-2-yl)ethyl)amino)-7-(1H-pyrazol-4-yl)imidazo[2,1-f][1,2,4]triazin-4(3H)-one 3-Isopropyl-2-(methyl(2-(tetrahydrofuran-2-yl)ethyl)amino)imidazo[2,1-f][1,2,4]triazin-4(3H)-one Prepared from 2-chloro-3-isopropylimidazo[2,1-f][1,2,4]triazin-4(3H)-one and N-methyl-2-tetrahydrofuran-2-yl-ethanamine by SnAr General Procedure 3 to give the title compound as a yellow oil (270 mg, 94%).

LCMS Method 4: r.t. 1.25 mins, [$MH^+$] 306.

7-Bromo-3-isopropyl-2-(methyl(2-(tetrahydrofuran-2-yl)ethyl)amino)imidazo[2,1-f][1,2,4]triazin-4(3H)-one Prepared from 3-isopropyl-2-(methyl(2-(tetrahydrofuran-2-yl)ethyl)amino)imidazo[2,1-f][1,2,4]triazin-4(3H)-one by Bromination General Procedure 1 to give the title compound as a yellow oil (340 mg, quantitative yield).

LCMS Method 4: r.t. 1.44 mins, [$MH^+$] 384, 386.

3-Isopropyl-2-(methyl(2-(tetrahydrofuran-2-yl)ethyl)amino)-7-(1-(tetrahydro-2H-pyran-2-yl)-1H-pyrazol-4-yl)imidazo[2,1-f][1,2,4]triazin-4(3H)-one Prepared from 7-bromo-3-isopropyl-2-(methyl(2-(tetrahydrofuran-2-yl)ethyl)amino)imidazo[2,1-f][1,2,4]triazin-4(3H)-one and 1-tetrahydropyran-2-yl-4-(4,4,5,5-tetramethyl-1,3,2-dioxaborolan-2-yl)pyrazole by Suzuki-Miyaura General Procedure 1 to give the title compound (480 mg, 96%).

LCMS Method 4: r.t. 1.44 mins, [$MH^+$] 456.

3-Isopropyl-2-(methyl(2-(tetrahydrofuran-2-yl)ethyl)amino)-7-(1H-pyrazol-4-yl)imidazo[2,1-f][1,2,4]triazin-4(3H)-one A suspension of 3-isopropyl-2-(methyl(2-(tetrahydrofuran-2-yl)ethyl)amino)-7-(1-(tetrahydro-2H-pyran-2-yl)-1H-pyrazol-4-yl)imidazo[2,1-f][1,2,4]triazin-4(3H)-one (419 mg, 0.91 mmol) in MeOH (10 mL) was treated with 1N HCl(aq) (30 eq.) and the reaction mixture was stirred at 50° C. for 16 h. The volatiles were concentrated in vacuo. The mixture was basified by adding saturated aqueous $NaHCO_3$ solution up to pH=8. The precipitate was filtered off. The aqueous phase was extracted with 10% MeOH in DCM (×3), combined with the precipitate and concentrated in vacuo. The residue was dissolved in DCM/MeOH, preadsorbed onto ISOLUTE® HM-N column (Biotage) and purified by silica gel chromatography eluting with a 0-5% gradient of MeOH in DCM, to afford the title compound as a white solid (108 mg, 32%).

LCMS Method 1: r.t. 3.48 mins, [$MH^+$] 372.3

$^1$H NMR (400 MHz, $d_6$-DMSO) δ, ppm 13.15 (1H, s), 8.34 (1H, s), 8.12 (1H, s), 7.67 (1H, s), 4.79-4.69 (1H, m), 3.82-3.71 (2H, m), 3.60-3.55 (1H, m), 3.29-3.20 (1H, m), 3.19-3.11 (1H, m), 2.84 (3H, s), 1.99-1.91 (1H, m), 1.88-1.70 (4H, m), 1.57 (6H, d, J=6.7 Hz), 1.48-1.38 (1H, m).

The enantiomers of EXAMPLE 61 were separated by chiral SFC using a LUX Cellulose-4 21×250 mm, 5 μm eluting with 40% IPA/ACN (50/50/0.1% DEA)/60% $CO_2$, 100 mL/min, 120 bar, 40° C. to afford:

Example 62

Enantiomer A: 40.6 mg of a white solid

Analytical SFC using LUX Cellulose-4 4.6×250 mm, 5 μm 40% IPA/ACN (50/50/0.1% DEA)/60% $CO_2$, 5.0 mL/min, 120 bar, 40° C., DAD 230 nm retention time 8.3 min Example 63

Enantiomer B: 41 mg of a white solid

Analytical SFC using LUX Cellulose-4 4.6×250 mm, 5 μm 40% IPA/ACN (50/50/0.1% DEA)/60% $CO_2$, 5.0 mL/min, 120 bar, 40° C., DAD 230 nm retention time 9.3 min Example 64

2-(1H-Indol-3-yl)-3-isopropyl-7-(1H-pyrazol-4-yl) imidazo[2,1-f][1,2,4]triazin-4(3H)-one tert-Butyl 3-(3-isopropyl-4-oxo-3,4-dihydroimidazo [2,1-f][1,2,4]triazin-2-yl)-1H-indole-1-carboxylate Prepared from 2-chloro-3-isopropylimidazo[2,1-f][1,2,4] triazin-4(3H)-one and tert-butyl 3-(4,4,5,5-tetramethyl-1,3,2-dioxaborolan-2-yl) indole-1-carboxylate by Suzuki-Miyaura General Procedure 1 to give the title compound as a brown oil (120 mg, 67%).

$^1$H NMR (400 MHz, $CDCl_3$) δ, ppm 8.27 (1H, d, J=8.5 Hz), 7.92 (1H, s), 7.57-7.56 (2H, m), 7.54-7.52 (1H, m), 7.48-7.44 (1H, m), 7.38-7.33 (1H, m), 4.47-4.36 (1H, m), 1.71 (9H, s), 1.61 (6H, d, J=6.9 Hz).

tert-Butyl 3-(7-bromo-3-isopropyl-4-oxo-3,4-dihydroimidazo[2,1-f][1,2,4]triazin-2-yl)-1H-indole-1-carboxylate Prepared from tert-butyl 3-(3-isopropyl-4-oxo-3,4-dihydroimidazo[2,1-f][1,2,4]triazin-2-yl)-1H-indole-1-carboxylate by Bromination General Procedure 1 to give the title compound as an orange oil (144 mg, quantitative yield).

$^1$H NMR (400 MHz, $CDCl_3$) δ, ppm 8.26 (1H, d, J=8.8 Hz), 7.96 (1H, s), 7.56-7.53 (2H, m), 7.47-7.44 (1H, m), 7.38-7.34 (1H, m), 4.49-4.39 (1H, m), 1.71 (9H, s), 1.60 (6H, d, J=6.1 Hz).

tert-Butyl 3-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl)-1H-indole-1-carboxylate Prepared from tert-butyl 3-(7-bromo-3-isopropyl-4-oxo-3,4-dihydroimidazo[2,1-f][1,2,4]triazin-2-yl)-1H-indole-1-carboxylate and 1-tetrahydropyran-2-yl-4-(4,4,5,5-tetramethyl-1,3,2-dioxaborolan-2-yl)pyrazole by Suzuki-Miyaura General Procedure 1 to give the title compound (106 mg, 64%).

$^1$H NMR (400 MHz, $CDCl_3$) δ, ppm 8.28 (1H, d, J=9.0 Hz), 8.17 (1H, s), 8.02 (1H, d, J=0.7 Hz), 7.93 (1H, s), 7.69-7.68 (1H, m), 7.63-7.61 (1H, m), 7.50-7.45 (1H, m), 7.39-7.35 (1H, m), 5.39-5.36 (2H, m), 4.53-4.43 (1H, m), 4.09-4.03 (2H, m), 3.72-3.65 (2H, m), 2.16-2.05 (2H, m), 1.76 (9H, s), 1.71-1.67 (1H, m), 1.63 (6H, dd, J=1.5, 6.8 Hz).

2-(1H-Indol-3-yl)-3-isopropyl-7-(1H-pyrazol-4-yl) imidazo[2,1-f][1,2,4]triazin-4(3H)-one A suspension of text-butyl 3-(3-isopropyl-4-oxo-7-(1-(tetrahydro-2H-pyran-2-yl)-1H-pyrazol-4-yl)-3,4-dihydroimidazo[2,1-f][1,2,4]triazin-2-yl)-1H-indole-1-carboxylate (106 mg, 0.19 mmol) in MeOH (5 mL) was treated with 1N HCl(aq) (30 eq.) and the reaction mixture was stirred at 50° C. for 16 h. The reaction was partitioned between DCM/MeOH (9/1) and saturated aqueous $NaHCO_3$ solution. The aqueous phase was extracted with 10% MeOH in DCM (×3) and concentrated in vacuo. The resulting off white solid was purified by reverse phase prep HPLC to afford the title compound as a white solid (22.5 mg, 32%).

LCMS Method 7: r.t. 3.6 mins, [$MH^+$] 360.

$^1$H NMR (400 MHz, $d_6$-DMSO) δ, ppm 13.10 (1H, s), 11.83 (1H, s), 8.17 (2H, s), 7.87 (1H, s), 7.79-7.76 (2H, m), 7.56 (1H, d, J=7.4 Hz), 7.27-7.23 (1H, m), 7.19-7.14 (1H, m), 4.62-4.52 (1H, m), 1.53 (6H, d, J=6.1 Hz).

Example 65

3-Isopropyl-2-(1-methyl-1H-pyrazol-3-yl)-7-(1H-pyrazol-4-yl)imidazo[2,1-f][1,2,4]triazin-4(3H)-one 2-Chloro-3-isopropylimidazo[2,1-f][1,2,4]triazin-4 (3H)-one 3-Isopropylimidazo[2,1-f][1,2,4]triazine-2,4 (1H,3H)-dione (460 mg, 2.37 mmol) was suspended in phosphorus oxychloride (5.0 mL) and stirred at 120° C. for 48 h. $POCl_3$ was added (5 mL) and it was stirred at 120° C. until the completion of the reaction was observed by LCMS. Water was added to the mixture and $NaHCO_3$ was added at 40° C. slowly portionwise to reach pH=6. DCM was added and the phases separated. The aqueous was extracted with DCM (×2) using a phase separator cartridge and the combined organic phase was concentrated in vacuo to afford the title compound (285 mg, 57%) as a pale yellow solid.

$^1$H NMR (400 MHz, $CDCl_3$) δ, ppm 7.54-7.52 (2H, m), 5.24-5.24 (1H, m), 1.67 (6H, d, J=6.9 Hz).

3-Isopropyl-2-(1-methyl-1H-pyrazol-3-yl)imidazo[2,1-f][1,2,4]triazin-4(3H)-one

Prepared from 2-chloro-3-isopropylimidazo[2,1-f][1,2,4] triazin-4(3H)-one and 1-methyl-3-(4,4,5,5-tetramethyl-1,3,2-dioxaborolan-2-yl)pyrazole by Suzuki-Miyaura General Procedure 1 to give the title compound as a yellow solid (167 mg, 92%).

$^1$H NMR (400 MHz, $CDCl_3$) δ, ppm 7.57 (1H, d, J=1.0 Hz), 7.53 (1H, d, J=1.1 Hz), 7.51 (1H, d, J=2.4 Hz), 6.60 (1H, d, J=2.4 Hz), 4.70-4.60 (1H, m), 4.03 (3H, s), 1.63 (6H, d, J=6.8 Hz).

7-Bromo-3-isopropyl-2-(1-methyl-1H-pyrazol-3-yl) imidazo[2,1-f][1,2,4]triazin-4(3H)-one Prepared from 3-isopropyl-2-(1-methyl-1H-pyrazol-3-yl) imidazo[2,1-f][1,2,4]triazin-4(3H)-one by Bromination General Procedure 1 to give the title compound as a yellow solid (118 mg, 54%).

LCMS Method 5: r.t. 1.7 mins, [$MH^+$] 337, 339.

3-Isopropyl-2-(1-methyl-1H-pyrazol-3-yl)-7-(1H-pyrazol-4-yl)imidazo[2,1-f][1,2,4]triazin-4(3H)-one Prepared from 7-bromo-3-isopropyl-2-(1-methyl-1H-pyrazol-3-yl)imidazo[2,1-f][1,2,4]triazin-4(3H)-one and 1-tetrahydropyran-2-yl-4-(4,4,5,5-tetramethyl-1,3,2-dioxaborolan-2-yl)pyrazole by Suzuki-Miyaura General Procedure 1 followed by THP Deprotection Procedure 1 and purification by precipitation in DMSO/$H_2O$ (9/1) to afford the title compound as a white solid, 56 mg (35% over two steps).

$^1$H NMR (400 MHz, $d_6$-DMSO) δ, ppm 13.15 (1H, s), 8.31 (1H, s), 8.09 (1H, s), 7.96 (1H, d, J=1.8 Hz), 7.79 (1H, s), 6.81 (1H, d, J=2.3 Hz), 4.74-4.64 (1H, m), 3.98 (3H, s), 1.54 (6H, d, J=7.4 Hz).

LCMS Method 3: r.t. 2.87 mins, [$MH^+$] 325.1

Example 66

2-(1-(tert-Butyl)-1H-pyrazol-4-yl)-3-isopropyl-7-(1H-pyrazol-4-yl)imidazo[2,1-f][1,2,4]triazin-4(3H)-one 2-Bromo-3-isopropylimidazo[2,1-f][1,2,4]triazin-4(3H)-one 3-Isopropylimidazo[2,1-f][1,2,4]triazine-2,4 (1H,3H)-dione (1.0 g, 5.1 mmol) and phosphorus oxybromide (7.4 g, 25.7 mmol) were heated at 135° C. for 16 h. The mixture was quenched with a saturated aqueous $NaHCO_3$ solution and sodium bicarbonate was added as a solid at 40° C. until pH=6. The mixture was extracted with DCM (×3) using a phase separator cartridge and the combined organic phase was concentrated in vacuo. The residue was dissolved in DCM/MeOH, preadsorbed onto ISOLUTE® HM-N column (Biotage) and purified by silica gel chromatography eluting with 0-20% EtOAc in DCM to afford the title compound (500 mg, 38%) as a fluffy yellow solid.

$^1$H NMR (400 MHz, $CDCl_3$) 0.5, ppm 7.52-7.51 (2H, m), 5.07-5.07 (1H, m), 1.68 (6H, d, J=6.7 Hz).

2-(1-(tert-Butyl)-1H-pyrazol-3-yl)-3-isopropylimidazo[2,1-f][1,2,4]triazin-4(3H)-one Prepared from 2-bromo-3-isopropylimidazo[2,1-f][1,2,4]triazin-4(3H)-one and 1-tert-butyl-3-(4,4,5,5-tetramethyl-1,3,2-dioxaborolan-2-yl)pyrazole by Suzuki-Miyaura General Procedure 2 to give the title compound as a yellow oil, 60 mg (50%).

LCMS Method 4: r.t. 1.22 mins, [$MH^+$] 301.

7-Bromo-2-(1-(tert-butyl)-1H-pyrazol-3-yl)-3-isopropylimidazo[2,1-f][1,2,4]triazin-4(3H)-one Prepared from 2-(1-(tert-butyl)-1H-pyrazol-3-yl)-3-isopropylimidazo[2,1-f][1,2,4]triazin-4(3H)-one by Bromination General Procedure 1 to give the title compound as a yellow oil.

LCMS Method 4: r.t. 1.38 mins, [$MH^+$] 379, 381.

2-(1-(tert-Butyl)-1H-pyrazol-4-yl)-3-isopropyl-7-(1H-pyrazol-4-yl)imidazo[2,1-f][1,2,4]triazin-4(3H)-one Prepared from 7-bromo-2-(1-(tert-butyl)-1H-pyrazol-3-yl)-3-isopropylimidazo[2,1-f][1,2,4]triazin-4(3H)-one and 1-tetrahydropyran-2-yl-4-(4,4,5,5-tetramethyl-1,3,2-dioxaborolan-2-yl)pyrazole by Suzuki-Miyaura General Procedure 2 followed by THP Deprotection Procedure 1 and purification by reverse phase preparative HPLC to afford the title compound as a white solid, 7 mg (8% over 2 steps).

$^1$H NMR (400 MHz, $CDCl_3$) δ, ppm 8.17 (2H, s), 7.87 (1H, d, J=0.8 Hz), 7.81 (1H, d, J=0.5 Hz), 7.67 (1H, s), 4.73-4.62 (1H, m), 1.69 (9H, s), 1.68 (6H, d, J=6.1 Hz) plus one exchangeable not observed.

LCMS Method 8: r.t. 3.91 mins, [$MH^+$] 367.0

Example 67

3-Isopropyl-2-methyl-7-(1-(5-methylpyridin-2-yl)-1H-pyrazol-4-yl)imidazo[2,1-f][1,2,4]triazin-4(3H)-one 3-Isopropyl-2-methylimidazo[2,1-f][1,2,4]triazin-4(3H)-one 1-Amino-N-isopropyl-1H-imidazole-2-carboxamide (200 mg, 1.19 mmol) was suspended in triethyl orthoacetate (2.0 mL) and stirred at 100° C. for 18 h. The reaction was cooled to rt and the volatiles were concentrated in vacuo to afford an orange sticky solid. The mixture was dissolved in ethanol (0.5 mL) and sodium ethoxide (21% in ethanol, 360 μL, 1.19 mmol) was added. The reaction mixture was heated at 110° C. for 1 h under microwave irradiation. Water was added and the volatiles were evaporated in vacuo. The mixture was partitioned between DCM and $H_2O$. The aqueous phase was extracted with 10% MeOH in DCM (×3) and the combined organic phase was concentrated in vacuo to afford a pale yellow solid (60 mg, 32%) which was used in the next step without further purification.

LCMS Method 2: r.t. 0.76 mins, [$MH^+$] 193.

7-Bromo-3-isopropyl-2-methylimidazo[2,1-f][1,2,4]triazin-4(3H)-one

Prepared from 3-isopropyl-2-methylimidazo[2,1-f][1,2,4]triazin-4(3H)-one using Bromination General Procedure 1 to afford the title compound as a brown solid 70 mg (quantitative yield).

$^1$H NMR (400 MHz, $CDCl_3$) δ, ppm 7.48 (1H, s), 4.55-4.55 (1H, m), 2.60 (3H, s), 1.67 (1H, d, J=7.2 Hz).

5-Methyl-2-(4-(4,4,5,5-tetramethyl-1,3,2-dioxaborolan-2-yl)-1H-pyrazol-1-yl)pyridine 4-Pyrazoleboronic acid pinacol ester (500 mg, 2.58 mmol), cesium carbonate (1.68 g, 5.15 mmol) and 2-fluoro-5-methylpyridine (0.27 mL, 2.58 mmol) were placed in dry DMF (10.0 mL) under argon and stirred at 100° C. for 16 h. After cooling to rt, the mixture was partitioned between EtOAc and $H_2O$. The aqueous phase was extracted with EtOAc (×3). The combined organic layers were washed with brine, dried ($MgSO_4$) and concentrated in vacuo to afford the title compound which was used in the next step without further purification.

$^1$H NMR (400 MHz, $CDCl_3$) δ, ppm 8.84 (1H, d, J=0.7 Hz), 8.23-8.21 (1H, m), 7.95 (1H, d, J=0.6 Hz), 7.90 (1H, s), 7.85 (1H, d, J=8.5 Hz), 2.36 (3H, s), 1.34 (12H, s).

3-Isopropyl-2-methyl-7-(1-(5-methylpyridin-2-yl)-1H-pyrazol-4-yl)imidazo[2,1-f][1,2,4]triazin-4(3H)-one Prepared from 7-bromo-3-isopropyl-2-methylimidazo[2,1-f][1,2,4]triazin-4(3H)-one and 5-Methyl-2-(4-(4,4,5,5-tetramethyl-1,3,2-dioxaborolan-2-yl)-1H-pyrazol-1-yl)pyridine by Suzuki-Miyaura General Procedure 1 using IMS/$H_2O$ (2.5/0.5 mL) as solvent to give the title compound as a white solid, 46 mg (36%).

$^1H$ NMR (400 MHz, $CDCl_3$) δ, ppm 9.10 (1H, s), 8.28-8.26 (1H, m), 8.23 (1H, d, J=0.7 Hz), 7.92 (1H, d, J=8.3 Hz), 7.68 (1H, s), 7.68-7.65 (1H, m), 4.58-4.58 (1H, m), 2.65 (3H, s), 2.39 (3H, s), 1.70 (6H, d, J=7.1 Hz).

LCMS Method 1: r.t. 4.37 mins, [$MH^+$] 350.2

Example 68

6-Isopropyl-3-(5-isopropyl-1H-pyrazole-3-carbonyl)-4-methyl-5-phenylpyrazolo[1,5-a]pyrimidin-7 (4H)-one Ethyl 2-benzoyl-3-methylbutanoate A solution of ethyl isovalerate (1.1 mL, 7.11 mmol) was placed in dry THF (15 mL) at −78° C. LDA (2M, 3.9 mL, 7.83 mmol) was added dropwise under argon and the reaction mixture was stirred 1 h at −78° C. Benzoyl chloride (0.83 mL, 7.11 mmol) in dry THF (5 mL) was added dropwise and the mixture was stirred 1 h at −78° C. then 2 h at rt. The volatiles were evaporated in vacuo and the residue partitioned between EtOAc and water. The phases were separated and the aqueous phase was extracted with EtOAc (×2). The combined organic phase was washed with brine, dried ($MgSO_4$), and concentrated in vacuo. The solid was dissolved in DCM, pre-adsorbed onto ISOLUTE® HM-N column (Biotage) and purified by silica gel chromatography eluting with 0-20% EtOAc in cyclohexane to afford the title compound (1.25 g, 75%) as a yellow oil. It was used in the next step without further purification.

$^1H$ NMR (400 MHz, $CDCl_3$) δ, ppm 8.04-8.00 (2H, m), 7.60-7.56 (1H, m), 7.50-7.45 (2H, m), 4.14 (2H, dq, J=1.3, 7.1 Hz), 4.09 (1H, d, J=9.2 Hz), 2.71-2.59 (1H, m), 1.18 (3H, t, J=7.1 Hz), 1.05 (3H, d, J=7.4 Hz), 0.95 (3H, d, J=6.6 Hz).

3-Bromo-6-isopropyl-5-phenylpyrazolo[1,5-a]pyrimidin-7 (4H)-one

Ethyl 2-benzoyl-3-methylbutanoate (1.0 g, 4.27 mmol) and 3-amino-4-bromo-1H-pyrazole (1.0 g, 6.4 mmol) were suspended in 2-MeTHF (20 mL), and a solution of titanium (IV) chloride in DCM (1M; 4.3 mL, 4.30 mmol) was added. The mixture was heated at 80° C. for 19 h. The precipitate was filtered off and the filtrate was partitioned between EtOAc and a saturated aqueous $NaHCO_3$ solution. The organic phase was washed with saturated aqueous $NaHCO_3$ solution (×2), water, dried ($MgSO_4$), and concentrated in vacuo to afford a white solid. The solid was dissolved in DCM and purified by silica gel chromatography eluting with 0-5% MeOH in DCM to afford the title compound as a grey solid (600 mg, 43%).

$^1H$ NMR (400 MHz, $CDCl_3$) δ, ppm 7.84 (1H, s), 7.72 (1H, s), 7.60-7.55 (3H, m), 7.48-7.44 (2H, m), 2.81-2.71 (1H, m), 1.34 (6H, d, J=6.9 Hz).

3-Bromo-6-isopropyl-4-methyl-5-phenylpyrazolo[1,5-a] pyrimidin-7 (4H)-one

3-Bromo-6-isopropyl-5-phenylpyrazolo[1,5-a]pyrimidin-7 (4H)-one (250 mg, 0.753 mmol) in THF (3.0 mL) was treated with sodium hydride (60%; 36 mg, 0.90 mmol) and after 30 min iodomethane (0.23 mL, 3.76 mmol) was added. After 18 h, the solvent was removed in vacuo, water was added and the product was extracted into DCM. The combined organic extracts were dried ($Na_2SO_4$), and concentrated in vacuo to give a yellow solid. The crude product was triturated using EtOAc-$Et_2O$ and the solids filtered off and dried to give the title compound as a white solid (120 mg, 46%).

LCMS Method 2: r.t. 1.57 mins, [$MH^+$] 346, 348

6-Isopropyl-3-(5-isopropyl-1H-pyrazole-3-carbonyl)-4-methyl-5-phenylpyrazolo[1,5-a]pyrimidin-7 (4H)-one A solution of 3-bromo-6-isopropyl-4-methyl-5-phenylpyrazolo[1,5-a]pyrimidin-7 (4H)-one (42 mg, 0.12 mmol) in THF (1.5 mL) was cooled to −78° C. and n-butyl lithium (1.6M; 0.083 mL, 0.13 mmol) was added. After 30 minutes a pre-cooled solution of 5-isopropyl-N-methoxy-N-methyl-1-(tetrahydro-2H-pyran-2-yl)-1H-pyrazole-3-carboxamide (34 mg, 0.121 mmol) in THF (1.5 mL) was added. The mixture was allowed to warm to rt during 18 h. The solvent was removed in vacuo, the residue re-dissolved in MeOH (3.0 mL) and TFA (1.0 mL) was added then the mixture was heated at 50° C. for 5 h. The reaction mixture was concentrated, loaded onto an SCX-2 cartridge and the cartridge eluted with MeOH. Evaporation of the eluent gave crude product which was purified by reverse phase preparative HPLC to give the title compound as a white solid (2.0 mg, 4%)

$^1H$ NMR (400 MHz, $d_6$-DMSO) δ, ppm 13.32 (1H, s), 8.59 (1H, s), 7.56-7.66 (3H, m), 7.46-7.52 (2H, m), 6.62 (1H, s), 3.29 (3H, s), 3.02 (1H, hept, J=7.2 Hz), 2.34 (11-1, hept, J=7.2 Hz), 1.26 (6H, d, J=6.9 Hz), 1.21 (6H, d, J=7.0 Hz)

LCMS Method 9: r.t. 4.84 mins, [$MH^+$] 404.3

Amide Coupling Procedure 1

A solution of cyclopropyl(2,6-diazaspiro[3.3]heptan-2-yl)methanone (2.8 mL at 0.22M, 0.615 mmol), $ArCO_2H$ (0.677 mmol) and triethylamine (0.51 mL, 3.69 mmol) in DCM (2.0 mL) was treated with HATU (257 mg, 0.677 mmol) and stirred at rt for 18 h. Solvent was removed in vacuo and crude product purified by reverse phase preparative HPLC or reverse phase chromatography (C18 cartridge) eluting with 10-98% $MeCN/H_2O$+0.1% $NH_4OH$.

Amide Coupling Procedure 2

A solution of amine (0.472 mmol), $ArCO_2H$ (0.567 mmol) and DIPEA (0.25 mL, 1.42 mmol) in DCM (10.0 mL) was treated with T3P (0.42 mL, 0.709 mmol) and stirred at rt for 2 h. Solvent was removed in vacuo and crude product purified by reverse phase preparative HPLC.

Amide Coupling Procedure 3

A solution of amine (2.74 mmol), $ArCO_2H$ (2.74 mmol) and DIPEA (1.40 mL, 8.21 mmol) in DMF (5.0 mL) was treated with HATU (1.093 g, 2.88 mmol) and stirred at rt for 18 h. Solvent was removed in vacuo and crude product purified by reverse phase preparative HPLC or reverse phase chromatography (C18 cartridge) eluting with 10-98% $MeCN/H_2O$+0.1% $NH_4OH$.

Amide Coupling Procedure 4

A solution of amine (0.548 mmol), $ArCO_2H$ (0.603 mmol) and triethylamine (0.23 mL, 1.64 mmol) in DCM (2.0 mL) was treated with HATU (229 mg, 0.603 mmol) and stirred at rt for 18 h. Solvent was removed in vacuo and crude product purified by reverse phase preparative HPLC or reverse phase chromatography ($C_{18}$ cartridge) eluting with 10-98% $MeCN/H_2O$+0.1% $NH_4OH$.

Amide Coupling Procedure 5

A solution of amine (0.439 mmol), $ArCO_2H$ (1.10 mmol) and triethylamine (0.24 mL, 1.76 mmol) in DMF (3.0 mL) was treated with HATU (334 mg, 0.878 mmol) and stirred at rt for 18 h. Solvent was removed in vacuo and crude product purified by reverse phase chromatography ($C1_8$ cartridge) eluting with 10-98% $MeCN/H_2O$+0.1% $NH_4OH$.

2,2-Dimethyl-1-(2,6-diazaspiro[3.3]heptan-2-yl) propan-1-one

A solution of text-butyl 6-pivaloyl-2,6-diazaspiro[3.3] heptane-2-carboxylate (0.20 g, 0.708 mmol) in MeOH (20 mL) was treated with pre-washed Amberlyst 15 (H form, 4.0 g) and stirred at rt for 20 h. The mixture was then treated with 2M ammonia in MeOH (20 mL), stirred for 2 h and filtered. The filtrate was concentrated in vacuo to give the title compound as a brown solid (130 mg, 100%)

LCMS Method 4: r.t. 0.96 mins, [$MH^+$] 183

(R)-1-(1-Hydroxypropan-2-yl)-1H-imidazole-4-carboxylic acid

The title compound was prepared according to a literature procedure (WO2013111105A1) using D-alinol to give the title compound as a white solid.

$^1$H NMR (400 MHz, $d_6$-DMSO) δ, ppm 7.83 (1H, d, J=1.3 Hz), 7.74 (1H, d, J=1.3 Hz), 4.25-4.35 (1H, m), 3.50-3.62 (3H, m), 1.37 (3H, d, J=6.9 Hz) plus one exchangeable proton not observed.

(S)-1-(1-Hydroxypropan-2-yl)-1H-imidazole-4-carboxylic acid

The title compound was prepared according to a literature procedure (WO2013111105A1) using L-alinol to give the title compound as a yellow solid.

$^1$H NMR (400 MHz, $d_6$-DMSO) δ, ppm 7.72 (1H, d, J=1.2 Hz), 7.69 (1H, d, J=1.2 Hz), 4.21-4.31 (1H, m), 3.50-3.62 (3H, m), 1.36 (3H, d, J=6.9 Hz) plus one exchangeable proton not observed.

(R)-1-(1-Fluoropropan-2-yl)-1H-imidazole-4-carboxylic acid

Ethyl (R)-1-(1-fluoropropan-2-yl)-1H-imidazole-4-carboxylate

A solution of (R)-1-(1-hydroxypropan-2-yl)-1H-imidazole-4-carboxylic acid (870 mg, 4.39 mmol) in DCM (10.0 mL) was cooled (ice/water bath) to 0° C., stirred and DAST (1.7 mL, 13.17 mmol) added dropwise. The mixture was allowed to warm to rt before solid $Na_2CO_3$ (550 mg, 5.19 mmol) was added and the mixture stirred for 20 h. It was diluted with DCM, filtered via Celite® and concentrated in vacuo to give a yellow oil. The crude product was purified by silica gel chromatography eluting with 0-10% MeOH in DCM to give the title compound as a yellow oil (120 mg, 13%).

LCMS Method 4: r.t. 0.99 mins, [$MH^+$] 201

(R)-1-(1-Fluoropropan-2-yl)-1H-imidazole-4-carboxylic acid

A mixture of ethyl (R)-1-(1-fluoropropan-2-yl)-1H-imidazole-4-carboxylate (140 mg, 0.699 mmol), $LiOH{\cdot}H_2O$ (88 mg, 2.10 mmol), THF (6.0 mL) and water (2.0 mL) was stirred and heated at 80° C. for 2 h. The cooled mixture was diluted with EtOAc, aqueous HCl (1N, 2.2 mL) added to attain pH5 then aqueous $NaHCO_3$ added. Phases were separated and the aqueous concentrated in vacuo to give a white solid. This was extracted into 20% IPA in DCM and filtered via Celite®. The filtrate was evaporated to give the title compound as a white solid (120 mg, 100%)

LCMS Method 4: r.t. 0.19 mins $^1$H NMR (400 MHz, $d_6$-DMSO) δ, ppm 7.55 (1H, s), 7.38 (1H, s), 4.47-4.69 (3H, m), 1.39 (3H, d, J=5.6 Hz) plus one exchangeable proton not observed.

(S)-1-(1-Fluoropropan-2-yl)-1H-imidazole-4-carboxylic acid

Ethyl (S)-1-(1-fluoropropan-2-yl)-1H-imidazole-4-carboxylate

A solution of (S)-1-(1-hydroxypropan-2-yl)-1H-imidazole-4-carboxylic acid (700 mg, 3.53 mmol) in DCM (10.0 mL) was cooled (ice/water bath) to 0° C., stirred and DAST (1.40 mL, 10.59 mmol) added dropwise. The mixture was allowed to warm to rt before solid $Na_2CO_3$ (550 mg, 5.19 mmol) was added and the mixture stirred for 20 h. It was diluted with DCM, filtered via Celite® and concentrated in vacuo to give a yellow oil. The crude product was purified by silica gel chromatography eluting with 0-10% MeOH in DCM to give the title compound as a yellow oil (100 mg, 14%).

LCMS Method 4: r.t. 0.99 mins, [$MH^+$] 201

(S)-1-(1-Fluoropropan-2-yl)-1H-imidazole-4-carboxylic acid

A mixture of ethyl (S)-1-(1-fluoropropan-2-yl)-1H-imidazole-4-carboxylate (120 mg, 0.599 mmol), $LiOH{\cdot}H_2O$ (75 mg, 1.80 mmol), THF (6.0 mL) and water (2.0 mL) was stirred and heated at 80° C. for 2 h. The cooled mixture was diluted with EtOAc, aqueous HCl (1N, 2.2 mL) added to attain pH5 then aqueous $NaHCO_3$ added. Phases were separated and the aqueous concentrated in vacuo to give a white solid. This was extracted into 20% IPA in DCM and filtered via Celite®. The filtrate was evaporated to give the title compound as a white solid (60 mg, 58%).

LCMS Method 4: r.t. 0.20 mins $^1$H NMR (400 MHz, $d_6$-DMSO) δ, ppm 7.58 (1H, s), 7.41 (1H, s), 4.44-4.70 (3H, m), 1.39 (3H, d, J=6.1 Hz) plus one exchangeable proton not observed.

5-Isopropyl-N-methoxy-N-methyl-1-(tetrahydro-2H-pyran-2-yl)-1H-pyrazole-3-carboxamide 5-Isopropyl-N-methoxy-N-methyl-1H-pyrazole-3-carboxamide A mixture of 3-isopropylpyrazole-5-carboxylic acid (750 mg, 4.86 mmol) in DCM (50 mL) was treated with N,O-dimethylhydroxylamine hydrochloride (949 mg, 9.73 mmol), 4-(dimethylamino)pyridine (2.377 g, 19.46 mmol) and N-(3-dimethylaminopropyl)-N'-ethylcarbodiimide hydrochloride (1.865 g, 9.73 mmol) and stirred for 18 h. It was poured into aqueous $NaHCO_3$ and extracted with DCM. The organic extracts were washed with brine, dried ($Na_2SO_4$), and evaporated to give a solid. The crude product was purified by silica gel chromatography eluting with 0-30% acetone in DCM to give the title compound as an oil (0.20 g, 21%).

$^1H$ NMR (300 MHz, $CDCl_3$) δ, ppm 6.63 (1H, s), 3.79 (3H, s), 3.39 (3H, s), 3.04 (1H, hept, J=7.0 Hz), 1.30 (6H, d, J=6.9 Hz)

5-Isopropyl-N-methoxy-N-methyl-1-(tetrahydro-2H-pyran-2-yl)-1H-pyrazole-3-carboxamide A solution of 5-isopropyl-N-methoxy-N-methyl-1H-pyrazole-3-carboxamide (200 mg, 1.01 mmol) and TFA (12 mg, 0.10 mmol) in DMF (2.0 mL) was heated to 85° C. and 3,4-dihydro-2H-pyran (0.14 mL, 1.52 mmol) added. It was stirred at 90° C. for 18 h. The solvent was removed in vacuo and the crude product purified by silica gel chromatography eluting with 0-7.5% (2M ammonia in MeOH) in DCM to give the title compound as a gum (0.24 g, 84%).

LCMS Method 2: r.t. 1.15 mins, [M+$Na^+$] 304

5-(1-Cyanopropan-2-yl)-1H-pyrazole-3-carboxylic acid

Ethyl 5-(1-cyanoprop-1-en-2-yl)-1H-pyrazole-3-carboxylate

Diethyl cyanomethylphosphonate (3.30 mL, 20.58 mmol) was added to sodium hydride (60%; 823 mg, 20.58 mmol) in THF (40 mL) at 0° C. (ice/water bath). After 30 minutes ethyl 3-acetyl-1H-pyrazole-5-carboxylate (750 mg, 4.12 mmol) was added, then the mixture allowed to warm to rt over 18 h. It was quenched with aqueous $NH_4Cl$ and extracted into EtOAc. The combined organic extracts were washed with brine, dried ($Na_2SO_4$), and evaporated to give a yellow oil. The crude product was purified by silica gel chromatography eluting with 0-30% EtOAc in cyclohexane to give the title compound as a white solid (0.84 g, 99%).

LCMS Method 5: r.t. 1.18 and 1.21 mins, [$M^-$] 204

Ethyl 5-(1-cyanopropan-2-yl)-1H-pyrazole-3-carboxylate

Ethyl 5-(1-cyanoprop-1-en-2-yl)-1H-pyrazole-3-carboxylate (810 mg, 3.95 mmol) was hydrogenated using 10% Pd/C (399 mg) in EtOAc (40 mL) under an atmosphere of hydrogen for 18 h. The resultant mixture was filtered via Celite® and the filtrate concentrated in vacuo to give the title compound as a white solid (0.81 g, 99%).

LCMS Method 5: r.t. 1.07 mins, [$M^-$] 206

5-(1-Cyanopropan-2-yl)-1H-pyrazole-3-carboxylic acid

A mixture of ethyl 5-(1-cyanopropan-2-yl)-1H-pyrazole-3-carboxylate (810 mg, 3.91 mmol), lithium hydroxide monohydrate (820 mg, 19.54 mmol), THF (15 mL) and water (15 mL) was stirred for 18 h. It was neutralised using aqueous HCl (1N; 20 mL), some aqueous $NaHCO_3$ added and then concentrated in vacuo. Residue was extracted into 5% MeOH/DCM and filtered. Filtrates were evaporated to give the title compound as a colourless semi-solid (0.48 g, 68%).

LCMS Method 5: r.t. 0.78 mins, [$MH^+$] 180 tert-Butyl 6-(1-isopropyl-1H-imidazole-4-carbonyl)-2,6-diazaspiro[3.3]heptane-2-carboxylate A solution of test-butyl 2,6-diazaspiro[3.3]heptane-2-carboxylate oxalate (288 mg, 1.00 mmol), 1-(propan-2-yl)-1H-imidazole-4-carboxylic acid hydrochloride (191 mg, 1.00 mmol) and DIPEA (775 mg, 6.00 mmol) in DCM (10 mL) was treated with HATU (456 mg, 1.20 mmol) and stirred at rt for 18 h. The reaction mixture was diluted with aqueous $NaHCO_3$ and extracted into DCM. The organic extracts were washed with water and brine then dried ($Na_2SO_4$), and evaporated to give the title compound as a brown solid (340 mg, 100%).

LCMS Method 2: r.t. 0.87 mins, [$MH^+$] 335.2

Example 69

(6-(Cyclopropanecarbonyl)-2,6-diazaspiro[3.3]heptan-2-yl)(5-isobutyl-1H-pyrazol-3-yl)methanone Amide Coupling Procedure 1 was employed using cyclopropyl(2,6-diazaspiro[3.3]heptan-2-yl)methanone (2.8 mL at 0.22M, 0.615 mmol) and 3-(2-methylpropyl)-1H-pyrazole-5-carboxylic acid (114 mg, 0.677 mmol) to give the title compound as an off-white solid (71.1 mg, 36%).

$^1H$ NMR (400 MHz, $d_6$-DMSO) δ, ppm 12.95 (1H, s), 6.35 (1H, s), 4.52-4.68 (2H, m), 4.36-4.46 (2H, m), 4.09-4.23 (2H, m), 3.94-4.08 (2H, m), 2.48 (2H, d, J=7.1 Hz), 1.87 (1H, hept, J=6.8 Hz), 1.45-1.53 (1H, m), 0.86 (6H, d, J=6.6 Hz), 0.64-0.73 (4H, m)

LCMS Method 8: r.t. 3.17 mins, [$MH^+$] 317.0

Example 70

(6-(Cyclopropanecarbonyl)-2,6-diazaspiro[3.3]heptan-2-yl) (5-cyclopropyl-1H-pyrazol-3-yl)methanone Amide Coupling Procedure 1 was employed using cyclopropyl(2,6-diazaspiro[3.3]heptan-2-yl)methanone (2.8 mL at 0.22M, 0.615 mmol) and 3-cyclopropyl-1H-pyrazole-5-carboxylic acid (103 mg, 0.677 mmol) to give the title compound as a white solid (46.3 mg, 25%).

$^1H$ NMR (400 MHz, $d_6$-DMSO) δ, ppm 13.00 (1H, s), 6.26 (1H, s), 4.50-4.66 (2H, m), 4.34-4.47 (2H, m), 4.08-4.22 (2H, m), 3.92-4.07 (2H, m), 1.84-1.95 (1H, m), 1.43-1.53 (1H, m), 0.61-0.99 (8H, m)

LCMS Method 8: r.t. 2.70 mins, [$MH^+$] 301.0

Example 71

(5-(tert-Butyl)-1H-pyrazol-3-yl)(6-(cyclopropanecarbonyl)-2,6-diazaspiro[3.3]heptan-2-yl)methanone Amide Coupling Procedure 1 was employed using cyclopropyl(2,6-diazaspiro[3.3]heptan-2-yl)methanone (2.8 mL at 0.22M, 0.615 mmol) and 3-tert-butyl-1H-pyrazole-5-carboxylic acid (114 mg, 0.677 mmol) to give the title compound as a white solid (5.0 mg, 2.5%).

$^1H$ NMR (400 MHz, $d_6$-DMSO) δ, ppm 12.88 (1H, br s), 6.36 (1H, s), 4.55-4.66 (2H, m), 4.37-4.46 (2H, m), 4.10-4.21 (2H, m), 3.97-4.06 (2H, m), 1.45-1.54 (1H, m), 1.27 (9H, s), 0.64-0.73 (4H, m)

LCMS Method 7: r.t. 3.22 mins, [$MH^+$] 317.0

Example 72

(5-Cyclobutyl-1H-pyrazol-3-yl)(6-(cyclopropanecarbonyl)-2,6-diazaspiro[3.3]heptan-2-yl)methanone Amide Coupling Procedure 1 was employed using cyclopropyl(2,6-diazaspiro[3.3]heptan-2-yl)methanone (2.8 mL at 0.22M, 0.615 mmol) and 3-cyclobutyl-1H-pyrazole-5-carboxylic acid (112 mg, 0.677 mmol) to give the title compound as a white solid (9.1 mg, 4.7%).

$^1$H NMR (400 MHz, $d_6$-DMSO) δ, ppm 13.00 (1H, s), 6.43 (1H, s), 4.54-4.66 (2H, m), 4.35-4.45 (2H, m), 4.10-4.22 (2H, m), 3.97-4.06 (2H, m), 3.51 (1H, hept, J=8.6 Hz), 2.23-2.34 (2H, m), 2.05-2.17 (2H, m), 1.89-2.00 (1H, m), 1.78-1.89 (1H, m), 1.44-1.53 (1H, m), 0.63-0.74 (4H, m)

LCMS Method 7: r.t. 3.12 mins, [$MH^+$] 315.0

Example 73

(5-Cyclohexyl-1H-pyrazol-3-yl)(6-(cyclopropanecarbonyl)-2,6-diazaspiro[3.3]heptan-2-yl)methanone Amide coupling procedure 1 was employed using cyclopropyl(2,6-diazaspiro[3.3]heptan-2-yl)methanone (2.8 mL at 0.22M, 0.615 mmol) and 3-cyclohexyl-1H-pyrazole-5-carboxylic acid (112 mg, 0.677 mmol) to give the title compound as a white solid (19.6 mg, 9%).

$^1$H NMR (400 MHz, $d_6$-DMSO) δ, ppm 12.58 (1H, br s), 6.34 (1H, s), 4.53-4.65 (2H, m), 4.35-4.45 (2H, m), 4.09-4.20 (2H, m), 3.96-4.00 (2H, m), 2.58-2.69 (1H, m), 1.84-1.96 (2H, m), 1.61-1.80 (3H, m), 1.43-1.54 (1H, m), 1.13-1.43 (5H, m), 0.62-0.74 (4H, m)

LCMS Method 1: r.t. 3.57 mins, [$MH^+$] 343.3

Example 74

(6-(Cyclobutanecarbonyl)-2,6-diazaspiro[3.3]heptan-2-yl)(5-isopropyl-1H-pyrazol-3-yl)methanone Pyrazole Spirodiazetidine Amide General Procedure 1 was employed using tert-butyl 6-(5-isopropyl-1H-pyrazole-3-carbonyl)-2,6-diazaspiro[3.3]heptane-2-carboxylate (75 mg, 0.22 mmol) and cyclobutane carboxylic acid (23 mg, 0.23 mmol) to give the title compound as a white solid (34.5 mg, 52%).

$^1$H NMR (400 MHz, $d_6$-DMSO) δ, ppm 12.98 (1H, s), 6.35 (1H, s), 4.51-4.62 (2H, m), 4.15-4.24 (2H, m), 4.08-4.15 (2H, m), 3.94-4.04 (2H, m), 3.04 (1H, pent, J=8.4 Hz), 2.95 (1H, hept, J=6.9 Hz), 1.95-2.15 (4H, m), 1.82-1.95 (1H, m), 1.68-1.78 (1H, m), 1.21 (6H, d, J=6.9 Hz)

LCMS Method 7: r.t. 3.31 mins, [$MH^+$] 317.0

Example 75

(5-Isopropyl-1H-pyrazol-3-yl)(6-(1-methyl-1H-imidazole-4-carbonyl)-2,6-diazaspiro[3.3]heptan-2-yl)methanone Pyrazole Spirodiazetidine Amide General Procedure 1 was employed using tert-butyl 6-(5-isopropyl-1H-pyrazole-3-carbonyl)-2,6-diazaspiro[3.3]heptane-2-carboxylate (75 mg, 0.22 mmol) and 1-methylimidazole-4-carboxylic acid (29 mg, 0.23 mmol) to give the title compound as a white solid (37.7 mg, 52%).

$^1$H NMR (400 MHz, $d_6$-DMSO) δ, ppm 12.98 (1H, s), 7.64 (2H, s), 6.36 (1H, s), 4.52-4.72 (4H, m), 4.06-4.28 (4H, m), 3.67 (3H, s), 2.95 (1H, hept, J=6.9 Hz), 1.21 (6H, d, J=6.9 Hz)

LCMS Method 1: r.t. 2.15 mins, [$MH^+$] 343.3

Example 76

(5-Isopropyl-1H-pyrazol-3-yl)(6-(thiazole-2-carbonyl)-2,6-diazaspiro[3.3]heptan-2-yl)methanone Pyrazole Spirodiazetidine Amide General Procedure 1 was employed using tert-butyl 6-(5-isopropyl-1H-pyrazole-3-carbonyl)-2,6-diazaspiro[3.3]heptane-2-carboxylate (75 mg, 0.22 mmol) and thiazole-2-carboxylic acid (30 mg, 0.23 mmol) to give the title compound as a white solid (20.0 mg, 28%).

$^1$H NMR (400 MHz, $d_6$-DMSO) δ, ppm 12.99 (1H, s), 8.04 (1H, d, J=3.1 Hz), 8.02 (1H, d, J=3.2 Hz), 6.36 (1H, s), 4.72-4.83 (2H, m), 4.59-4.68 (2H, m), 4.24-4.35 (2H, m), 4.15-4.24 (2H, m), 2.95 (1H, hept, J=6.8 Hz), 1.21 (6H, d, J=6.9 Hz)

LCMS Method 1: r.t. 3.08 mins, [$MH^+$] 346.3

Example 77

(5-Isopropyl-1H-pyrazol-3-yl)(6-(1-methyl-1H-pyrazole-3-carbonyl)-2,6-diazaspiro[3.3]heptan-2-yl)methanone Pyrazole Spirodiazetidine Amide General Procedure 1 was employed using tert-butyl 6-(5-isopropyl-1H-pyrazole-3-carbonyl)-2,6-diazaspiro[3.3]heptane-2-carboxylate (75 mg, 0.22 mmol) and 1-methyl-1H-pyrazole carboxylic acid (29 mg, 0.23 mmol) to give the title compound as a white solid (43.0 mg, 60%).

$^1$H NMR (400 MHz, $d_6$-DMSO) δ, ppm 12.98 (1H, s), 7.75 (1H, d, J=2.2 Hz), 6.59 (1H, d, J=2.2 Hz), 6.36 (1H, s), 4.58-4.66 (4H, m), 4.13-4.22 (4H, m), 3.88 (3H, s), 2.95 (1H, hept, J=6.8 Hz), 1.21 (6H, d, J=6.9 Hz)

LCMS Method 1: r.t. 2.73 mins, [$MH^+$] 343.3

Example 78

(5-Isopropyl-1H-pyrazol-3-yl)(6-(thiazole-4-carbonyl)-2,6-diazaspiro[3.3]heptan-2-yl)methanone Pyrazole Spirodiazetidine Amide General Procedure 1 was employed using tert-butyl 6-(5-isopropyl-1H-pyrazole-3-carbonyl)-2,6-diazaspiro[3.3]heptane-2-carboxylate (75 mg, 0.22 mmol) and 4-thiazole carboxylic acid (30 mg, 0.23 mmol) to give the title compound as a white solid (30.7 mg, 43%).

$^1$H NMR (400 MHz, $d_6$-DMSO) δ, ppm 12.99 (1H, s), 9.17 (1H, d, J=2.0 Hz), 8.35 (1H, d, J=2.1 Hz), 6.36 (1H, s), 4.67-4.72 (2H, m), 4.59-4.66 (2H, m), 4.21-4.28 (2H, m), 4.13-4.21 (2H, m), 2.95 (1H, hept, J=6.8 Hz), 1.21 (6H, d, J=6.9 Hz)

LCMS Method 3: r.t. 2.92 mins, [$MH^+$] 345.0

Example 79

(S)-(6-(Cyclopropanecarbonyl)-2,6-diazaspiro[3.3]heptan-2-yl)(1-(1-hydroxypropan-2-yl)-1H-imidazol-4-yl)methanone Amide coupling procedure 1 was employed using cyclopropyl(2,6-diazaspiro[3.3]heptan-2-yl)methanone (2.8 mL at 0.22M, 0.615 mmol) and (S)-1-(1-hydroxypropan-2-yl)-1H-imidazole-4-carboxylic acid (70 mg, 0.413 mmol) to give the title compound as a white solid (24.3 mg, 20%).

$^1$H NMR (400 MHz, $d_6$-DMSO) δ, ppm 7.74 (1H, d, J=1.2 Hz), 7.71 (1H, d, J=1.2 Hz), 5.00 (1H, br s), 4.58-4.69 (2H, m), 4.36-4.43 (2H, m), 4.23-4.33 (1H, m), 4.08-4.18 (2H, m), 3.97-4.05 (2H, m), 3.49-3.62 (2H, m), 1.44-1.53 (1H, m), 1.36 (3H, d, J=6.9 Hz), 0.64-0.73 (4H, m)

LCMS Method 1: r.t. 1.80 mins, [$MH^+$] 319.2

Example 80

N-(1-(5-Isopropyl-1H-pyrazole-3-carbonyl)azetidin-3-yl)cyclopropanecarboxamide tert-Butyl 3-(cyclopropanecarboxamido)azetidine-1-carboxylate A stirred solution of 3-amino-1-N-Boc-azetidine (1.00 g, 5.81 mmol) and triethylamine (1.6 mL, 11.6 mmol) in DCM (50 mL) was cooled to 0° C. and treated with cyclopropanecarbonyl chloride (0.59 mL, 6.39 mmol). The mixture was allowed to warm to rt for 18 h then diluted with aqueous $NaHCO_3$ and extracted into DCM. The combined organic extracts were washed with water and brine, dried ($Na_2SO_4$), and evaporated to give an oil. The crude product was purified by silica gel chromatography eluting with 0-5% (2M ammonia in MeOH)/DCM to give the title compound as an oil (1.08 mg, 77%).

LCMS Method 2: r.t. 1.00 mins, [$MH^+$-Boc] 141

N-(Azetidin-3-yl)cyclopropanecarboxamide

A solution of TFA (1.0 mL) in DCM (2.0 mL) was added to tert-butyl-3-(cyclopropanecarboxamido)azetidine-1-carboxylate (500 mg, 2.08 mmol). After 1 h the solution was loaded onto a pre-wetted SCX-2 cartridge, and the cartridge was washed through with MeOH then the product eluted using 2M ammonia in MeOH. Evaporation of the solution gave the title compound as an oil (285 mg, 97%).

LCMS Method 4: r.t. 0.30 mins, [$MH^+$] 141

N-(1-(5-Isopropyl-1H-pyrazole-3-carbonyl)azetidin-3-yl)cyclopropanecarboxamide

Amide Coupling Procedure 3 was employed using N-(azetidin-3-yl)cyclopropanecarboxamide (285 mg, 2.03 mmol) and 3-isopropylpyrazole-5-carboxylic acid (313 mg, 2.03 mmol) to give an oil. The crude product was purified by silica gel chromatography eluting with 0-10% (2M ammonia in MeOH)/DCM to give the title compound as a white solid (30 mg, 5%).

$^1H$ NMR (400 MHz, $d_6$-DMSO) δ, ppm 12.98 (1H, s), 8.74 (1H, d, J=7.1 Hz), 6.37 (1H, s), 4.64-4.73 (1H, m), 4.47-4.58 (1H, m), 4.18-4.30 (2H, m) 3.75-3.84 (1H, m), 2.96 (1H, hept, J=6.9 Hz), 1.47-1.56 (1H, m), 1.12 (6H, d, J=6.9 Hz), 0.64-0.73 (4H, m)

LCMS Method 1: r.t. 2.75 mins, [$MH^+$] 277.2

Example 81

(6-(Cyclopropanecarbonyl)-2,6-diazaspiro[3.3]heptan-2-yl)(1-isopropyl-1H-imidazol-4-yl)methanone Pyrazole Spirodiazetidine Amide General Procedure 1 was employed using tert-butyl 6-(1-isopropyl-1H-imidazole-4-carbonyl)-2,6-diazaspiro[3.3]heptane-2-carboxylate (75 mg, 0.22 mmol) and cyclopropane carboxylic acid (21 mg, 0.25 mmol) to give the title compound as a white solid (39 mg, 57%).

$^1H$ NMR (400 MHz, $d_6$-DMSO) δ, ppm 7.79 (1H, d, J=1.4 Hz), 7.77 (1H, d, J=1.4 Hz), 4.58-4.69 (2H, m), 4.44 (1H, hept, J=6.7 Hz), 4.37-4.42 (2H, m), 4.07-4.18 (2H, m), 3.96-4.05 (2H, m), 1.44-1.53 (1H, m), 1.40 (6H, d, J=6.7 Hz), 0.64-0.73 (4H, m)

LCMS Method 8: r.t. 2.60 mins, [$MH^+$] 303.0

Example 82

1-(6-(1-Isopropyl-1H-imidazole-4-carbonyl)-2,6-diazaspiro[3.3]heptan-2-yl)-2,2-dimethylpropan-1-one Pyrazole Spirodiazetidine Amide General Procedure 1 was employed using tert-butyl 6-(1-isopropyl-1H-imidazole-4-carbonyl)-2,6-diazaspiro[3.3]heptane-2-carboxylate (200 mg, 0.365 mmol) and pivalic acid (41 mg, 0.401 mmol) to give the title compound as a white solid (25 mg, 21%).

$^1H$ NMR (400 MHz, $d_6$-DMSO) δ, ppm 7.78 (1H, d, J=1.4 Hz), 7.76 (1H, d, J=1.3 Hz), 4.48-4.67 (4H, m), 4.44 (1H, hept, J=6.7 Hz), 3.91-4.15 (4H, m), 1.39 (6H, d, J=6.9 Hz), 1.09 (9H, s)

LCMS Method 1: r.t. 2.49 mins, [$MH^+$] 319.3

Cyclopropyl Amides tert-Butyl 6-(cyclopropanecarbonyl)-2,6-diazaspiro[3.3]heptane-2-carboxylate To a suspension of tert-butyl 2,6-diazaspiro[3.3]heptane-2-carboxylate oxalate (2.70 g, 9.37 mmol) in DCM (54 ml) was added cyclopropanecarboxylic acid (0.75 ml, 9.37 mmol) and triethylamine (5.2 ml, 37.5 mmol). HATU (4.63 g, 12.2 mmol) was added and the reaction was stirred at rt for 60 h. The reaction mixture was concentrated in vacuo and the resulting residue was taken up in EtOAc then washed with water (×3) then brine. The organic phase was dried ($Na_2SO_4$) and concentrated in vacuo to give the crude product as a yellow oil. Purification by silica gel chromatography (80 g cartridge) eluting with 0-15% MeOH in DCM gave the target compound as a yellow oil (1.49 g, 60%).

LCMS Method 4: r.t 1.18 mins [$MH^+$] 267

Cyclopropyl Spirodiazetidine Amide General Procedure

To a solution of tert-butyl 6-(cyclopropanecarbonyl)-2,6-diazaspiro[3.3]heptane-2-carboxylate (1.0 eq) in DCM (3 ml) was added methanesulfonic acid (4 eq). The reaction was stirred at room temperature for 75 min then triethylamine (6 eq) was added followed by carboxylic acid (1.1 eq) and HATU (1.3 eq). The reaction was stirred at room temperature for 16-60 h then concentrated in vacuo to give the crude amide product.

Example 83

(6-(Cyclopropanecarbonyl)-2,6-diazaspiro[3.3]heptan-2-yl)(5-isopropyl-1H-pyrazol-3-yl)methanone Prepared from tert-butyl 6-(cyclopropanecarbonyl)-2,6-diazaspiro[3.3]heptane-2-carboxylate and 5-isopropyl-1H-pyrazole-3-carboxylic acid using Cyclopropyl Spirodiazetidine Amide General Procedure. Purification of the crude product by reverse phase preparative HPLC to afford the title compound as a white solid (18 mg, 26%).

$^1H$ NMR (400 MHz, $d_6$-DMSO) δ, ppm 13.01 (1H, s), 6.37 (1H, s), 4.64-4.57 (2H, m), 4.43-4.38 (2H, m), 4.19-

4.12 (2H, m), 4.04-3.98 (2H, m), 3.01-2.90 (1H, m), 1.52-1.45 (1H, m), 1.21 (6H, d, J=6.8 Hz), 0.73-0.64 (4H, m).

LCMS Method 7: r.t 3.02 mins [$MH^+$] 303.0

Example 84

(6-(Cyclopropanecarbonyl)-2,6-diazaspiro[3.3]heptan-2-yl)(5-methyl-1H-pyrazol-3-yl)methanone Prepared from tert-butyl 6-(cyclopropanecarbonyl)-2,6-diazaspiro[3.3]heptane-2-carboxylate and 5-methyl-1H-pyrazole-3-carboxylic acid using Cyclopropyl Spirodiazetidine Amide General Procedure. Purification of the crude product by reverse phase preparative HPLC (Luna Phenyl-Hexyl 21.2×150 mm, 10 μM column) to afford the title compound as a white solid (59.1 mg, 35%).

$^1$H NMR (400 MHz, $d_6$-DMSO) δ, ppm 12.94 (1H, s), 6.34 (1H, s), 4.62-4.56 (2H, m), 4.43-4.38 (2H, m), 4.18-4.11 (2H, m), 4.04-3.97 (2H, m), 2.25 (3H, s), 1.52-1.45 (1H, m), 0.72-0.65 (4H, m).

LCMS Method 8: r.t 2.88 mins [$MH^+$] 275.0

Example 85

(6-(Cyclopropanecarbonyl)-2,6-diazaspiro[3.3]heptan-2-yl)(5-propyl-1H-pyrazol-3-yl)methanone Prepared from tert-butyl 6-(cyclopropanecarbonyl)-2,6-diazaspiro[3.3]heptane-2-carboxylate and 5-propyl-1H-pyrazole-3-carboxylic acid using Cyclopropyl Spirodiazetidine Amide General Procedure. Purification of the crude product by reverse phase preparative HPLC to afford the title compound as a white solid (35.2 mg, 19%).

$^1$H NMR (400 MHz, $d_6$-DMSO) δ, ppm 12.96 (1H, s), 6.37 (1H, s), 4.64-4.57 (2H, m), 4.44-4.38 (2H, m), 4.19-4.12 (2H, m), 4.05-3.98 (2H, m), 2.57 (2H, t, J=7.4 Hz), 1.64-1.55 (2H, m), 1.52-1.45 (1H, m), 0.89 (3H, t, J=7.1 Hz), 0.72-0.65 (4H, m).

LCMS Method 7: r.t 2.99 mins [$MH^+$] 303.0

Example 86

(6-(Cyclopropanecarbonyl)-2,6-diazaspiro[3.3]heptan-2-yl)(5-ethyl-1H-pyrazol-3-yl)methanone Prepared from tert-butyl 6-(cyclopropanecarbonyl)-2,6-diazaspiro[3.3]heptane-2-carboxylate and 5-ethyl-1H-pyrazole-3-carboxylic acid using Cyclopropyl Spirodiazetidine Amide General Procedure. Purification of the crude product was by silica gel chromatography (25 g cartridge) eluting with 0-10% MeOH in DCM followed by reverse phase preparative HPLC (Luna Phenyl-Hexyl 21.2×150 mm, 10 μM column) to afford the title compound as a white solid (21 mg, 19% yield).

$^1$H NMR (400 MHz, $d_6$-DMSO) δ, ppm 12.96 (1H, s), 6.38 (1H, s), 4.63-4.57 (2H, m), 4.44-4.39 (2H, m), 4.19-4.12 (2H, m), 4.04-3.99 (2H, m), 2.61 (2H, q, J=7.5 Hz), 1.52-1.45 (1H, m), 1.18 (3H, t, J=7.5 Hz), 0.73-0.65 (4H, m).

LCMS Method 8: r.t 2.97 mins [$MH^+$] 289

Example 87

(6-(Cyclopropanecarbonyl)-2,6-diazaspiro[3.3]heptan-2-yl)(5-(1-phenylethyl)-1H-pyrazol-3-yl)methanone Prepared from tert-butyl 6-(cyclopropanecarbonyl)-2,6-diazaspiro[3.3]heptane-2-carboxylate and 5-(1-phenylethyl)-1H-pyrazole-3-carboxylic acid using Cyclopropyl Spirodiazetidine Amide General Procedure. Purification of the crude product was by silica gel chromatography (40 g cartridge) eluting with 0-10% MeOH in DCM followed by reverse phase preparative HPLC (Luna Phenyl-Hexyl 21.2×150 mm, 10 μM column) to afford the title compound as a white solid (73 mg, 27%).

$^1$H NMR (400 MHz, $d_6$-DMSO) δ, ppm 13.08 (1H, s), 7.33-7.29 (2H, m), 7.26-7.18 (3H, m), 6.42 (1H, s), 4.63-4.53 (2H, m), 4.39 (2H, s), 4.24-4.11 (3H, m), 4.03-3.98 (2H, m), 1.57 (3H, d, J=7.0 Hz), 1.51-1.44 (1H, m), 0.72-0.64 (4H, m).

LCMS Method 8: r.t 3.64 mins [$MH^+$] 365

The enantiomers of EXAMPLE 87 were separated by chiral SFC using a LUX Cellulose-3 4.6×250 mm, 5 μM column eluting with 30% MeOH (+0.1% diethylamine): 70% $CO_2$, 15 mL/min, 120 bar, 40° C., DAD 230 nm to afford Enantiomer A (EXAMPLE 88), 28 mg as a white solid and Enantiomer B (EXAMPLE 89), 28 mg as a white solid.

Example 88

Enantiomer A

Analytical SFC using LUX Cellulose-3 (2×150 mm, 5 μM) eluting with 25% MeOH (+0.1% diethylamine): 75% $CO_2$, 0.95 mL/min, 120 bar, 40° C., DAD 230 nm retention time 1.0 min Example 89

Enantiomer B

Analytical SFC using LUX Cellulose-3 (2×150 mm, 5 μM) eluting with 25% MeOH (+0.1% diethylamine) 75% $CO_2$, 0.95 mL/min, 120 bar, 40° C., DAD 230 nm retention time 2.1 min Example 90

[2-(Cyclopropanecarbonyl)-3-methyl-2,6-diazaspiro[3.3]heptan-6-yl]-(5-isopropyl-1H-pyrazol-3-yl)methanone 2-(tert-Butylsulfinyl)-1-methyl-6-tosyl-2,6-diazaspiro[3.3]heptane 2-(tert-Butylsulfinyl)-1-methyl-6-tosyl-2,6-diazaspiro[3.3]heptane was prepared according to the procedure reported in J. A. Burkhard, B. Wagner, H. Fischer, F. Schuler, K. Muller and E. M. Carreira, *Angew. Chem. Int. Ed*, 2010, 49, 3524, using racemic tert-butylsulfinamide in the second step 6-(tert-Butylsulfinyl)-5-methyl-2,6-diazaspiro[3.3]heptan-2-yl)(5-isopropyl-1H-pyrazol-3-yl)methanone Magnesium powder (1.31 g, 54.0 mmol) was stirred in anhydrous MeOH (50 ml). To this mixture was added a crystal of iodine and the resulting mixture was stirred at rt until the yellow colour faded (an ice bath was used periodically to lower the temperature of the reaction and prevent boiling of the solvent). To the resulting mixture was added 2-(tert-butylsulfinyl)-1-methyl-6-tosyl-2,6-diazaspiro[3.3]heptane (1.0 g, 2.70 mmol) and the reaction was sonicated at rt for 60 min. The reaction mixture was concentrated in vacuo and taken up in $Et_2O$ then $Na_2SO_4.10H_2O$ (approx. 12 g) was added and the resulting mixture was stirred vigorously for 30 min then filtered through Celite® until all of the white solids were removed. The filtrate was dried ($Na_2SO_4$) and concentrated in vacuo to give a yellow residue which was subsequently dissolved in DMF (5 ml). To this solution was added 5-isopropyl-1H-pyrazole-3-carboxylic acid (458 mg, 1.73 mmol) followed by triethylamine (1.1 ml, 8.10 mmol) then HATU (1.33 g, 3.51 mmol). The reaction was stirred at rt for 60 min then concentrated in vacuo. The resulting residue was dissolved in DCM and filtered. The filtrate was purified by silica gel chromatography (80 g cartridge) eluting with 0-100% MeCN in DCM then 0-10% MeOH in DCM to afford the title compound (as a mixture of diastereoisomers) as an orange oil (118 mg, 21%)

LCMS Method 4: r.t 1.23 mins [$MH^+$] 353

[2-(Cyclopropanecarbonyl)-3-methyl-2,6-diazaspiro[3.3]heptan-6-yl]-(5-isopropyl-1H-pyrazol-3-yl)methanone To a solution of (6-(tert-butylsulfinyl)-5-methyl-2,6-diazaspiro[3.3]heptan-2-yl)(5-isopropyl-1H-pyrazol-3-yl)methanone (mixture of diastereoisomers, 118 mg, 0.20 mmol) in THF (2 ml) was added 2 M HCl in $Et_2O$ (0.60 ml, 1.21 mmol). The reaction was stirred at rt for 25 min then then the solvent was decanted off and the residue triturated three times with $Et_2O$. The product was suspended in DCM (2 ml) then triethylamine (0.22 ml, 1.61 mmol) was added followed by cyclopropanecarboxylic acid (18 µl, 0.22 mmol) then HATU (99 mg, 0.26 mmol). The reaction was stirred at rt for 1 h then the solvent was removed by blowing down under a stream of nitrogen gas. The residue was purified by reverse phase chromatography eluting with 20-98% MeCN in 0.1% $NH_4OH$ solution to afford the title compound as a white solid (21 mg, 33%).

$^1H$ NMR (400 MHz, $d_6$-DMSO) δ, ppm 13.14-12.96 (1H, m), 6.39 (1H, s), 4.64-4.51 (2H, m), 4.46-4.29 (2H, m), 4.20-3.91 (3H, m), 2.99-2.90 (1H, m), 1.56-1.39 (1H, m), 1.50-1.32 (3H, m), 1.23-1.19 (6H, m), 0.76-0.62 (4H, m).

LCMS Method 1: r.t 3.01 mins [$MH^+$] 317.2

The enantiomers of EXAMPLE 90 were separated by chiral SFC using a YMC Amylose-C (10×250 mm, 5 µm) column eluting with 40% MeOH (+0.1% diethylamine): 60% $CO_2$, 15 mL/min, 120 bar, 40° C., DAD 230 nm to afford Enantiomer A (EXAMPLE 91), 10 mg as a white solid and Enantiomer B (EXAMPLE 92), 8 mg as a white solid.

Example 91

Enantiomer A

Analytical SFC using YMC-Amylose C (4.6×250 mm, 5 µm) eluting with 40% MeOH (+0.1% diethylamine): 60% $CO_2$, 5 mL/min, 120 bar, 40° C., DAD 230 nm retention time 1.33 mins Example 92

Enantiomer B

Analytical SFC using YMC-Amylose C (4.6×250 mm, 5 µm) eluting with 40% MeOH (+0.1% diethylamine): 60% $CO_2$, 5 mL/min, 120 bar, 40° C., DAD 230 nm retention time 2.38 mins Example 93

(5-Isopropyl-1H-pyrazol-3-yl)-[2-(4-methylthiazole-2-carbonyl)-2,6-diazaspiro[3.3]heptan-6-yl]methanone Prepared from (5-isopropyl-1H-pyrazol-3-yl)(2,6-diazaspiro[3.3]heptan-2-yl)methanone and 4-methylthiazole-2-carboxylic acid using Pyrazole Spirodiazetidine Amide General Procedure 4. Purification of the crude product by reverse phase chromatography eluting with 10-98% MeCN in 0.1% $NH_4OH$ solution to afford the title compound as a white solid (41 mg, 53%).

$^1H$ NMR (400 MHz, $d_6$-DMSO) δ, ppm 12.98 (1H, s), 7.58 (1H, d, J=0.9 Hz), 6.37 (1H, s), 4.77 (2H, s), 4.66-4.61 (2H, m), 4.30-4.24 (2H, m), 4.22-4.15 (2H, m), 3.01-2.90 (1H, m), 2.43 (3H, s), 1.22 (6H, d, J=7.8 Hz).

LCMS Method 1: r.t 3.38 mins [$MH^+$] 360.1

Example 94

((1R,5S,6r)-6-(cyclopropanecarbonyl)-3-azabicyclo[3.1.0]hexan-3-yl)(5-isopropyl-1H-pyrazol-3-yl)methanone tert-Butyl (1R,5S,6r)-6-(cyclopropanecarbonyl)-3-azabicyclo[3.1.0]hexane-3-carboxylate To a solution of text-butyl (1R,5S,6r)-6-(methoxy(methyl)carbamoyl)-3-azabicyclo[3.1.0]hexane-3-carboxylate (233 mg, 0.83 mmol) in THF (4 mL) at 0° C. was added, dropwise, cyclopropylmagnesium bromide in THF (8.3 mL, 0.5 M, 4.12 mmol) and the reaction mixture stirred at 0° C. for 2 h. Sat. aq. $NH_4Cl$ was added and the mixture stirred at rt for 3 h before being extracted with ethyl acetate (×3). The combined organic fractions were washed with brine, dried ($Na_2SO_4$) and concentrated in vacuo. The product was purified by silica gel chromatography eluting with 0-25% ethyl acetate in cyclohexane to yield the title compound as a white solid (167 mg, 81%).

$^1H$ NMR (400 MHz, $CDCl_3$) δ, ppm 3.69 (1H, d, J=11.3 Hz), 3.61 (1H, dd, J=11.2 Hz), 3.48-3.36 (2H, m), 2.14-1.98 (3H, m), 1.90 (1H, t, J=3.1 Hz), 1.45 (9H, s), 1.08-1.02 (2H, m), 0.95-0.88 (2H, m).

((1R,5S,6r)-3-Azabicyclo[3.1.0] hexan-6-yl)(cyclopropyl)methanone hydrochloride

A solution of tert-butyl (1R,5S,6r)-6-(cyclopropanecarbonyl)-3-azabicyclo[3.1.0]hexane-3-carboxylate (167 mg, 0.66 mmol) in HCl in dioxane (5 mL, 4 N, 20 mmol) was stirred at rt for 1 h. The reaction mixture was concentrated in vacuo to give the title compound as a white solid (125 mg, 100%).

$^1H$ NMR (400 MHz, $d_6$-DMSO) δ, ppm 9.39 (2H, br s), 3.41-3.35 (2H, m), 3.34-3.25 (3H, s), 2.16-2.09 (2H, m), 2.05-1.96 (1H, m), 1.00-0.88 (4H, m).

((1R,5S,6r)-6-(cyclopropanecarbonyl)-3-azabicyclo[3.1.0]hexan-3-yl)(5-isopropyl-pyrazol-3-yl)methanone To a solution of ((1R,5S,6r)-3-azabicyclo[3.1.0]hexan-6-yl)(cyclopropyl)methanone hydrochloride (125 mg, 0.68 mmol) and 3-isopropyl-1H-pyrazole-5-carboxylic acid (113 mg, 0.73 mmol) in DMF (5.0 mL) was added DIPEA (0.35 mL, 1.99 mmol) and HATU (328 mg, 0.86 mmol) and the reaction mixture stirred at rt for 19 h. The reaction mixture was diluted with water and extracted with ethyl acetate (×3). The combined organic fractions were washed with brine, dried ($Na_2SO_4$) and concentrated in vacuo. The product was purified by reverse phase preparative HPLC (Sunfire $C_{18}$ 19×150 mm, 10 μm) to yield the title compound as a white solid (140 mg, 73%).

$^1$H NMR (400 MHz, $d_6$-DMSO) δ, ppm 12.94 (1H, s), 6.38 (1H, s), 4.34 (1H, d, J=12.1 Hz), 3.93 (1H, d, J=12.5 Hz), 3.85 (1H, dd, J=12.1, 3.9 Hz), 3.50 (1H, dd, J=12.4, 3.7 Hz), 2.96 (1H, sept, J=6.7 Hz), 2.22-2.10 (2H, m), 2.10-1.98 (2H, m), 1.22 (6H, d, J=6.85 Hz), 0.92-0.84 (4H, m).

LCMS Method 8: r.t. 3.37 mins, [MH$^+$] 288

Example 95

7-Isopropyl-8-oxo-6-phenyl-5,8-dihydroimidazo[1,2-b]pyridazine-3-carbonitrile

A mixture of 3-bromo-7-isopropyl-6-phenylimidazo[1,2-b]pyridazin-8 (5H)-one (86 mg, 0.26 mmol), zinc cyanide (30 mg, 0.26 mmol), dichloro[9,9-dimethyl-4,5-bis(diphenylphosphino)xanthene] palladium(II) (98 mg, 0.13 mmol) and DIPEA (0.01 mL, 0.06 mmol) were degassed with argon and heated at 100° C. for 30 min. DIPEA (0.09 mL, 0.52 mmol) was added, the mixture degassed then heated at 100° C. for 30 min. DIPEA (0.91 mL, 0.52 mmol), zinc cyanide (30 mg, 0.26 mmol) and dichloro[9,9-dimethyl-4,5-bis(diphenylphosphino)xanthene]palladium(II) (98 mg, 0.13 mmol) were added, the mixture degassed and heated at 100° C. for 30 min. The reaction mixture was cooled to rt, filtered and the filtrate diluted with water. The mixture was extracted with ethyl acetate/MeOH and the combined organic fractions washed with brine, dried ($Na_2SO_4$) and concentrated in vacuo. The residue was purified by purified by reverse phase preparative HPLC to yield the title compound as a white solid (8 mg, 11%).

$^1$H NMR (400 MHz DMSO) δ, ppm 8.47 (1H, s), 7.58-7.51 (3H, m), 7.50-7.43 (2H, m), 2.80 (1H, sept, J=7.0 Hz), 1.28 (6H, d, J=7.0 Hz).

LCMS Method 8: r.t. 3.31 mins, [MH$^+$] 279

Example 96

(5-Isopropyl-1H-pyrazol-3-yl)(6-(1-methylcyclopropane-1-carbonyl)-2,6-diazaspiro[3.3]heptan-2-yl) methanone Prepared from tert-butyl 6-(5-isopropyl-1H-pyrazole-3-carbonyl)-2,6-diazaspiro[3.3]heptane-2-carboxylate (75 mg, 0.22 mmol) and 1-methylcyclopropanecarboxylic acid using Pyrazole Spirodiazetidine Amide General Procedure 1 to yield the title compound as a white solid (19 mg, 27%).

$^1$H NMR (400 MHz DMSO) δ, ppm 12.97 (1H, s), 6.36 (1H, s), 4.62-4.41 (4H, m), 4.2-3.96 (4H, m), 2.95 (1H, sept, J=6.9 Hz), 1.22 (3H, s), 1.21 (6H, d, J=6.9 Hz), 0.89 (2H, dd, J=6.4, 3.8 Hz), 0.45 (2H, dd, J=6.3, 3.6 Hz).

LCMS Method 8: r.t. 3.09 mins, [MH$^+$] 317

Example 97

(5-Isopropyl-1H-pyrazol-3-yl)(6-(1-methylcyclobutane-1-carbonyl)-2,6-diazaspiro[3.3]heptan-2-yl) methanone Prepared from tert-butyl 6-(5-isopropyl-1H-pyrazole-3-carbonyl)-2,6-diazaspiro[3.3]heptane-2-carboxylate (75 mg, 0.22 mmol) and 1-methylcyclobutanecarboxylic acid using Pyrazole Spirodiazetidine Amide General Procedure 1 to yield the title compound as a white solid (18 mg, 24%).

$^1$H NMR (400 MHz $d_6$-DMSO) δ, ppm 12.97 (1H, s), 6.36 (1H, s), 4.63-4.53 (2H, m), 4.31-4.21 (2H, m), 4.18-4.08 (2H, m), 4.06-3.94 (2H, m), 2.95 (1H, sept, J=6.9 Hz), 2.37-2.25 (2H, m), 1.97-1.84 (1H, m), 1.69-1.56 (3H, m), 1.30 (3H, s), 1.21 (6H, d, J=6.9 Hz).

LCMS Method 8: r.t. 3.3 mins, [MH$^+$] 331

Example 98

Bicyclo[1.1.1]pentan-1-yl(6-(5-isopropyl-1H-pyrazole-3-carbonyl)-2,6-diazaspiro[3.3]heptan-2-yl) methanone Prepared from tert-butyl 6-(5-isopropyl-1H-pyrazole-3-carbonyl)-2,6-diazaspiro[3.3]heptane-2-carboxylate (75 mg, 0.22 mmol) and bicycle[1.1.1]pentane-3-carboxylic acid using Pyrazole Spirodiazetidine Amide General Procedure 1 to yield the title compound as a white solid (32 mg, 43%).

$^1$H NMR (400 MHz $d_6$-DMSO) δ, ppm 12.97 (1H, s), 6.35 (1H, s), 4.61-4.53 (2H, m), 4.45-4.37 (2H, m), 4.18-4.08 (2H, m), 4.06-3.97 (2H, m), 2.95 (1H, sept, J=6.7 Hz), 2.42 (1H, s), 1.99 (6H, s), 1.21 (6H, d, J=6.8 Hz).

LCMS Method 8: r.t. 3.18 mins, [MH$^+$] 329

Example 99

(5-Isopropyl-1H-pyrazol-3-yl)(6-(thiophene-2-carbonyl)-2,6-diazaspiro[3.3]heptan-2-yl)methanone Prepared from tert-butyl 6-(5-isopropyl-1H-pyrazole-3-carbonyl)-2,6-diazaspiro[3.3]heptane-2-carboxylate (75 mg, 0.22 mmol) and thiophene-2-carboxylic acid using Pyrazole Spirodiazetidine Amide General Procedure 1 to yield the title compound as a white solid (17 mg, 22%).

$^1$H NMR (400 MHz $d_6$-DMSO) δ, ppm 12.98 (1H, s), 7.81 (1H, dd, J=5.0, 1.1 Hz), 7.48 (1H, dd, J=3.8, 1.1 Hz), 7.18 (1H, dd, J=5.0, 3.8 Hz), 6.36 (1H, s), 4.72-4.59 (4H, m), 4.29-4.15 (4H, m), 2.95 (1H, sept, J=7.0 Hz), 1.21 (6H, d, J=7.0 Hz).

LCMS Method 7: r.t. 3.30 mins, [MH$^+$] 345

Example 100

3-Isopropyl-2-(1-methyl-1H-pyrrol-3-yl)-7-(1H-pyrazol-4-yl)imidazo[2,1-f][1,2,4]triazin-4(3H)-one 3-Isopropyl-2-(1-methyl-1H-pyrrol-3-yl)-7-(1-(tetrahydro-2H-pyran-2-yl)-1H-pyrazol-4-yl)imidazo[2,1-f][1,2,4]triazin-4(3H)-one A mixture of 2-chloro-3-isopropyl-7-(1-(tetrahydro-2H-pyran-2-yl)-1H-pyrazol-4-yl)imidazo[2,1-f][1,2,4]triazin-4 (3H)-one (75 mg, 0.21 mmol), 1-methyl-3-(4,4,5,5-tetramethyl-1,3,2-dioxaborolan-2-yl)-1H-pyrrole (64 mg, 0.31 mmol), XphosPdG2 (16 mg, 0.02 mmol), Xphos (10 mg, 0.02 mmol) and potassium carbonate (57 mg, 0.41 mmol) in dioxane (2.7 mL) and water (0.3 mL) was degassed with argon and heated at 80° C. for 16 h. The reaction mixture was diluted with water and extracted with ethyl acetate. The combined organic fractions were washed with brine, dried ($Na_2SO_4$) and concentrated in vacuo. The residue was purified by silica gel chromatography eluting with 0-2.5% MeOH in DCM to yield the title compound as a white solid (28 mg, 33%).

LCMS Method 2: r.t. 1.18 mins, [$MH^+$] 408

3-Isopropyl-2-(1-methyl-1H-pyrrol-3-yl)-7-(1H-pyrazol-4-yl)imidazo[2,1-f][1,2,4]triazin-4(3H)-one To a solution of 3-isopropyl-2-(1-methyl-1H-pyrrol-3-yl)-7-(1-(tetrahydro-2H-pyran-2-yl)-1H-pyrazol-4-yl)imidazo [2,1-f][1,2,4]triazin-4(3H)-one (25 mg, 0.06 mmol) in MeOH (1.5 mL) was added HCl aq. (1.0 mL, 1 N, 1 mmol) and the reaction mixture stirred at rt for 16 h. The reaction mixture was concentrated in vacuo and the residue purified by reverse phase chromatography eluting with 10-98% MeCN in water (formic acid modifier) to yield the title compound as a white solid (3.3 mg, 16%).

$^1$H NMR (400 MHz, $d_6$-DMSO) δ, ppm 13.15 (1H, s), 8.33 (1H, s), 8.11 (1H, s), 7.74 (1H, s), 7.37 (1H, t, J=1.9 Hz), 6.94 (1H, t, J=2.5 Hz), 6.40 (1H, dd, J=2.7, 1.8 Hz), 4.79 (1H, sept, J=6.8 Hz), 3.74 (3H, s), 1.55 (6H, d, J=6.8 Hz).

LCMS Method 1: r.t. 3.26 mins, [$MH^+$] 324

Example 101

3-Isopropyl-2-(1-methyl-1H-indol-3-yl)-7-(1H-pyrazol-4-yl)imidazo[2,1-f][1,2,4]triazin-4(3H)-one 3-Isopropyl-2-(1-methyl-1H-indol-3-yl)-7-(1-(tetrahydro-2H-pyran-2-yl)-1H-pyrazol-4-yl)imidazo[2,1-f][1,2,4]triazin-4(3H)-one A mixture of 2-chloro-3-isopropyl-7-(1-(tetrahydro-2H-pyran-2-yl)-1H-pyrazol-4-yl)imidazo[2,1-f][1,2,4]triazin-4 (3H)-one (75 mg, 0.21 mmol), 1-methyl-3-(4,4,5,5-tetramethyl-1,3,2-dioxaborolan-2-yl)-1H-indole (80 mg, 0.31 mmol), XphosPdG2 (16 mg, 0.02 mmol), Xphos (10 mg, 0.02 mmol) and potassium carbonate (57 mg, 0.41 mmol) in dioxane (2.7 mL) and water (0.3 mL) was degassed with argon and heated at 80° C. for 16 h. The reaction mixture was diluted with water and extracted with ethyl acetate. The combined organic fractions were washed with brine, dried ($Na_2SO_4$) and concentrated in vacuo. The residue was purified by silica gel chromatography eluting with 0-2% MeOH in DCM to yield the title compound as a white solid (21 mg, 22%).

LCMS Method 2: r.t. 1.29 mins, [$MH^+$] 458

3-Isopropyl-2-(1-methyl-1H-indol-3-yl)-7-(1H-pyrazol-4-yl)imidazo[2,1-f][1,2,4]triazin-4(3H)-one To a solution of 3-isopropyl-2-(1-methyl-1H-indol-3-yl)-7-(1-(tetrahydro-2H-pyran-2-yl)-1H-pyrazol-4-yl)imidazo [2,1-f][1,2,4]triazin-4(3H)-one (21 mg, 0.05 mmol) in MeOH (1.5 mL) was added HCl aq. (1 mL, 1 N, 1 mmol) and the reaction mixture stirred at rt for 16 h. The reaction mixture was concentrated in vacuo and the residue purified by reverse phase chromatography eluting with 10-98% MeCN in water (formic acid modifier) to yield the title compound as a white solid (7 mg, 41%).

$^1$H NMR (400 MHz, $d_6$-DMSO) δ, ppm 13.11 (1H, s), 8.26 (1H, s), 8.07 (1H, s), 7.88 (1H, s), 7.81-7.76 (2H, m), 7.61 (1H, d, J=8.3 Hz), 7.31 (1H, ddd, J=8.2, 7.0, 1.1 Hz), 7.20 (1H, ddd, J=8.0, 7.2, 0.9 Hz), 4.58 (1H, sept, J=6.8 Hz), 3.93 (3H, s), 1.53 (6H, d, J=6.8 Hz).

LCMS Method 1: r.t. 3.83 mins, [$MH^+$] 374

Example 102

N-(1-(5-Cyclopropyl-1H-pyrazole-3-carbonyl)azetidin-3-yl)cyclopropanecarboxamide tert-Butyl (1-(5-cyclopropyl-1H-pyrazole-3-carbonyl)azetidin-3-yl) carbamate A mixture of 5-cyclopropyl-1H-pyrazole-3-carboxylic acid (200 mg, 1.31 mmol), tert-butyl azetidin-3-ylcarbamate (226 mg, 1.31 mmol), DIPEA (0.69 mL, 3.94 mmol) and HATU (600 mg, 1.58 mmol) in DMF (5.0 mL) was stirred at rt for 16 h. The reaction mixture was diluted with water and extracted with ethyl acetate. The combined organic fractions were washed with brine, dried ($Na_2SO_4$) and concentrated in vacuo. The residue was purified by silica gel chromatography eluting with 0-100% ethyl acetate in cyclohexane to yield the title compound as a white solid. A further quantity of product precipitated out of the aqueous fraction on standing, this was collected by filtration and dried in vacuo. Both samples were combined to give the title compound as an off-white solid (335 mg, 83%).

LCMS Method 2: r.t. 0.98 mins, [$MH^+$] 307

(3-Aminoazetidin-1-yl)(5-cyclopropyl-1H-pyrazol-3-yl)methanone

To a solution of tert-butyl (1-(5-cyclopropyl-1H-pyrazole-3-carbonyl)azetidin-3-yl)carbamate (330 mg, 1.08 mmol), in MeOH (1.0 mL) was added DCM (4.0 mL) and TFA (1.0 mL, 13.1 mmol) and the reaction mixture stirred at rt for 16 h. A further quantity of TFA (2.0 mL, 26.2 mmol) and MeOH (1.0 mL) was added and the reaction stirred for 16 h. The reaction mixture was concentrated in vacuo and the residue dissolved in TFA (4.0 mL) and stirred at rt for 16 h. The reaction mixture was concentrated in vacuo and the residue purified by SCX-2 Cartridge eluting with 7 N $NH_3$ in MeOH to yield the title compound as a yellow oil (138 mg, 62%).

LCMS Method 4: r.t. 0.78 mins, [$MH^+$] 207

N-(1-(5-Cyclopropyl-1H-pyrazole-3-carbonyl)azetidin-3-yl)cyclopropanecarboxamide A mixture of cyclopropane carboxylic acid (36 mg, 0.27 mmol), (3-aminoazetidin-1-yl)(5-cyclopropyl-1H-pyrazol-3-yl)methanone (46 mg, 0.22 mmol), DIPEA (0.12 mL, 0.67 mmol) and HATU (110 mg, 0.29 mmol) in DMF (3.0 mL) was stirred at rt for 16 h. The reaction mixture was concentrated in vacuo and the residue purified by reverse phase chromatography eluting with 10-98% MeCN in water (formic acid modifier) to yield the title compound as a white solid (47 mg, 77%).

$^1$H NMR (400 MHz, $d_6$-DMSO) δ, ppm 12.98 (1H, s), 8.74 (1H, d, J=7.7 Hz), 6.27 (1H, s), 4.70-4.47 (2H, m), 4.30-4.10 (2H, m), 3.82-3.74 (1H, m), 1.95-1.85 (1H, m), 1.56-1.46 (1H, in), 0.98-0.80 (2H, m), 0.73-0.63 (6H, m).

LCMS Method 3: r.t 2.6 mins, [$MH^+$] 275

Example 103

N-(1-(5-cyclopropyl-1H-pyrazole-3-carbonyl)azetidin-3-yl)spiro[2.2]pentane-1-carboxamide A mixture of spiro[2.2]pentane-1-carboxylic acid (60 mg, 0.54 mmol), (3-aminoazetidin-1-yl)(5-cyclopropyl-1H- pyrazol-3-yl)methanone (90 mg, 0.45 mmol), DIPEA (0.23 mL, 1.34 mmol) and HATU (220 mg, 0.58 mmol) in DMF (3.0 mL) was stirred at rt for 16 h. The reaction mixture was concentrated in vacuo and the residue purified by reverse phase chromatography eluting with 10-98% MeCN in water (formic acid modifier) to yield the title compound as a white solid (107 mg, 80%).

$^1H$ NMR (400 MHz, $d_6$-DMSO) δ, ppm 12.98 (1H, s), 8.54 (1H, d, J=6.8 Hz), 6.27 (1H, s), 4.70-4.44 (2H, m), 4.30-4.07 (2H, m), 3.88-3.72 (1H, m), 1.95-1.83 (2H, m), 1.27 (1H, t, J=3.4 Hz), 1.20 (1H, dd, J=7.5, 3.8 Hz), 0.98-0.87 (2H, m), 0.87-0.75 (3H, m), 0.74-0.63 (3H, m).

LCMS Method 3: r.t. 2.95 mins, [$MH^+$] 301

The enantiomers of EXAMPLE 103 were separated by chiral SFC (YMC Cellulose-SC 10×250 mm, 5 μm column) eluting with 20% EtOH (0.1% diethylamine)/80% $CO_2$, 15 ml/min, 120 bar, 40° C. to afford EXAMPLE 104 and EXAMPLE 105.

Example 104

Enantiomer A: 44.1 mg as a white solid

Analytical SFC using YMC Cellulose-SC (4.6×250 mm, 5 μm) eluting with 20% EtOH (+0.1% diethylamine)/80% $CO_2$, 5.0 ml/min, 120 bar, 40° C. Enantiomer A: r.t. 7.54 min

Example 105

Enantiomer B: 44 mg as a white solid

Analytical SFC using YMC Cellulose-SC (4.6×250 mm, 5 μm) eluting with 20% EtOH (+0.1% diethylamine)/80% $CO_2$, 5.0 ml/min, 120 bar, 40° C. Enantiomer B: r.t. 8.94 min

Example 106

1-(6-(5-(1-Hydroxypropan-2-yl)-1H-pyrazole-3-carbonyl)-2,6-diazaspiro[3.3]heptan-2-yl)-2,2-dimethylpropan-1-one tert-Butyl 6-(3-bromo-1-((2-(trimethylsilyl)ethoxy)methyl)-1H-pyrazole-5-carbonyl)-2,6-diazaspiro[3.3]heptane-2-carboxylate A mixture of 3-bromo-14 (2-(trimethylsilyl)ethoxy)methyl)-1H-pyrazole-5-carboxylic acid (5.05 g, 15.7 mmol), tert-butyl 2,6-diazaspiro[3.3]heptane-2-carboxylate oxalate (4.53 g, 15.7 mmol), triethylamine (8.8 mL, 62.8 mmol) and HATU (7.76 g, 20.4 mmol) in DMF (50 mL) was stirred at rt for 16 h. The reaction mixture was diluted with water and extracted with ethyl acetate. The combined organic fractions were washed with brine, dried ($Na_2SO_4$) and concentrated in vacuo. The residue was purified by silica gel chromatography eluting with 0-40% ethyl acetate in cyclohexane to yield the title compound as a white solid (2.36 g, 30%).

LCMS Method 2: r.t. 1.55 mins, [$MH^+$-56] 443, 445 tert-Butyl 6-(3-(prop-1-en-2-yl)-1-((2-(trimethylsilyl)ethoxy)methyl)-1H-pyrazole-5-carbonyl)-2,6-diazaspiro[3.3]heptane-2-carboxylate A mixture of tert-butyl 6-(3-bromo-1-((2-(trimethylsilyl)ethoxy)methyl)-1H-pyrazole-5-carbonyl)-2,6-diazaspiro[3.3]heptane-2-carboxylate (855 mg, 1.70 mmol), 4,4,5,5-tetramethyl-2-(prop-1-en-2-yl)-1,3,2-dioxaborolane (344 mg, 2.05 mmol), [1,1'-bis(diphenylphosphino)ferrocene] dichloropalladium(II) (125 mg, 0.17 mmol) and sodium carbonate (723 mg, 6.82 mmol) in dioxane (17 mL) and water (3.0 mL) was degassed with argon and the mixture heated at 100° C. for 1 h. The reaction mixture was diluted with water and extracted with ethyl acetate (×3). The combined organic fractions were washed with brine, dried ($Na_2SO_4$) and concentrated in vacuo. The residue was purified by silica gel chromatography eluting with 0-50% ethyl acetate in cyclohexane to yield the title compound as a yellow gum (799 mg, 101%)

LCMS Method 2: r.t. 1.63 mins, [$MNa^+$] 485 tert-Butyl 6-(3-(1-hydroxypropan-2-yl)-1-((2-(trimethylsilyl)ethoxy)methyl)-1H-pyrazole-5-carbonyl)-2,6-diazaspiro[3.3]heptane-2-carboxylate To a solution of tert-butyl 6-(3-(prop-1-en-2-yl)-1-((2-(trimethylsilyl)ethoxy)methyl)-1H-pyrazole-5-carbonyl)-2,6-diazaspiro[3.3]heptane-2-carboxylate (384 mg, 0.83 mmol) in THF (2.0 mL) at 0° C. was added, dropwise, 9-BBN in THF (3.3 mL, 0.5 M, 1.66 mmol) and the reaction stirred at rt for 16 h. The reaction mixture was cooled to 0° C. and hydrogen peroxide (0.37 mL, 30%, 3.73 mmol) and sodium hydroxide aq. (0.17 mL, 10 M, 1.7 mmol) added. The reaction mixture was stirred at 0° C. for 30 min then at 10° C. for 1 h. The reaction mixture was quenched with sodium sulphite aq. and extracted with ethyl acetate (×3). The combined organic fractions were washed with brine, dried ($Na_2SO_4$) and concentrated in vacuo. The residue was purified by silica gel chromatography eluting with 0-100% ethyl acetate in cyclohexane to yield the title compound as a colourless gum (325 mg, 81%)

LCMS Method 2: r.t. 1.42 mins, [$MNa^+$] 503

(5-(1-Hydroxypropan-2-yl)-1H-pyrazol-3-yl)(2,6-diazaspiro[3.3]heptan-2-yl)methanone To a solution of tert-butyl 6-(3-(1-hydroxypropan-2-yl)-1-((2-(trimethylsilyl)ethoxy)methyl)-1H-pyrazole-5-carbonyl)-2,6-diazaspiro[3.3]heptane-2-carboxylate (320 mg, 0.67 mmol) in DCM (2.0 mL) was added TFA (2.0 mL, 26.1 mmol) and the reaction mixture stirred at rt for 1.5 h. The reaction mixture was concentrated in vacuo and the residue dissolved in 2N $NH_3$ in MeOH (4.0 mL). The mixture was stirred at rt for 16 h then concentrated in vacuo. The residue purified by SCX-2 Cartridge eluting with 7N $NH_3$ in MeOH to yield the title compound as a yellow gum (94 mg, 56%).

LCMS Method 4: r.t. 0.74 mins, [$MH^+$] 251

1-(6-(5-(1-Hydroxypropan-2-yl)-1H-pyrazole-3-carbonyl)-2,6-diazaspiro[3.3]heptan-2-yl)-2,2-dimethylpropan-1-one A mixture of (5-(1-hydroxypropan-2-yl)-1H-pyrazol-3-yl)(2,6-diazaspiro[3.3]heptan-2-yl)methanone (94 mg, 0.38 mmol), pivalic acid (38 mg, 0.38 mmol), DIPEA (0.20 mL, 1.13 mmol) and HATU (186 mg, 0.49 mmol) in DMF (3.0 mL) was stirred at rt for 16 h. The reaction mixture was concentrated in vacuo and the residue purified by reverse phase chromatography eluting with 10-98% MeCN in water (formic acid modifier) to yield the title compound as a white solid (40 mg, 32%).

$^1H$ NMR (400 MHz, $CDCl_3$) δ, ppm 6.53 (1H, s), 4.76-4.63 (2H, m), 4.60-4.37 (2H, m), 4.35-4.05 (4H, m), 3.86 (1H, dd, J=10.4, 4.4 Hz), 3.68 (1H, dd, J=10.3, 8.2 Hz), 3.14-3.04 (1H, m), 1.29 (3H, d, J=7.1 Hz), 1.20 (9H, s).

LCMS Method 1: r.t. 2.58 mins, [$MH^+$] 335

The enantiomers of EXAMPLE 106 were separated by chiral SFC (YMC Amylose-C 10×250 mm, 5 μm column)

eluting with 40% MeOH (0.1% diethylamine)/60% $CO_2$, 15 ml/min, 120 bar, 40° C. to afford EXAMPLE 107 and EXAMPLE 108.

Example 107

Enantiomer A

Analytical SFC using YMC Amylose-C 4.6×250 mm, 5 μm column eluting with 40% MeOH (0.1% diethylamine)/60% $CO_2$, 5.0 ml/min, 120 bar, 40° C., retention time 4.1 mins Enantiomer A was freeze-dried to afford the title compound (12 mg) as a white solid.

Example 108

Enantiomer B

Analytical SFC using YMC Amylose-C 4.6×250 mm, 5 μm column eluting with 40% MeOH (0.1% diethylamine)/60% $CO_2$, 5.0 ml/min, 120 bar, 40° C., retention time 5.8 mins Enantiomer B was further purified by silica gel chromatography eluting with 0-10% MeOH/DCM to afford the title compound (7 mg) as a white solid after freeze-drying from MeCN/$H_2O$.

Example 109

1-(6-(3-(1-(Benzyloxy)-2-methylpropan-2-yl)-1H-pyrazole-5-carbonyl)-2,6-diazaspiro[3.3]heptan-2-yl)-2,2-dimethylpropan-1-one tert-Butyl 6-pivaloyl-2,6-diazaspiro[3.3]heptane-2-carboxylate To a stirred solution of tert-butyl 2,6-diazaspiro[3.3]heptane-2-carboxylate hemi-oxylate (2.0 g, 4.11 mmol) in DMF (20 mL) was added pivalic acid (0.84 g, 8.22 mmol) and $NEt_3$ (3.4 mL, 24.66 mmol). HATU (6.25 g, 16.44 mmol) was slowly added to the mixture, observing evolution of gas. The reaction was stirred at rt for 2 h, then water (20 mL) was added, followed by EtOAc (30 mL). The organics were separated and water (70 mL) added to the aqueous layer which was then extracted with 2-methyl-THF (100 mL). The aqueous layer was further extracted with 2-methyl-THF (2×50 mL), and the combined organics concentrated in vacuo to ~50 mL then washed with aqueous citric acid (10%, 20 mL), then saturated aqueous $NaHCO_3$ (20 mL), and brine (20 mL). The organics were dried ($MgSO_4$), and concentrated in vacuo to give a yellow residue which was purified by silicas gel chromatography eluting with 0-30% EtOAc in cyclohexane, then 10% MeOH in EtOAc to give the product as a white solid (740 mg, 32%).

$^1$H NMR (400 MHz, $d_6$-DMSO) δ, ppm 4.57-4.34 (2H, m), 4.08-3.77 (6H, m), 1.36 (9H, s), 1.07 (9H, s).

LCMS Method 5: r.t. 1.38 min, $[MH]^+$283

2,2-Dimethyl-1-(2,6-diazaspiro[3.3]heptan-2-yl)propan-1-one

To a stirred solution of text-butyl 6-pivaloyl-2,6-diazaspiro[3.3]heptane-2-carboxylate (740 mg, 2.62 mmol) in MeOH (50 mL) was added Amberlyst® 15 hydrogen form (24 g). The reaction was stirred for 24 h, after which time $NH_3$ in MeOH (2 M, 150 mL) was added and the reaction stirred for a further 1.5 h. The reaction was filtered and solvent removed in vacuo to give a brown residue which was loaded onto a preconditioned (MeOH) SCX-2 cartridge as a solution in MeOH. After washing with MeOH the compound was eluted from the cartridge with 2N $NH_3$ in MeOH and solvent removed in vacuo to give the product as a white solid (340 mg, 63%).

$^1$H NMR (400 MHz, $d_6$-DMSO) δ, ppm 4.56-4.15 (2H, m), 4.10-3.69 (2H, m), 3.63-3.43 (4H, m), 1.08 (9H, s) plus one exchangeable not observed.

LCMS Method 4: r.t. 0.92 min, $[MH]^+$183

Ethyl 3-(1-(benzyloxy)-2-methylpropan-2-yl)-1H-pyrazole-5-carboxylate

To a stirred solution of (((2,2-dimethylbut-3-yn-1-yl)oxy)methyl)benzene (2.0 g, 10.62 mmol) in anhydrous toluene (30 mL) was slowly added ethyl diazoacetate (1.21 g, 10.62 mmol) as a solution in anhydrous toluene (10 mL). The reaction was heated at 120° C. After 16 h the reaction was cooled to rt and solvent removed in vacuo to give a yellow residue which was purified by silica gel chromatography eluting with 0-50% EtOAc in cyclohexane to give the product as a yellow sticky oil (612 mg, 19%).

$^1$H NMR (400 MHz, $CDCl_3$) δ, ppm 7.39-7.26 (5H, m), 6.61 (1H, s), 4.56 (2H, s), 4.38 (2H, q, J=7.14 Hz), 3.47 (2H, s), 1.39 (3H, t, J=7.14 Hz), 1.30 (6H, s).

3-(1-(Benzyloxy)-2-methylpropan-2-yl)-1H-pyrazole-5-carboxylic acid

To a stirred solution of ethyl 3-(1-(benzyloxy)-2-methylpropan-2-yl)-1H-pyrazole-5-carboxylate (612 mg, 2.02 mmol) in THF (3.0 mL) was added $LiOH \cdot H_2O$ (255 mg, 6.07 mmol) as a solution in $H_2O$ (3 mL). After 3 h the reaction was quenched by slow addition of aqueous HCl (2 M, 20 mL). The aqueous was extracted with EtOAc (3×25 mL), and the combined organics washed with brine (20 mL), and solvent removed in vacuo to give a yellow gum that was purified by silica gel chromatography eluting with 0-100% EtOAc (containing 1% AcOH) in cyclohexane to give the product as an off-white solid (282 mg, 51%).

LCMS Method 5: r.t. 1.36 min, $[MH]^+$275.4.

1-(6-(3-(1-(Benzyloxy)-2-methylpropan-2-yl)-1H-pyrazole-5-carbonyl)-2,6-diazaspiro[3.3]heptan-2-yl)-2,2-dimethylpropan-1-one To a stirred solution of 3-(1-(benzyloxy)-2-methylpropan-2-yl)-1H-pyrazole-5-carboxylic acid (280 mg, 1.02 mmol) in DMF (3 mL) was added 2,2-dimethyl-1-(2,6-diazaspiro[3.3]heptan-2-yl)propan-1-one (205 mg, 1.12 mmol) then $NEt_3$ (0.43 mL, 3.06 mmol), then HATU (466 mg, 1.22 mmol). After 4 h the reaction was concentrated in vacuo and $H_2O$ (20 mL) and DCM (20 mL) added. The organics were separated and the aqueous extracted with DCM (2×20 mL). The combined organics were concentrated in vacuo to give a white residue which was purified by silica gel chromatography eluting with 0-10% MeOH in EtOAc to give the product as a white solid (230 mg, 51%). A portion (50 mg) was further purified by reverse phase chromatography eluting with 5-95% MeCN/water (containing 0.1% formic acid). The product (31 mg) was obtained as a white solid after freeze drying.

$^1$H NMR (400 MHz, $CD_3OD$) δ, ppm 7.34-7.20 (5H, m), 6.50 (1H, s), 4.77-4.55 (4H, m), 4.48 (2H, s), 4.35-4.05 (4H, m), 3.43 (2H, s), 1.33 (6H, s), 1.19 (9H, s) plus one exchangeable proton not observed.

LCMS Method 1: r.t. 4.28 min $[MH]^+$ 439.1

Example 110

1-(6-(5-(1-hydroxy-2-methylpropan-2-yl)-1H-pyrazole-3-carbonyl)-2,6-diazaspiro[3.3]heptan-2-yl)-2,2-dimethylpropan-1-one To a solution of 1-(6-(3-(1-(benzyloxy)-2-methylpropan-2-yl)-1H-pyrazole-5-carbonyl)-2,6-diazaspiro[3.3]heptan-2-yl)-2,2-dimethylpropan-1-one (100 mg, 0.228 mmol) in EtOH (9 mL) was added Pd/C (20 mg, 20% wt). The reaction was charged with $H_2$ gas and stirred for 72 h. The reaction was filtered through Celite® and solvent removed in vacuo to give a white residue that was purified by silica gel chromatography eluting with 0-100% EtOAc in cyclohexane to give the product as a white solid (15 mg, 19%).

$^1$H NMR (400 MHz, $CD_3OD$) δ, ppm 6.51 (1H, s), 4.78-4.54 (4H, m), 4.44-4.21 (2H, m), 4.20-4.06 (2H, m) 3.52 (2H, s), 1.30 (6H, s), 1.19 (9H, s).

LCMS Method 1: r.t. 2.81, $[MH]^+$349.2

Example 111

(4-Cyclopropylthiazol-2-14)(6-(5-isopropyl-1H-pyrazole-3-carbonyl)-2,6-diazaspiro[3.3]heptan-2-yl)methanone To a solution of (5-isopropyl-1H-pyrazol-3-yl)(2,6-diazaspiro[3.3]heptan-2-yl)methanone (100 mg, 0.42 mmol) and potassium 4-cyclopropyl-1,3-thiazole-2-carboxylate (100 mg, 0.47 mmol) in DMF (2.0 mL) was added DIPEA (165 mg, 1.28 mmol) and HATU (211 mg, 0.55 mmol). The resulting mixture was stirred at rt for 1 h, then partitioned between water and EtOAc. The phases were separated and the aqueous phase was extracted with EtOAc (×2). The combined organic layers were dried ($MgSO_4$), concentrated in vacuo and purified by silica gel chromatography eluting with 0 to 5% MeOH in DCM. The fractions were concentrated in vacuo to give an orange gummy solid, which was triturated with DMSO (2 mL) to afford the title compound as a white solid (23 mg, 14%).

$^1$H NMR (400 MHz, $d_6$-DMSO) δ, ppm 12.98 (1H, s), 7.57 (1H, s), 6.36 (1H, s), 4.72 (2H, s), 4.63 (2H, dd, J=10.6, 15.4 Hz), 4.25 (2H, s), 4.18 (2H, dd, J=10.3, 18.1 Hz), 2.95 (1H, q, J=9.2 Hz), 2.16-2.08 (1H, m), 1.21 (6H, d, J=6.9 Hz), 0.97-0.92 (2H, m), 0.90-0.84 (2H, m).

LCMS Method 1: r.t=3.81 min, $[MH^+]$ 386.1

Example 112

N-(3-(7-(1H-Imidazol-4-yl)-3-isopropyl-4-oxo-3,4-dihydroimidazo[2,1-f][1,2,4]triazin-2-yl)phenethyl)acetamide

N-(3-(3-isopropyl-4-oxo-7-(1-trityl-1H-imidazol-4-yl)-3,4-dihydroimidazo[2,1-f][1,2,4]triazin-2-yl)phenethyl)acetamide Prepared from 2-chloro-3-isopropyl-7-(1-trityl-1H-imidazol-4-yl)imidazo[2,1-f][1,2,4]triazin-4(3H)-one and [3-(2-acetamidoethyl)phenyl]boronic acid by Suzuki-Miyaura General Procedure 2 to give the title compound as an orange gum (31 mg, 8%).

LCMS Method 4: r.t. 2.88 mins, $[MH^+]$ 648

N-(3-(7-(1H-imidazol-4-yl)-3-isopropyl-4-oxo-3,4-dihydroimidazo[2,1-f][1,2,4]triazin-2-yl)phenethyl)acetamide Prepared from N-(3-(3-isopropyl-4-oxo-7-(1-trityl-1H-imidazol-4-yl)-3,4-dihydroimidazo[2,1-f][1,2,4]triazin-2-yl)phenethyl)acetamide by Trityl Deprotection Procedure 2 to give the title compound as a white solid.

$^1$H NMR (400 MHz, $d_6$-DMSO) δ, ppm 12.26 (1H, s), 7.94 (1H, t, J=5.8 Hz), 7.76 (2H, d, J=16.4 Hz), 7.58-7.51 (4H, m), 7.47-7.45 (1H, m), 4.13-4.02 (1H, m), 2.84-2.78 (2H, m), 2.52-2.49 (2H, m), 1.78 (3H, s), 1.50 (6H, d, J=6.8 Hz).

LCMS Method 8: r.t=2.92 min, $[MH^+]$ 406.0

Example 113

N-(4-(7-(1H-imidazol-4-yl)-3-isopropyl-4-oxo-3,4-dihydroimidazo[2,1-f][1,2,4]triazin-2-yl)phenethyl)acetamide

N-(4-(3-isopropyl-4-oxo-7-(1-trityl-1H-imidazol-4-yl)-3,4-dihydroimidazo[2,1-f][1,2,4]triazin-2-yl)benzyl)acetamide Prepared from 2-chloro-3-isopropyl-7-(1-trityl-1H-imidazol-4-yl)imidazo[2,1-f][1,2,4]triazin-4(3H)-one and [4-(2-acetamidoethyl)phenyl]boronic acid by Suzuki-Miyaura General Procedure 1 to give the title compound as an orange gum (21 mg, 8%).

LCMS Method 4: r.t. 2.77 mins, $[MH^+]$ 648

N-(4-(7-(1H-imidazol-4-yl)-3-isopropyl-4-oxo-3,4-dihydroimidazo[2,1-f][1,2,4]triazin-2-yl)phenethyl)acetamide Prepared from N-(4-(3-isopropyl-4-oxo-7-(1-trityl-1H-imidazol-4-yl)-3,4-dihydroimidazo[2,1-f][1,2,4]triazin-2-yl)benzyl)acetamide by Trityl Deprotection Procedure 2 to give the title compound as a white solid.

$^1$H NMR (400 MHz, $d_6$-DMSO) δ, ppm 12.29-12.26 (1H, m), 7.93 (1H, t, J=5.6 Hz), 7.78 (1H, s), 7.74 (1H, s), 7.57-7.50 (4H, m), 7.48-7.44 (1H, m), 4.13-4.02 (1H, m), 2.82 (2H, t, J=6.8 Hz), 2.53 (2H, t, J=6.8 Hz), 1.78 (3H, s), 1.49 (6H, d, J=6.8 Hz).

LCMS Method 1: r.t.=2.39 min, $[MH^+]$ 406.1

Example 114

N-(2-(4-(7-(1H-imidazol-4-yl)-3-isopropyl-4-oxo-3,4-dihydroimidazo[2,1][1,2,4]triazin-2-yl)-1H-pyrazol-1-yl)ethyl)pivalamide tert-Butyl (2-(4-(4,4,5,5-tetramethyl-1,3,2-dioxaborolan-2-yl)-1H-pyrazol-1-yl)ethyl)carbamate A solution of 4-pyrazoleboronic acid pinacol ester (7.22 g, 37.1 mmol), 2-(Boc-amino)ethyl bromide (10.00 g, 44.6 mmol), potassium iodide (3.09 g, 18.6 mmol) and cesium carbonate (36.35 g, 111.6 mmol) in DMF (100 mL) was stirred at 70° C. for 3 h. The volatiles were then evaporated in vacuo. The residue was dissolved in EtOAc and diluted with water. The phases were separated and the aqueous phase was extracted with EtOAc (×3). The combined organic layers were dried ($MgSO_4$), concentrated in vacuo then purified by silica gel chromatography eluting with 0 to 10% MeOH in DCM. The fractions were concentrated in vacuo to give a white solid (6.27 g, 50%).

$^1$H NMR (300 MHz, $CDCl_3$) δ, ppm, 7.81 (1H, s), 7.68 (1H, s), 4.88 (1H, s), 4.23 (2H, t, J=5.7 Hz), 3.58 (2H, dd, J=5.3, 11.0 Hz), 1.44 (9H, s), 1.33 (12H, s).

2-(4-(4,4,5,5-tetramethyl-1,3,2-dioxaborolan-2-yl)-1H-pyrazol-1-yl)ethan-1-amine. nTFA Salt tert-Butyl (2-(4-(4,4,5,5-tetramethyl-1,3,2-dioxaborolan-2-yl)-1H-pyrazol-1-yl)ethyl)carbamate (0.50 g, 1.48 mmol) was dissolved in DCM (4.0 mL) and TFA (3.4 mL) was added. This mixture was stirred at rt for 2 h and concentrated in vacuo to give a colourless gum (800 mg, quant.).

$^1$H NMR (300 MHz, $CDCl_3$) δ, ppm 8.02-7.98 (2H, m), 7.87 (2H, s), 4.73 (2H, d, J=4.0 Hz), 3.69 (2H, s), 1.34 (12H, s).

N-(2-(4-(4,4,5,5-tetramethyl-1,3,2-dioxaborolan-2-yl)-1H-pyrazol-1-yl)ethyl)pivalamide A solution of 2-(4-(4,4,5,5-tetramethyl-1,3,2-dioxaborolan-2-yl)-1H-pyrazol-1-yl)ethan-1-amine. nTFA (218 mg, 9.20 mmol) in DCM (10.0 mL) was treated with triethylamine (931 mg, 22.0 mmol) followed by trimethylacetyl chloride (116 mg, 96.6 mmol). This mixture was left at rt for 4 h. The mixture was partitioned between water and EtOAc. The phases were separated and the aqueous phase was extracted with EtOAc (×3). The combined organic phases were dried ($MgSO_4$), concentrated in vacuo and purified by silica gel chromatography eluting with 0 to 10% MeOH in DCM. The fractions were concentrated in vacuo to give a clear oil (230 mg, 79%).

$^1$H NMR (300 MHz, $CDCl_3$) δ, ppm 7.81 (1H, s), 7.65 (1H, s), 6.32 (1H, s), 4.26 (2H, t, J=5.6 Hz), 3.66 (2H, q, J=5.5 Hz), 1.31 (12H, s), 1.14 (9H, s).

N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)pivalamide To a solution of 2-chloro-3-isopropyl-7-(1-trityl-1H-imidazol-4-yl)imidazo[2,1-f][1,2,4]triazin-4(3H)-one (50 mg, 0.096 mmol) and N-(2-(4-(4,4,5,5-tetramethyl-1,3,2-dioxaborolan-2-yl)-1H-pyrazol-1-yl)ethyl)pivalamide (70 mg, 0.218 mmol) in dioxane (5.0 mL) was added tetrakis(triphenylphosphine)palladium (0) (11 mg, 0.0096 mmol) followed by cesium carbonate (78 mg, 0.240 mol) in water (1 mL). The mixture was degassed and stirred at 100° C. for 7 h. The mixture was partitioned between water and DCM. The phases were separated and the aqueous phase was extracted with DCM (×3). The combined organic phases were dried ($MgSO_4$), concentrated in vacuo (×3) and purified by silica gel chromatography eluting with 0 to 6% (2N $NH_3$ in MeOH) in DCM. The fractions were concentrated in vacuo to give an orange gum (23 mg, 35%).

LCMS Method 4: r.t. 2.87 mins, [$MH^+$] 680

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)pivalamide To a solution of N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)pivalamide (20 mg, 0.0294 mmol) in DCM (1.0 mL) was added TFA (1.0 mL). This mixture was stirred for 1 h at rt, concentrated in vacuo and purified by reverse phase preparative HPLC to afford the title compound as a white solid.

LCMS Method 1: r.t.=2.51 min, [$MH^+$] 438.1

$^1$H NMR (400 MHz, $d_6$-DMSO) δ, ppm 12.37 (1H, s), 8.21 (1H, s), 7.91-7.90 (1H, m), 7.79 (1H, d, J=1.0 Hz), 7.72-7.69 (2H, m), 7.61 (1H, t, J=5.6 Hz), 4.62-4.52 (1H, m), 4.30 (2H, t, J=6.1 Hz), 3.53 (2H, dd, J=6.4, 11.5 Hz), 1.55 (6H, d, J=6.8 Hz), 1.05 (9H, s).

Example 115

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)cyclopropanecarboxamide N-(2-(4-(4,4,5,5-tetramethyl-1,3,2-dioxaborolan-2-yl)-1H-pyrazol-1-yl)ethyl)cyclopropanecarboxamide A solution of 2-(4-(4,4,5,5-tetramethyl-1,3,2-dioxaborolan-2-yl)-1H-pyrazol-1-yl)ethan-1-amine. nTFA (116 mg, 0.00490 mol) in DCM (5.0 mL) was treated with triethylamine (496 mg, 4.9 mmol) followed by cyclopropanecarbonyl chloride (56 mg, 0.539 mmol). This mixture was left at rt for 4 h then partitioned between water and EtOAc. The phases were separated and the aqueous phase was extracted with EtOAc (×3). The combined organic phases were dried ($MgSO_4$), concentrated in vacuo and purified by silica gel chromatography eluting with 0 to 10% MeOH in DCM. The fractions were concentrated in vacuo to give a clear oil (110 mg, 73%).

$^1$H NMR (300 MHz, $CDCl_3$) δ, ppm 7.82 (1H, s), 7.68 (1H, s), 6.27 (1H, s), 4.25 (2H, t, J=5.5 Hz), 3.71 (2H, dd, J=6.0, 11.3 Hz), 1.33-1.31 (13H, m), 0.95 (2H, tt, J=3.8, 3.9 Hz), 0.77-0.68 (2H, m).

N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)cyclopropanecarboxamide To a solution of 2-chloro-3-isopropyl-7-(1-trityl-1H-imidazol-4-yl)imidazo[2,1-f][1,2,4]triazin-4(3H)-one (100 mg, 0.192 mmol) and N-(2-(4-(4,4,5,5-tetramethyl-1,3,2-dioxaborolan-2-yl)-1H-pyrazol-1-yl)ethyl)cyclopropanecarboxamide (100 mg, 0.325 mmol) in dioxane (4.0 mL) was added tetrakis(triphenylphosphine)palladium (0) (22 mg, 0.0192 mmol) followed by cesium carbonate (156 mg, 0.48 mol) in water (1 mL). The mixture was degassed and stirred at 90° C. for 10 h then partitioned between water and EtOAc. The phases were separated and the aqueous phase was extracted with EtOAc (×3). The combined organic phases were dried ($MgSO_4$), concentrated in vacuo and purified by silica gel chromatography eluting with 0 to 5% (2N $NH_3$ in MeOH) in DCM. The fractions were concentrated in vacuo to give an orange gum (32 mg, 35%).

LCMS Method 4: r.t. 2.75 mins, [$MH^+$] 664.

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)cyclopropanecarboxamide To a solution of N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)cyclopropanecarboxamide (30 mg, 0.0452 mmol) in DCM (1.0 mL) was added TFA (1.0 mL). The mixture was stirred for 1 h at rt, concentrated in vacuo and purified by reverse phase preparative HPLC to afford the title compound as a white solid (5.0 mg, 29%).

LCMS Method 7: r.t.=2.26 min, [$MH^+$] 422.0

$^1$H NMR (400 MHz, $d_6$-DMSO) δ, ppm 12.40 (1H, s), 8.25-8.23 (2H, m), 7.93 (1H, s), 7.80 (1H, d, J=1.1 Hz), 7.72 (2H, d, J=3.1 Hz), 4.63-4.54 (1H, m), 4.29 (2H, t, J=6.1 Hz), 3.54 (2H, q, J=5.9 Hz), 1.57 (6H, d, J=6.7 Hz), 1.54-1.49 (1H, m), 0.68-0.60 (4H, m).

Example 116

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)-N-methylpivalamide tert-Butyl methyl(2-(4-(4,4,5,5-tetramethyl-1,3,2-dioxaborolan-2-yl)-1H-pyrazol-1-yl)ethyl)carbamate text-Butyl (2-(4-(4,4,5,5-tetramethyl-1,3,2-dioxaborolan-2-yl)-1H-pyrazol-1-yl)ethyl)carbamate (2.00 g, 14.8 mmol) was dissolved in THF (40 mL) and sodium bis(trimethylsilyl)amide (1N in THF, 14.83 mL, 0.0148 mol) was added followed by iodomethane (4.21 g, 29.6 mmol). This mixture was stirred at rt for 1 h and iodomethane (4.21 g, 29.65 mmol) was added followed by sodium bis(trimethylsilyl) amide (1N in THF, 3.0 mL, 3.0 mmol). This mixture was stirred for a further hour. The mixture was partitioned between water and EtOAc. The phases were separated and the aqueous phase was extracted with EtOAc (×3). The combined organic phases were dried ($MgSO_4$), concentrated in vacuo and purified by silica gel chromatography eluting with 0 to 6% MeOH in DCM. The fractions were concentrated in vacuo to give a white solid (960 mg, 34%).

$^1$H NMR (300 MHz, $d_6$-DMSO) δ, ppm 7.79 (1H, s), 7.51 (1H, s), 4.16 (2H, t, J=5.5 Hz), 3.49-3.37 (2H, m), 2.43 (3H, s), 1.27 (9H, s), 1.17 (12H, s).

N-methyl-2-(4-(4,4,5,5-tetramethyl-1,3,2-dioxaborolan-2-yl)-1H-pyrazol-1-yl)ethane-1-amine. nTFA tert-Butyl methyl(2-(4-(4,4,5,5-tetramethyl-1,3,2-dioxaborolan-2-yl)-1H-pyrazol-1-yl)ethyl)carbamate (0.50 g, 1.42 mmol) was dissolved in DCM (5.0 mL) and TFA (4.0 mL) was added. This mixture was stirred at rt for 2 h and concentrated in vacuo to give the title compound as a colourless gum (800 mg, quant.).

$^1$H NMR (300 MHz, $CDCl_3$) δ, ppm 8.62 (1H, s), 8.04 (1H, s), 4.80-4.68 (2H, m), 3.77-3.67 (2H, m), 2.88 (3H, t, J=4.8 Hz), 1.33 (12H, s).

N-methyl-N-(2-(4-(4,4,5,5-tetramethyl-1,3,2-dioxaborolan-2-yl)-1H-pyrazol-1-yl)ethyl)pivalamide A solution of N-methyl-2-(4-(4,4,5,5-tetramethyl-1,3,2-dioxaborolan-2-yl)-1H-pyrazol-1-yl)ethan-1-amine. nTFA (118 mg, 4.70 mmol) in DCM (5.0 mL) was treated with triethylamine (476 mg, 4.7 mmol) followed by trimethylacetyl chloride (62 mg, 0.517 mmol). This mixture was left at rt for 2 h. The mixture was partitioned between water and DCM. The phases were separated and the aqueous phase was extracted with DCM (×3). The combined organic phases were dried ($MgSO_4$), concentrated in vacuo and purified by silica gel chromatography eluting with 0 to 10% MeOH in DCM. The fractions were concentrated in vacuo to give the title compound as a clear oil (130 mg, 82%).

$^1$H NMR (300 MHz, $CDCl_3$) δ, ppm 7.79 (1H, s), 7.61 (1H, s), 4.34 (2H, t, J=6.2 Hz), 3.72 (2H, t, J=2.9 Hz), 2.72 (3H, s), 1.31 (12H, s), 1.24 (9H, s).

N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)-N-methylpivalamide To a solution of 2-chloro-3-isopropyl-7-(1-trityl-1H-imidazol-4-yl)imidazo[2,1-f][1,2,4]triazin-4(3H)-one (100 mg, 0.192 mmol) and N-methyl-N-(2-(4-(4,4,5,5-tetramethyl-1,3,2-dioxaborolan-2-yl)-1H-pyrazol-1-yl)ethyl)pivalamide (120 mg, 0.358 mmol) in dioxane (4.0 mL) was added tetrakis(triphenylphosphine)palladium (0) (22 mg, 0.0192 mmol) followed by cesium carbonate (156 mg, 0.48 mmol) in water (1 mL). This mixture was degassed and stirred at 90° C. for 10 h. The mixture was partitioned between water and EtOAc. The phases were separated and the aqueous phase was extracted with EtOAc (×3). The combined organic phases were dried ($MgSO_4$), concentrated in vacuo and purified by silica gel chromatography eluting with 0 to 5% (2N $NH_3$ in MeOH) in DCM. The fractions were concentrated in vacuo to give an orange gum (44 mg, 33%).

LCMS Method 4: r.t. 3.14 mins, [$MH^+$] 694.

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)-N-methylpivalamide To a solution of N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)-N-methylpivalamide (40 mg, 0.0576 mmol) in DCM (1.0 mL) was added TFA (1.0 mL). This mixture was stirred for 1 h at rt then evaporated to dryness and purified by reverse phase preparative HPLC to afford the title compound as a white solid (8.0 mg, 32%).

LCMS Method 7: r.t.=2.81 min, $[MH]^+$452.0

$^1$H NMR (400 MHz, $d_6$-DMSO) δ, ppm 12.32 (1H, s), 8.29 (1H, s), 7.90 (1H, s), 7.80 (1H, s), 7.71 (1H, s), 7.69 (1H, s), 4.53 (1H, m), 4.40 (2H, t, J=5.7 Hz), 3.76 (2H, t, J=5.8 Hz), 2.90 (3H, s), 1.56 (6H, d, J=6.8 Hz), 1.15 (9H, s).

Example 117

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)-N-methylcyclopropanecarboxamide N-methyl-N-(2-(4-(4,4,5,5-tetramethyl-1,3,2-dioxaborolan-2-yl)-1H-pyrazol-1-yl)ethyl)cyclopropanecarboxamide A solution of N-methyl-2-(4-(4,4,5,5-tetramethyl-1,3,2-dioxaborolan-2-yl)-1H-pyrazol-1-yl)ethan-1-amine. nTFA (118 mg, 4.70 mmol) in DCM (5.0 mL) was treated with triethylamine (476 mg, 4.7 mmol) followed by cyclopropanecarbonyl chloride (54 mg, 0.517 mmol). This mixture was left at rt for 3 h. The mixture was partitioned between water and DCM. The phases were separated and the aqueous phase was extracted with DCM (×3). The combined organic phases were dried ($MgSO_4$), concentrated in vacuo and purified by silica gel chromatography eluting with 0 to 10% MeOH in DCM. The relevant fractions were concentrated in vacuo to give a clear oil (116 mg, 77%).

$^1$H NMR (300 MHz, $CDCl_3$) δ, ppm 7.81 (11-1, s), 7.63 (1H, s), 4.39-4.26 (2H, m), 3.93 (1H, t, J=5.7 Hz), 3.79 (2H, t, J=6.0 Hz), 2.82 (3H, s), 1.32 (12H, s), 1.02-0.95 (2H, m), 0.80-0.72 (2H, m).

N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)-N-methylcyclopropanecarboxamide To a solution of 2-chloro-3-isopropyl-7-(1-trityl-1H-imidazol-4-yl)imidazo[2,1-f][1,2,4]triazin-4(3H)-one (100 mg, 0.192 mmol) and N-methyl-N-(2-(4-(4,4,5,5-tetramethyl-1,3,2-dioxaborolan-2-yl)-1H-pyrazol-1-yl)ethyl)cyclopropanecarboxamide (100 mg, 0.313 mmol) in dioxane (4.0 mL) was added tetrakis(triphenylphosphine)palladium (0) (22 mg, 0.0192 mmol) followed by cesium carbonate (156 mg, 0.48 mmol) in water (1 mL). This mixture was degassed and stirred at 90° C. for 10 h. The mixture was partitioned between water and EtOAc. The phases were separated and the aqueous phase was extracted with EtOAc (×3). The combined organic phases were dried ($MgSO_4$), concentrated in vacuo and purified by silica gel chromatography eluting with 0 to 5% (2N $NH_3$ in MeOH) in DCM. The fractions were concentrated in vacuo to give an orange gum (55 mg, 42%).

LCMS Method 4: r.t. 2.87 mins, [$MH^+$] 678.

N-(2-(4-(7-(1H-imidazol-4-yl)-3-isopropyl-4-oxo-3,4-dihydroimidazo[2,1-f][1,2,4]triazin-2-yl)-1H-pyrazol-1-yl)ethyl)-N-methylcyclopropanecarboxamide To a solution of N-(2-(4-(3-isopropyl-4-oxo-7-(1-trityl-1H-imidazol-4-yl)-3,4-dihydroimidazo[2,1-f][1,2,4]triazin-2-yl)-1H-pyrazol-1-yl)ethyl)-N-methylcyclopropanecarboxamide (50 mg, 0.0753 mmol) in DCM (1.0 mL) was added TFA (1.0 mL). This mixture was stirred for 1 h at rt then evaporated to dryness and purified by reverse phase preparative HPLC to afford the title compound as a white solid (9.9 mg, 30%).

LCMS Method 7: r.t.=2.43 min, [$MH^+$] 436.0

$^1$H NMR (400 MHz, $d_6$-DMSO) δ, ppm 12.38 (1H, s), 8.29 (1H, s), 7.93 (1H, d, J=19.1 Hz), 7.81 (1H, s), 7.74 (1H, s), 7.72 (1H, s), 4.57-4.48 (2H, m), 4.40-4.35 (1H, m), 4.01-3.96 (1H, m), 3.77 (1H, t, J=5.8 Hz), 3.02 (1H, s), 2.86 (1.4H, s), 2.56 (1.6H, s), 1.90-1.84 (0.4H, m), 1.59-1.55 (6.6H, m), 1.03 (0.4H, d, J=6.6 Hz), 0.69 (1.6H, d, J=6.1 Hz), 0.58-0.53 (2H, m).

Pyrazole Azetidine Amide General Procedure

To a solution of (3-aminoazetidin-1-yl)(5-isopropyl-1H-pyrazol-3-yl)methanone in DMF (2.0 mL) was added carboxylic acid (1.1 eq) followed by DIPEA (3.0 eq) and HATU (1.2 eq). This mixture was stirred at rt for 1 h. The volatiles were concentrated in vacuo and the residue was purified by silica gel chromatography eluting with 0 to 10% MeOH in DCM followed by reverse phase preparative HPLC to afford the desired product.

Example 118

N-(1-(5-Isopropyl-1H-pyrazole-3-carbonyl)azetidin-3-yl)spiro[2.2]pentane-1-carboxamide Prepared from (3-aminoazetidin-1-yl)(5-isopropyl-1H-pyrazol-3-yl)methanone and spiro[2.2]pentane-2-carboxylic acid by Pyrazole Azetidine Amide General Procedure.

$^1$H NMR (300 MHz, $d_6$-DMSO) δ, ppm 12.98 (1H, s), 8.54 (1H, d, J=7.0 Hz), 6.37 (1H, s), 4.67 (1H, t, J=8.8 Hz), 4.58-4.44 (1H, m), 4.26-4.17 (2H, m), 3.82-3.73 (1H, m), 3.01-2.90 (1H, m), 1.87 (1H, dd, J=4.3, 7.5 Hz), 1.28 (1H, t, J=3.9 Hz), 1.23-1.19 (7H, m), 0.87-0.76 (3H, m), 0.72-0.67 (1H, m).

The enantiomers of EXAMPLE 118 were separated by chiral SFC using a YMC Amylose-SC 10×250 mm, 5 μm column eluting with 20% EtOH (0.1% diethylamine)/80% $CO_2$, 15 ml/min, 120 bar, 40° C. to afford EXAMPLE 119 and EXAMPLE 120.

Example 119

Enantiomer A: 41.5 mg $^1$H NMR (300 MHz, $d_6$-DMSO) δ, ppm 12.98 (1H, s), 8.54 (1H, d, J=7.0 Hz), 6.37 (1H, s), 4.67 (1H, t, J=8.8 Hz), 4.58-4.44 (1H, m), 4.26-4.17 (2H, m), 3.82-3.73 (1H, m), 3.01-2.90 (1H, m), 1.87 (1H, dd, J=4.3, 7.5 Hz), 1.28 (1H, t, J=3.9 Hz), 1.23-1.19 (7H, m), 0.87-0.76 (3H, m), 0.72-0.67 (1H, m).

LCMS Method 8: r.t.=3.06 min, [$MH^+$] 303.0

Analytical SFC using YMC Amylose-SC 2×150 mm, 5 μm column eluting with 20% EtOH (0.1% diethylamine)/80% $CO_2$, 0.95 ml/min, 120 bar, 40° C., retention time 4.20 min Example 120

Enantiomer B: 45.3 mg $^1$H NMR (300 MHz, $d_6$-DMSO) δ, ppm 12.95 (1H, s), 8.54 (1H, d, J=7.2 Hz), 6.37 (1H, s), 4.71-4.62 (1H, m), 4.55-4.47 (1H, m), 4.25-4.17 (2H, m), 3.83-3.75 (1H, m), 3.02-2.87 (1H, m), 1.87 (1H, dd, J=4.3, 7.5 Hz), 1.28 (1H, t, J=4.2 Hz), 1.23-1.19 (7H, m), 0.88-0.75 (3H, m), 0.73-0.64 (1H, m).

LCMS Method 8: r.t.=3.06 min, [$MH^+$] 303.

Analytical SFC using YMC Amylose-SC 2×150 mm, 5 μm column eluting with 20% EtOH (0.1% diethylamine)/80% $CO_2$, 0.95 ml/min, 120 bar, 40° C., retention time 5.19 min Example 121

N-(2-(4-(7-(1H-Imidazol-4-yl)-3-isopropyl-4-oxo-3,4-dihydroimidazo[2,1-f][1,2,4]triazin-2-yl)-1H-pyrazol-1-yl)ethyl)acetamide N-(2-O-(4,4,5,5-tetramethyl-1,3,2-dioxaborolan-2-yl)-1H-pyrazol-1-yl)ethyl)acetamide 2-(4-(4,4,5,5-tetramethyl-1,3,2-dioxaborolan-2-yl)-1H-pyrazol-1-yl)ethan-1-amine.TFA (1.28 g, 2.97 mmol) was dissolved in DCM (20 mL). Triethylamine (1.2 mL, 3.0 mmol) then acetic anhydride (0.29 mL, 3.12 mmol) were added. The reaction mixture was stirred overnight at rt then partitioned between water and DCM. The phases were separated and the aqueous phase was extracted with DCM (×2). The combined organic layers were dried ($MgSO_4$) and concentrated in vacuo to afford the title compound as a colourless oil.

LCMS Method 2: r.t. 0.96 mins, [$MH^+$] 280.

N-(2-(4-(3-Isopropyl-4-oxo-7-(1-trityl-1H-imidazol-4-yl)-3,4-dihydroimidazo[2,1-f][1,2,4]triazin-2-yl)-1H-pyrazol-1-yl)ethyl)acetamide Prepared from 2-chloro-3-isopropyl-7-(1-trityl-1H-imidazol-4-yl)imidazo[2,1-f][1,2,4]triazin-4(3H)-one and N-(2-(4-(4,4,5,5-tetramethyl-1,3,2-dioxaborolan-2-yl)-1H-pyrazol-1-yl)ethyl)acetamide by Suzuki-Miyaura General Procedure 2 to give the title compound as a white solid (50 mg, 41%).

LCMS Method 4: r.t. 1.44 mins, [$MH^+$] 638.

N-(2-(4-(7-(1H-Imidazol-4-yl)-3-isopropyl-4-oxo-3,4-dihydroimidazo[2,1-f][1,2,4]triazin-2-yl)-1H-pyrazol-1-yl)ethyl) acetamide Prepared from N-(2-(4-(3-Isopropyl-4-oxo-7-(1-trityl-1H-imidazol-4-yl)-3,4-dihydroimidazo[2,1-f][1,2,4]triazin-2-yl)-1H-pyrazol-1-yl)ethyl)acetamide by Trityl Deprotection Procedure 1 to give the title compound as a white solid (11 mg, 41%). $^{1}$H NMR (400 MHz, $d_6$-DMSO) δ, ppm 12.34 (1H, s), 8.26 (1H, s), 8.03 (1H, t, J=5.9 Hz), 7.92 (1H, s), 7.80 (1H, s), 7.74 (1H, s), 7.72 (1H, s), 4.62-4.53 (1H, m), 4.28 (2H, t, J=5.7 Hz), 3.50 (2H, dt, J=5.8, 5.6 Hz), 1.80 (3H, s), 1.57 (6H, d, J=6.6 Hz).

LCMS Method 1: r.t. 1.95 mins, [$MH^+$] 396.1

Example 122

7-(1H-Imidazol-4-yl)-3-isopropyl-2-(4-methyl-3,4-dihydro-2H-benzo[b][1,4]oxazin-7-yl)imidazo[2,1-f][1,2,4]triazin-4(3H)-one 3-Isopropyl-2-(4-methyl-3,4-dihydro-2H-benzo[b][1,4] oxazin-7-yl)-7-(1-trityl-1H-imidazol-4-yl)imidazo[2,1-f][1,2,4]triazin-4(3H)-one Prepared from 2-chloro-3-isopropyl-7-(1-trityl-1H-imidazol-4-yl)imidazo[2,1-f][1,2,4]triazin-4(3H)-one and 4-methyl-7-(4,4,5,5-tetramethyl-1,3,2-dioxaborolan-2-yl)-2,3-dihydro-1,4-benzoxazine by Suzuki-Miyaura General Procedure 2 to give the title compound as a yellow solid (50 mg, 41%).

LCMS Method 4: r.t. 1.81 mins, [$MH^+$] 634.

7-(1H-Imidazol-4-yl)-3-isopropyl-2-(4-methyl-3,4-dihydro-2H-benzo[b][1,4]oxazin-7-yl)imidazo[2,1-f][1,2,4]triazin-4(3H)-one Prepared from 3-isopropyl-2-(4-methyl-3,4-dihydro-2H-benzo[b][1,4]oxazin-7-yl)-7-(1-trityl-1H-imidazol-4-yl)imidazo[2,1-f][1,2,4]triazin-4(3H)-one by Trityl Deprotection Procedure 1 to give the title compound as a white solid as a formate salt (6 mg, 19%). 1H NMR (400 MHz, $d_6$-DMSO) δ, ppm 12.29 (1H, s), 7.79 (1H, d, J=1.0 Hz), 7.72 (1H, s), 7.58 (1H, s), 7.10 (1H, dd, J=1.9, 8.3 Hz), 7.02 (1H, d, J=2.1 Hz), 6.84 (1H, d, J=8.3 Hz), 4.32-4.23 (2H, m), 3.45-3.35 (2H, m), 2.93 (3H, s), 1.51 (6H, d, J=6.4 Hz).

LCMS Method 1: r.t. 3.04 mins, [$MH^+$] 392.1

Example 123

6-(5-(1-Hydroxypropan-2-yl)-1H-pyrazole-3-carbonyl)-N-isopropyl-2,6-diazaspiro[3.3]heptane-2-carboxamide A suspension of (5-(1-hydroxypropan-2-yl)-1H-pyrazol-3-yl)(2,6-diazaspiro[3.3]heptan-2-yl)methanone (90 mg, 0.36 mmol) in DCM (3.0 mL) and MeCN (1.0 mL) was treated at 0° C. with isopropyl isocyanate (0.037 mL, 0.38 mmol) and the mixture was allowed to warm up to rt and stirred for 16 h. The volatiles were evaporated in vacuo and the residue was purified by reverse phase chromatography to afford the title compound (50 mg, 41%) as a white solid after freeze-drying.

$^{1}$H NMR (400 MHz, $d_6$-DMSO) δ., ppm 12.93 (1H, s), 6.38 (1H, s), 6.08 (1H, d, J=7.9 Hz), 4.79 (1H, s), 4.54 (2H, s), 4.10 (2H, s), 3.94-3.89 (4H, m), 3.72-3.61 (1H, m), 3.52 (1H, s), 3.41 (1H, s), 2.93-2.85 (1H, m), 1.18 (3H, d, J=7.0 Hz), 1.02 (6H, d, J=6.6 Hz).

LCMS Method 1: r.t. 2.25 min, [$MH^+$] 336.1

Example 124

1-(6-(5-(1-Hydroxyethyl)-1H-pyrazole-3-carbonyl)-2,6-diazaspiro[3.3]heptan-2-yl)-2,2-dimethylpropan-1-one Ethyl 5-acetyl-14 (2-(trimethylsilyl)ethoxy)methyl)-1H-pyrazole-3-carboxylate A solution of ethyl 3-acetyl-1H-pyrazole-5-carboxylate (1.00 g, 5.49 mmol) in DMF (10 mL) was cooled to 0° C. (ice/water bath) and treated with sodium hydride (60%; 263 mg, 6.59 mmol). After 45 minutes SEM-C1 (1.2 mL, 6.59 mmol) was added and the mixture allowed to warm to rt during 18 h. The mixture was diluted with EtOAc and brine and EtOAc extracts washed with water and brine then dried ($Na_2SO_4$), filtered and evaporated to give a yellow oil. The crude product was purified by silica gel chromatography eluting with 0-45% EtOAc/cyclohexane to give the title compound as a colourless oil (1.52 g, 88%).

LCMS Method 5: r.t. 1.96 mins $^{1}$H NMR (400 MHz, $CDCl_3$) δ, ppm 7.40 (1H, s), 5.93 (2H, s), 4.40 (2H, quart, J=7.1 Hz), 3.63-3.70 (2H, m), 2.64 (3H, s), 1.41 (31-1, t, J=7.2 Hz), 0.91-0.99 (2H, m), 0.00 (9H, s)

5-Acetyl-1-((2-(trimethylsilyl)ethoxy)methyl)-1H-pyrazole-3-carboxylic acid

A solution of ethyl 5-acetyl-1-((2-(trimethylsilyl)ethoxy)methyl)-1H-pyrazole-3-carboxylate (1.00 g, 3.20 mmol) in THF (15 mL) was treated with lithium hydroxide monohydrate (671 mg, 16.00 mmol) in water (15 mL) and stirred for 18 h. The mixture was acidified using aqueous HCl (1N, 17 mL) and $NaHCO_3$ was added to achieve pH7. The volatiles were removed in vacuo and the resultant solid extracted into 5% MeOH/DCM. Filtrate was evaporated to give the title compound as a white solid (0.73 g, 80%)

LCMS Method 5: r.t. 1.60 mins [$MH^+$] 283

1-(6-(5-Acetyl-1-((2-(trimethylsilyl)ethoxy)methyl)-1H-pyrazole-3-carbonyl)-2,6-diazaspiro[3.3]heptan-2-yl)-2,2-dimethylpropan-1-one Amide Coupling Procedure 5 was employed using 2,2-dimethyl-1-(2,6-diazaspiro[3.3]heptan-2-yl)propan-1-one (180 mg, 0.988 mmol) and 5-acetyl-1-((2-(trimethylsilyl)ethoxy)methyl)-1H-pyrazole-3-carboxylic acid (281 mg, 0.988 mmol) to give the title compound as a white solid (38 mg, 8.6%)

LCMS Method 5: r.t. 1.66 mins [$MH^+$] 449.1

1-(6-(5-(1-Hydroxyethyl)-1-((2-(trimethylsilyl)ethoxy)methyl)-1H-pyrazole-3-carbonyl)-2,6-diazaspiro[3.3]heptan-2-yl)-2,2-dimethylpropan-1-one A solution of 1-(6-(5-acetyl-1-((2-(trimethylsilyl)ethoxy)methyl)-1H-pyrazole-3-carbonyl)-2,6-diazaspiro[3.3]heptan-2-yl)-2,2-dimethylpropan-1-one (36 mg, 0.080 mmol) in MeOH (1.0 mL) was treated with sodium borohydride (15 mg, 0.401 mmol). After 1 h the mixture was quenched with water and concentrated to near dryness. It was extracted into DCM, filtered via a phase separation cartridge and evaporated to give the title compound as a white solid (26 mg, 72%)

LCMS Method 5: r.t. 1.46 mins [$MH^+$] 451.2

1-(6-(5-(1-Hydroxyethyl)-1H-pyrazole-3-carbonyl)-2,6-diazaspiro[3.3]heptan-2-yl)-2,2-dimethylpropan-1-one A solution of TFA (0.5 mL) in DCM (1.0 mL) was added to 1-(6-(5-(1-hydroxyethyl)-1-((2-(trimethylsilyl)ethoxy)methyl)-1H-pyrazole-3-carbonyl)-2,6-diazaspiro[3.3]heptan-2-yl)-2,2-dimethylpropan-1-one (26 mg, 0.0577 mmol). After 1 h the solution was loaded onto a pre-wetted SCX-2 cartridge, washed through with MeOH then product recovered using 2M ammonia in MeOH. The filtrate was evaporated and the residue freeze dried to give impure product as an off-white solid (19 mg, quant.; 90% purity). The crude product was purified by reverse phase chromatography ($C_{18}$ cartridge) eluting with 10-98% MeCN/$H_2O$+0.1% $NH_4OH$ and freeze dried to give the title compound as a white solid (14 mg, 78%).

LCMS Method 1: r.t. 2.52 mins [$MH^+$] 321.1

$^1H$ NMR (400 MHz, $d_6$-DMSO) δ, ppm 13.08 (1H, s), 6.43 (1H, s), 5.40 (1H, d, J=5.0 Hz), 4.72-4.83 (1H, m), 4.40-4.66 (4H, m), 3.83-4.23 (4H, m), 1.37 (3H, d, J=6.5 Hz), 1.09 (9H, s).

Example 125

(5-Isopropyl-1H-pyrazol-3-yl)-[2-[4-(4-methoxyphenyl)thiophene-2-carbonyl]-2,6-diazaspiro[3.3]heptan-6-yl]methanone Prepared from (5-isopropyl-1H-pyrazol-3-yl)(2,6-diazaspiro[3.3]heptan-2-yl)methanone and 4-(4-methoxyphenyl)thiophene-2-carboxylic acid using Pyrazole Spirodiazetidine Amide General Procedure 4. Purification of the crude product by trituration with water afforded the title compound as a white solid (58 mg, 60%).

$^1H$ NMR (300 MHz, $d_6$-DMSO) δ, ppm 13.02-12.98 (1H, m), 7.99 (1H, s), 7.78 (1H, s), 7.68 (2H, d, J=8.7 Hz), 6.99 (1H, s), 6.98 (1H, s), 6.37 (1H, s), 4.76 (2H, s), 4.65 (2H, s), 4.25-4.19 (4H, m), 3.79 (3H, s), 3.01-2.86 (1H, m), 1.21 (6H, d, J=7.0 Hz).

LCMS Method 1: r.t 4.06 mins [$MH^+$] 451.0

Example 126

[2-(4-Fluoro-1-methyl-pyrazole-3-carbonyl)-2,6-diazaspiro[3.3]heptan-6-yl]-(5-isopropyl-1H-pyrazol-3-yl)methanone Prepared from (5-isopropyl-1H-pyrazol-3-yl)(2,6-diazaspiro[3.3]heptan-2-yl)methanone and 1-methyl-4-fluoro-pyrazole-3-carboxylic acid using Pyrazole Spirodiazetidine Amide General Procedure 4. Purification of the crude product by reverse phase chromatography eluting with 10-98% MeCN in 0.1% $NH_4OH$ solution afforded the title compound as a white solid (22 mg, 29%).

$^1H$ NMR (400 MHz, $d_6$-DMSO) δ, ppm 12.98-12.98 (1H, m), 7.94 (1H, d, J=4.5 Hz), 6.36 (1H, s), 4.61 (2H, s), 4.55 (2H, s), 4.22-4.14 (4H, m), 3.81 (3H, s), 3.00-2.90 (1H, m), 1.21 (6H, d, J=6.9 Hz).

LCMS Method 1: r.t 2.88 mins [$MH^+$] 361.1

Example 127

(5-Isopropyl-1H-pyrazol-3-yl)-[2-(4-phenylthiophene-2-carbonyl)-2,6-diazaspiro[3.3]heptan-6-yl]methanone Prepared from (5-isopropyl-1H-pyrazol-3-yl)(2,6-diazaspiro[3.3]heptan-2-yl)methanone and 4-phenylthiophene-2-carboxylic acid using Pyrazole Spirodiazetidine Amide General Procedure 4. Purification of the crude product by trituration with water followed by silica gel chromatography eluting with 0-10% MeOH in DCM to afford the title compound as a white solid (23 mg, 26%).

$^1H$ NMR (400 MHz, $d_6$-DMSO) δ, ppm 12.99 (1H, d, J=1.3 Hz), 8.13 (1H, d, J=1.4 Hz), 7.84 (1H, d, J=1.4 Hz), 7.77-7.74 (2H, m), 7.46-7.41 (2H, m), 7.35-7.31 (1H, m), 6.37 (1H, d, J=1.5 Hz), 4.79 (2H, s), 4.66 (2H, s), 4.26-4.19 (4H, m), 3.01-2.91 (1H, m), 1.21 (6H, d, J=6.9 Hz).

LCMS Method 1: r.t 4.11 mins [$MH^+$] 421.0

Example 128

(5-Isopropyl-1H-pyrazol-3-yl)-[2-(4-methoxythiophene-2-carbonyl)-2,6-diazaspiro[3.3]heptan-6-yl]methanone Prepared from (5-isopropyl-1H-pyrazol-3-yl)(2,6-diazaspiro[3.3]heptan-2-yl)methanone and 4-methoxythiophene-2-carboxylic acid using Pyrazole Spirodiazetidine Amide General Procedure 4. Purification of the crude product by trituration with water followed by silica gel chromatography eluting with 0-10% MeOH in DCM to afford the title compound as a white solid (23 mg, 29%).

$^1H$ NMR (400 MHz, $d_6$-DMSO) δ, ppm 12.98 (1H, s), 7.10 (1H, d, J=1.7 Hz), 6.90 (1H, d, J=1.6 Hz), 6.36 (1H, d, J=1.3 Hz), 4.62 (4H, s), 4.24-4.15 (4H, m), 3.76 (3H, s), 3.01-2.90 (1H, m), 1.21 (6H, d, J=6.9 Hz).

LCMS Method 1: r.t 3.33 mins [$MH^+$] 375.0

Pyrrolidine Amide General Procedure 1

To a solution of (1R,5S,6R)-3-(tert-butoxycarbonyl)-3-azabicyclo[3.1.0]hexane-6-carboxylic acid (1 eq) and triethylamine (3 eq) in DCM (0.55 M) was added HATU (1.2 eq). The resulting mixture was stirred at rt for 10 min then the appropriately substituted pyrrolidine hydrochloride salt (1.2 eq) was added and the reaction was stirred for one hour. The reaction mixture was washed twice with water and once with 10% aqueous citric acid solution, then passed through a hydrophobic frit and concentrated in vacuo to yield the crude product which was used in the next step without further purification.

Pyrrolidine Boc Deprotection General Procedure

The appropriately substituted Boc protected pyrrolidine (1 eq) was dissolved in 4 M HCl in dioxane (4 eq) and the reaction was stirred at rt for 1 h. The reaction mixture was concentrated in vacuo to yield the crude product which was used in the next step without further purification.

Pyrrolidine Amide General Procedure 2

To a solution of 5-isopropyl-1H-pyrazole-3-carboxylic acid (2 eq) and triethylamine (4.8 eq) in DCM (0.13 M) was added HATU (2.2 eq). The reaction was stirred at rt for 10 min then the appropriately substituted pyrrolidine hydrochloride salt (1 eq) was added and the reaction was stirred at rt for 16 h. The solvent was removed in vacuo then the residue was taken up in EtOAc and washed once with 1 M HCl and once with water. The organic phase was passed through a phase separator and concentrated in vacuo to give the crude product.

Example 129

(5-isopropyl-1H-pyrazol-3-yl)((1R,5S,6r)-6-((R)-2-methylpyrrolidine-1-carbonyl)-3-azabicyclo[3.1.0]hexan-3-yl)methanone tert-Butyl-(1R,5S,6r)-6-((R)-2-methylpyrrolidine-1-carbonyl)-3-azabicyclo[3.1.0]hexane-3-carboxylate Prepared from (1R,5S,6R)-3-(tert-butoxycarbonyl)-3-azabicyclo[3.1.0]hexane-6-carboxylic acid and (2R)-2-methylpyrrolidine hydrochloride using Pyrrolidine Amide General Procedure 1. The crude product was isolated in quantitative yield (assumed 100%).

LCMS Method 4: r.t 1.37 mins [$MH^+$] 295

((1R,5S,6r)-3-Azabicyclo[3.1.0]hexan-6-yl)((R)-2-methylpyrrolidin-1-yl)methanone hydrochloride Prepared from tert-butyl-(1R,5S,6r)-6-((R)-2-methylpyrrolidine-1-carbonyl)-3-azabicyclo[3.1.0]hexane-3-carboxylate using Pyrrolidine Boc Deprotection General Procedure. The crude product was isolated in quantitative yield (assumed 100%).

LCMS Method 4: r.t 0.91 mins [$MH^+$] 195

(5-isopropyl-1H-pyrazol-3-yl)((1R,5S,6r)-6-((R)-2-methylpyrrolidine-1-carbonyl)-3-azabicyclo[3.1.0]hexan-3-yl)methanone Prepared from ((1R,5S,6r)-3-Azabicyclo[3.1.0]hexan-6-yl)((R)-2-methylpyrrolidin-1-yl)methanone hydrochloride and 3-isopropyl-1H-pyrazole-5-carboxylic acid using Pyrrolidine Amide General Procedure 2. Purification of the crude product by trituration with DCM followed by reverse phase chromatography eluting with 10-98% MeCN in 0.1% $NH_4OH$ solution to afford the title compound as a white solid (20 mg, 12%).

$^1H$ NMR (400 MHz, $d_6$-DMSO) δ, ppm 12.87 (1H, s), 6.40-6.38 (1H, m), 4.24-4.20 (1H, m), 4.00-3.84 (3H, m), 3.62-3.49 (2H, m), 3.00-2.90 (1H, m), 2.14-1.78 (5H, m), 1.55-1.49 (2H, m), 1.21 (6H, d, J=7.0 Hz), 1.17-1.05 (3H, m) plus one proton obscured by the water peak.

LCMS Method 1: r.t 3.29 mins [$MH^+$] 331.1

Example 130

(5-Isopropyl-1H-pyrazol-3-yl)((1R,5S,6r)-6-((S)-2-methylpyrrolidine-1-carbonyl)-3-azabicyclo[3.1.0]hexan-3-yl)methanone tert-Butyl-(1R,5S,6r)-6-((S)-2-methylpyrrolidine-1-carbonyl)-3-azabicyclo[3.1.0]hexane-3-carboxylate Prepared from (1R,5S,6R)-3-(tert-butoxycarbonyl)-3-azabicyclo[3.1.0]hexane-6-carboxylic acid and (2S)-2-methylpyrrolidine hydrochloride using Pyrrolidine Amide General Procedure 1. The crude product was isolated in quantitative yield (assumed 100%).

LCMS Method 4: r.t 1.37 mins [$MH^+$] 295

((1R,5S,6r)-3-Azabicyclo[3.1.0]hexan-6-yl)((S)-2-methylpyrrolidin-1-yl)methanone hydrochloride Prepared from tert-butyl-(1R,5S,6r)-6-((S)-2-methylpyrrolidine-1-carbonyl)-3-azabicyclo[3.1.0]hexane-3-carboxylate using Pyrrolidine Boc Deprotection General Procedure. The crude product was isolated in quantitative yield (assumed 100%).

LCMS Method 4: r.t 0.91 mins [$MH^+$] 195

(5-Isopropyl-1H-pyrazol-3-yl)((1R,5S,6r)-6-((S)-2-methylpyrrolidine-1-carbonyl)-3-azabicyclo[3.1.0]hexan-3-yl)methanone Prepared from ((1R,5S,6r)-3-Azabicyclo[3.1.0]hexan-6-yl)((S)-2-methylpyrrolidin-1-yl)methanone hydrochloride and 3-isopropyl-1H-pyrazole-5-carboxylic acid using Pyrrolidine Amide General Procedure 2. Purification of the crude product by reverse phase chromatography eluting with 10-98% MeCN in 0.1% $NH_4OH$ solution to afford the title compound as a white solid (115 mg, 32%).

LCMS Method 1: r.t 3.29 mins [$MH^+$] 331.2

$^1H$ NMR (400 MHz, $d_6$-DMSO) δ, ppm 12.93 (1H, s), 6.38 (1H, s), 4.27-4.19 (1H, m), 3.99-3.83 (3H, m), 3.61-3.50 (2H, m), 3.00-2.90 (1H, m), 2.15-1.73 (5H, m), 1.65-1.46 (2H, m), 1.22 (6H, d, J=6.9 Hz), 1.18-1.04 (3H, m) plus one proton obscured by the water peak.

Example 131

(2,2-Dimethylpyrrolidin-1-yl)((1R,5S,6r)-3-(5-isopropyl-1H-pyrazole-3-carbonyl)-3-azabicyclo[3.1.0]hexan-6-yl)methanone tert-Butyl-(1R,5S,6r)-6-(2,2-dimethylpyrrolidine-1-carbonyl)-3-azabicyclo[3.1.0]hexane-3-carboxylate Prepared from (1R,5S,6R)-3-(tert-butoxycarbonyl)-3-azabicyclo[3.1.0]hexane-6-carboxylic acid and 2,2-dimethylpyrrolidine hydrochloride using Pyrrolidine Amide General Procedure 1. The crude product was isolated in quantitative yield (assumed 100%).

LCMS Method 4: r.t 1.50 mins [$MH^+$] 309

((1R,5S,6r)-3-Azabicyclo[3.1.0]hexan-6-yl)(2,2-dimethylpyrrolidin-1-yl)methanone hydrochloride Prepared from tert-butyl-(1R,5S,6r)-6-(2,2-dimethylpyrrolidine-1-carbonyl)-3-azabicyclo[3.1.0]hexane-3-carboxylate using Pyrrolidine Boc Deprotection General Procedure. The crude product was isolated in quantitative yield (assumed 100%).

LCMS Method 4: r.t 1.03 mins [$MH^+$] 209

(2,2-Dimethylpyrrolidin-1-yl)((1R,5S,6r)-3-(5-isopropyl-1H-pyrazole-3-carbonyl)-3-azabicyclo[3.1.0]hexan-6-yl)methanone Prepared from ((1R,5 S, 6r)-3-azabicyclo[3.1.0] hexan-6-yl) (2,2-dimethylpyrrolidin-1-yl)methanone hydrochloride and 3-isopropyl-1H-pyrazole-5-carboxylic acid using Pyrrolidine Amide General Procedure 2. Purification of the crude product by reverse phase chromatography eluting with 10-98% MeCN in 0.1% $NH_4OH$ solution to afford the title compound as a white solid (173 mg, 46%).

$^1$H NMR (400 MHz, $d_6$-DMSO) δ, ppm 12.91 (1H, s), 6.37 (1H, s), 4.27 (1H, d, J=12.0 Hz), 3.90-3.83 (2H, m), 3.63-3.59 (2H, m), 3.51 (1H, dd, J=4.0, 12.3 Hz), 3.00-2.90 (1H, m), 2.03-1.97 (1H, m), 1.93-1.81 (1H, m), 1.80-1.68 (4H, m), 1.52-1.44 (1H, m), 1.41-1.32 (6H, m), 1.21 (6H, d, J=7.0 Hz).

LCMS Method 1: r.t 3.66 mins [$MH^+$] 345.1

Example 132

1-[2-(5-Isopropyl-1H-pyrazole-3-carbonyl)-6-oxa-2,7-diazaspiro[3.4]octan-7-yl]-2,2-dimethyl-propan-1-one

N-hydroxypivalamide

The title compound was prepared according to the procedure detailed in J. E. Johnson, A. Ghafouripour and Y. K. Haug, *J. Org. Chem,* 1985, 50, 993

2,2-Dimethyl-1-(2-tosyl-6-oxa-2,7-diazaspiro[3.4]octan-7-yl)propan-1-one

To a stirred suspension of 3,3-bis(bromomethyl)-1-(p-toluenesulfonyl)azetidine (300 mg, 0.76 mmol), N-hydroxypivalamide (177 mg, 1.51 mmol) and cesium carbonate (738 mg, 2.27 mmol) in DMF (10 mL) was added water (1 mL). The reaction mixture was stirred at 60° C. for 24 h then cooled to rt and water (~40 mL) was added. The resulting precipitate was filtered off and washed with water to provide the title compound as a white solid (196 mg, 74%).

LCMS Method 2: r.t 1.35 mins [$MH^+$] 353

2,2-Dimethyl-1-(6-oxa-2,7-diazaspiro[3.4]octan-7-yl)propan-1-one

To a stirred mixture of magnesium powder (414 mg, 17.0 mmol) in anhydrous MeOH (5 mL) was added a crystal of iodine. The resulting mixture was stirred until the green colour of the iodine faded. An ice bath was used periodically to prevent boiling of the solvent. A solution of 2,2-dimethyl-1-(2-tosyl-6-oxa-2,7-diazaspiro[3.4]octan-7-yl)propan-1-one (150 mg, 0.43 mmol) in anhydrous MeOH (4 mL) was added and the reaction was sonicated at rt for 30 min. The reaction mixture was diluted with DCM and concentrated in vacuo. The crude product was taken up in MeOH and filtered through a pad of Celite®. The Celite® pad was washed with MeOH then DCM. The MeOH/DCM filtrate was discarded and the Celite® pad was washed with water and the filtrate was freeze-dried. The resulting product was washed with DCM and the DCM filtrate was concentrated in vacuo to provide the title compound as a yellow oil (35 mg, 42%).

LCMS Method 4: r.t 1.03 mins [$MH^+$] 199

1-[2-(5-Isopropyl-1H-pyrazole-3-carbonyl)-6-oxa-2,7-diazaspiro[3.4]octan-7-yl]-2,2-dimethyl-propan-1-one To a solution of 5-isopropyl-1H-pyrazole-3-carboxylic acid (27 mg, 0.18 mmol) and triethylamine (0.06 mL, 0.42 mmol) in DCM (0.5 mL) was added HATU (81 mg, 0.21 mmol). The reaction was stirred at room temperature for 10 min then a solution of 2,2-dimethyl-1-(6-oxa-2,7-diazaspiro[3.4]octan-7-yl)propan-1-one (35 mg, 0.18 mmol) in DCM (0.5 mL) was added and the resulting mixture was stirred at room temperature for 16 h. The reaction mixture was diluted with DCM and washed with water. The aqueous phase was extracted once with DCM then the combined organic phases were passed through a phase separator and concentrated in vacuo. Purification of the crude product by reverse phase chromatography eluting with 5-70% MeCN in 0.1% $NH_4OH$ solution to afford the title compound as a white solid (12 mg, 20%).

$^1$H NMR (400 MHz, $d_6$-DMSO) δ, ppm 13.00 (1H, s), 6.38 (1H, s), 4.58-4.52 (2H, m), 4.20-4.05 (4H, m), 3.94-3.87 (2H, m), 3.01-2.91 (1H, m), 1.21 (6H, d, J=7.0 Hz), 1.17 (9H, s).

LCMS Method 1: r.t 3.68 mins [$MH^+$] 335.1

Example 133

(4-(Difluoromethyl)-1-methyl-1H-pyrazol-3-yl)(6-(5-isopropyl-1H-pyrazole-3-carbonyl)-2,6-diazaspiro[3.3]heptan-2-yl)methanone

Ethyl 4-(difluoromethyl)-1-methyl-1H-pyrazole-3-carboxylate

A solution of ethyl 4-formyl-1-methyl-1H-pyrazole-3-carboxylate (600 mg, 3.6 mmol) in DCM (20 mL) was added DAST (1150 mg, 7.1 mmol) and MeOH (11 mg, 3.6 mmol). The resulting mixture was mechanically stirred at rt for 12 h then partitioned between saturated sodium hydrogen carbonate solution and DCM (×3). The combined DCM layers were dried over solid magnesium sulphate and evaporated to dryness then purified by silica gel chromatography eluting with 0 to 60% ethylacetate in cyclohexane. The relevant fractions were collected and concentrated in vacuo to yield 540 mg of a white solid (79%).

$^1$H NMR (300 MHz, $CDCl_3$) δ, ppm 7.67 (1H, s), 7.14 (1H, t, J=55.7 Hz), 4.43 (2H, q, J=7.1 Hz), 4.01-4.00 (3H, m), 1.42 (3H, t, J=7.0 Hz).

4-(Difluoromethyl)-1-methyl-1H-pyrazole-3-carboxylic acid

A solution of ethyl 4-(difluoromethyl)-1-methyl-1H-pyrazole-3-carboxylate (540 mg, 2.6 mmol) in dioxane (4.0 mL) was added lithium hydroxide hydrate (444 mg, 106 mmol) in water (4.0 mL). The resulting mixture was stirred at 50° C. for 0.5 h then diluted with water (10 mL) and concentrated in vacuo to remove the volatile organics. This solution was then acidified (1N HCl soln., pH=1) and partitioned with ethylacetate (×3). The combined ethylacetate extracts were dried over solid magnesium sulphate and evaporated to dryness to yield 380 mg of a white solid (81%).

$^1$H NMR (300 MHz, $CDCl_3$) δ, ppm 7.72 (1H, s), 7.14 (1H, t, J=55.5 Hz), 4.03-4.02 (3H, in).

(4-(Difluoromethyl)-1-methyl-1H-pyrazol-3-yl)(6-(5-isopropyl-1H-pyrazole-3-carbonyl)-2,6-diazaspiro[3.3]heptan-2-yl)methanone To a solution of (5-isopropyl-1H-pyrazol-3-yl)(2,6-diazaspiro[3.3]heptan-2-yl)methanone (170 mg, 0.73 mmol) and 4-(difluoromethyl)-1-methyl-1H-pyrazole-3-carboxylic acid (153 mg, 0.87 mmol) in DMF (3.0 mL) was added diisopropylethylamine (375 mg, 2.90 mmol) and HATU (386 mg, 1.0 mmol). The resulting mixture was stirred at rt for 1.5 h then partitioned between water and ethylacetate (×3). The combined ethylacetate extracts were dried over solid magnesium sulphate and evaporated to dryness then purified by silica gel chromatography eluting 0 to 6% MeOH in DCM.

The relevant fractions were collected and concentrated in vacuo to yield 160 mg white solid (56%).

$^1H$ NMR (400 MHz, $d_6$-DMSO) δ, ppm 12.98 (1H, s), 8.19 (1H, s), 7.26 (1H, t, J=56.0 Hz), 6.36 (1H, d, J=1.7 Hz), 4.64 (41-1, d, J=6.7 Hz), 4.23-4.16 (4H, m), 3.92-3.91 (3H, m), 3.00-2.91 (1H, m), 1.23-1.20 (6H, m).

LCMS Method 5: r.t. 3.36 min, [$M^+$] 393

Example 134

(5-Isopropyl-1H-pyrazol-3-yl)((1R,5S,6r)-6-(5-methyl-4-phenylisoxazol-3-yl)-3-azabicyclo[3.1.0]hexan-3-yl)methanone tert-Butyl (1R,5S,6r)-6-((E)-(hydroxyimino)methyl)-3-azabicyclo[3.1.0]hexane-3-carboxylate To a solution of tert-butyl (1R,5S,6r)-6-formyl-3-azabicyclo[3.1.0]hexane-3-carboxylate (100 mg, 0.47 mmol) in EtOH (2 mL) was added HOAc (28.4 mg, 0.47 mmol), KOAc (46.5 mg, 0.47 mmol). Then hydroxylamine hydrochloride (39.5 mg, 0.57 mmol) was added to the mixture. The mixture was stirred at 25° C. for 2 h to give white suspension. The reaction mixture was poured into water (10 mL) and extracted with EtOAc (20 mL×3). The combined organic layers were washed with brine (30 mL), dried over $Na_2SO_4$, filtered and concentrated under reduced pressure to give tert-butyl (1R,5S,6r)-6-((E)-(hydroxyimino)methyl)-3-azabicyclo[3.1.0]hexane-3-carboxylate (100 mg, 0.44 mmol, 93.4% yield) as a colorless oil.

$^1H$ NMR (400 MHz, $d_6$-DMSO) δ, ppm 7.14 (1H, d, J=7.6 Hz), 6.12 (1H, d, J=8.8 Hz), 3.75-3.55 (2H, m), 3.50-3.35 (2H, m), 2.20-2.15 (1H, m), 1.85-1.75 (1H, m), 1.44 (9H, s).

LCMS Method 11: r.t. 0.79 min, [$MH^+$] 227.0 tert-Butyl (1R,5S,6r)-6-((Z)-chloro(hydroxyimino)methyl)-3-azabicyclo[3.1.0]hexane-3-carboxylate To a solution of tert-butyl (1R,5S,6r)-6-((E)-(hydroxyimino)methyl)-3-azabicyclo[3.1.0]hexane-3-carboxylate (100 mg, 0.44 mmol) in DMF (1 mL) was added NCS (62.0 mg, 0.46 mmol). The reaction mixture was stirred at 15° C. for 2 h to give a colorless mixture. The reaction mixture was diluted with water (50 mL) and extracted with EtOAc (30 mL×2). The organic layer was dried over anhydrous $Na_2SO_4$, filtrated and concentrated under reduced pressure to give tert-butyl (1R,5S,6r)-6-((Z)-chloro(hydroxyimino)methyl)-3-azabicyclo[3.1.0]hexane-3-carboxylate (100 mg, 0.38 mmol, 86.8% yield) as a colorless gum.

$^1H$ NMR (400 MHz, $d_6$-DMSO) δ, ppm 3.70-3.45 (2H, m), 3.45-3.25 (2H, m), 2.10-2.00 (2H, m), 1.65-1.60 (1H, m), 1.38 (9H, s).

LCMS Method 11: r.t. 0.79 min, [$MH^+$] 261 tert-Butyl (1R,5S,6r)-6-(5-methylisoxazol-3-yl)-3-azabicyclo[3.1.0]hexane-3-carboxylate To a solution of tert-butyl (1R,5S,6r)-6-((Z)-chloro(hydroxyimino)methyl)-3-azabicyclo[3.1.0]hexane-3-carboxylate (255 mg, 0.98 mmol) and prop-1-en-2-yl acetate (2.1 mL, 19.6 mmol) in DCM (3.3 mL) was added TEA (0.25 mL, 2.0 mmol) dropwise at 0-5° C. The resulting mixture was stirred at 15° C. for 16 h to give a light yellow suspension. The reaction was concentrated to dryness. The residue was partitioned between EtOAc (5 mL) and 0.1 M HCl aq. (15 mL). The organic layer was washed with 0.1 M HCl aq. (5 mL). The above aqueous layers were extracted with EtOAc (5 mL). The combined organic layers were washed with $Na_2CO_3$ aq. (5 mL), brine (5 mL), dried over $Na_2SO_4$, filtered and concentrated to afford tert-butyl (1R,5S,6r)-6-(5-methylisoxazol-3-yl)-3-azabicyclo[3.1.0]hexane-3-carboxylate (258 mg, 0.98 mmol, 99.8% yield) as light yellow oil.

$^1H$ NMR (400 MHz, $CDCl_3$) δ, ppm 5.70 (1H, s), 3.76 (1H, d, J=12.0 Hz), 3.67 (1H, d, J=12.0 Hz), 3.60-3.40 (2H, m), 2.36 (3H, s), 2.00-1.90 (2H, m), 1.76-1.73 (1H, m), 1.45 (9H, s).

LCMS Method 11: r.t. 0.89 min, [$MH^+$] 264 tert-Butyl (1R,5S,6r)-6-(4-bromo-5-methylisoxazol-3-yl)-3-azabicyclo[3.1.0]hexane-3-carboxylate To a solution of tert-butyl (1R,5S,6r)-6-(5-methylisoxazol-3-yl)-3-azabicyclo[3.1.0]hexane-3-carboxylate (258 mg, 0.98 mmol) in DMF (2 mL) was added NBS (173.7 mg, 0.98 mmol) at 0-5° C. The reaction was stirred at 15° C. for 16 h to give a yellow solution. The reaction was diluted with water (15 mL) and extracted with EtOAc (5 mL×3). The combined organic layers were washed with $NH_4Cl$ aq. (5 mL×2), $NaHCO_3$ aq. (5 mL), brine (5 mL), dried over $Na_2SO_4$, filtered and concentrated to afford tert-butyl (1R,5S,6r)-6-(4-bromo-5-methylisoxazol-3-yl)-3-azabicyclo[3.1.0]hexane-3-carboxylate (251 mg, 0.73 mmol, 74.9% yield) as a light yellow oil.

$^1H$ NMR (400 MHz, $CDCl_3$) δ, ppm 3.78 (1H, d, J=10.8 Hz), 3.70 (1H, d, J=10.8 Hz), 3.46 (2H, d, J=10.8 Hz), 2.39 (3H, s), 2.20-2.05 (2H, m), 1.70-1.65 (1H, m), 1.46 (9H, s).

tert-Butyl (1R,5S,6r)-6-(5-methyl-4-phenylisoxazol-3-yl)-3-azabicyclo[3.1.0]hexane-3-carboxylate To a solution of tert-butyl (1R,5S,6r)-6-(4-bromo-5-methylisoxazol-3-yl)-3-azabicyclo[3.1.0]hexane-3-carboxylate (200 mg, 0.58 mmol) in DMF (2 mL) and water (0.2 mL) was added phenylboronic acid (85.3 mg, 0.7 mmol), $NaHCO_3$ (146.9 mg, 1.8 mmol) and $Pd(PPh_3)_2C12$ (40.9 mg, 0.06 mmol) under nitrogen. The resulting mixture was stirred at 90° C. for 16 h to give a black brown solution. The reaction was diluted with water (20 mL) and extracted with EtOAc (5 mL×3). The combined organic layers were washed with $NH_4Cl$ aq. (5 mL×2), brine (5 mL), dried over $Na_2SO_4$, filtered and concentrated to dryness.

The residue was purified by prep-TLC (PE/EtOAc=4/1, Rf=0.6) to afford tert-butyl (1R,5 S,6r)-6-(5-methyl-4-phenylisoxazol-3-yl)-3-azabicyclo[3.1.0]hexane-3-carboxylate (105 mg, 0.31 mmol, 52.9% yield) as a white solid.

LCMS Method 11: r.t. 0.98 [$MH^+$] 341

3-((1R,5S,6r)-3-azabicyclo[3.1.0]hexan-6-yl)-5-methyl-4-phenylisoxazole hydrochloride A mixture of tert-butyl (1R,5S,6r)-6-(5-methyl-4-phenylisoxazol-3-yl)-3-azabicyclo[3.1.0]hexane-3-carboxylate (50 mg, 0.1500 mmol) in 4M HCl/dioxane (5 mL, 0.15 mmol) was stirred at 0° C. for 50 min to give colorless solution. The reaction was concentrated in vacuo to give 3-((1R,5S,6r)-3-azabicyclo[3.1.0] hexan-6-yl)-5-methyl-4-phenylisoxazole hydrochloride (50 mg, 0.18 mmol, 123% yield) as a pale yellow gum which was used directly in the next step.

LCMS Method 11: r.t. 0.66 [$MH^+$] 240.9

(5-isopropyl-1H-pyrazol-3-yl)((1R,5S,6r)-6-(5-methyl-4-phenylisoxazol-3-yl)-3-azabicyclo[3.1.0]hexan-3-yl)methanone To a solution of 3-((1R,5S,6r)-3-azabicyclo[3.1.0]hexan-6-yl)-5-methyl-4-phenylisoxazole hydrochloride (86 mg, 0.36 mmol) in DMF (1 mL) was added 5-isopropyl-1H-pyrazole-3-carboxylic acid (55.2 mg, 0.36 mmol), DIEA (0.18 mL, 1.1 mmol) and HATU (204 mg, 0.54 mmol) at 0-5° C. The resulting mixture was stirred at 15° C. for 16 h to give a light brown solution. The reaction was diluted with water (15 mL) and extracted with EtOAc (5 mL×3). The combined organic layers were washed with $NH_4Cl$ aq. (5 mL×2), brine (5 mL), dried over $Na_2SO_4$, filtered and concentrated to dryness. The residue was purified by prep-TLC (DCM/EtOAc/MeOH=10/5/1, Rf=0.6) and lyophilized to afford (5-isopropyl-1H-pyrazol-3-yl)((1R,5S,6r)-6-(5-methyl-4-phenylisoxazol-3-yl)-3-azabicyclo[3.1.0]hexan-3-yl)methanone (52.7 mg, 0.14 mmol, 39.1% yield) as a white solid.

$^1$H NMR (400 MHz, $CDCl_3$) δ, ppm 7.50-7.40 (2H, m), 7.35-7.30 (1H, m), 7.30-7.25 (2H, m), 6.44 (1H, s), 4.22 (1H, d, J=11.2 Hz), 4.15 (1H, d, J=11.2 Hz), 3.99 (1H, dd, 11.2, 4.4 Hz), 3.72 (1H, dd, J=11.2, 4.4 Hz), 3.01 (1H, qn, J=7.2 Hz), 2.50-2.40 (1H, m), 2.40 (3H, s), 2.25-2.15 (1H, m), 1.60-1.55 (1H, m), 1.28 (6H, d, J=7.2 Hz).

LCMS Method 11: r.t 0.87 min [$MH^+$] 377.0

Biological Example 1

Biochemical KDM5A Inhibition Assay

Using 384-well white ProxiPlates (PerkinElmer), representative compounds were characterized for their inhibition of KDM5A using HTRF® technology (Cisbio Bioassays). Briefly, the test compounds, reference compounds, and DMSO control (typical compound concentration range 300 pM-10 μM, final assay concentration (FAC) of DMSO 0.5%) were added to 384-well plate by the Echo® acoustic dispensing platform (Labcyte). Three (3) μl of KDM5A protein (BPS Bioscience, Cat #50110)(10 or 20 nM FAC) in assay buffer (50 mM MES, 50 mM NaCl, 2 mM ascorbic acid, 0.01% v/v Tween 20, pH 6.5) was added to wells and plates were incubated for 10 minutes at room temperature. Then, 3 μl of biotin-labelled H3K4-me3 substrate (Anaspec Cat #AS-64357-1; 100 nM FAC), alpha-ketoglutaric acid (100 FAC) and Fe(II)$SO_4$ (FAC 100 μM) in assay buffer was added and plates were incubated for 60 minutes at room temperature. The reaction was stopped with the addition of 6 μl of anti-H3-K4-Met-Eu(K) (Cisbio Bioassays Cat #61KA2KAE; 0.025 μg/ml FAC)+Streptavidin XL665 (Cisbio Bioassays Cat #610SAXLA; 0.5 μg/ml FAC) in HTRF detection buffer (Cisbio Bioassays Cat #62SDBRDD). The mixture was incubated for 90 minutes at room temperature before 340 nm excitation and measurement of dual emission at 620 nm and 665 nm. The raw data (a 665 nm and a 620 nm reading from each well) for individual assay plates were analyzed. The ratio of emissions was calculated using the following calculation:

$$Ratio=(665\ nm\ emission/620\ nm\ emission)*10000.$$

Using DMSO control (maximum response or 0% inhibition) and 1 μM reference control compound (minimum response or 100% inhibition), percentage inhibition values for each well were calculated using the median values of the minimum and maximum control wells and the following calculation:

$$\%\ Inhibition=(Well\ ratio-max\ control\ ratio)/(min\ control\ ratio-max\ control\ ratio)*100.$$

Compound $IC_{50}$ values were calculated from graphs of % inhibition plotted against compound concentration, using a four parameter curve fit.

Results

The present compounds exhibited a strong KDM5 inhibitory activity. $IC_{50}$ values (μM) of representative present compounds are shown in the table below. In the table, * represents the results measured at 10 nM and the others at 20 nM enzyme concentration. $IC_{50}$ values (μM) of comparative compound, (R)—N-(1-(3-isopropyl-1H-pyrazole-5-carbonyl)pyrrolidin-3-yl)cyclopropane carboxamide (the compound of Examples 29 described in the pamphlet of International Publication No. WO2016057924) and 5-(1-(cyclopropylmethyl)-1H-pyrazol-4-yl)-6-isopropyl-7-oxo-4,7-dihydropyrazolo[1,5-a]pyrimidine-3-carbonitrile (the compound of Example 6 described in the pamphlet of International Publication No. WO2014139326) were 0.02 and 0.005 μM, respectively.

| EXAMPLE No. | $IC_{50}$ value (μM) |
|---|---|
| EXAMPLE 8 | 0.04 |
| EXAMPLE 19 | 0.03 |
| EXAMPLE 20 | 0.04 |
| EXAMPLE 21 | 0.04 |
| EXAMPLE 26 | 0.2 |
| EXAMPLE 27 | 0.05 |
| EXAMPLE 30 | 0.3 |
| EXAMPLE 31 | 0.2 |
| EXAMPLE 41 | 0.03 |
| EXAMPLE 47 | 0.05 |
| EXAMPLE 62 | 1.0 |
| EXAMPLE 67 | 2.9 |
| EXAMPLE 68 | 0.4 |
| EXAMPLE 80 | 0.2 |
| EXAMPLE 81 | 0.1 |
| EXAMPLE 92 | 0.6 |
| EXAMPLE 94 | 1.5* |
| EXAMPLE 95 | 0.4 |
| EXAMPLE 96 | 0.03 |
| EXAMPLE 121 | 0.09 |
| EXAMPLE 126 | 0.008 |

Biological Example 2

Permeability in Wild Type MDCK Cell Lines (MDCK-WT)

Wild type MDCKII cells were seeded onto an apical chamber 3 days prior to running the assay at a density of $2.3\times10^5$ cells per well. The integrity of cell monolayers was evaluated by examining the permeability of lucifer yellow assay using a Spectramax Gemini XS with excitation and emission at 426 nm and 538 nm respectively. Permeation of Lucifer Yellow should be $\leq10\times10^{-6}$ cm/s for the experimental data to be accepted. The cell monolayers were preincubated in transport buffer (HBSS with $CaCl_2$ and $MgCl_2$)+25 mM HEPES, adjust to pH 7.4) at 37° C. or more than 20 min. Transport experiment was initiated by adding test compound solution (10 μM) to the apical chamber. Samples were obtained from basal chamber at 60 min, followed by addition of ice-cold acetonitrile containing internal standard. LC-MS/MS analysis was conducted as specified below. Standard calibration samples were prepared using the same matrix and analysed in the same manner.

| | | |
|---|---|---|
| LC | System | Waters TQD |
| | Column | Kinetix XB-C18 100 A 50 × 2.1 mm 2.6 μM |
| | Elution conditions | Column temperature: Room temperature |
| | | Mobile phase: |
| | | A: 0.1% Formic acid in water (v/v) |
| | | B: 0.1% Formic acid in acetonitrile (v/v) |
| | | Gradient program: |
| | | Time (min) 0 0.5 0.85 0.9 1.1 |
| | | Mobile phase B (%) 5 95 95 5 5 |
| | | Flow rate: 0.7 mL/min |
| MS | Condition | Electrospray ionization, positive ion mode, multiple reaction monitoring mode |

The apparent permeability in apical to basal direction ($P_{app}$, cm/s) of test compound was calculated according to the formula described below.

$$P_{app}(cm/s)=(dC_B/dt)\times V_B/(A\times C_A)$$

$dC_B/dt$ is the slope of the cumulative concentration in basal side versus time $V_B$ is the volume of the basal compartment A is the area of the membrane surface area $C_A$ is the initial concentration in apical side

Results

The permeability in MDCK-WT of the present compounds was high. The permeabilities in MDCK-WT of representative present compounds are shown in the table below. The permeabilities in MDCK-WT of comparative compound, (R)—N-(1-(3-isopropyl-1H-pyrazole-5-carbonyl)pyrrolidin-3-yl)cyclopropanecarboxamide (the compound of Example 29 described in the pamphlet of International Publication No. WO2016057924) and 5-(1-(cyclopropylmethyl)-1H-pyrazol-4-yl)-6-isopropyl-7-oxo-4,7-dihydropyrazolo[1,5-a]pyrimidine-3-carbonitrile (the compound of Example 6 described in the pamphlet of International Publication No. WO2014139326) were $4.9\times10^{-6}$ and $5.6\times10^{-6}$ cm/s, respectively.

| EXAMPLE No. | MDCK-WT ($P_{app}$) [$10^{-6}$ cm/s] |
|---|---|
| EXAMPLE 8 | 23 |
| EXAMPLE 20 | 25 |
| EXAMPLE 21 | 10 |
| EXAMPLE 26 | 20 |
| EXAMPLE 30 | 37 |
| EXAMPLE 31 | 64 |
| EXAMPLE 73 | 16 |
| EXAMPLE 89 | 9 |
| EXAMPLE 92 | 8 |
| EXAMPLE 94 | 68 |
| EXAMPLE 95 | 66 |
| EXAMPLE 99 | 20 |
| EXAMPLE 104 | 8 |
| EXAMPLE 105 | 6 |
| EXAMPLE 131 | 20 |
| EXAMPLE 132 | 19 |
| EXAMPLE 134 | 24 |

Formulation Example 1

Tablets containing 5 mg of 3-isopropyl-4-oxo-2-phenyl-3,4-dihydropyrido[3,2-cl]pyrimidine-8-carboxamide The following components can be mixed and compressed to tablets according to standard methods to obtain 10,000 tablets containing 5 mg of the active component.

3-isopropyl-4-oxo-2-phenyl-3,4-dihydropyrido[3,2-d]pyrimidine-8-carboxamide: 50 g Carboxymethylcellulose calcium (disintegrating agent): 20 g Magnesium stearate (lubricant): 10 g Microcrystalline cellulose: 920 g

Formulation Example 2

Tablets containing 5 mg of ((1R,5S,6r)-6-(cyclopropanecarbonyl)-3-azabicyclo[3.1.0]hexan-3-yl)(5-isopropyl-1H-pyrazol-3-yl)methanone The following components can be mixed and compressed to tablets according to standard methods to obtain 10,000 tablets containing 5 mg of the active component.

((1R,5S,6r)-6-(cyclopropanecarbonyl)-3-azabicyclo[3.1.0]hexan-3-yl)(5-isopropyl-1H-pyrazol-3-yl)methanone: 50 g Carboxymethylcellulose calcium (disintegrating agent): 20 g Magnesium stearate (lubricant): 10 g Microcrystalline cellulose: 920 g

Formulation Example 3

Injections containing 20 mg of (5-Isopropyl-1H-pyrazol-3-yl)(6-(1-methylcyclopropane-1-carbonyl)-2,6-diazaspiro[3.3]heptan-2-yl)methanone The following components can be mixed according to the standard method, and the solution can be then sterilised according to the standard method, divided into ampoules at 5-mL aliquot and lyophilised according to the standard method to obtain 10,000 ampoules containing 20 mg of the active component.

(5-Isopropyl-1H-pyrazol-3-yl)(6-(1-methylcyclopropane-1-carbonyl)-2,6-diazaspiro[3.3]heptan-2-yl)methanone: 200 g Mannitol: 20 g Distilled water: 50 L

INDUSTRIAL APPLICABILITY

The present compound has KDM5 inhibitory activity, and thus is useful as a prophylactic and/or therapeutic agent for cancer, Huntington's disease, or Alzheimer's disease and the like.

The invention claimed is:

1. A compound of the following formula (II-1-1):

(II-1-1)

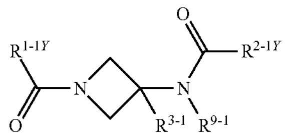

wherein $R^{1-1Y}$ represents

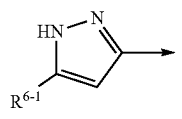 or 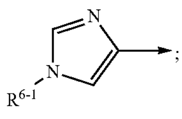;

in the group, the arrow indicates a binding to the carbon atom of carbonyl;

$R^{6-1}$ represents a C1-4 alkyl which is optionally substituted with 1 to 4 $R^{8-1}$, C3-8 cycloalkyl, C3-8 cycloalkyl which is substituted with C1-4 alkyl, C1-4 haloalkyl, or halogen atom;

$R^{8-1}$ represents a hydroxy, halogen atom, nitrile, benzyloxy, or 5- or 6-membered monocyclic carbocycle;

$R^{2-1Y}$ represents a 3- to 8-membered monocyclic carbocycle which is optionally substituted with 1 to 4 $R^{13-1}$ or 4- to 15-membered bicyclic carbocycle which is optionally substituted with 1 to 4 $R^{14-1}$;

$R^{13-1}$ represents a C1-4 alkyl, C3-8 cycloalkyl, halogen atom, or C1-4 haloalkyl;

$R^{14-1}$ represents a C1-4 alkyl, C3-8 cycloalkyl, halogen atom, or C1-4 haloalkyl;

when being substituted with a plurality of $R^{8-1}$, $R^{13-1}$ or $R^{14-1}$, $R^{8-1}$, $R^{13-1}$ or $R^{14-1}$ are the same or different from each other;

$R^{3-1}$ represents a hydrogen atom, C1-4 alkyl, C1-4 haloalkyl, or halogen atom;

$R^{9-1}$ represents a hydrogen atom, or C1-4 alkyl; and

 represents α-configuration, β-configuration or a mixture of α-configuration and β-configuration, or a salt thereof.

2. The compound according to claim 1, wherein the compound is N-(1-(5-isopropyl-1H-pyrazole-3-carbonyl) azetidin-3-yl) cyclopropanecarboxamide or a salt thereof.

3. A pharmaceutical composition comprising the compound or the salt thereof according to claim 1, and a pharmaceutically acceptable carrier.

4. The pharmaceutical composition according to claim 3, which is a KDM5 inhibitor.

5. The pharmaceutical composition according to claim 3, further comprising one or more drug selected from the group consisting of donepezil hydrochloride, galantamine hydrobromide, huperzine A, idebenone, levacecarnine hydrochloride, memantine hydrochloride, memantine hydrochloride/ donepezil hydrochloride, proteolytic peptide fraction from porcine brain protein, rivastigmine tartrate, tacrine hydrochloride, and aducanumab.

6. A method for inhibiting KDM5 in a subject in need thereof, comprising administering to the subject an effective amount of the compound or the salt thereof according to claim 1.

7. The method according to claim 6, wherein the subject has cancer or Alzheimer's disease.

* * * * *